(12) United States Patent
Vogt et al.

(10) Patent No.: US 11,180,470 B2
(45) Date of Patent: Nov. 23, 2021

(54) HERBICIDAL PYRIMIDINE COMPOUNDS

(71) Applicant: BASF SE, Ludwigshafen am Rhein (DE)

(72) Inventors: Florian Vogt, Ludwigshafen (DE); Matthias Witschel, Ludwigshafen (DE); Veronica Lopez Carrillo, Ludwigshafen (DE); Tobias Seiser, Limburgerhof (DE); Thomas Seitz, Ludwigshafen (DE); Gerd Kraemer, Limburgerhof (DE); Klaus Reinhard, Limburgerhof (DE); Trevor William Newton, Limburgerhof (DE); Doreen Schachtschabel, Ludwigshafen (DE); Kristin Hanzlik, Limburgerhof (DE)

(73) Assignee: BASF SE, Ludwigshafen (DE)

( * ) Notice: Subject to any disclaimer, the term of this patent is extended or adjusted under 35 U.S.C. 154(b) by 113 days.

(21) Appl. No.: 16/319,871

(22) PCT Filed: Jul. 10, 2017

(86) PCT No.: PCT/EP2017/067261
§ 371 (c)(1),
(2) Date: Jan. 23, 2019

(87) PCT Pub. No.: WO2018/019552
PCT Pub. Date: Feb. 1, 2018

(65) Prior Publication Data
US 2019/0225594 A1     Jul. 25, 2019

(30) Foreign Application Priority Data

Jul. 25, 2016  (EP) ..................................... 16180948
Jul. 28, 2016  (EP) ..................................... 16181597

(51) Int. Cl.
| | | |
|---|---|---|
| *C07D 401/04* | (2006.01) | |
| *A01N 43/54* | (2006.01) | |
| *C07D 405/04* | (2006.01) | |
| *C07D 409/04* | (2006.01) | |
| *A01N 25/32* | (2006.01) | |

(52) U.S. Cl.
CPC .......... *C07D 401/04* (2013.01); *A01N 43/54* (2013.01); *C07D 405/04* (2013.01); *C07D 409/04* (2013.01); *A01N 25/32* (2013.01)

(58) Field of Classification Search
CPC .................................................. C07D 401/04
See application file for complete search history.

(56) References Cited

FOREIGN PATENT DOCUMENTS

| | | |
|---|---|---|
| WO | 0073278 A2 | 12/2000 |
| WO | 05063721 A1 | 7/2005 |
| WO | 11057935 A1 | 5/2011 |
| WO | 13178585 A1 | 12/2013 |
| WO | 16120116 A1 | 8/2016 |
| WO | 16120355 A2 | 8/2016 |
| WO | 18015180 A1 | 1/2018 |
| WO | 18019554 A1 | 2/2018 |
| WO | 18019555 A1 | 2/2018 |
| WO | 18019574 A1 | 2/2018 |
| WO | 18019765 A1 | 2/2018 |
| WO | 18019860 A1 | 2/2018 |

OTHER PUBLICATIONS

Search Report, issued in EP Application No. 16180948.8, dated Oct. 7, 2016.
International Search Report, issued in PCT/EP2017/067261, dated Aug. 4, 2017.
International Preliminary Report on Patentability, issued in PCT/EP2017/067261, dated Jan. 29, 2019.

*Primary Examiner* — Yong S. Chong
(74) *Attorney, Agent, or Firm* — Marshall, Gerstein & Borun LLP

(57) ABSTRACT

The present invention relates to the pyrimidine compounds of formula (I),

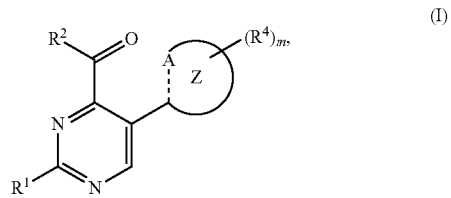

or their agriculturally acceptable salts or derivatives as herbicides, wherein the variables are defined according to the description, use of pyrimidine compounds of formula (I) as herbicide, compositions comprising them and their use as herbicides, i.e. for controlling harmful plants, and also a method for controlling unwanted vegetation which comprises allowing a herbicidal effective amount of at least one pyrimidine compounds of the formula (I) to act on plants, their seed and/or their habitat.

16 Claims, No Drawings

HERBICIDAL PYRIMIDINE COMPOUNDS

This application is a National Stage application of International Application No. PCT/EP2017/067261, filed Jul. 10, 2017. This application also claims priority under 35 U.S.C. § 119 to European Patent Application No. 16180948.8, filed Jul. 25, 2016, and European Patent Application No. 16181597.2, filed Jul. 28, 2016.

The present invention relates to pyrimidine compounds of the general formula (I) defined below and to their use as herbicides. Moreover, the invention relates to compositions for crop protection and to a method for controlling unwanted vegetation.

Compounds having a 5-phenyl pyrimidine moiety are known in the art. WO 2000/073278 describes such compounds being antagonists of the Neurokinin 1 receptor and thus having pharmaceutical properties.

In agriculture, there is a constant demand to develop novel active ingredients, which complement or outperform present methods of treatment regarding activity, selectivity and environmental safety.

These and further objects are achieved by pyrimidine compounds of formula (I), defined below, and by their agriculturally suitable salts.

Accordingly, the present invention provides the pyrimidine compounds of formula (I)

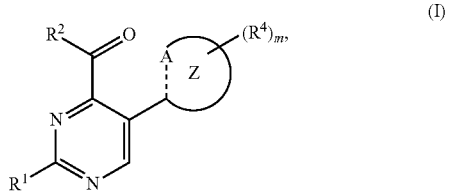

wherein
the dotted line (------) is a single bond or a double bond;
$R^1$ is $C_1$-$C_6$-alkyl, $C_1$-$C_6$-haloalkyl, OH—$C_1$-$C_6$-alkyl, $C_3$-$C_6$-alkenyl, $C_3$-$C_6$-haloalkenyl, $C_2$-$C_6$-alkynyl, $C_3$-$C_6$-haloalkynyl, $C_1$-$C_6$-alkoxy-$C_1$-$C_6$-alkyl, $C_1$-$C_6$-alkoxy, $C_3$-$C_6$-alkenyloxy, $C_3$-$C_6$-haloalkenyloxy, $C_3$-$C_6$-alkynyloxy, $C_3$-$C_6$-haloalkynyloxy, $C_1$-$C_6$-haloalkoxy, $C_3$-$C_6$-cycloalkoxy, $C_3$-$C_6$-halocycloalkoxy, $C_3$-$C_6$-cycloalkenyloxy, $C_3$-$C_6$-halocycloalkenyloxy, $C_1$-$C_6$-alkylthio, $C_1$-$C_6$-haloalkylthio, ($C_1$-$C_6$-alkyl)amino, di($C_1$-$C_6$-alkyl)amino, $C_1$-$C_6$-alkylsulfinyl, $C_1$-$C_6$-alkylsulfonyl, $C_3$-$C_6$-cycloalkyl, $C_3$-$C_6$-cycloalkenyl, $C_3$-$C_6$-halocycloalkyl, $C_3$-$C_6$-halocycloalkenyl, [1-($C_1$-$C_6$-alkyl)]-$C_3$-$C_6$-cycloalkyl, [1-($C_3$-$C_6$-alkenyl)]-$C_3$-$C_6$-cycloalkyl, [1-($C_2$-$C_6$-alkynyl)]-$C_3$-$C_6$-cycloalkyl, [1-($C_1$-$C_6$-haloalkyl)]-$C_3$-$C_6$-cycloalkyl, [1-($C_3$-$C_6$-haloalkenyl)]-$C_3$-$C_6$-cycloalkyl, [1-($C_3$-$C_6$-haloalkynyl)]-$C_3$-$C_6$-cycloalkyl, $C_3$-$C_6$-cycloalkyl-$C_1$-$C_6$-alkyl, $C_3$-$C_6$-cycloalkyl-$C_1$-$C_6$-haloalkyl, $C_3$-$C_6$-cycloalkyl-$C_1$-$C_6$-alkoxy, $C_3$-$C_6$-cycloalkyl-$C_1$-$C_6$-haloalkoxy, phenyl, 5- or 6-membered heteroaryl, or 3- to 6-membered heterocyclyl;
wherein the cyclic groups of $R^1$ are unsubstituted or substituted by $R^a$;
$R^2$ is H, halogen, $C_1$-$C_6$-alkyl, $C_1$-$C_6$-haloalkyl, $C_1$-$C_6$-alkylcarbonyl-$C_1$-$C_6$-alkyl, $C_1$-$C_6$-alkoxycarbonyl-$C_1$-$C_6$-alkyl, $C_1$-$C_6$-haloalkylcarbonyl-$C_1$-$C_6$-alkyl, $C_1$-$C_6$-haloalkoxycarbonyl-$C_1$-$C_6$-alkyl, $C_1$-$C_6$-alkylcarbonyl-$C_1$-$C_6$-haloalkyl, $C_1$-$C_6$-alkoxycarbonyl-$C_1$-$C_6$-haloalkyl, $C_1$-$C_6$-haloalkylcarbonyl-$C_1$-$C_6$-haloalkyl, $C_1$-$C_6$-haloalkoxycarbonyl-$C_1$-$C_6$-haloalkyl, OH, $C_1$-$C_6$-alkoxy, $C_1$-$C_6$-alkoxy-$C_1$-$C_6$-alkoxy, $C_1$-$C_6$-haloalkoxy-$C_1$-$C_6$-alkoxy, $C_1$-$C_6$-alkoxy-$C_1$-$C_6$-haloalkoxy, $C_1$-$C_6$-haloalkoxy-$C_1$-$C_6$-haloalkoxy, $C_1$-$C_6$-alkoxy-$C_1$-$C_6$-alkoxy-$C_1$-$C_6$-alkoxy, $C_1$-$C_6$-haloalkoxy, $C_1$-$C_6$-cyanoalkoxy, $C_1$-$C_6$-hydroxyalkoxy, $C_3$-$C_6$-alkenyloxy, $C_3$-$C_6$-alkenyloxy-$C_1$-$C_6$-alkoxy, $C_3$-$C_6$-haloalkenyloxy-$C_1$-$C_6$-haloalkoxy, $C_3$-$C_6$-alkenyloxy-$C_1$-$C_6$-haloalkoxy, $C_3$-$C_6$-haloalkenyloxy, $C_3$-$C_6$-alkynyloxy, $C_3$-$C_6$-haloalkynyloxy, $C_3$-$C_6$-alkynyloxy-$C_1$-$C_6$-alkoxy, $C_3$-$C_6$-haloalkynyloxy-$C_1$-$C_6$-haloalkoxy, $C_3$-$C_6$-alkynyloxy-$C_1$-$C_6$-haloalkoxy, $C_3$-$C_6$-alkynyloxy-$C_3$-$C_6$-alkenyloxy, $C_3$-$C_6$-haloalkynyloxy-$C_3$-$C_6$-alkenyloxy, $C_3$-$C_6$-alkynyloxy-$C_3$-$C_6$-haloalkenyloxy, $C_3$-$C_6$-haloalkynyloxy-$C_3$-$C_6$-haloalkenyloxy, $C_3$-$C_6$-alkynyloxy-$C_3$-$C_6$-alkynyloxy, $C_3$-$C_6$-haloalkynyloxy-$C_3$-$C_6$-alkynyloxy, $C_3$-$C_6$-alkynyloxy-$C_3$-$C_6$-haloalkynyloxy, $C_3$-$C_6$-haloalkynyloxy-$C_3$-$C_6$-haloalkynyloxy, ($C_1$-$C_6$-alkyl)carbonyl-$C_1$-$C_6$-alkoxy, ($C_1$-$C_6$-haloalkyl)carbonyl-$C_1$-$C_6$-haloalkoxy, ($C_1$-$C_6$-haloalkyl)carbonyl-$C_1$-$C_6$-alkoxy, ($C_1$-$C_6$-alkyl)carbonyl-$C_1$-$C_6$-haloalkoxy, ($C_1$-$C_6$-alkoxy)carbonyl-$C_1$-$C_6$-alkoxy, ($C_1$-$C_6$-haloalkoxy)carbonyl-$C_1$-$C_6$-alkoxy, ($C_1$-$C_6$-alkoxy)carbonyl-$C_1$-$C_6$-haloalkoxy, ($C_1$-$C_6$-haloalkoxy)carbonyl-$C_1$-$C_6$-haloalkoxy, ($C_1$-$C_6$-alkoxy-$C_1$-$C_6$-alkyl)carbonyl-$C_1$-$C_6$-alkoxy, ($C_1$-$C_6$-haloalkoxy-$C_1$-$C_6$-alkyl)carbonyl-$C_1$-$C_6$-alkoxy, ($C_1$-$C_6$-alkoxy-$C_1$-$C_6$-haloalkyl)carbonyl-$C_1$-$C_6$-alkoxy, ($C_1$-$C_6$-alkoxy-$C_1$-$C_6$-alkyl)carbonyl-$C_1$-$C_6$-haloalkoxy, ($C_1$-$C_6$-haloalkoxy-$C_1$-$C_6$-haloalkyl)carbonyl-$C_1$-$C_6$-alkoxy, ($C_1$-$C_6$-haloalkoxy-$C_1$-$C_6$-alkyl)carbonyl-$C_1$-$C_6$-haloalkoxy, ($C_1$-$C_6$-alkoxy-$C_1$-$C_6$-haloalkyl)carbonyl-$C_1$-$C_6$-haloalkoxy, ($C_1$-$C_6$-haloalkoxy-$C_1$-$C_6$-haloalkyl)carbonyl-$C_1$-$C_6$-haloalkoxy, ($C_1$-$C_6$-alkylthio)carbonyl-$C_1$-$C_6$-alkoxy, ($C_1$-$C_6$-haloalkylthio)carbonyl-$C_1$-$C_6$-alkoxy, ($C_1$-$C_6$-alkylthio)carbonyl-$C_1$-$C_6$-haloalkoxy, ($C_1$-$C_6$-haloalkylthio)carbonyl-$C_1$-$C_6$-haloalkoxy, ($C_1$-$C_6$-alkylthio-$C_1$-$C_6$-alkyl)carbonyl-$C_1$-$C_6$-alkoxy, ($C_1$-$C_6$-haloalkylthio-$C_1$-$C_6$-alkyl)carbonyl-$C_1$-$C_6$-alkoxy, ($C_1$-$C_6$-alkylthio-$C_1$-$C_6$-haloalkyl)carbonyl-$C_1$-$C_6$-alkoxy, ($C_1$-$C_6$-alkylthio-$C_1$-$C_6$-alkyl)carbonyl-$C_1$-$C_6$-haloalkoxy, ($C_1$-$C_6$-haloalkylthio-$C_1$-$C_6$-haloalkyl)carbonyl-$C_1$-$C_6$-alkoxy, ($C_1$-$C_6$-haloalkylthio-$C_1$-$C_6$-alkyl)carbonyl-$C_1$-$C_6$-haloalkoxy, ($C_1$-$C_6$-alkylthio-$C_1$-$C_6$-haloalkyl)carbonyl-$C_1$-$C_6$-haloalkoxy, ($C_1$-$C_6$-haloalkylthio-$C_1$-$C_6$-haloalkyl)carbonyl-$C_1$-$C_6$-haloalkoxy, $C_3$-$C_6$-cycloalkoxy, $C_3$-$C_6$-halocycloalkoxy, ($C_3$-$C_6$-cycloalkyl)$C_1$-$C_6$-alkoxy, ($C_3$-$C_6$-halocycloalkyl)$C_1$-$C_6$-alkoxy, ($C_3$-$C_6$-cycloalkyl)$C_1$-$C_6$-haloalkoxy, $C_1$-$C_6$-alkylcarbonylamino, [($C_1$-$C_6$-alkyl)carbonyl]($C_1$-$C_6$-alkyl)amino, $C_1$-$C_6$-haloalkylcarbonylamino, [($C_1$-$C_6$-haloalkyl)carbonyl]($C_1$-$C_6$-alkyl)amino, $C_3$-$C_6$-cycloalkylcarbonylamino, [($C_3$-$C_6$-cycloalkyl)carbonyl]($C_1$-$C_6$-alkyl)amino, phenylcarbonylamino, (phenylcarbonyl)($C_1$-$C_6$-alkyl)amino, heterocyclylcarbonylamino, (heterocyclylcarbonyl)($C_1$-$C_6$-alkyl)amino, heteroarylcarbonylamino, (heteroarylcarbonyl)($C_1$-$C_6$-alkyl)amino, [($C_1$-$C_6$-alkyl)carbonyl]($C_1$-$C_6$-alkoxy)amino, [($C_1$-$C_6$-haloalkyl)carbonyl]($C_1$-$C_6$-alkoxy)amino, [($C_3$-$C_6$-cycloalkyl)carbonyl]($C_1$-$C_6$-alkyloxy)amino, (phenylcarbonyl)($C_1$-$C_6$-alkoxy)amino, (heterocyclylcarbonyl)($C_1$-$C_6$-alkoxy)amino, (heteroarylcarbonyl)($C_1$-$C_6$-alkoxy)amino, [($C_1$-$C_6$-alkyl)carbonyl]($C_2$-$C_6$-alkenyl)amino, [($C_1$-$C_6$-haloalkyl)carbonyl]($C_2$-$C_6$-alkenyl)amino, [($C_3$-$C_6$-cycloalkyl)carbonyl]($C_2$-$C_6$-alkenyl)amino, (phenylcarbonyl)($C_2$-$C_6$-alkenyl)amino, (heterocyclylcarbonyl)($C_2$-$C_6$-alkenyl)amino, (heteroarylcarbonyl)($C_2$-$C_6$-alkenyl)amino, [($C_1$-$C_6$-alkyl)

carbonyl](C$_3$-C$_6$-alkynyl)amino, [(C$_1$-C$_6$-haloalkyl)carbonyl](C$_3$-C$_6$-alkynyl)amino, [(C$_3$-C$_6$-cycloalkyl)carbonyl](C$_3$-C$_6$-alkynyl)amino, (phenylcarbonyl)(C$_3$-C$_6$-alkynyl)amino, (heterocyclylcarbonyl)(C$_3$-C$_6$-alkynyl)amino, (heteroarylcarbonyl)(C$_3$-C$_6$-alkynyl)amino, [(C$_2$-C$_6$-alkenyl)carbonyl]amino, [(C$_2$-C$_6$-alkenyl)carbonyl](C$_1$-C$_6$-alkyl)amino, [(C$_2$-C$_6$-alkenyl)carbonyl](C$_1$-C$_6$-alkoxy)amino, [(C$_3$-C$_6$-alkynyl)carbonyl]amino, [(C$_3$-C$_6$-alkynyl)carbonyl](C$_1$-C$_6$-alkyl)amino, [(C$_3$-C$_6$-alkynyl)carbonyl](C$_1$-C$_6$-alkoxy)amino, [di(C$_1$-C$_6$-alkyl)amino]carbonylamino, [di(C$_1$-C$_6$-alkyl)aminocarbonyl](C$_1$-C$_6$-alkyl)amino, [di(C$_1$-C$_6$-alkyl)aminocarbonyl](C$_1$-C$_6$-alkoxy)amino, aminocarbonyl-C$_1$-C$_6$-alkoxy, (C$_3$-C$_6$-halocycloalkyl)C$_1$-C$_6$-haloalkoxy, aminocarbonyl-C$_1$-C$_6$-haloalkoxy, N—(C$_1$-C$_6$-alkyl)aminocarbonyl-C$_6$-C$_6$-alkoxy, N—(C$_1$-C$_6$-alkyl)-aminocarbonyl-C$_1$-C$_6$-haloalkoxy, N,N-di(C$_1$-C$_6$-alkyl)aminocarbonyl-C$_1$-C$_6$-alkoxy, N,N-di(C$_1$-C$_6$-alkyl)aminocarbonyl-C$_1$-C$_6$-haloalkoxy, (diphenyl)C=N—O, (C$_1$-C$_6$-alkyl)(phenyl)C=N—O, (di(C$_1$-C$_6$-alkyl))C=N—O, (C$_1$-C$_6$-alkyl)-3-silyl-C$_1$-C$_6$-alkoxy, C$_1$-C$_6$-alkylthio, C$_1$-C$_6$-haloalkylthio, C$_1$-C$_6$-alkoxy-C$_1$-C$_6$-alkylthio, C$_1$-C$_6$-haloalkoxy-C$_1$-C$_6$-alkylthio, C$_1$-C$_6$-alkoxy-C$_1$-C$_6$-haloalkylthio, C$_1$-C$_6$-haloalkoxy-C$_1$-C$_6$-haloalkylthio, C$_1$-C$_6$-alkoxy-C$_1$-C$_6$-alkoxy-C$_1$-C$_6$-alkylthio, C$_1$-C$_6$-cyanoalkylthio, C$_3$-C$_6$-alkenylthio, C$_3$-C$_6$-haloalkenylthio, C$_3$-C$_6$-alkenyloxy-C$_1$-C$_6$-alkylthio, C$_3$-C$_6$-haloalkenyloxy-C$_1$-C$_6$-alkylthio, C$_3$-C$_6$-alkenyloxy-C$_1$-C$_6$-haloalkylthio, C$_3$-C$_6$-haloalkenyloxy-C$_1$-C$_6$-haloalkylthio, C$_3$-C$_6$-alkynylthio, C$_3$-C$_6$-haloalkynylthio, C$_3$-C$_6$-alkynyloxy-C$_1$-C$_6$-alkylthio, C$_3$-C$_6$-haloalkynyloxy-C$_1$-C$_6$-haloalkylthio, C$_3$-C$_6$-alkynyloxy-C$_1$-C$_6$-haloalkylthio, C$_3$-C$_6$-alkynyloxy-C$_3$-C$_6$-alkenylthio, C$_3$-C$_6$-haloalkynyloxy-C$_3$-C$_6$-alkenylthio, C$_3$-C$_6$-alkynyloxy-C$_3$-C$_6$-haloalkenylthio, C$_3$-C$_6$-haloalkynyloxy-C$_3$-C$_6$-haloalkenylthio, C$_3$-C$_6$-alkynyloxy-C$_2$-C$_6$-alkynylthio, C$_3$-C$_6$-haloalkynyloxy-C$_3$-C$_6$-alkynylthio, C$_3$-C$_6$-alkynyloxy-C$_3$-C$_6$-haloalkynylthio, C$_3$-C$_6$-haloalkynyloxy-C$_3$-C$_6$-haloalkynylthio, (C$_1$-C$_6$-alkyl)carbonyl-C$_1$-C$_6$-alkylthio, (C$_1$-C$_6$-haloalkyl)carbonyl-C$_1$-C$_6$-alkylthio, (C$_1$-C$_6$-alkyl)carbonyl-C$_1$-C$_6$-haloalkylthio, (C$_1$-C$_6$-haloalkyl)carbonyl-C$_1$-C$_6$-haloalkylthio, (C$_1$-C$_6$-alkoxy)carbonyl-C$_1$-C$_6$-alkylthio, (C$_1$-C$_6$-haloalkoxy)carbonyl-C$_1$-C$_6$-alkylthio, (C$_1$-C$_6$-alkoxy)carbonyl-C$_1$-C$_6$-haloalkylthio, (C$_1$-C$_6$-haloalkoxy)carbonyl-C$_1$-C$_6$-haloalkylthio, (C$_1$-C$_6$-alkoxy-C$_1$-C$_6$-alkyl)carbonyl-C$_1$-C$_6$-alkylthio, (C$_1$-C$_6$-haloalkoxy-C$_1$-C$_6$-alkyl)carbonyl-C$_1$-C$_6$-alkylthio, (C$_1$-C$_6$-alkoxy-C$_1$-C$_6$-haloalkyl)carbonyl-C$_1$-C$_6$-alkylthio, (C$_1$-C$_6$-alkoxy-C$_1$-C$_6$-alkyl)carbonyl-C$_1$-C$_6$-haloalkylthio, (C$_1$-C$_6$-haloalkoxy-C$_1$-C$_6$-haloalkyl)carbonyl-C$_1$-C$_6$-alkylthio, (C$_1$-C$_6$-haloalkoxy-C$_1$-C$_6$-alkyl)carbonyl-C$_1$-C$_6$-haloalkylthio, (C$_1$-C$_6$-alkoxy-C$_1$-C$_6$-haloalkyl)carbonyl-C$_1$-C$_6$-haloalkylthio, (C$_1$-C$_6$-haloalkoxy-C$_1$-C$_6$-haloalkyl)carbonyl-C$_1$-C$_6$-haloalkylthio, (C$_1$-C$_6$-alkylthio)carbonyl-C$_1$-C$_6$-alkylthio, (C$_1$-C$_6$-haloalkylthio)carbonyl-C$_1$-C$_6$-alkylthio, (C$_1$-C$_6$-alkylthio)carbonyl-C$_1$-C$_6$-haloalkylthio, (C$_1$-C$_6$-haloalkylthio)carbonyl-C$_1$-C$_6$-haloalkylthio, (C$_1$-C$_6$-alkylthio-C$_1$-C$_6$-alkyl)carbonyl-C$_1$-C$_6$-alkylthio, (C$_1$-C$_6$-haloalkylthio-C$_1$-C$_6$-alkyl)carbonyl-C$_1$-C$_6$-alkylthio, (C$_1$-C$_6$-alkylthio-C$_1$-C$_6$-haloalkyl)carbonyl-C$_1$-C$_6$-alkylthio, (C$_1$-C$_6$-alkylthio-C$_1$-C$_6$-haloalkyl)carbonyl-C$_1$-C$_6$-haloalkylthio, (C$_1$-C$_6$-haloalkylthio-C$_1$-C$_6$-haloalkyl)carbonyl-C$_1$-C$_6$-haloalkylthio, C$_3$-C$_6$-cycloalkylthio, C$_3$-C$_6$-halocycloalkylthio, (C$_3$-C$_6$-cycloalkyl)C$_1$-C$_6$-alkylthio, (C$_3$-C$_6$-cycloalkyl)C$_1$-C$_6$-haloalkylthio, (C$_3$-C$_6$-halocycloalkyl)C$_1$-C$_6$-alkylthio, (C$_3$-C$_6$-halocycloalkyl)C$_1$-C$_6$-haloalkylthio, aminocarbonyl-C$_1$-C$_6$-alkylthio, aminocarbonyl-C$_1$-C$_6$-haloalkylthio, N—(C$_1$-C$_6$-alkyl)-aminocarbonyl-C$_1$-C$_6$-alkylthio, N—(C$_1$-C$_6$-haloalkyl)-aminocarbonyl-C$_1$-C$_6$-alkylthio, N—(C$_1$-C$_6$-alkyl)-aminocarbonyl-C$_1$-C$_6$-haloalkylthio, N—(C$_1$-C$_6$-haloalkyl)-aminocarbonyl-C$_1$-C$_6$-haloalkylthio, N,N-di(C$_1$-C$_6$-alkyl)-aminocarbonyl-C$_1$-C$_6$-alkylthio, N,N-di(C$_1$-C$_6$-haloalkyl)aminocarbonyl-C$_1$-C$_6$-alkylthio, N,N-di(C$_1$-C$_6$-alkyl)-aminocarbonyl-C$_1$-C$_6$-haloalkylthio, N,N-di(C$_1$-C$_6$-haloalkyl)-aminocarbonyl-C$_1$-C$_6$-haloalkylthio, NH$_2$, (C$_1$-C$_6$-alkyl)amino, hydroxyamino, (C$_1$-C$_6$-alkoxy)amino, (C$_3$-C$_6$-cycloalkoxy)amino, (C$_1$-C$_6$-alkyl)sulfinylamino, (C$_1$-C$_6$-alkyl)sulfonylamino, (amino)sulfinylamino, [(C$_1$-C$_6$-alkyl)amino]sulfinylamino, (amino)sulfonylamino, [(C$_1$-C$_6$-alkyl)amino]sulfonylamino, [di(C$_1$-C$_6$-alkyl)amino]sulfonylamino, di(C$_1$-C$_6$-alkyl)amino, (hydroxy)(C$_1$-C$_6$-alkyl)amino, (hydroxy)(C$_1$-C$_6$-cycloalkyl)amino, (C$_1$-C$_6$-alkoxy)(C$_1$-C$_6$-alkyl)amino, (C$_1$-C$_6$-alkoxy)(C$_3$-C$_6$-cycloalkyl)amino, (C$_3$-C$_6$-cycloalkoxy)(C$_1$-C$_6$-alkyl)amino, (C$_3$-C$_6$-cycloalkoxy)(C$_3$-C$_6$-cycloalkyl)amino, [(C$_1$-C$_6$-alkyl)sulfinyl](C$_1$-C$_6$-alkyl)amino, [(C$_1$-C$_6$-alkyl)sulfonyl](C$_1$-C$_6$-alkyl)amino, [di(C$_1$-C$_6$-alkyl)amino]sulfinylamino, [di(C$_1$-C$_6$-alkyl)amino]sulfonylamino, phenyloxy, phenyl-C$_1$-C$_6$-alkoxy, phenylthio, phenyl-C$_1$-C$_6$-alkylthio, phenylamino, (C$_1$-C$_6$-alkyl)(phenyl)amino, (heteroaryl)oxy, heteroaryl-C$_1$-C$_6$-alkoxy, (heterocyclyl)oxy, or heterocyclyl-C$_1$-C$_6$-alkoxy;

wherein the cyclic groups of R$^2$ are unsubstituted or substituted by R$^a$;

A is CR$^3$ or NR$^{3A}$;

Z is a 5 or 6 membered heteroaryl ring comprising A;

R$^3$ is halogen, CN, NO$_2$, CHO, C$_1$-C$_6$-alkyl, C$_1$-C$_6$-haloalkyl, C$_1$-C$_6$-alkylcarbonyl, C$_3$-C$_6$-alkenyl, C$_3$-C$_6$-haloalkenyl, C$_2$-C$_6$-alkynyl, C$_3$-C$_6$-haloalkynyl, C$_1$-C$_6$-alkoxy, C$_1$-C$_6$-haloalkoxy, C$_3$-C$_6$-alkenyloxy, C$_3$-C$_6$-haloalkenyloxy, C$_3$-C$_6$-alkynyloxy, C$_3$-C$_6$-haloalkynyloxy, C$_1$-C$_6$-alkoxy-C$_1$-C$_6$-alkoxy, hydroxycarbonyl, C$_1$-C$_6$-alkoxycarbonyl, C$_1$-C$_6$-alkylthio, C$_1$-C$_6$-haloalkylthio, NH$_2$, (C$_1$-C$_6$-alkyl)amino, di(C$_1$-C$_6$-alkyl)amino, (C$_1$-C$_6$-alkyl)sulfinyl, (C$_1$-C$_6$-alkyl)sulfonyl, C$_3$-C$_6$-cycloalkyl, (C$_3$-C$_6$-cycloalkyl)oxy, or phenyl;

wherein the cyclic groups of R$^3$ are unsubstituted or substituted by substituents R$^a$;

R$^{3A}$ is H, C$_1$-C$_6$-alkyl, C$_1$-C$_6$-haloalkyl, C$_1$-C$_6$-alkylcarbonyl, C$_3$-C$_6$-alkenyl, C$_3$-C$_6$-haloalkenyl, C$_2$-C$_6$-alkynyl, C$_3$-C$_6$-haloalkynyl, C$_1$-C$_6$-alkoxy, C$_1$-C$_6$-haloalkoxy, C$_3$-C$_6$-alkenyloxy, C$_3$-C$_6$-haloalkenyloxy, C$_3$-C$_6$-alkynyloxy, C$_3$-C$_6$-haloalkynyloxy, C$_1$-C$_6$-alkoxy-C$_1$-C$_6$-alkoxy, hydroxycarbonyl, C$_1$-C$_6$-alkoxycarbonyl, C$_1$-C$_6$-alkylthio, C$_1$-C$_6$-haloalkylthio, NH$_2$, (C$_1$-C$_6$-alkyl)amino, di(C$_1$-C$_6$-alkyl)amino, (C$_1$-C$_6$-alkyl)sulfinyl, (C$_1$-C$_6$-alkyl)sulfonyl, C$_3$-C$_6$-cycloalkyl, (C$_3$-C$_6$-cycloalkyl)oxy, or phenyl;

wherein the cyclic groups of R$^{3A}$ are unsubstituted or substituted by R$^a$;

R$^4$ is halogen, CN, NO$_2$, CHO, C$_1$-C$_6$-alkyl, C$_1$-C$_6$-haloalkyl, C$_1$-C$_6$-alkylcarbonyl, C$_3$-C$_6$-alkenyl, C$_3$-C$_6$-haloalkenyl, C$_3$-C$_6$-alkenyl, C$_3$-C$_6$-haloalkenyl, C$_1$-C$_6$-alkoxy, C$_1$-C$_6$-haloalkoxy, C$_3$-C$_6$-alkenyloxy, C$_3$-C$_6$-haloalkenyloxy, C$_3$-C$_6$-alkenyloxy, C$_3$-C$_6$-haloalkenyloxy, C$_1$-C$_6$-alkoxy-C$_1$-C$_6$-alkoxy, hydroxycarbonyl, C$_1$-C$_6$-alkoxycarbonyl, $C_1$-$C_6$-alkylthio, $C_1$-$C_6$-haloalkylthio, $NH_2$, ($C_1$-$C_6$-alkyl)amino, di($C_1$-$C_6$-alkyl)amino, ($C_1$-$C_6$-alkyl)sulfinyl, ($C_1$-$C_6$-alkyl)sulfonyl, $C_3$-$C_6$-cycloalkyl, ($C_3$-$C_6$-cycloalkyl)oxy, or phenyl;
wherein the cyclic groups of $R^4$ are unsubstituted or substituted by $R^a$;
$R^a$ is halogen, CN, $NO_2$, $C_1$-$C_6$-alkyl, $C_1$-$C_6$-haloalkyl, $C_1$-$C_6$-alkoxy, or $C_1$-$C_6$-haloalkoxy;
m is 0, 1, 2, or 3;
and agriculturally acceptable salts or derivatives of the compounds of formula (I) having an acidic functionality.

The present invention also provides the use of pyrimidine compounds of formula (I) and agriculturally acceptable salts or derivatives of the compounds of formula (I) having an acidic functionality, as herbicide.

The pyrimidine compounds of formula (I) according to the invention can be prepared by standard processes of organic chemistry, e.g. by the following processes:

Process A:

The pyrimidine compounds of formula (I) can be obtained by reacting respective pyrimidines of formula (II) with boronic acids of formula (III):

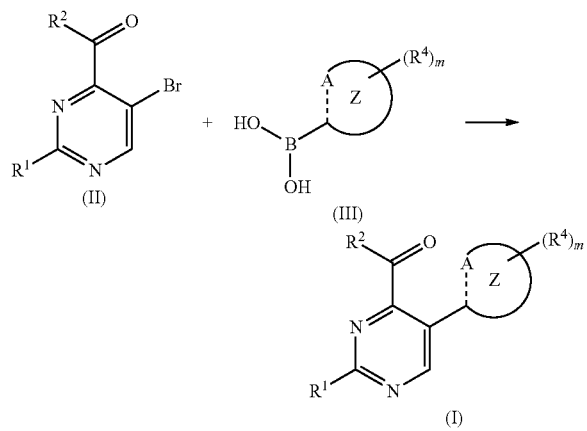

The reaction of the pyrimidine (II) with boronic acids (III) is usually carried out at from 0° C. to the boiling point of the reaction mixture, preferably at from 15° C. to 110° C., particularly preferably at from 40° C. to 100° C., in an inert organic solvent in the presence of a base and a catalyst.

The reaction may in principle be carried out in substance. However, preference is given to reacting the pyrimidines (II) with the boronic acids (III) in an organic solvent with or without water as co-solvent.

Suitable in principle are all solvents which are capable of dissolving the pyrimidines (II) and the boronic acids (III) at least partly and preferably fully under the reaction conditions.

Examples of suitable solvents are aromatic hydrocarbons such as benzene, chlorobenzene, toluene, cresols, o-, m- and p-xylene, ethers such as diethyl ether, diisopropyl ether, tert.-butyl methylether (TBME), dioxane, anisole and tetrahydrofuran (THF), as well as dipolar aprotic solvents such as sulfolane, dimethylsulfoxide, N,N-dimethylformamide (DMF), N,N-dimethylacetamide (DMAC), 1,3-dimethyl-2-imidazolidinone (DMI), N,N'-dimethylpropylene urea (DMPU), dimethyl sulfoxide (DMSO) and 1-methyl-2 pyrrolidinone (NMP).

Preferred solvents are ethers such as diethyl ether, diisopropyl ether, TBME, dioxane, anisole and THF and dipolar aprotic solvents such as sulfolane, dimethylsulfoxide, DMF, DMAC, DMI, N,N'-dimethyl¬propylene urea (DMPU), DMSO and 1-methyl-2 pyrroli-dinone (NMP).

More preferred solvents are ethers such as diethyl ether, diisopropyl ether, TBME, dioxane, anisole and THF.

It is also possible to use mixtures of the solvents mentioned.

Examples of suitable metal-containing bases are inorganic compounds including metal-containing bases such as alkali metal and alkaline earth metal hydroxides, and other metal hydroxides, such as LiOH, NaOH, KOH, MgOH, CaOH and AlOH; alkali metal and alkaline earth metal oxide, and other metal oxides, such as $Li_2O$, $Na_2O$, $K_2O$, MgO, CaO, $Fe_2O_3$, and $Ag_2O$; alkali metal and alkaline earth metal carbonates such as $Li_2CO_3$, $Na_2CO_3$, $K_2CO_3$, $Cs_2CO_3$, $MgCO_3$, and $CaCO_3$, as well as alkali metal hydrogen carbonates (bicarbonates) such as $LiHCO_3$, $NaHCO_3$, $KHCO_3$; alkali metal and alkaline earth metal phosphates such as potassium phosphate, calcium phosphate.

The term base as used herein also includes mixtures of two or more, preferably two of the above bases. Particular preference is given to the use of one base.

The bases are used preferably at from 1 to 10 equivalents based on the pyrimidine (II), more preferably at from 1.0 to 5.0 equivalents based on the pyrimidine (II), most preferably from 1.2 to 2.5 equivalents based on the pyrimidine (II).

It may be advantageous to add the base offset over a period of time.

The reaction of the pyrimidines (II) with the boronic acids (II) is carried out in the presence of a catalyst. Examples of suitable catalysts include e.g., palladium based catalysts like, e.g., Palladium(II)acetate, tetrakis(triphenylphosphine) palladium(0), bis(triphenylphosphine)palladium(II)chloride, or (1,1,-bis(diphenylphosphino)ferrocene)-dichloropalladium(II), and optionally suitable additives such as, e.g., phosphines like, e.g., P(o-tolyl)3, tr phenylphosphine, or BINAP (2,2'-Bis(diphenylphospino)-1,1'-binaphthyl).

The amount of catalyst is usually 0.01 to 20 mol % (0.0001 to 0.2 equivalents) based on the pyrimidine (II).

Pyrimidine compounds (I) wherein $R^2$ is OH can be easily obtained from a corresponding ester (I) in which $R^2$ equals an alkoxy group (e.g. $R=CH_3$) by methods known to a person skilled in the art.

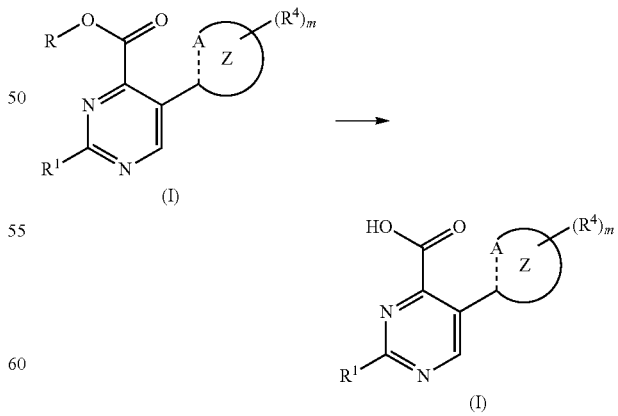

Alternatively pyrimidine compounds (I), wherein $R^2$ has any one of the above mentioned meanings except OH, can also be obtained by modifying pyrimidine compounds (I) wherein $R^2$ is OH by known methods (e.g. "oxy-substituents" except "OH" analogous to Arnab, P. et. al. Angew. Chem. Int. Ed. 2010, 49, 1492-1495; "thio-substituents" analogous to Silvestri, M. A. et. al. J. Med. Chem. 2004, 47, 3149-3162; "amino-sustituents" analogous to Kuhn, B. et. al. J. Med. Chem. 2010, 53, 2601-2611).

The pyrimidines (II) wherein $R^2$ is OH are known from the literature (e.g. WO 06/004532) or are commercially available.

To obtain the other pyrimidines (II), wherein $R^2$ has any one of the above mentioned meanings except OH, the pyrimidines (II) wherein $R^2$ is OH can easily be modified by known methods (e.g. "oxy-substituents" except "OH" analogous to Arnab, P. et. al. Angew. Chem. Int. Ed. 2010, 49, 1492-1495; "thio-substituents" analogous to Silvestri, M. A. et. al. J. Med. Chem. 2004, 47, 3149-3162; "amino-substituents" analogous to Kuhn, B. et. al. J. Med. Chem. 2010, 53, 2601-2611).

The boronic acids (III) required for the preparation of pyrimidine compounds of formula (I) are known from the literature, are commercially available or can easily prepared by methods known to a person skilled in the art.

Process B:

The pyrimidine compounds of formula (I) can in addition be obtained by reacting respective pyrimidine boronic acid esters of formula (IV) with halides of formula (V) in which X equals Cl, Br, or I:

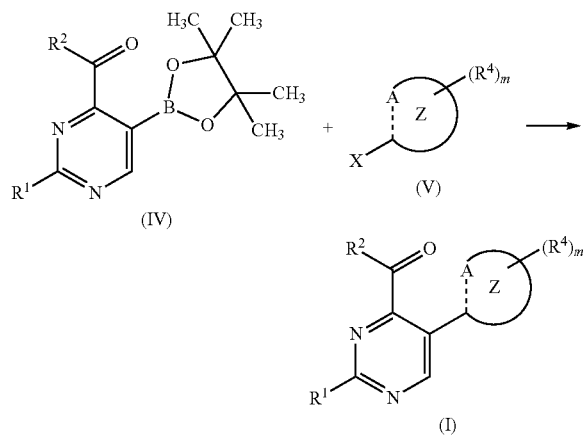

The reaction of the pyrimidine (IV) with halides (V) is usually carried out at from 0° C. to the boiling point of the reaction mixture, preferably at from 15° C. to 110° C., particularly preferably at from 40° C. to 100° C., in an inert organic solvent in the presence of a base and a catalyst.

The reaction may in principle be carried out in substance. However, preference is given to reacting the pyrimidines (IV) with the halides (V) in an organic solvent with or without water as co-solvent.

Suitable in principle are all solvents which are capable of dissolving the pyrimidines (IV) and the halides (V) at least partly and preferably fully under reaction conditions.

Examples of suitable solvents are aromatic hydrocarbons such as benzene, chlorobenzene, toluene, cresols, o-, m- and p-xylene, ethers such as diethyl ether, diisopropyl ether, TBME, dioxane, anisole and THF, as well as dipolar aprotic solvents such as sulfolane, dimethylsulfoxide, DMF, DMAC, DMI, DMPU, DMSO and NMP.

Preferred solvents are ethers such as diethyl ether, diisopropyl ether, TBME, dioxane, anisole and THF and dipolar aprotic solvents such as sulfolane, dimethylsulfoxide, DMF, DMAC, DMI, N,N'-dimethyl-propylene urea (DMPU), DMSO and 1-methyl-2 pyrroli-dinone (NMP).

More preferred solvents are ethers such as diethyl ether, diisopropyl ether, TBME, dioxane, anisole and THF.

It is also possible to use mixtures of the solvents mentioned.

Examples of suitable metal-containing bases are inorganic compounds including metal-containing bases such as alkali metal and alkaline earth metal hydroxides, and other metal hydroxides, such as LiOH, NaOH, KOH, MgOH, CaOH and AlOH; alkali metal and alkaline earth metal oxide, and other metal oxides, such as $Li_2O$, $Na_2O$, $K_2O$, MgO, CaO, $Fe_2O_3$, and $Ag_2O$; alkali metal and alkaline earth metal carbonates such as $Li_2CO_3$, $Na_2CO_3$, $K_2CO_3$, $Cs_2CO_3$, $MgCO_3$, and $CaCO_3$, as well as alkali metal hydrogen carbonates (bicarbonates) such as $LiHCO_3$, $NaHCO_3$, $KHCO_3$; alkali metal and alkaline earth metal phosphates such as potassium phosphate, calcium phosphate.

The term base as used herein also includes mixtures of two or more, preferably two of the above bases. Particular preference is given to the use of one base.

The bases are used preferably at from 1 to 10 equivalents based on the pyrimidine (IV), more preferably at from 1.0 to 5.0 equivalents based on the pyrimidine (IV), most preferably from 1.2 to 2.5 equivalents based on the pyrimidine (IV).

It may be advantageous to add the base offset over a period of time.

The reaction of the pyrimidines (IV) with the boronic acids (V) is carried out in the presence of a catalyst. Examples of suitable catalysts include e.g., palladium based catalysts like, e.g., Palladium(II)acetate, tetrakis(triphenylphosphine)palladium(0), bis(triphenylphosphine)palladium(II)chloride or (1,1, -bis(diphenylphosphino)ferrocene)-dichloropalladium(II), and optionally suitable additives such as, e.g., phosphines like, e.g., P(o-tolyl)3, tri-phenylphosphine or BINAP (2,2'-Bis(diphenylphospino)-1,1'-binaphthyl).

The amount of catalyst is usually 0.01 to 20 mol % (0.0001 to 0.2 equivalents) based on the pyrimidine (IV).

The halides (V) required for the preparation of pyrimidine compounds of formula (I) are known from the literature or are commercially available.

The pyrimidines of formula (IV) can be obtained by reacting the respective pyrimidines (II) with Bis(pinacolato) diboron VI.

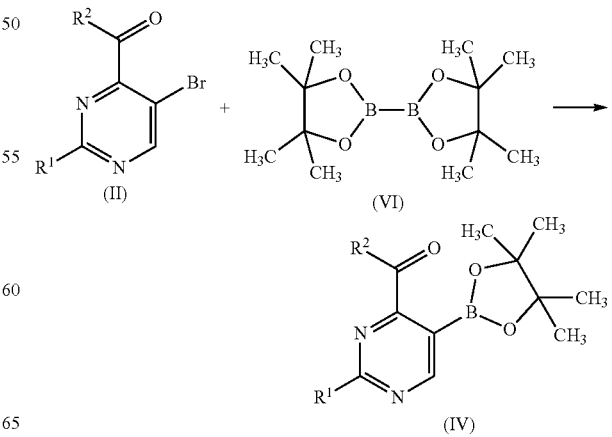

The reaction of the pyrimidine (II) with Bis(pinacolato) diboron VI is usually carried out at from 0° C. to the boiling point of the reaction mixture, preferably at from 15° C. to 110° C., particularly preferably at from 40° C. to 100° C., in an inert organic solvent in the presence of a base and a catalyst.

The reaction may in principle be carried out in substance. However, preference is given to reacting the pyrimidines (II) with Bis(pinacolato)diboron VI in an organic solvent with or without water as co-solvent.

Suitable in principle are all solvents which are capable of dissolving the pyrimidines (II) and the Bis(pinacolato)diboron VI at least partly and preferably fully under reaction conditions.

Examples of suitable solvents are aromatic hydrocarbons such as benzene, chlorobenzene, toluene, cresols, o-, m- and p-xylene, ethers such as diethyl ether, diisopropyl ether, TBME, dioxane, anisole and THF, as well as dipolar aprotic solvents such as sulfolane, dimethylsulfoxide, DMF, DMAC, DMI, DMPU, DMSO and NMP.

Preferred solvents are ethers such as diethyl ether, diisopropyl ether, TBME, dioxane, anisole and THF and dipolar aprotic solvents such as sulfolane, dimethylsulfoxide, DMF, DMAC, DMI, N,N'-dimethyl¬propylene urea (DMPU), DMSO and 1-methyl-2 pyrroli-dinone (NMP).

More preferred solvents are ethers such as diethyl ether, diisopropyl ether, TBME, dioxane, anisole and THF.

It is also possible to use mixtures of the solvents mentioned.

Examples of suitable metal-containing bases are inorganic compounds including metal-containing bases such as alkali metal and alkaline earth metal hydroxides, and other metal hydroxides, such as LiOH, NaOH, KOH, MgOH, CaOH and AlOH; alkali metal and alkaline earth metal oxide, and other metal oxides, such as $Li_2O$, $Na_2O$, $K_2O$, MgO, CaO, $Fe_2O_3$, and $Ag_2O$; alkali metal and alkaline earth metal carbonates such as $Li_2CO_3$, $Na_2CO_3$, $K_2CO_3$, $Cs_2CO_3$, $MgCO_3$, and $CaCO_3$, as well as alkali metal hydrogen carbonates (bicarbonates) such as $LiHCO_3$, $NaHCO_3$, $KHCO_3$; alkali metal and alkaline earth metal phosphates such as potassium phosphate, calcium phosphate; alkali metal and alkaline earth metal acetates such as sodium acetate or potassium acetate.

The term base as used herein also includes mixtures of two or more, preferably two of the above bases. Particular preference is given to the use of one base.

The bases are used preferably at from 1 to 10 equivalents based on the pyrimidine (II), more preferably at from 1.0 to 5.0 equivalents based on the pyrimidine (II), most preferably from 1.2 to 2.5 equivalents based on the pyrimidine (II).

It may be advantageous to add the base offset over a period of time.

The reaction of the pyrimidines (II) with Bis(pinacolato) diboron VI is carried out in the presence of a catalyst. Examples of suitable catalysts include e.g., palladium based catalysts like, e.g., Palladium(II)acetate, tetrakis(triphenylphosphine)palladium(0), bis(triphenylphosphine)palladium(II)chloride or (1,1, -bis(diphenylphosphino)ferrocene)-dichloropalladium(II), and optionally suitable additives such as, e.g., phosphines like, e.g., P(o-tolyl)3, tri-phenylphosphine or BINAP (2,2'-Bis(diphenylphospino)-1,1'-binaphthyl).

The amount of catalyst is usually 0.01 to 20 mol % (0.0001 to 0.2 equivalents) based on the pyrimidine (II).

The end of the reaction can easily be determined by the skilled worker by means of routine methods.

The reaction mixtures are worked up in a customary manner, e.g. by mixing with water, separation of the phases and, if appropriate, chromatographic purification of the crude product.

Some of the intermediates and end products are obtained in the form of viscous oils, which can be purified or freed from volatile components under reduced pressure and at moderately elevated temperature.

If the intermediates and the end products are obtained as solid, purification can also be carried out by recrystallization or digestion.

The present invention also provides compound of formula (III),

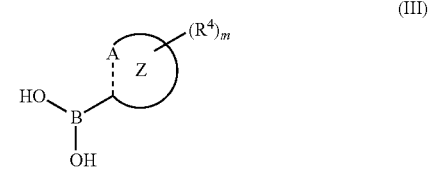

(III)

Wherein the dotted line (------) is a single bond or a double bond; and A, ring Z, $R^4$, and m are as defined for pyrimidine compounds of formula (I).

The present invention also provides compound of formula (IV),

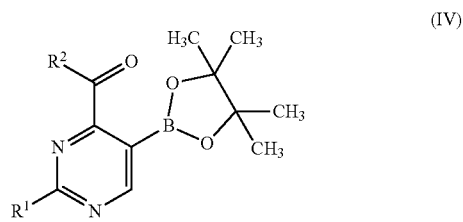

(IV)

Wherein $R^1$ and $R^2$ are as defined for pyrimidine compounds of formula (I).

The present invention also provides agrochemical compositions comprising at least one pyrimidine compounds of formula (I) and auxiliaries customary for formulating crop protection agents.

The present invention furthermore provides a method for controlling unwanted vegetation where a herbicidal effective amount of at least one pyrimidine compounds of formula (I) is allowed to act on plants, their seeds and/or their habitat. Application can be done before, during and/or after, preferably during and/or after, the emergence of the undesirable plants.

Further embodiments of the present invention are evident from the claims, the description and the examples. It is to be understood that the features mentioned above and still to be illustrated below of the subject matter of the invention can be applied not only in the combination given in each particular case but also in other combinations, without leaving the scope of the invention.

As used herein, the terms "controlling" and "combating" are synonyms.

As used herein, the terms "undesirable vegetation" and "harmful plants" are synonyms.

If the pyrimidine compounds of formula (I) as described herein are capable of forming geometrical isomers, e.g. E/Z isomers, it is possible to use both, the pure isomers and mixtures thereof, in the compositions according to the invention.

If the pyrimidine compounds of formula (I) as described herein have one or more centres of chirality and, as a consequence, are present as enantiomers or diastereomers, it is possible to use both, the pure enantiomers and diastereomers and their mixtures, in the compositions according to the invention.

If the pyrimidine compounds of formula (I) as described herein have ionisable functional groups, they can also be employed in the form of their agriculturally acceptable salts. Suitable are, in general, the salts of those cations and the acid addition salts of those acids whose cations and anions, respectively, have no adverse effect on the activity of the active compounds.

Preferred cations are the ions of the alkali metals, preferably of lithium, sodium and potassium, of the alkaline earth metals, preferably of calcium and magnesium, and of the transition metals, preferably of manganese, copper, zinc and iron, further ammonium and substituted ammonium in which one to four H atoms are replaced by $C_1$-$C_4$-alkyl, OH—$C_1$-$C_4$-alkyl, $C_1$-$C_4$-alkoxy-$C_1$-$C_4$-alkyl, OH—$C_1$-$C_4$-alkoxy-$C_1$-$C_4$-alkyl, phenyl or benzyl, preferably ammonium, methyl-ammonium, isopropylammonium, dimethylammonium, diisopropylammonium, trimethylammonium, heptylammonium, dodecylammonium, tetradecylammonium, tetramethylammonium, tetraethylammonium, tetrabutylammonium, 2-hydroxyethylammonium (olamine salt), 2-(2-hydroxyeth-1-oxy)eth-1-ylammonium (diglycolamine salt), di(2-hydroxyeth-1-yl)ammonium (diolamine salt), tris (2-OH-ethyl)ammonium (trolamine salt), tris(2-hydroxypropyl)ammonium, benzyltrimethylammonium, benzyltriethylammonium, N,N,N-trimethylethanolammonium (choline salt), furthermore phosphon-ium ions, sulfonium ions, preferably tri($C_1$-$C_4$-alkyl)sulfonium, such as trimethylsulfonium, and sulfoxonium ions, preferably tri($C_1$-$C_4$-alkyl)sulfoxonium, and finally the salts of polybasic amines such as N,N-bis-(3-aminopropyl)methylamine and diethylenetriamine.

Anions of useful acid addition salts are primarily chloride, bromide, fluoride, iodide, hydrogensulfate, methylsulfate, sulfate, dihydrogenphosphate, hydrogenphosphate, nitrate, bicarbonate, carbonate, hexafluorosilicate, hexafluorophosphate, benzoate and also the anions of $C_1$-$C_4$-alkanoic acids, preferably formate, acetate, propionate and butyrate.

Pyrimidine compounds of formula (I) as described herein having a carboxyl group can be employed, if applicable, in the form of the acid, in the form of an agriculturally suitable salt as mentioned above or else in the form of an agriculturally acceptable derivative, e.g. as amides, such as mono- and di-$C_1$-$C_6$-alkylamides or arylamides, as esters, e.g. as allyl esters, propargyl esters, $C_1$-$C_{10}$-alkyl esters, alkoxyalkyl esters, tefuryl ((tetrahydrofuran-2-yl)methyl) esters and also as thioesters, e.g. as $C_1$-$C_{10}$-alkylthio esters. Preferred mono- and di-$C_1$-$C_6$-alkylamides are the $CH_3$ and the dimethylamides. Preferred arylamides are, e.g., the anilides and the 2-chloroanilides. Preferred alkyl esters are, e.g., the methyl, ethyl, propyl, isopropyl, butyl, isobutyl, pentyl, mexyl (1-methylhexyl), meptyl (1-methylheptyl), heptyl, octyl or isooctyl (2-ethylhexyl) esters. Preferred $C_1$-$C_4$-alkoxy-$C_1$-$C_4$-alkyl esters are the straight-chain or branched $C_1$-$C_4$-alkoxy ethyl esters, e.g. the 2-methoxyethyl, 2-ethoxyethyl, 2-butoxyethyl (butotyl), 2-butoxypropyl or 3-butoxypropyl ester. An example of a straight-chain or branched $C_1$-$C_{10}$-alkylthio ester is the ethylthio ester.

The organic moieties mentioned in the definition of the variables $R^1$, $R^2$, A, Z, $R^3$, $R^{3A}$, and $R^4$, are—like the term halogen—collective terms for individual enumerations of the individual group members. The term halogen denotes in each case F, Cl, Br, or I. All hydrocarbon chains, e.g. all alkyl, alkenyl, alkynyl, alkoxy chains can be straight-chain or branched, the prefix $C_n$-$C_m$ denoting in each case the possible number of carbon atoms in the group.

Examples of Such Meanings are:

$C_1$-$C_4$-alkyl: e.g. $CH_3$, $C_2H_5$, n-propyl, $CH(CH_3)_2$, n-butyl, $CH(CH_3)$—$C_2H_5$, $CH_2$—$CH(CH_3)_2$, and $C(CH_3)_3$;

$C_1$-$C_6$-alkyl: $C_1$-$C_4$-alkyl as mentioned above, and also, e.g., n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl or 1-ethyl-2-methylpropyl, preferably methyl, ethyl, n-propyl, 1-methylethyl, n-butyl, 1,1-dimethylethyl, n-pentyl, or n-hexyl;

$C_1$-$C_4$-haloalkyl: $C_1$-$C_4$-alkyl as mentioned above which is partially or fully substituted by fluorine, chlorine, bromine and/or iodine, e.g., chloromethyl, dichloromethyl, trichloromethyl, fluoromethyl, difluoromethyl, trifluoromethyl, chlorofluoromethyl, dichlorofluoromethyl, chlorodifluoromethyl, bromomethyl, iodomethyl, 2-fluoroethyl, 2-chloroethyl, 2-bromoethyl, 2-iodoethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, 2-fluoropropyl, 3-fluoropropyl, 2,2-difluoropropyl, 2,3-difluoropropyl, 2-chloropropyl, 3-chloropropyl, 2,3-dichloropropyl, 2-bromopropyl, 3-bromopropyl, 3,3,3-trifluoropropyl, 3,3,3-trichloropropyl, 2,2,3,3,3-pentafluoropropyl, heptafluoro-propyl, 1-(fluoromethyl)-2-fluoroethyl, 1-(chloromethyl)-2-chloroethyl, 1-(bromomethyl)-2-bromo-ethyl, 4-fluorobutyl, 4-chlorobutyl, 4-bromobutyl, nonafluorobutyl, 1,1,2,2,-tetrafluoroethyl, and 1-trifluoromethyl-1,2,2,2-tetrafluoroethyl;

$C_1$-$C_6$-haloalkyl: $C_1$-$C_4$-haloalkyl as mentioned above, and also, e.g., 5-fluoropentyl, 5-chloropentyl, 5-bromopentyl, 5-iodopentyl, undecafluoropentyl, 6-fluorohexyl, 6-chlorohexyl, 6-bromohexyl, 6-iodohexyl, and dodecafluorohexyl;

$C_3$-$C_6$-cycloalkyl: monocyclic saturated hydrocarbons having 3 to 6 ring members, such as cyclopropyl, cyclobutyl, cyclopentyl, and cyclohexyl;

$C_3$-$C_6$-alkenyl: e.g. 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl- 3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl, and 1-ethyl-2-methyl-2-propenyl;

$C_3$-$C_6$-haloalkenyl: a $C_3$-$C_6$-alkenyl substituent as mentioned above which is partially or fully substituted by fluorine, chlorine, bromine and/or iodine, e.g. 2-chloroprop-2-en-1-yl, 3-chloroprop-2-en-1-yl, 2,3-dichloroprop-2-en-1-yl, 3,3-dichloroprop-2-en-1-yl, 2,3,3-trichloro-2-en-1-yl, 2,3-dichlorobut-2-en-1-yl, 2-bromoprop-2-en-1-yl, 3-bromoprop-2-en-1-yl, 2,3-dibromoprop-2-en-1-yl, 3,3-dibromoprop-2-en-1-yl, 2,3,3-tribromo-2-en-1-yl, or 2,3-dibromobut-2-en-1-yl;

$C_3$-$C_6$-alkynyl: e.g. 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl, and 1-ethyl-1-methyl-2-propynyl;

$C_2$-$C_6$-alkynyl: $C_3$-$C_6$-alkynyl as mentioned above and also ethynyl;

$C_3$-$C_6$-haloalkynyl: a $C_3$-$C_6$-alkynyl group as mentioned above which is partially or fully substituted by F, Cl, Br and/or I, e.g. 1,1-difluoroprop-2-yn-1-yl, 3-chloroprop-2-yn-1-yl, 3-bromoprop-2-yn-1-yl, 3-iodoprop-2-yn-1-yl, 4-fluorobut-2-yn-1-yl, 4-chlorobut-2-yn-1-yl, 1,1-difluorobut-2-yn-1-yl, 4-iodobut-3-yn-1-yl, 5-fluoropent-3-yn-1-yl, 5-iodopent-4-yn-1-yl, 6-fluorohex-4-yn-1-yl, or 6-iodohex-5-yn-1-yl;

$C_1$-$C_4$-alkoxy: e.g. methoxy, ethoxy, propoxy, 1-methylethoxy butoxy, 1-methylpropoxy, 2-methylpropoxy, and 1,1-dimethylethoxy;

$C_1$-$C_6$-alkoxy: $C_1$-$C_4$-alkoxy as mentioned above, and also, e.g., pentoxy, 1-methylbutoxy, 2-methylbutoxy, 3-methoxybutoxy, 1,1-dimethylpropoxy, 1,2-dimethylpropoxy, 2,2-dimethylpropoxy, 1-ethylpropoxy, hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy, and 1-ethyl-2-methylpropoxy.

$C_1$-$C_4$-haloalkoxy: a $C_1$-$C_4$-alkoxy group as mentioned above which is partially or fully substituted by fluorine, chlorine, bromine and/or iodine, i.e., e.g., fluoromethoxy, difluoromethoxy, trifluoromethoxy, chlorodifluoromethoxy, bromodifluoromethoxy, 2-fluoroethoxy, 2-chloroethoxy, 2-bromomethoxy, 2-iodoethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, pentafluoroethoxy, 2-fluoropropoxy, 3-fluoropropoxy, 2-chloropropoxy, 3-chloropropoxy, 2-bromopropoxy, 3-bromopropoxy, 2,2-difluoropropoxy, 2,3-difluoropropoxy, 2,3-dichloropropoxy, 3,3,3-trifluoropropoxy, 3,3,3-trichloropropoxy, 2,2,3,3,3-pentafluoropropoxy, heptafluoropropoxy, 1-(fluoromethyl)-2-fluoroethoxy, 1-(chloromethyl)-2-chloroethoxy, 1-(bromomethyl)-2-bromoethoxy, 4-fluorobutoxy, 4-chlorobutoxy, 4-bromobutoxy, and nonafluorobutoxy;

$C_1$-$C_6$-haloalkoxy: a $C_1$-$C_4$-haloalkoxy as mentioned above, and also, e.g., 5-fluoropentoxy, 5-chloropentoxy, 5-bromopentoxy, 5-iodopentoxy, undecafluoropentoxy, 6-fluorohexoxy, 6-chlorohexoxy, 6-bromohexoxy, 6-iodohexoxy and dodecafluorohexoxy;

$C_1$-$C_4$-alkylthio: e.g. methylthio, ethylthio, propylthio, 1-methylethylthio, butylthio, 1-methylpropylthio, 2-methylpropylthio, and 1,1-dimethylethylthio;

$C_1$-$C_6$-alkylthio: $C_1$-$C_4$-alkylthio as mentioned above, and also, e.g., pentylthio, 1-methylbutylthio, 2-methylbutylthio, 3-methylbutylthio, 2,2-dimethylpropylthio, 1-ethylpropylthio, hexylthio, 1,1-dimethylpropylthio, 1,2-dimethylpropylthio, 1-methylpentylthio, 2-methylpentylthio, 3-methylpentylthio, 4-methylpentylthio, 1,1-dimethylbutylthio, 1,2-dimethylbutylthio, 1,3-dimethylbutylthio, 2,2-dimethylbutylthio, 2,3-dimethylbutylthio, 3,3-dimethylbutylthio, 1-ethylbutylthio, 2-ethylbutylthio, 1,1,2-trimethylpropylthio, 1,2,2-trimethylpropylthio, 1-ethyl-1-methylpropylthio, and 1-ethyl-2-methylpropylthio;

($C_1$-$C_4$-alkyl)amino: e.g. methylamino, ethylamino, propylamino, 1-methylethylamino, butylamino, 1-methylpropylamino, 2-methylpropylamino, or 1,1-dimethylethylamino;

($C_1$-$C_6$-alkyl)amino: ($C_1$-$C_4$-alkylamino) as mentioned above, and also, e.g., pentylamino, 1-methylbutylamino, 2-methylbutylamino, 3-methylbutylamino, 2,2-dimethylpropylamino, 1-ethylpropylamino, hexylamino, 1,1-dimethylpropylamino, 1,2-dimethylpropylamino, 1-methylpentylamino, 2-methylpentylamino, 3-methylpentylamino, 4-methylpentylamino, 1,1-dimethylbutyl-amino, 1,2-dimethylbutylamino, 1,3-dimethylbutylamino, 2,2-dimethylbutylamino, 2,3-dimethylbutyl-amino 3,3-dimethylbutylamino, 1-ethylbutylamino, 2-ethylbutylamino, 1,1,2-trimethyl-propylamino, 1,2,2-trimethyl-propylamino, 1-ethyl-1-methylpropylamino, or 1-ethyl-2-methylpropylamino;

di($C_1$-$C_4$-alkyl)amino: e.g. N,N-dimethylamino, N,N-diethylamino, N,N-di(1-methylethyl)amino, N,N-dipropylamino, N,N-dibutylamino, N,N-di(1-methylpropyl)amino, N,N-di(2-methylpropyl)amino, N,N-di(1,1-dimethylethyl)amino, N-ethyl-N-methylamino, N-methyl-N-propylamino, N-methyl-N-(1-methylethyl)amino, N-butyl-N-methylamino, N-methyl-N-(1-methylpropyl)amino, N-methyl-N-(2-methylpropyl)amino, N-(1,1-dimethylethyl)-N-methylamino, N-ethyl-N-propylamino, N-ethyl-N-(1-methylethyl)amino, N-butyl-N-ethylamino, N-ethyl-N-(1-methylpropyl)amino, N-ethyl-N-(2-methylpropyl)amino, N-ethyl-N-(1,1-dimethylethyl)amino, N-(1-methylethyl)-N-propylamino, N-butyl-N-propylamino, N-(1-methylpropyl)-N-propylamino, N-(2-methylpropyl)-N- propylamino, N-(1,1-dimethylethyl)-N-propylamino, N-butyl-N-(1-methylethyl)amino, N-(1-methylethyl)-N-(1-methylpropyl)amino, N-(1-methylethyl)-N-(2-methylpropyl)amino, N-(1,1-dimethylethyl)-N-(1-methylethyl)amino, N-butyl-N-(1-methylpropyl) amino, N-butyl-N-(2-methylpropyl)amino, N-butyl-N-(1,1-dimethylethyl)amino, N-(1-methylpropyl)-N-(2-methylpropyl)amino, N-(1,1-dimethylethyl)-N-(1-methylpropyl)amino, or N-(1,1-dimethylethyl)-N-(2-methylpropyl)amino;

di($C_1$-$C_6$-alkyl)amino: di($C_1$-$C_4$-alkyl)amino as mentioned above, and also, e.g., N-methyl-N-pentylamino, N-methyl-N-(1-methylbutyl)amino, N-methyl-N-(2-methylbutyl)amino, N-methyl-N-(3-methylbutyl) amino, N-methyl-N-(2,2-dimethylpropyl)amino, N-methyl-N-(1-ethylpropyl)amino, N-methyl-N-hexylamino, N-methyl-N-(1,1-dimethylpropyl)amino, N-methyl-N-(1,2-dimethylpropyl)amino, N-methyl-N-(1-methylpentyl)amino, N-methyl-N-(2-methylpentyl) amino, N-methyl-N-(3-methylpentyl)amino, N-methyl-N-(4-methylpentyl)amino, N-methyl-N-(1,1-dimethylbutyl)amino, N-methyl-N-(1,2-dimethylbutyl)amino, N-methyl-N-(1,3-dimethylbutyl)amino, N-methyl-N-(2,2-dimethylbutyl)amino, N-methyl-N-(2,3-dimethylbutyl)amino, N-methyl-N-(3,3-dimethylbutyl)amino, N-methyl-N-(1-ethylbutyl)amino, N-methyl-N-(2-ethylbutyl)amino, N-methyl-N-(1,1,2-trimethylpropyl)amino, N-methyl-N-(1,2,2-trimethylpropyl)amino, N-methyl-N-(1-ethyl-1-methylpropyl) amino, N-methyl-N-(1-ethyl-2-methylpropyl)amino, N-ethyl-N-pentylamino, N-ethyl-N-(1-methylbutyl) amino, N-ethyl-N-(2-methylbutyl)amino, N-ethyl-N-(3-methylbutyl)amino, N-ethyl-N-(2,2-dimethylpropyl)amino, N-ethyl-N-(1-ethylpropyl)amino, N-ethyl-N-hexylamino, N-ethyl-N-(1,1-dimethylpropyl)amino, N-ethyl-N-(1,2-dimethylpropyl)amino, N-ethyl-N-(1-methylpentyl)amino, N-ethyl-N-(2-methylpentyl) amino, N-ethyl-N-(3-methylpentyl)amino, N-ethyl-N-(4-methylpentyl)amino, N-ethyl-N-(1,1-dimethylbutyl)amino, N-ethyl-N-(1,2-dimethylbutyl) amino, N-ethyl-N-(1,3-dimethylbutyl)amino, N-ethyl-N-(2,2-dimethylbutyl)amino, N-ethyl-N-(2,3-dimethylbutyl)amino, N-ethyl-N-(3,3-dimethylbutyl) amino, N-ethyl-N-(1-ethylbutyl)amino, N-ethyl-N-(2-ethylbutyl)amino, N-ethyl-N-(1,1,2-trimethylpropyl) amino, N-ethyl-N-(1,2,2-trimethylpropyl)amino, N-ethyl-N-(1-ethyl-1-methylpropyl)amino, N-ethyl-N-(1-ethyl-2-methylpropyl)amino, N-propyl-N-pentylamino, N-butyl-N-pentylamino, N,N-dipentylamino, N-propyl-N-hexylamino, N-butyl-N-hexylamino, N-pentyl-N-hexylamino, or N,N-dihexylamino;

$C_1$-$C_6$-alkylsulfinyl ($C_1$-$C_6$-Alkyl-S(=O)—): e.g. methylsulfinyl, ethylsulfinyl, propylsulfinyl, 1-methylethylsulfinyl, butylsulfinyl, 1-methylpropylsulfinyl, 2-methylpropylsulfinyl, 1,1-dimethylethylsulfinyl, pentylsulfinyl, 1-methylbutylsulfinyl, 2-methylbutylsulfinyl, 3-methylbutylsulfinyl, 2,2-dimethylpropylsulfinyl, 1-ethylpropylsulfinyl, 1,1-dimethylpropylsulfinyl, 1,2-dimethylpropyl-sulfinyl, hexylsulfinyl, 1-methylpentylsulfinyl, 2-methylpentylsulfinyl, 3-methylpentyl-sulfinyl, 4-methylpentyl-sulfinyl, 1,1-dimethylbutylsulfinyl, 1,2-dimethylbutyl-sulfinyl, 1,3-dimethylbutylsulfinyl, 2,2-dimethylbutylsulfinyl, 2,3-dimethylbutylsulfinyl, 3,3-dimethylbutyl-sulfinyl, 1-ethylbutylsulfinyl, 2-ethylbutylsulfinyl, 1,1,2-trimethyl-propylsulfinyl, 1,2,2-trimethylpropylsulfinyl, 1-ethyl-1-methylpropyl-sulfinyl, and 1-ethyl-2-methylpropylsulfinyl;

$C_1$-$C_6$-alkylsulfonyl ($C_1$-$C_6$-alkyl-S(O)$_2$—): e.g. methylsulfonyl, ethylsulfonyl, propylsulfonyl, 1-methylethylsulfonyl, butylsulfonyl, 1-methylpropylsulfonyl, 2-methyl-propylsulfonyl, 1,1-dimethylethylsulfonyl, pentylsulfonyl, 1-methylbutylsulfonyl, 2-methylbutylsulfonyl, 3-methylbutylsulfonyl, 1,1-dimethylpropylsulfonyl, 1,2-dimethylpropylsulfonyl, 2,2-dimethylpropylsulfonyl, 1-ethylpropylsulfonyl, hexylsulfonyl, 1-methylpentylsulfonyl, 2-methylpentylsulfonyl, 3-methylpentylsulfonyl, 4-methylpentylsulfonyl, 1,1-dimethylbutylsulfonyl, 1,2-dimethylbutylsulfonyl, 1,3-dimethylbutylsulfonyl, 2,2-dimethylbutylsulfonyl, 2,3-dimethylbutylsulfonyl, 3,3-dimethylbutyl-sulfonyl, 1-ethylbutylsulfonyl, 2-ethylbutylsulfonyl, 1,1,2-trimethyl-propylsulfonyl, 1,2,2-trimethyl-propylsulfonyl, 1-ethyl-1-methylpropylsulfonyl, and 1-ethyl-2-methylpropylsulfonyl;

$C_3$-$C_6$-cycloalkyl: a monocyclic saturated hydrocarbon having 3 to 6 ring members, such as cyclopropyl, cyclobutyl, cyclopentyl, and cyclohexyl;

$C_3$-$C_6$-cycloalkenyl: 1-cyclopropenyl, 2-cyclopropenyl, 1-cyclobutenyl, 2-cyclobutenyl, 1-cyclopentenyl, 2-cyclopentenyl, 1,3-cyclopentadienyl, 1,4-cyclopentadienyl, 2,4-cyclopentadienyl, 1-cyclohexenyl, 2-cyclohexenyl, 3-cyclohexenyl, 1,3-cyclohexadienyl, 1,4-cyclohexadienyl, or 2,5-cyclohexadienyl;

heterocyclyl: a 3- to 6-membered heterocyclyl: a saturated or partial unsaturated cycle having three to six ring members which comprises apart from carbon atoms one to four nitrogen atoms, or one or two oxygen atoms, or one or two sulfur atoms, or one to three nitrogen atoms and an oxygen atom, or one to three nitrogen atoms and a sulfur atom, or one sulfur and one oxygen atom, e.g.

3- or 4-membered heterocycles like 2-oxiranyl, 2-aziridinyl, 2-thiiranyl, 2-oxetanyl, 3-oxetanyl, 2-thietanyl, 3-thietanyl, 1-azetidinyl, 2-azetidinyl, 1-azetinyl, or 2-azetinyl;

5-membered saturated heterocycles like 2-tetrahydrofuranyl, 3-tetrahydrofuranyl, 2-tetrahydrothienyl, 3-tetrahydrothienyl, 1-pyrrolidinyl, 2-pyrrolidinyl, 3-pyrrolidinyl, 3-isoxazolidinyl, 4-isoxazolidinyl, 5-isoxazolidinyl, 2-isothiazolidinyl, 3-isothiazolidinyl, 4-isothiazolidinyl, 5-isothiazolidinyl, 1-pyrazolidinyl, 3-pyrazolidinyl, 4-pyrazolidinyl, 5-pyrazolidinyl, 2-oxazolidinyl, 4-oxazolidinyl, 5-oxazolidinyl, 2-thiazolidinyl, 4-thiazolidinyl, 5-thiazolidinyl, 1-imidazolidinyl, 2-imidazolidinyl, 4-imidazolidinyl, 3-oxazolidinyl, 1,2,4-oxadiazolidin-3-yl, 1,2,4-oxadiazolidin-5-yl, 3-thiazolidinyl, 1,2,4-thiadiazolidin-3-yl, 1,2,4-thiadiazolidin-5-yl, 1,2,4-triazolidin-3-yl, 1,2,4-oxadiazolidin-2-yl, 1,2,4-oxadiazolidin-4-yl, 1,3,4-oxadiazolidin-2-yl, 1,2,4-thiadiazolidin-2-yl, 1,2,4-thiadiazolidin-4-yl, 1,3,4-thiadiazolidin-2-yl, 1,2,4-triazolidin-1-yl, or 1,3,4-triazolidin-2-yl;

5-membered partial unsaturated heterocycles like 2,3-dihydrofur-2-yl, 2,3-dihydrofur-3-yl, 2,4-dihydrofur-2-yl, 2,4-dihydrofur-3-yl, dioxolan-2-yl, 1,3-dioxol-2-yl, 2,3-dihydrothien-2-yl, 2,3-dihydrothien-3-yl, 2,4-dihydrothien-2-yl, 2,4-dihydrothien-3-yl, 4,5-dihydropyrrol-1-yl, 4,5-dihydropyrrol-2-yl, 4,5-dihydropyrrol-3-yl, 2,5-dihydropyrrol-1-yl, 2,5-dihydropyrrol-2-yl, 2,5-dihydropyrrol-3-yl, 2,3-dihydroisoxazol-1-yl, 2,3-dihydroisoxazol-3-yl, 2,3-dihydroisoxazol-4-yl, 2,3-dihydroisoxazol-5-yl, 2,5-dihydroisoxazol-3-yl, 2,5-dihydroisoxazol-4-yl, 2,5-dihydroisoxazol-5-yl, 4,5-dihydroisoxazol-2-yl, 4,5- dihydroisoxazol-3-yl, 4,5-dihydroisoxazol-4-yl, 4,5-dihydroisoxazol-5-yl, 2,3-dihydroisothiazol-1-yl, 2,3-dihydroisothiazol-3-yl, 2,3-dihydroisothiazol-4-yl, 2,3-dihydroisothiazol-5-yl, 2,5-dihydroisothiazol-3-yl, 2,5-dihydroisothiazol-4-yl, 2,5-dihydroisothiazol-5-yl, 4,5-dihydroisothiazol-1-yl, 4,5-dihydroisothiazol-3-yl, 4,5-dihydroisothiazol-4-yl, 4,5-dihydroisothiazol-5-yl, 2,3-dihydropyrazol-1-yl, 2,3-dihydropyrazol-2-yl, 2,3-dihydropyrazol-3-yl, 2,3-dihydropyrazol-4-yl, 2,3-dihydropyrazol-5-yl, 3,4-dihydropyrazol-1-yl, 3,4-dihydropyrazol-3-yl, 3,4-dihydropyrazol-4-yl, 3,4-dihydropyrazol-5-yl, 4,5-dihydropyrazol-1-yl, 4,5-dihydropyrazol-3-yl, 4,5-dihydropyrazol-4-yl, 4,5-dihydropyrazol-5-yl, 2,3-dihydroimidazol-1-yl, 2,3-dihydroimidazol-2-yl, 2,3-dihydroimidazol-3-yl, 2,3-dihydroimidazol-4-yl, 2,3-dihydroimidazol-5-yl, 4,5-dihydroimidazol-1-yl, 4,5-dihydroimidazol-2-yl, 4,5-dihydroimidazol-4-yl, 4,5-dihydroimidazol-5-yl, 2,5-dihydroimidazol-1-yl, 2,5-dihydroimidazol-2-yl, 2,5-dihydroimidazol-4-yl, 2,5-dihydroimidazol-5-yl, 2,3-dihydrooxazol-2-yl, 2,3-dihydrooxazol-3-yl, 2,3-dihydrooxazol-4-yl, 2,3-dihydrooxazol-5-yl, 3,4-dihydrooxazol-2-yl, 3,4-dihydrooxazol-3-yl, 3,4-dihydrooxazol-4-yl, 3,4-dihydrooxazol-5-yl, 2,3-dihydrothiazol-2-yl, 2,3-dihydrothiazol-3-yl, 2,3-dihydrothiazol-4-yl, 2,3-dihydrothiazol-5-yl, 3,4-dihydrothiazol-2-yl, 3,4-dihydrothiazol-3-yl, 3,4-dihydrothiazol-4-yl, 3,4-dihydrothiazol-5-yl, 3,4-dihydrothiazol-2-yl, 3,4-dihydrothiazol-3-yl, or 3,4-dihydrothiazol-4-yl;

6-membered saturated heterocycles like 1-piperidinyl, 2-piperidinyl, 3-piperidinyl, 4-piperidinyl, 1,3-dioxan-5-yl, 1,4-dioxanyl, 1,3-dithian-5-yl, 1,3-dithianyl, 1,3-oxathian-5-yl, 1,4-oxathianyl, 2-tetrahydropyranyl, 3-tetrahydopyranyl, 4-tetrahydropyranyl, 2-tetrahydrothiopyranyl, 3-tetrahydrothiopyranyl, 4-tetrahydrothiopyranyl, 1-hexahydropyridazinyl, 3-hexahydropyridazinyl, 4-hexahydropyridazinyl, 1-hexahydropyrimidinyl, 2-hexahydropyrimidinyl, 4-hexahydropyrimidinyl, 5-hexahydropyrimidinyl, 1-piperazinyl, 2-piperazinyl, 1,3,5-hexahydrotriazin-1-yl, 1,3,5-hexahydrotriazin-2-yl, 1,2,4-hexahydrotriazin-1-yl, 1,2,4-hexahydrotriazin-3-yl, tetrahydro-1,3-oxazin-1-yl, tetrahydro-1,3-oxazin-2-yl, tetrahydro-1,3-oxazin-6-yl, 1-morpholinyl, or 2-morpholinyl, 3-morpholinyl;

6-membered partial unsaturated heterocycles like 2H-pyran-2-yl, 2H-pyran-3-yl, 2H-pyran-4-yl, 2H-pyran-5-yl, 2H-pyran-6-yl, 2H-thiopyran-2-yl, 2H-thiopyran-3-yl, 2H-thiopyran-4-yl, 2H-thiopyran-5-yl, 2H-thiopyran-6-yl, or 5,6-dihydro-4H-1,3-oxazin-2-yl.

heteroaryl: a 5- or 6-membered heteroaryl: monocyclic aromatic heteroaryl having 5 to 6 ring members which, in addition to carbon atoms and independent of their position in the ring, contains 1 to 4 nitrogen atoms, or 1 to 3 nitrogen atoms and an oxygen or sulfur atom, or an oxygen or a sulfur atom, e.g. 5-membered aromatic rings like furyl (e.g. 2-furyl, 3-furyl), thienyl (e.g. 2-thienyl, 3-thienyl), pyrrolyl (e.g. pyrrol-2-yl, pyrrol-3-yl), pyrazolyl (e.g. pyrazol-3-yl, pyrazol-4-yl), isoxazolyl (e.g. isoxazol-3-yl, isoxazol-4-yl, isoxazol-5-yl), isothiazolyl (e.g. isothiazol-3-yl, isothiazol-4-yl, isothiazol-5-yl), imidazolyl (e.g. imidazole-2-yl, imidazole-4-yl), oxazolyl (e.g. oxazol-2-yl, oxazol-4-yl, oxazol-5-yl), thiazolyl (e.g. thiazol-2-yl, thiazol-4-yl, thiazol-5-yl), oxadiazolyl (e.g. 1,2,3-oxadiazol-4-yl, 1,2,3-oxadiazol-5-yl, 1,2,4-oxadiazol-3-yl, 1,2,4-oxadiazol-5-yl, 1,3,4-oxadiazol-2-yl), thiadiazolyl (e.g. 1,2,3-thiadiazol-4-yl, 1,2,3-thiadiazol-5-yl, 1,2,4-thiadiazol-3-yl, 1,2,4-thiadiazol-5-yl, 1,3,4-thiadiazolyl-2-yl), triazolyl (e.g. 1,2,3-triazol-4-yl, 1,2,4-triazol-3-yl); 1-tetrazolyl; 6-membered aromatic rings like pyridyl (e.g. pyridine-2-yl, pyridine-3-yl, pyridine-4-yl), pyrazinyl (e.g. pyridazin-3-yl, pyridazin-4-yl), pyrimidinyl (e.g. pyrimidin-2-yl, pyrimidin-4-yl, pyrimidin-5-yl), pyrazin-2-yl, triazinyl (e.g. 1,3,5-triazin-2-yl, or 1,2,4-triazin-3-yl, 1,2,4-triazin-5-yl, 1,2,4-triazin-6-yl);

The term "substituted" if not specified otherwise refers to substituted by 1, 2 or maximum possible number of substituents. If substituents as defined in compounds of formula I are more than one then they are independently from each other are same or different if not mentioned otherwise.

The term "acidic functionality" if not specified otherwise refers to a functionality capable of donating a hydrogen (proton or hydrogen ion $H^+$), such as a carboxylic group or sulphonic group, or, alternatively, capable of forming a covalent bond with an electron pair.

The terms "compounds of formula (I)", "Pyrimidine compounds of formula (I)", "Compounds I" and "compounds of invention" are synonyms.

The preferred embodiments of the invention mentioned herein below have to be understood as being preferred either independently from each other or in combination with one another.

In general, pyrimidine compounds of formula (I) are suitable as herbicides.

According to a preferred embodiment of the invention preference is given pyrimidine compounds of formula (I), and their use as herbicides, wherein the variables, either independently of one another or in combination with one another, have the following meanings:

Preferred $R^1$ is $C_1$-$C_6$-alkyl, $C_1$-$C_6$-alkoxy, $C_1$-$C_6$-haloalkoxy, $C_3$-$C_6$-alkenyloxy, $C_3$-$C_6$-haloalkenyloxy $C_3$-$C_6$-alkynyloxy, $C_3$-$C_6$-haloalkynyloxy, $C_1$-$C_6$-alkylthio, or $C_3$-$C_6$-cycloalkyl, wherein the cycloalkyl substituent is unsubstituted or substituted by halogen;

Also preferred $R^1$ is $C_1$-$C_6$-alkyl, $C_1$-$C_6$-alkoxy, $C_1$-$C_6$-haloalkoxy, $C_3$-$C_6$-alkenyloxy, $C_3$-$C_6$-haloalkenyloxy $C_3$-$C_6$-alkynyloxy, $C_3$-$C_6$-haloalkynyloxy, $C_1$-$C_6$-alkylthio, or $C_3$-$C_6$-cycloalkyl, wherein the cycloalkyl substituent is unsubstituted;

particularly preferred $R^1$ is $C_1$-$C_6$-alkyl, $C_1$-$C_6$-alkoxy, or $C_3$-$C_6$-cycloalkyl, wherein the cycloalkyl substituent is unsubstituted;

also particularly preferred $R^1$ is $C_1$-$C_6$-alkyl, $C_1$-$C_6$-alkoxy, or $C_3$-$C_6$-cycloalkyl, wherein the cycloalkyl substituent is unsubstituted or substituted by fluorine;

especially preferred $R^1$ is $C_3$-$C_6$-cycloalkyl, wherein the cycloalkyl substituent is unsubstituted;

also especially preferred $R^1$ is $C_2H_5$, i-$C_3H_7$, i-$C_4H_9$, $OCH_3$, c-$O_3H_5$, or c-$C_4H_9$;

more preferred $R^1$ is $C_2H_5$, $OCH_3$, or c-$C_3H_5$;

most preferred $R^1$ is c-$C_3H_5$.

Preferred $R^2$ is OH, $C_1$-$C_6$-alkoxy, $C_1$-$C_6$-haloalkoxy, $C_3$-$C_6$-alkenyloxy, $C_3$-$C_6$-haloalkenyloxy, $C_3$-$C_6$-alkynyloxy, $C_3$-$C_6$-haloalkynyloxy, $C_1$-$C_6$-alkoxy-$C_1$-$C_6$-alkoxy, ($C_1$-$C_6$-alkoxy)carbonyl-$C_1$-$C_6$-alkoxy, $C_1$-$C_6$-alkylthio, ($C_1$-$C_6$-alkoxy)carbonyl-$C_1$-$C_6$-alkylthio, N $H_2$, $C_1$-$C_6$-alkylcarbonylamino, $C_1$-$C_6$-haloalkylcarbonylamino, $C_3$-$C_6$-cycloalkylcarbonylamino, phenylcarbonylamino, heterocyclylcarbonylamino, heteroarylcarbonylamino, ($C_1$-$C_6$-alkyl)amino, ($C_1$-$C_6$-alkoxy)amino, ($C_1$-$C_6$-alkoxy)($C_1$-$C_6$-alkyl)amino, hydroxy($C_1$-$C_6$-alkyl)amino, hydroxyamino, ($C_1$-$C_6$-alkyl)sulfonylamino, [di($C_1$-$C_6$-alkyl)amino]

sulfonylamino, phenyloxy, phenyl-$C_1$-$C_6$-alkoxy, or phenyl-$C_1$-$C_6$-alkylthio, wherein the phenyl substituent is unsubstituted;

Also preferred $R^2$ is OH, $C_1$-$C_6$-alkoxy, $C_1$-$C_6$-haloalkoxy, $C_3$-$C_6$-alkenyloxy, $C_3$-$C_6$-haloalkenyloxy, $C_3$-$C_6$-alkynyloxy, $C_3$-$C_6$-haloalkynyloxy, ($C_1$-$C_6$-alkoxy)carbonyl-$C_1$-$C_6$-alkoxy, $C_1$-$C_6$-alkylthio, ($C_1$-$C_6$-alkoxy)carbonyl-$C_1$-$C_6$-alkylthio, $NH_2$, $C_1$-$C_6$-alkylcarbonylamino, $C_1$-$C_6$-haloalkylcarbonylamino, $C_3$-$C_6$-cycloalkylcarbonylamino, phenylcarbonylamino, heterocyclylcarbonylamino, heteroarylcarbonylamino, ($C_1$-$C_6$-alkyl)amino, ($C_1$-$C_6$-alkoxy)amino, ($C_1$-$C_6$-alkoxy)($C_1$-$C_6$-alkyl)amino, hydroxy($C_1$-$C_6$-alkyl)amino, hydroxyamino, ($C_1$-$C_6$-alkyl)sulfonylamino, [di($C_1$-$C_6$-alkyl)amino]sulfonylamino, phenyloxy, phenyl-$C_1$-$C_6$-alkoxy, or phenyl-$C_1$-$C_6$-alkylthio, wherein the phenyl substituent is unsubstituted;

particularly preferred $R^2$ is OH, $C_1$-$C_6$-alkoxy, $C_1$-$C_6$-haloalkoxy, $C_3$-$C_6$-alkenyloxy, $C_3$-$C_6$-alkynyloxy, $C_1$-$C_6$-alkylthio, phenyloxy, $C_1$-$C_6$-alkylcarbonylamino, $C_1$-$C_6$-haloalkylcarbonylamino, phenylcarbonylamino, heterocyclylcarbonylamino, heteroarylcarbonylamino, ($C_1$-$C_6$-alkoxy)amino, ($C_1$-$C_6$-alkoxy)($C_1$-$C_6$-alkyl)amino, hydroxy($C_1$-$C_6$-alkyl)amino, hydroxyamino, or phenyl-$C_1$-$C_6$-alkoxy, wherein the phenyl substituent is unsubstituted;

also particularly preferred $R^2$ is OH, $C_1$-$C_6$-alkoxy, $C_1$-$C_6$-haloalkoxy, $C_3$-$C_6$-alkynyloxy, $C_1$-$C_6$-alkylthio, phenyloxy, $C_1$-$C_6$-alkylcarbonylamino, $C_1$-$C_6$-haloalkylcarbonylamino, phenylcarbonylamino, heterocyclylcarbonylamino, heteroarylcarbonylamino, ($C_1$-$C_6$-alkoxy)amino, ($C_1$-$C_6$-alkoxy)($C_1$-$C_6$-alkyl)amino, hydroxy($C_1$-$C_6$-alkyl)amino, hydroxyamino, or phenyl-$C_1$-$C_6$-alkoxy, wherein the phenyl substituent is unsubstituted;

also particularly preferred $R^2$ is OH, $C_1$-$C_6$-alkoxy, $C_3$-$C_6$-alkynyloxy or $C_1$-$C_6$-haloalkoxy;

especially preferred $C_1$-$C_6$-alkoxy, $C_3$-$C_6$-alkynyloxy, $C_1$-$C_6$-haloalkoxy, ($C_1$-$C_6$-alkoxy)amino or $C_1$-$C_6$-alkylcarbonylamino;

also especially preferred $R^2$ is OH, $C_1$-$C_6$-alkoxy, or $C_1$-$C_6$-haloalkoxy;

more preferred $R^2$ is OH, $C_3$-$C_6$-alkynyloxy, or $C_1$-$C_6$-alkoxy, most preferred $R^2$ is OH, also most preferred $R^2$ is $C_3$-$C_6$-alkynyloxy, also most preferred $R^2$ is $C_1$-$C_6$-alkoxy.

Preferred A is $CR^3$ or $NR^{3A}$;

most preferred A is $CR^3$;

also most preferred A is $NR^{3A}$.

Preferred Z is 6-membered heteroaryl ring, preferably triazine, pyrimidine, or pyridine;

particularly preferred Z is pyrimidine or pyridine;

especially preferred Z is pyridine.

Also preferred Z is 5-membered heteroaryl ring, preferably thiadiazole, oxadiazole, triazole, thiazole, isothiazole, oxazole, isoxazole, pyrazole, imidazole, thiophene, furan, or pyrrole;

particularly preferred Z is thiazole, isothiazole, oxazole, isoxazole, pyrazole, imidazole, thiophene, furan, or pyrrole;

especially preferred Z is thiophene, furan, or pyrrole.

Particularly preferred Z is selected from below groups A to G,

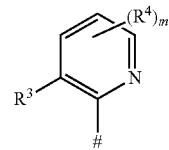
A

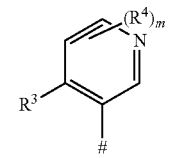
B

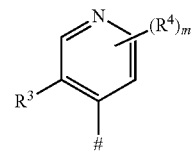
C

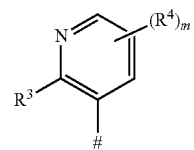
D

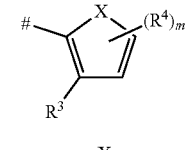
E

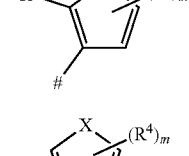
F

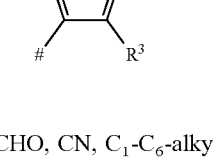
G wherein
$R^3$ is halogen, CHO, CN, $C_1$-$C_6$-alkyl, $C_1$-$C_6$-haloalkyl, or $C_1$-$C_6$-alkoxy;
m is 0 or 1;
$R^4$ is halogen, CHO, CN, $C_1$-$C_6$-alkyl, $C_1$-$C_6$-haloalkyl, or $C_1$-$C_6$-alkoxy;
X is O, S, or $NR^{3A}$;
$R^{3A}$ is H, $C_1$-$C_6$-alkyl, $C_1$-$C_6$-haloalkyl, $C_1$-$C_6$-alkylcarbonyl, $C_3$-$C_6$-alkenyl, $C_3$-$C_6$-haloalkenyl, $C_3$-$C_6$-alkenyl, $C_3$-$C_6$-haloalkenyl, or $C_3$-$C_6$-cycloalkyl; and
denotes the point of attachment to the pyrimidine ring.

Preferred $R^3$ is halogen, CN, $NO_2$, $C_1$-$C_6$-alkyl, $C_1$-$C_6$-haloalkyl, $C_1$-$C_6$-alkoxy, or $C_3$-$C_6$-cycloalkyl;

also preferred $R^3$ is halogen, CN, $C_1$-$C_6$-alkyl, $C_1$-$C_6$-haloalkyl, or $C_1$-$C_6$-alkoxy, particularly preferred $R^3$ is halogen, CN, $C_1$-$C_6$-alkyl, or $C_1$-$C_6$-alkoxy;

especially preferred halogen, or $CH_3$;

also especially preferred $R^3$ is halogen;

more preferred $R^3$ is Cl, Br, or I;

most preferred $R^3$ is Cl or Br.

Preferred $R^{3A}$ is H, $C_1$-$C_6$-alkyl, $C_1$-$C_6$-haloalkyl, $C_1$-$C_6$-alkylcarbonyl, $C_3$-$C_6$-alkenyl, $C_3$-$C_6$-haloalkenyl, $C_3$-$C_6$-alkenyl, $C_3$-$C_6$-haloalkenyl, or $C_3$-$C_6$-cycloalkyl;

also preferred $R^{3A}$ is H, $C_1$-$C_6$-alkyl, $C_1$-$C_6$-haloalkyl, or $C_1$-$C_6$-alkylcarbonyl;

particularly preferred $R^{3A}$ is H, $C_1$-$C_6$-alkyl, or $C_1$-$C_6$-alkylcarbonyl;

especially preferred $R^{3A}$ is H, or $C_1$-$C_6$-alkyl;

most preferred $R^{3A}$ is H, or $CH_3$.

Preferred $R^4$ is halogen, CN, $C_1$-$C_6$-alkyl, $C_1$-$C_6$-haloalkyl, or $C_1$-$C_6$-alkoxy;

particularly preferred $R^4$ is halogen, $C_1$-$C_6$-haloalkyl, or $C_1$-$C_6$-alkyl;

especially preferred $R^4$ is halogen;

also especially preferred $R^4$ is $C_1$-$C_6$-haloalkyl, or $C_1$-$C_6$-alkyl;

more preferred $R^4$ is F, Cl, $CHF_2$, $CF_3$, $CH_3$, or $C_2H_5$;

most preferred $R^4$ is F;

also most preferred $R^4$ is $CH_3$;

also most preferred $R^4$ is Cl.

also most preferred $R^4$ is $CF_3$.

Preferred m is 0, 1, or 2;

more preferred m is 0 or 1;

most preferred m is 0.

also most preferred m is 1.

Also preferred is the pyrimidine compounds of formula (I), and their use as herbicide, wherein $R^1$ is preferably $C_1$-$C_6$-alkyl, $C_1$-$C_6$-alkoxy, or $C_3$-$C_6$-cycloalkyl, wherein the cycloalkyl substituent is unsubstituted or substituted by fluorine;

also $R^1$ is preferably $C_1$-$C_6$-alkyl, $C_1$-$C_6$-alkoxy, or $C_3$-$C_6$-cycloalkyl, wherein the cycloalkyl substituent is unsubstituted;

particularly preferred $R^1$ is $C_3$-$C_6$-cycloalkyl, wherein the cycloalkyl substituent is unsubstituted;

$R^2$ is preferably OH, $C_1$-$C_6$-alkoxy, $C_3$-$C_6$-alkynyloxy, or $C_1$-$C_6$-haloalkoxy;

particularly preferred $R^2$ is $C_1$-$C_6$-alkoxy, $C_3$-$C_6$-alkynyloxy, or $C_1$-$C_6$-haloalkoxy also particularly preferred $R^2$ is OH or $C_1$-$C_6$-alkoxy, more preferred $R^2$ is OH;

also more preferred $R^2$ is $C_1$-$C_6$-alkoxy;

A is preferably $CR^3$ or $NR^{3A}$;

particularly preferred A is $CR^3$;

also particularly preferred A is $NR^{3A}$;

Z is preferably pyridine, pyrrole, furan, or thiophene;

particularly preferred Z is pyridine;

also particularly preferred Z is pyrrole, furan, or thiophene;

more preferred Z is pyridine, furan, or thiophene;

most preferred Z is selected from groups A to G, as defined above;

$R^3$ is preferably halogen, CN, $C_1$-$C_6$-alkyl, $C_1$-$C_6$-haloalkyl, or $C_1$-$C_6$-alkoxy;

particularly preferred $R^3$ is halogen or $CH_3$;

$R^{3A}$ is preferably H or $C_1$-$C_6$-alkyl;

particularly preferred $R^{3A}$ is H or $CH_3$;

m is preferably 0 or 1;

$R^4$ is preferably halogen or $CF_3$.

Also preferred are the pyrimidine compounds of formula (I) wherein $R^1$ is $C_1$-$C_6$-alkyl, $C_1$-$C_6$-alkoxy, or $C_3$-$C_6$-cycloalkyl, wherein the cycloalkyl substituent is unsubstituted;

$R^2$ is OH or $C_1$-$C_6$-alkoxy;

Z is selected from rings A to G

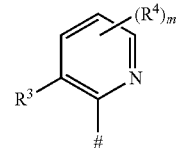

A

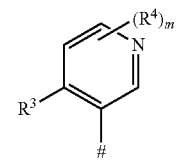

B

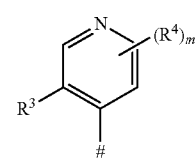

C

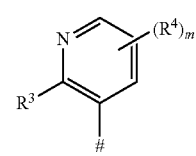

D

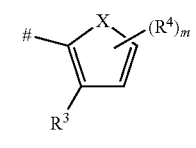

E

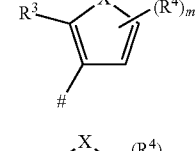

F

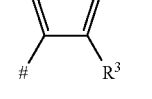

G wherein

X is O or S;

$R^3$ is halogen, CHO, $C_1$-$C_6$-alkyl, $C_1$-$C_6$-haloalkyl, or $C_1$-$C_6$-alkoxy;

m is 0 or 1;

$R^4$ is halogen or $C_1$-$C_6$-haloalkyl;

more preferred are the pyrimidine compounds of formula (I) wherein $R^1$ is $C_2H_5$, $OCH_3$, or $c$-$C_3H_5$;

$R^2$ is OH or $OCH_3$;

Z is selected from rings A to G

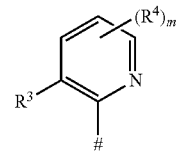

A

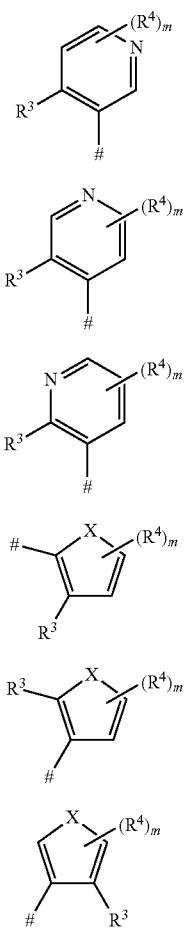

wherein
X is O or S;
R³ is halogen, CHO, CH₃, CHF₂, or OCH₃;
m is 0 or 1;
R⁴ is F or CF₃;

Also preferred are the pyrimidine compounds of formula (I.1) (corresponds to pyrimidine compounds of formula (I) wherein R² is OH), and their use as herbicide,

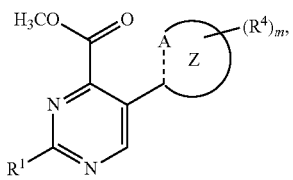

wherein the dotted line (------) is a single bond or a double bond;
R¹ is $C_3$-$C_6$-cycloalkyl, $C_1$-$C_6$-alkyl, or $C_1$-$C_6$-alkoxy;
A is CR³ or NR³ᴬ;
R³ is halogen, $C_1$-$C_6$-alkyl, $C_1$-$C_6$-haloalkyl, or $C_1$-$C_6$-alkoxy;
R³ᴬ is H or $C_1$-$C_6$-alkyl;
Z is pyridine, thiophene, furan, or pyrrol;
m is 0 or 1;
R⁴ is F, Cl, CHF₂, CH₃, CF₃, or C₂H₅.

Also preferred is the pyrimidine compounds of formula (I.2) (corresponds to pyrimidine compounds of formula (I) wherein R² is OCH₃), and their use as herbicide,

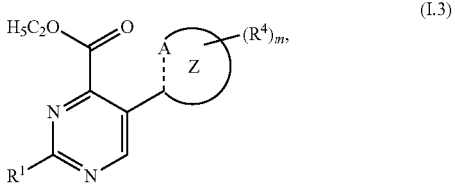

wherein the dotted line (------) is a single bond or a double bond;
R¹ is $C_3$-$C_6$-cycloalkyl, $C_1$-$C_6$-alkyl, or $C_1$-$C_6$-alkoxy;
A is CR³;
R³ is halogen, $C_1$-$C_6$-alkyl, $C_1$-$C_6$-haloalkyl, or $C_1$-$C_6$-alkoxy;
Z is pyridine, thiophene, furan, or pyrrol;
m is 0 or 1;
R⁴ is F, Cl, CHF₂, CH₃, CF₃, or C₂H₅.

Also preferred is the pyrimidine compounds of formula (I.3) (corresponds to pyrimidine compounds of formula (I) wherein R² is OC₂H₅), and their use as herbicide,

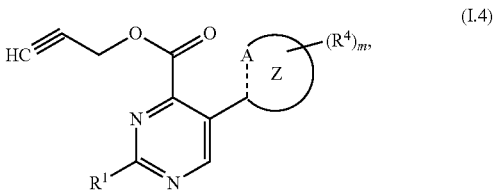

wherein the dotted line (------) is a single bond or a double bond;
R¹ is $C_3$-$C_6$-cycloalkyl, $C_1$-$C_6$-alkyl, or $C_1$-$C_6$-alkoxy;
A is CR³;
R³ is halogen, $C_1$-$C_6$-alkyl, $C_1$-$C_6$-haloalkyl, or $C_1$-$C_6$-alkoxy;
Z is pyridine, thiophene, furan, or pyrrol;
m is 0 or 1;
R⁴ is F, Cl, CHF₂, CH₃, CF₃, or C₂H₅.

Also preferred is the pyrimidine compounds of formula (I.4) (corresponds to pyrimidine compounds of formula (I) wherein R² is OCH₂C≡CH, and their use as herbicide, wherein the dotted line (------) is a single bond or a double bond;
R¹ is $C_3$-$C_6$-cycloalkyl, $C_1$-$C_6$-alkyl, or $C_1$-$C_6$-alkoxy;
A is CR³;
R³ is halogen, $C_1$-$C_6$-alkyl, $C_1$-$C_6$-haloalkyl, or $C_1$-$C_6$-alkoxy;
Z is pyridine, thiophene, furan, or pyrrol;
m is 0 or 1;
R⁴ is F, Cl, CHF₂, CH₃, CF₃, or C₂H₅.

Also preferred is the pyrimidine compounds of formula (I.4) (corresponds to pyrimidine compounds of formula (I) wherein $R^2$ is $OCH_2CHF_2$), and their use as herbicide,

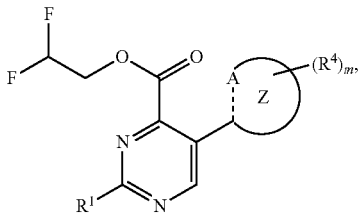

(I.5)

wherein the dotted line (------) is a single bond or a double bond;
$R^1$ is $C_3$-$C_6$-cycloalkyl, $C_1$-$C_6$-alkyl, or $C_1$-$C_6$-alkoxy;
A is $CR^3$;
$R^3$ is halogen, $C_1$-$C_6$-alkyl, $C_1$-$C_6$-haloalkyl, or $C_1$-$C_6$-alkoxy;
Z is pyridine, thiophene, furan, or pyrrol;
m is 0 or 1;
$R^4$ is F, Cl, $CHF_2$, $CH_3$, $CF_3$, or $C_2H_5$.

Also preferred is the pyrimidine compounds of formula (I.4) (corresponds to pyrimidine compounds of formula (I) wherein $R^2$ is $NHOCH_3$), and their use as herbicide,

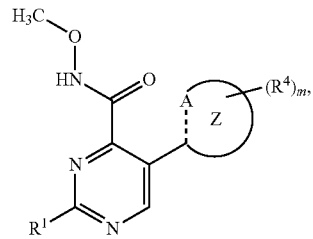

(I.6)

wherein the dotted line (------) is a single bond or a double bond;
$R^1$ is $C_3$-$C_6$-cycloalkyl, $C_1$-$C_6$-alkyl, or $C_1$-$C_6$-alkoxy;
A is $CR^3$;
$R^3$ is halogen, $C_1$-$C_6$-alkyl, $C_1$-$C_6$-haloalkyl, or $C_1$-$C_6$-alkoxy;
Z is pyridine, thiophene, furan, or pyrrol;
m is 0 or 1;
$R^4$ is F, Cl, $CHF_2$, $CH_3$, $CF_3$, or $C_2H_5$.

Also preferred is the pyrimidine compounds of formula (I.4) (corresponds to pyrimidine compounds of formula (I) wherein $R^2$ is $NHCOCH_3$), and their use as herbicide,

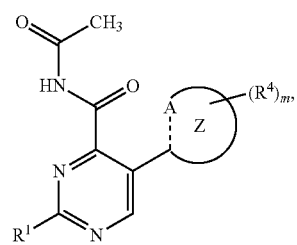

(I.7)

wherein the dotted line (------) is a single bond or a double bond;
$R^1$ is $C_3$-$C_6$-cycloalkyl, $C_1$-$C_6$-alkyl, or $C_1$-$C_6$-alkoxy;
A is $CR^3$;
$R^3$ is halogen, $C_1$-$C_6$-alkyl, $C_1$-$C_6$-haloalkyl, or $C_1$-$C_6$-alkoxy;
Z is pyridine, thiophene, furan, or pyrrol;
m is 0 or 1;
$R^4$ is F, Cl, $CHF_2$, $CH_3$, $CF_3$, or $C_2H_5$.

Particular preference is given to the pyrimidine compounds of formula I.A to I.G (corresponds to pyrimidine compounds of formula (I)), and their use as herbicide, wherein X is O, $NR^{3.4}$, or S.

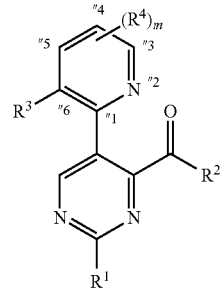

I.A

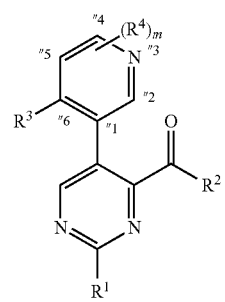

I.B

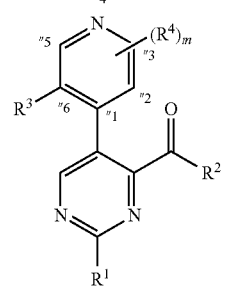

I.C

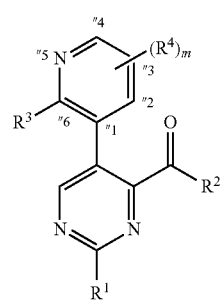

I.D

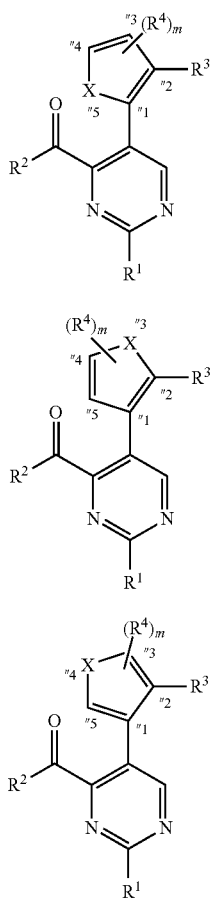

Preferred compounds of formula I, and their use as herbicide, are the compounds of the formulae I.A to I.G wherein
R$^1$ is C$_2$H$_5$, c-C$_3$H$_5$, c-C$_4$H$_7$, or OCH$_3$;
R$^2$ is OH, OCH$_3$, OC$_2$H$_5$, OCH$_2$C≡CH, OCH$_2$CHF$_2$, NHOCH$_3$, or NHCOCH$_3$;
R$^3$ is CH$_3$, OCH$_3$, Cl, Br, CHF$_2$, F, or I;
X is O, S, or NR$^{3A}$;
m is 0 or 1;
R$^4$ is F or CF$_3$.

Each of the groups mentioned for a substituent in the tables is furthermore per se, independently of the combination in which it is mentioned, a particularly preferred aspect of the substituent in question.

According to particularly preferred embodiment of the compound of formula I, and their use as herbicide, compounds of the invention are the compounds of the formulae I-A to I-G that are compiled in the Tables 1 to 26.

Table 1. Compounds of formula I.A, wherein m is 0 (=compounds of formula 1.1), and the meaning for the combination of R$^1$, R$^2$, and R$^3$ for each individual compound corresponds in each case to one line of Table A.

Table 2. Compounds of formula I.A, wherein m is 1, R$^4$ is 4"-F (=compounds of formula 1.2), and the meaning for the combination of R$^1$, R$^2$, and R$^3$ for each individual compound corresponds in each case to one line of Table A.

Table 3. Compounds of formula I.B, wherein m is 0 (=compounds of formula 1.3), and the meaning for the combination of R$^1$, R$^2$, and R$^3$ for each individual compound corresponds in each case to one line of Table A.

Table 4. Compounds of formula I.B, wherein m is 1, R$^4$ is 4"-F (=compounds of formula 1.4), and the meaning for the combination of R$^1$, R$^2$, and R$^3$ for each individual compound corresponds in each case to one line of Table A.

Table 5. Compounds of formula I.C, wherein m is 0 (=compounds of formula 1.5), and the meaning for the combination of R$^1$, R$^2$, and R$^3$ for each individual compound corresponds in each case to one line of Table A.

Table 6. Compounds of formula I.C, wherein m is 1, R$^4$ is 2"-F (=compounds of formula 1.6), and the meaning for the combination of R$^1$, R$^2$, and R$^3$ for each individual compound corresponds in each case to one line of Table A.

Table 7. Compounds of formula I.D, wherein m is 0 (=compounds of formula 1.7), and the meaning for the combination of R$^1$, R$^2$, and R$^3$ for each individual compound corresponds in each case to one line of Table A.

Table 8. Compounds of formula I.D, wherein m is 1, R$^4$ is 4"-F (=compounds of formula 1.8), and the meaning for the combination of R$^1$, R$^2$, and R$^3$ for each individual compound corresponds in each case to one line of Table A.

Table 9. Compounds of formula I.E, wherein m is 0, X is O (=compounds of formula 1.9), and the meaning for the combination of R$^1$, R$^2$, and R$^3$ for each individual compound corresponds in each case to one line of Table A.

Table 10. Compounds of formula I.E, wherein m is 1, X is O, R$^4$ is 3"-F (=compounds of formula 1.10), and the meaning for the combination of R$^1$, R$^2$, and R$^3$ for each individual compound corresponds in each case to one line of Table A.

Table 11. Compounds of formula I.E, wherein m is 0, X is S (=compounds of formula 1.11), and the meaning for the combination of R$^1$, R$^2$, and R$^3$ for each individual compound corresponds in each case to one line of Table A.

Table 12. Compounds of formula I.E, wherein m is 1, X is S, R$^4$ is 3"-F (=compounds of formula 1.12), and the meaning for the combination of R$^1$, R$^2$, and R$^3$ for each individual compound corresponds in each case to one line of Table A.

Table 13. Compounds of formula I.E, wherein m is 0, X is NCH$_3$ (=compounds of formula 1.13), and the meaning for the combination of R$^1$, R$^2$, and R$^3$ for each individual compound corresponds in each case to one line of Table A.

Table 14. Compounds of formula I.E, wherein m is 1, X is NCH$_3$, R$^4$ is 3"-F (=compounds of formula 1.14), and the meaning for the combination of R$^1$, R$^2$, and R$^3$ for each individual compound corresponds in each case to one line of Table A.

Table 15. Compounds of formula I.F, wherein m is 0, X is O (=compounds of formula 1.15), and the meaning for the combination of R$^1$, R$^2$, and R$^3$ for each individual compound corresponds in each case to one line of Table A.

Table 16. Compounds of formula I.F, wherein m is 1, X is O, R$^4$ is 5"-F (=compounds of formula 1.16), and the meaning for the combination of R$^1$, R$^2$, and R$^3$ for each individual compound corresponds in each case to one line of Table A.

Table 17. Compounds of formula I.F, wherein m is 0, X is S (=compounds of formula 1.17), and the meaning for the combination of R$^1$, R$^2$, and R$^3$ for each individual compound corresponds in each case to one line of Table A.

Table 18. Compounds of formula I.F, wherein m is 1, X is S, R$^4$ is 5"-F (=compounds of formula 1.18), and the meaning for the combination of R$^1$, R$^2$, and R$^3$ for each individual compound corresponds in each case to one line of Table A.

Table 19. Compounds of formula I.F, wherein m is 0, X is NH (=compounds of formula 1.19), and the meaning for the combination of $R^1$, $R^2$, and $R^3$ for each individual compound corresponds in each case to one line of Table A.

Table 20. Compounds of formula I.F, wherein m is 1, X is NH, $R^4$ is 5"-F (=compounds of formula 1.20), and the meaning for the combination of $R^1$, $R^2$, and $R^3$ for each individual compound corresponds in each case to one line of Table A.

Table 21. Compounds of formula I.G, wherein m is 0, X is O (=compounds of formula 1.21), and the meaning for the combination of $R^1$, $R^2$, and $R^3$ for each individual compound corresponds in each case to one line of Table A.

Table 22. Compounds of formula I.G, wherein m is 1, X is O, $R^4$ is 5"-F (=compounds of formula 1.22), and the meaning for the combination of $R^1$, $R^2$, and $R^3$ for each individual compound corresponds in each case to one line of Table A.

Table 23. Compounds of formula I.G, wherein m is 0, X is S (=compounds of formula 1.23), and the meaning for the combination of $R^1$, $R^2$, and $R^3$ for each individual compound corresponds in each case to one line of Table A.

Table 24. Compounds of formula I.G, wherein m is 1, X is S, $R^4$ is 5"-F (=compounds of formula 1.24), and the meaning for the combination of $R^1$, $R^2$, and $R^3$ for each individual compound corresponds in each case to one line of Table A.

Table 25. Compounds of formula I.G, wherein m is 0, X is NH (=compounds of formula 1.25), and the meaning for the combination of $R^1$, $R^2$, and $R^3$ for each individual compound corresponds in each case to one line of Table A.

Table 26. Compounds of formula I.G, wherein m is 1, X is NH, $R^4$ is 5"-F (=compounds of formula 1.26), and the meaning for the combination of $R^1$, $R^2$, and $R^3$ for each individual compound corresponds in each case to one line of Table A.

TABLE A

| Line | $R^1$ | $R^2$ | $R^3$ |
|---|---|---|---|
| I-1 | c-C$_3$H$_5$ | OH | CH$_3$ |
| I-2 | c-C$_3$H$_5$ | OH | OCH$_3$ |
| I-3 | c-C$_3$H$_5$ | OH | Cl |
| I-4 | c-C$_3$H$_5$ | OH | Br |
| I-5 | c-C$_3$H$_5$ | OH | CHF$_2$ |
| I-6 | c-C$_3$H$_5$ | OH | F |
| I-7 | c-C$_3$H$_5$ | OH | I |
| I-8 | c-C$_3$H$_5$ | OCH$_3$ | CH$_3$ |
| I-9 | c-C$_3$H$_5$ | OCH$_3$ | OCH$_3$ |
| I-10 | c-C$_3$H$_5$ | OCH$_3$ | Cl |
| I-11 | c-C$_3$H$_5$ | OCH$_3$ | Br |
| I-12 | c-C$_3$H$_5$ | OCH$_3$ | CHF$_2$ |
| I-13 | c-C$_3$H$_5$ | OCH$_3$ | F |
| I-14 | c-C$_3$H$_5$ | OCH$_3$ | I |
| I-15 | c-C$_3$H$_5$ | OC$_2$H$_5$ | CH$_3$ |
| I-16 | c-C$_3$H$_5$ | OC$_2$H$_5$ | OCH$_3$ |
| I-17 | c-C$_3$H$_5$ | OC$_2$H$_5$ | Cl |
| I-18 | c-C$_3$H$_5$ | OC$_2$H$_5$ | Br |
| I-19 | c-C$_3$H$_5$ | OC$_2$H$_5$ | CHF$_2$ |
| I-20 | c-C$_3$H$_5$ | OC$_2$H$_5$ | F |
| I-21 | c-C$_3$H$_5$ | OC$_2$H$_5$ | I |
| I-22 | c-C$_3$H$_5$ | OCH$_2$C≡CH | CH$_3$ |
| I-23 | c-C$_3$H$_5$ | OCH$_2$C≡CH | OCH$_3$ |
| I-24 | c-C$_3$H$_5$ | OCH$_2$C≡CH | Cl |
| I-25 | c-C$_3$H$_5$ | OCH$_2$C≡CH | Br |
| I-26 | c-C$_3$H$_5$ | OCH$_2$C≡CH | CHF$_2$ |
| I-27 | c-C$_3$H$_5$ | OCH$_2$C≡CH | F |
| I-28 | c-C$_3$H$_5$ | OCH$_2$C≡CH | I |
| I-29 | c-C$_3$H$_5$ | OCH$_2$CHF$_2$ | CH$_3$ |
| I-30 | c-C$_3$H$_5$ | OCH$_2$CHF$_2$ | OCH$_3$ |
| I-31 | c-C$_3$H$_5$ | OCH$_2$CHF$_2$ | Cl |
| I-32 | c-C$_3$H$_5$ | OCH$_2$CHF$_2$ | Br |
| I-33 | c-C$_3$H$_5$ | OCH$_2$CHF$_2$ | CHF$_2$ |
| I-34 | c-C$_3$H$_5$ | OCH$_2$CHF$_2$ | F |
| I-35 | c-C$_3$H$_5$ | OCH$_2$CHF$_2$ | I |
| I-36 | c-C$_3$H$_5$ | NHOCH$_3$ | CH$_3$ |
| I-37 | c-C$_3$H$_5$ | NHOCH$_3$ | OCH$_3$ |
| I-38 | c-C$_3$H$_5$ | NHOCH$_3$ | Cl |
| I-39 | c-C$_3$H$_5$ | NHOCH$_3$ | Br |
| I-40 | c-C$_3$H$_5$ | NHOCH$_3$ | CHF$_2$ |
| I-41 | c-C$_3$H$_5$ | NHOCH$_3$ | F |
| I-42 | c-C$_3$H$_5$ | NHOCH$_3$ | I |
| I-43 | c-C$_3$H$_5$ | NHCOCH$_3$ | CH$_3$ |
| I-44 | c-C$_3$H$_5$ | NHCOCH$_3$ | OCH$_3$ |
| I-45 | c-C$_3$H$_5$ | NHCOCH$_3$ | Cl |
| I-46 | c-C$_3$H$_5$ | NHCOCH$_3$ | Br |
| I-47 | c-C$_3$H$_5$ | NHCOCH$_3$ | CHF$_2$ |
| I-48 | c-C$_3$H$_5$ | NHCOCH$_3$ | F |
| I-49 | c-C$_3$H$_5$ | NHCOCH$_3$ | I |
| I-50 | c-C$_4$H$_7$ | OH | CH$_3$ |
| I-51 | c-C$_4$H$_7$ | OH | OCH$_3$ |
| I-52 | c-C$_4$H$_7$ | OH | Cl |
| I-53 | c-C$_4$H$_7$ | OH | Br |
| I-54 | c-C$_4$H$_7$ | OH | CHF$_2$ |
| I-55 | c-C$_4$H$_7$ | OH | F |
| I-56 | c-C$_4$H$_7$ | OH | I |
| I-57 | c-C$_4$H$_7$ | OCH$_3$ | CH$_3$ |
| I-58 | c-C$_4$H$_7$ | OCH$_3$ | OCH$_3$ |
| I-59 | c-C$_4$H$_7$ | OCH$_3$ | Cl |
| I-60 | c-C$_4$H$_7$ | OCH$_3$ | Br |
| I-61 | c-C$_4$H$_7$ | OCH$_3$ | CHF$_2$ |
| I-62 | c-C$_4$H$_7$ | OCH$_3$ | F |
| I-63 | c-C$_4$H$_7$ | OCH$_3$ | I |
| I-64 | c-C$_4$H$_7$ | OC$_2$H$_5$ | CH$_3$ |
| I-65 | c-C$_4$H$_7$ | OC$_2$H$_5$ | OCH$_3$ |
| I-66 | c-C$_4$H$_7$ | OC$_2$H$_5$ | Cl |
| I-67 | c-C$_4$H$_7$ | OC$_2$H$_5$ | Br |
| I-68 | c-C$_4$H$_7$ | OC$_2$H$_5$ | CHF$_2$ |
| I-69 | c-C$_4$H$_7$ | OC$_2$H$_5$ | F |
| I-70 | c-C$_4$H$_7$ | OC$_2$H$_5$ | I |
| I-71 | c-C$_4$H$_7$ | OCH$_2$C≡CH | CH$_3$ |
| I-72 | c-C$_4$H$_7$ | OCH$_2$C≡CH | OCH$_3$ |
| I-73 | c-C$_4$H$_7$ | OCH$_2$C≡CH | Cl |
| I-74 | c-C$_4$H$_7$ | OCH$_2$C≡CH | Br |
| I-75 | c-C$_4$H$_7$ | OCH$_2$C≡CH | CHF$_2$ |
| I-76 | c-C$_4$H$_7$ | OCH$_2$C≡CH | F |
| I-77 | c-C$_4$H$_7$ | OCH$_2$C≡CH | I |
| I-78 | c-C$_4$H$_7$ | OCH$_2$CHF$_2$ | CH$_3$ |
| I-79 | c-C$_4$H$_7$ | OCH$_2$CHF$_2$ | OCH$_3$ |
| I-80 | c-C$_4$H$_7$ | OCH$_2$CHF$_2$ | Cl |
| I-81 | c-C$_4$H$_7$ | OCH$_2$CHF$_2$ | Br |
| I-82 | c-C$_4$H$_7$ | OCH$_2$CHF$_2$ | CHF$_2$ |
| I-83 | c-C$_4$H$_7$ | OCH$_2$CHF$_2$ | F |
| I-84 | c-C$_4$H$_7$ | OCH$_2$CHF$_2$ | I |
| I-85 | c-C$_4$H$_7$ | NHOCH$_3$ | CH$_3$ |
| I-86 | c-C$_4$H$_7$ | NHOCH$_3$ | OCH$_3$ |
| I-87 | c-C$_4$H$_7$ | NHOCH$_3$ | Cl |
| I-88 | c-C$_4$H$_7$ | NHOCH$_3$ | Br |
| I-89 | c-C$_4$H$_7$ | NHOCH$_3$ | CHF$_2$ |
| I-90 | c-C$_4$H$_7$ | NHOCH$_3$ | F |
| I-91 | c-C$_4$H$_7$ | NHOCH$_3$ | I |
| I-92 | c-C$_4$H$_7$ | NHCOCH$_3$ | CH$_3$ |
| I-93 | c-C$_4$H$_7$ | NHCOCH$_3$ | OCH$_3$ |
| I-94 | c-C$_4$H$_7$ | NHCOCH$_3$ | Cl |
| I-95 | c-C$_4$H$_7$ | NHCOCH$_3$ | Br |
| I-96 | c-C$_4$H$_7$ | NHCOCH$_3$ | CHF$_2$ |
| I-97 | c-C$_4$H$_7$ | NHCOCH$_3$ | F |
| I-98 | c-C$_4$H$_7$ | NHCOCH$_3$ | I |
| I-99 | C$_2$H$_5$ | OH | CH$_3$ |
| I-100 | C$_2$H$_5$ | OH | OCH$_3$ |
| I-101 | C$_2$H$_5$ | OH | Cl |
| I-102 | C$_2$H$_5$ | OH | Br |
| I-103 | C$_2$H$_5$ | OH | CHF$_2$ |
| I-104 | C$_2$H$_5$ | OH | F |
| I-105 | C$_2$H$_5$ | OH | I |
| I-106 | C$_2$H$_5$ | OCH$_3$ | CH$_3$ |
| I-107 | C$_2$H$_5$ | OCH$_3$ | OCH$_3$ |
| I-108 | C$_2$H$_5$ | OCH$_3$ | Cl |
| I-109 | C$_2$H$_5$ | OCH$_3$ | Br |
| I-110 | C$_2$H$_5$ | OCH$_3$ | CHF$_2$ |
| I-111 | C$_2$H$_5$ | OCH$_3$ | F |
| I-112 | C$_2$H$_5$ | OCH$_3$ | I |

TABLE A-continued

| Line | $R^1$ | $R^2$ | $R^3$ |
|---|---|---|---|
| I-113 | $C_2H_5$ | $OC_2H_5$ | $CH_3$ |
| I-114 | $C_2H_5$ | $OC_2H_5$ | $OCH_3$ |
| I-115 | $C_2H_5$ | $OC_2H_5$ | Cl |
| I-116 | $C_2H_5$ | $OC_2H_5$ | Br |
| I-117 | $C_2H_5$ | $OC_2H_5$ | $CHF_2$ |
| I-118 | $C_2H_5$ | $OC_2H_5$ | F |
| I-119 | $C_2H_5$ | $OC_2H_5$ | I |
| I-120 | $C_2H_5$ | $OCH_2C\equiv CH$ | $CH_3$ |
| I-121 | $C_2H_5$ | $OCH_2C\equiv CH$ | $OCH_3$ |
| I-122 | $C_2H_5$ | $OCH_2C\equiv CH$ | Cl |
| I-123 | $C_2H_5$ | $OCH_2C\equiv CH$ | Br |
| I-124 | $C_2H_5$ | $OCH_2C\equiv CH$ | $CHF_2$ |
| I-125 | $C_2H_5$ | $OCH_2C\equiv CH$ | F |
| I-126 | $C_2H_5$ | $OCH_2C\equiv CH$ | I |
| I-127 | $C_2H_5$ | $OCH_2CHF_2$ | $CH_3$ |
| I-128 | $C_2H_5$ | $OCH_2CHF_2$ | $OCH_3$ |
| I-129 | $C_2H_5$ | $OCH_2CHF_2$ | Cl |
| I-130 | $C_2H_5$ | $OCH_2CHF_2$ | Br |
| I-131 | $C_2H_5$ | $OCH_2CHF_2$ | $CHF_2$ |
| I-132 | $C_2H_5$ | $OCH_2CHF_2$ | F |
| I-133 | $C_2H_5$ | $OCH_2CHF_2$ | I |
| I-134 | $C_2H_5$ | $NHOCH_3$ | $CH_3$ |
| I-135 | $C_2H_5$ | $NHOCH_3$ | $OCH_3$ |
| I-136 | $C_2H_5$ | $NHOCH_3$ | Cl |
| I-137 | $C_2H_5$ | $NHOCH_3$ | Br |
| I-138 | $C_2H_5$ | $NHOCH_3$ | $CHF_2$ |
| I-139 | $C_2H_5$ | $NHOCH_3$ | F |
| I-140 | $C_2H_5$ | $NHOCH_3$ | I |
| I-141 | $C_2H_5$ | $NHCOCH_3$ | $CH_3$ |
| I-142 | $C_2H_5$ | $NHCOCH_3$ | $OCH_3$ |
| I-143 | $C_2H_5$ | $NHCOCH_3$ | Cl |
| I-144 | $C_2H_5$ | $NHCOCH_3$ | Br |
| I-145 | $C_2H_5$ | $NHCOCH_3$ | $CHF_2$ |
| I-146 | $C_2H_5$ | $NHCOCH_3$ | F |
| I-147 | $C_2H_5$ | $NHCOCH_3$ | I |
| I-148 | $OCH_3$ | OH | $CH_3$ |
| I-149 | $OCH_3$ | OH | $OCH_3$ |
| I-150 | $OCH_3$ | OH | Cl |
| I-151 | $OCH_3$ | OH | Br |
| I-152 | $OCH_3$ | OH | $CHF_2$ |
| I-153 | $OCH_3$ | OH | F |
| I-154 | $OCH_3$ | OH | I |
| I-155 | $OCH_3$ | $OCH_3$ | $CH_3$ |
| I-156 | $OCH_3$ | $OCH_3$ | $OCH_3$ |
| I-157 | $OCH_3$ | $OCH_3$ | Cl |
| I-158 | $OCH_3$ | $OCH_3$ | Br |
| I-159 | $OCH_3$ | $OCH_3$ | $CHF_2$ |
| I-160 | $OCH_3$ | $OCH_3$ | F |
| I-161 | $OCH_3$ | $OCH_3$ | I |
| I-162 | $OCH_3$ | $OC_2H_5$ | $CH_3$ |
| I-163 | $OCH_3$ | $OC_2H_5$ | $OCH_3$ |
| I-164 | $OCH_3$ | $OC_2H_5$ | Cl |
| I-165 | $OCH_3$ | $OC_2H_5$ | Br |
| I-166 | $OCH_3$ | $OC_2H_5$ | $CHF_2$ |
| I-167 | $OCH_3$ | $OC_2H_5$ | F |
| I-168 | $OCH_3$ | $OC_2H_5$ | I |
| I-169 | $OCH_3$ | $OCH_2C\equiv CH$ | $CH_3$ |
| I-170 | $OCH_3$ | $OCH_2C\equiv CH$ | $OCH_3$ |
| I-171 | $OCH_3$ | $OCH_2C\equiv CH$ | Cl |
| I-172 | $OCH_3$ | $OCH_2C\equiv CH$ | Br |
| I-173 | $OCH_3$ | $OCH_2C\equiv CH$ | $CHF_2$ |
| I-174 | $OCH_3$ | $OCH_2C\equiv CH$ | F |
| I-175 | $OCH_3$ | $OCH_2C\equiv CH$ | I |
| I-176 | $OCH_3$ | $OCH_2CHF_2$ | $CH_3$ |
| I-177 | $OCH_3$ | $OCH_2CHF_2$ | $OCH_3$ |
| I-178 | $OCH_3$ | $OCH_2CHF_2$ | Cl |
| I-179 | $OCH_3$ | $OCH_2CHF_2$ | Br |
| I-180 | $OCH_3$ | $OCH_2CHF_2$ | $CHF_2$ |
| I-181 | $OCH_3$ | $OCH_2CHF_2$ | F |
| I-182 | $OCH_3$ | $OCH_2CHF_2$ | I |
| I-183 | $OCH_3$ | $NHOCH_3$ | $CH_3$ |
| I-184 | $OCH_3$ | $NHOCH_3$ | $OCH_3$ |
| I-185 | $OCH_3$ | $NHOCH_3$ | Cl |
| I-186 | $OCH_3$ | $NHOCH_3$ | Br |
| I-187 | $OCH_3$ | $NHOCH_3$ | $CHF_2$ |
| I-188 | $OCH_3$ | $NHOCH_3$ | F |
| I-189 | $OCH_3$ | $NHOCH_3$ | I |
| I-190 | $OCH_3$ | $NHCOCH_3$ | $CH_3$ |
| I-191 | $OCH_3$ | $NHCOCH_3$ | $OCH_3$ |
| I-192 | $OCH_3$ | $NHCOCH_3$ | Cl |
| I-193 | $OCH_3$ | $NHCOCH_3$ | Br |
| I-194 | $OCH_3$ | $NHCOCH_3$ | $CHF_2$ |
| I-195 | $OCH_3$ | $NHCOCH_3$ | F |
| I-196 | $OCH_3$ | $NHCOCH_3$ | I |

The specific number for each single compound is deductible as follows:

Compound 1.1.I-3 e.g. comprises the compound of formula 1.1 from Table 1 and line I-3 from Table A.

To widen the spectrum of action and to achieve synergistic effects, the pyrimidine compounds of formula (I) may be mixed with a large number of representatives of other herbicidal or growth-regulating active ingredient groups and then applied concomitantly. Suitable components for mixtures are, e.g., herbicides from the classes of the acetamides, amides, aryloxyphenoxypropionates, benzamides, benzofuran, benzoic acids, benzothiadiazinones, bipyridylium, carbamates, chloroacetamides, chlorocarboxylic acids, cyclohexanediones, dinitroanilines, dinitrophenol, diphenyl ether, glycines, imidazolinones, isoxazoles, isoxazolidinones, nitriles, N-phenylphthalimides, oxadiazoles, oxazolidinediones, oxyacetamides, phenoxycarboxylic acids, phenylcarbamates, phenylpyrazoles, phenylpyrazolines, phenylpyridazines, phosphinic acids, phosphoroamidates, phosphorodithioates, phthalamates, pyrazoles, pyridazinones, pyridines, pyridinecarboxylic acids, pyridinecarboxamides, pyrimidinediones, pyrimidinyl(thio)benzoates, quinolinecarboxylic acids, semicarbazones, sulfonylaminocarbonyltriazolinones, sulfonylureas, tetrazolinones, thiadiazoles, thiocarbamates, triazines, triazinones, triazoles, triazolinones, triazolocarboxamides, triazolopyrimidines, triketones, uracils, or ureas.

It may furthermore be beneficial to apply the pyrimidine compounds of formula (I) alone or in combination with other herbicides, or else in the form of a mixture with other crop protection agents, e.g. together with agents for controlling pests or phytopathogenic fungi or bacteria. Also of interest is the miscibility with mineral salt solutions, which are employed for treating nutritional and trace element deficiencies. Other additives such as non-phytotoxic oils and oil concentrates may also be added.

In one embodiment of the present invention the compositions according to the present invention comprise at least one pyrimidine compound of formula (I) (compound A) and at least one further active compound selected from herbicides B, preferably herbicides B of class b1) to b15), and safeners C (compound C).

In a preferred embodiment of the invention, the composition comprises as active compound A or component A at least one, preferably exactly one, pyrimidine compound of formula (I.1) (corresponds to pyrimidine compound of formula (I)), as defined herein;

In another preferred embodiment of the invention, the composition comprises as active compound A or component A at least one, preferably exactly one, pyrimidine compound of formula (I.2) (corresponds to pyrimidine compound of formula (I)), as defined herein;

In another preferred embodiment of the invention, the composition comprises as active compound A or component A at least one, preferably exactly one, pyrimidine compound of formula (I.3) (corresponds to pyrimidine compound of formula (I)), as defined herein;

In another preferred embodiment of the invention, the composition comprises as active compound A or component A at least one, preferably exactly one, pyrimidine compound of formula (I.4) (corresponds to pyrimidine compound of formula (I)), as defined herein;

In another preferred embodiment of the invention, the composition comprises as active compound A or component A at least one, preferably exactly one, pyrimidine compound of formula (I.5) (corresponds to pyrimidine compound of formula (I)), as defined herein;

In another preferred embodiment of the invention, the composition comprises as active compound A or component A at least one, preferably exactly one, pyrimidine compound of formula (I.6) (corresponds to pyrimidine compound of formula (I)), as defined herein;

In another preferred embodiment of the invention, the composition comprises as active compound A or component A at least one, preferably exactly one, pyrimidine compound of formula (I.7) (corresponds to pyrimidine compound of formula (I)), as defined herein;

Preferred compounds of the formula (I) which, as component A, are constituent of the composition according to the invention are the compounds 1.1 to 1.7, as defined above;

In another embodiment of the present invention the compositions according to the present invention comprise at least one pyrimidine compound of formula (I) and at least one further active compound B (herbicide B).

The further herbicidal compound B (component B) is preferably selected from the herbicides of class b1) to b15):

Mixing partners for the composition can be selected from below herbicides B as defined below:

B) herbicides of class b1) to b15):
b1) lipid biosynthesis inhibitors;
b2) acetolactate synthase inhibitors (ALS inhibitors);
b3) photosynthesis inhibitors;
b4) protoporphyrinogen-IX oxidase inhibitors (PPO inhibitors);
b5) bleacher herbicides;
b6) enolpyruvyl shikimate 3-phosphate synthase inhibitors (EPSP inhibitors);
b7) glutamine synthetase inhibitors;
b8) 7,8-dihydropteroate synthase inhibitors (DHP inhibitors);
b9) mitosis inhibitors;
b10) inhibitors of the synthesis of very long chain fatty acids (VLCFA inhibitors);
b11) cellulose biosynthesis inhibitors;
b12) decoupler herbicides;
b13) auxinic herbicides;
b14) auxin transport inhibitors; and
b15) other herbicides selected from the group consisting of bromobutide, chlorflurenol, chlorflurenol-methyl, cinmethylin, cumyluron, dalapon, dazomet, difenzoquat, difenzoquat-metilsulfate, dimethipin, DSMA, dymron, endothal and its salts, etobenzanid, flamprop, flamprop-isopropyl, flamprop-methyl, flamprop-M-isopropyl, flamprop-M-methyl, flurenol, flurenol-butyl, flurprimidol, fosamine, fosamine-ammonium, indanofan, indaziflam, maleic hydrazide, mefluidide, metam, methiozolin (CAS 403640-27-7), methyl azide, methyl bromide, methyl-dymron, methyl iodide, MSMA, oleic acid, oxaziclomefone, pelargonic acid, pyributicarb, quinoclamine, triaziflam, tridiphane and 6-chloro-3-(2-cyclopropyl-6-methylphenoxy)-4-pyridazinol (CAS 499223-49-3) and its salts and esters;

including their agriculturally acceptable salts or derivatives;

In one embodiment of the invention, the compositions contain at least one inhibitor of the lipid biosynthesis (herbicide b1). These compounds inhibit lipid biosynthesis. Inhibition of the lipid biosynthesis can be affected either through inhibition of acetylCoA carboxylase (hereinafter-termed ACCase herbicides) or through a different mode of action (hereinafter termed non-ACCase herbicides). The ACCase herbicides belong to the group A of the HRAC classification system whereas the non-ACCase herbicides belong to the group N of the HRAC classification.

In another embodiment of the invention, the compositions contain at least one ALS inhibitor (herbicide b2). The herbicidal activity of these compounds is based on the inhibition of acetolactate synthase and thus on the inhibition of the branched chain amino acid biosynthesis. These inhibitors belong to the group B of the HRAC classification system.

In another embodiment of the invention, the compositions contain at least one inhibitor of photosynthesis (herbicide b3). The herbicidal activity of these compounds is based either on the inhibition of the photosystem II in plants (so-called PSII inhibitors, groups C1, C2 and C3 of HRAC classification) or on diverting the electron transfer in photosystem I in plants (so-called PSI inhibitors, group D of HRAC classification) and thus on an inhibition of photosynthesis. Amongst these, PSII inhibitors are preferred.

In another embodiment of the invention, the compositions contain at least one inhibitor of protoporphyrinogen-IX-oxidase (herbicide b4). The herbicidal activity of these compounds is based on the inhibition of the protoporphyrinogen-IX-oxidase. These inhibitors belong to the group E of the HRAC classification system.

In another embodiment of the invention, the compositions contain at least one bleacher-herbicide (herbicide b5). The herbicidal activity of these compounds is based on the inhibition of the carotenoid biosynthesis. These include compounds which inhibit carotenoid biosynthesis by inhibition of phytoene desaturase (so-called PDS inhibitors, group F1 of HRAC classification), compounds that inhibit the 4-hydroxyphenylpyruvate-dioxygenase (HPPD inhibitors, group F2 of HRAC classification), compounds that inhibit DOXsynthase (group F4 of HRAC class) and compounds which inhibit carotenoid biosynthesis by an unknown mode of action (bleacher—unknown target, group F3 of HRAC classification).

In another embodiment of the invention, the compositions contain at least one EPSP synthase inhibitor (herbicide b6). The herbicidal activity of these compounds is based on the inhibition of enolpyruvyl shikimate 3-phosphate synthase, and thus on the inhibition of the amino acid biosynthesis in plants. These inhibitors belong to the group G of the HRAC classification system.

In another embodiment of the invention, the compositions contain at least one glutamine synthetase inhibitor (herbicide b7). The herbicidal activity of these compounds is based on the inhibition of glutamine synthetase, and thus on the inhibition of the aminoacid biosynthesis in plants. These inhibitors belong to the group H of the HRAC classification system.

In another embodiment of the invention, the compositions contain at least one DHP synthase inhibitor (herbicide b8). The herbicidal activity of these compounds is based on the inhibition of 7,8-dihydropteroate synthase. These inhibitors belong to the group I of the HRAC classification system.

In another embodiment of the invention, the compositions contain at least one mitosis inhibitor (herbicide b9). The herbicidal activity of these compounds is based on the disturbance or inhibition of microtubule formation or organization, and thus on the inhibition of mitosis. These inhibitors belong to the groups K1 and K2 of the HRAC classification system. Among these, compounds of the group K1, in particular dinitroanilines, are preferred.

In another embodiment of the invention, the compositions contain at least one VLCFA inhibitor (herbicide b10). The herbicidal activity of these compounds is based on the inhibition of the synthesis of very long chain fatty acids and thus on the disturbance or inhibition of cell division in plants. These inhibitors belong to the group K3 of the HRAC classification system.

In another embodiment of the invention, the compositions contain at least one cellulose biosynthesis inhibitor (herbicide b11). The herbicidal activity of these compounds is based on the inhibition of the biosynthesis of cellulose and thus on the inhibition of the synthesis of cell walls in plants. These inhibitors belong to the group L of the HRAC classification system.

In another embodiment of the invention, the compositions contain at least one decoupler herbicide (herbicide b12). The herbicidal activity of these compounds is based on the disruption of the cell membrane. These inhibitors belong to the group M of the HRAC classification system.

In another embodiment of the invention, the compositions contain at least one auxinic herbicide (herbicide b13). These include compounds that mimic auxins, i.e. plant hormones, and affect the growth of the plants. These compounds belong to the group O of the HRAC classification system.

In another embodiment of the invention, the compositions contain at least one auxin transport inhibitor (herbicide b14). The herbicidal activity of these compounds is based on the inhibition of the auxin transport in plants. These compounds belong to the group P of the HRAC classification system.

As to the given mechanisms of action and classification of the active substances, see e.g. "HRAC, Classification of Herbicides According to Mode of Action", http://www-.plantprotection.org/hrac/MOA.html).

Preference is given to those compositions according to the present invention comprising at least one herbicide B selected from herbicides of class b1, b2, b3, b4, b5, b6, b9, b10, b13, and b14.

Specific preference is given to those compositions according to the present invention which comprise at least one herbicide B selected from the herbicides of class b1, b2, b4, b5, b9, b10, b13, and b14.

Particular preference is given to those compositions according to the present invention which comprise at least one herbicide B selected from the herbicides of class b1, b2, b4, b5, b9, b10, and b13 Examples of herbicides B which can be used in combination with the compound of formula (I) according to the present invention are:

b1) from the group of the lipid biosynthesis inhibitors:

ACC-herbicides such as alloxydim, alloxydim-sodium, butroxydim, clethodim, clodinafop, clodinafop-propargyl, cycloxydim, cyhalofop, cyhalofop-butyl, diclofop, diclofop-methyl, fenoxaprop, fenoxaprop-ethyl, fenoxaprop-P, fenoxaprop-P-ethyl, fluazifop, fluazifop-butyl, fluazifop-P, fluazifop-P-butyl, haloxyfop, haloxyfop-methyl, haloxyfop-P, haloxyfop-P-methyl, metamifop, pinoxaden, profoxydim, propaquizafop, quizalofop, quizalofop-ethyl, quizalofop-tefuryl, quizalofop-P, quizalofop-P-ethyl, quizalofop-P-tefuryl, sethoxydim, tepraloxydim, tralkoxydim, 4-(4'-Chloro-4-cyclopropyl-2'-fluoro[1,1'-biphenyl]-3-yl)-5-hydroxy-2,2,6,6-tetramethyl-2H-pyran-3(6H)-one (CAS 1312337-72-6); 4-(2',4'-Dichloro-4-cyclopropyl[1,1'-biphenyl]-3-yl)-5-hydroxy-2,2,6,6-tetramethyl-2H-pyran-3 (6H)-one (CAS 1312337-45-3); 4-(4'-Chloro-4-ethyl-2'-fluoro[1,1'-biphenyl]-3-yl)-5-hydroxy-2,2,6,6-tetramethyl-2H-pyran-3(6H)-one (CAS 1033757-93-5); 4-(2',4'-Dichloro-4-ethyl[1,1'-biphenyl]-3-yl)-2,2,6,6-tetramethyl-2H-pyran-3,5(4H,6H)-dione (CAS 1312340-84-3); 5-(Acetyloxy)-4-(4'-chloro-4-cyclopropyl-2'-fluoro[1,1'-biphenyl]-3-yl)-3,6-dihydro-2,2,6,6-tetramethyl-2H-pyran-3-one (CAS 1312337-48-6); 5-(Acetyloxy)-4-(2',4'-dichloro-4-cyclopropyl-[1,1'-biphenyl]-3-yl)-3,6-dihydro-2,2,6,6-tetramethyl-2H-pyran-3-one; 5-(Acetyloxy)-4-(4'-chloro-4-ethyl-2'-fluoro[1,1'-biphenyl]-3-yl)-3,6-dihydro-2,2,6,6-tetramethyl-2H-pyran-3-one (CAS 1312340-82-1); 5-(Acetyloxy)-4-(2',4'-dichloro-4-ethyl[1,1'-biphenyl]-3-yl)-3,6-dihydro-2,2,6,6-tetramethyl-2H-pyran-3-one (CAS 1033760-55-2); 4-(4'-Chloro-4-cyclopropyl-2'-fluoro[1,1'-biphenyl]-3-yl)-5,6-dihydro-2,2,6,6-tetramethyl-5-oxo-2H-pyran-3-yl carbonic acid methyl ester (CAS 1312337-51-1); 4-(2',4'-Dichloro-4-cyclopropyl-[1,1'-biphenyl]-3-yl)-5,6-dihydro-2,2,6,6-tetramethyl-5-oxo-2H-pyran-3-yl carbonic acid methyl ester; 4-(4'-Chloro-4-ethyl-2'-fluoro[1,1'-biphenyl]-3-yl)-5,6-dihydro-2,2,6,6-tetramethyl-5-oxo-2H-pyran-3-yl carbonic acid methyl ester (CAS 1312340-83-2); 4-(2',4'-Dichloro-4-ethyl[1,1'-biphenyl]-3-yl)-5,6-dihydro-2,2,6,6-tetramethyl-5-oxo-2H-pyran-3-yl carbonic acid methyl ester (CAS 1033760-58-5); and non ACC herbicides such as benfuresate, butylate, cycloate, dalapon, dimepiperate, EPTC, esprocarb, ethofumesate, flupropanate, molinate, orbencarb, pebulate, prosulfocarb, TCA, thiobencarb, tiocarbazil, triallate and vernolate;

b2) from the group of the ALS inhibitors:

sulfonylureas such as amidosulfuron, azimsulfuron, bensulfuron, bensulfuron-methyl, chlorimuron, chlorimuron-ethyl, chlorsulfuron, cinosulfuron, cyclosulfamuron, ethametsulfuron, ethametsulfuron-methyl, ethoxysulfuron, flazasulfuron, flucetosulfuron, flupyrsulfuron, flupyrsulfuron-methyl-sodium, foramsulfuron, halosulfuron, halosulfuron-methyl, imazosulfuron, iodosulfuron, iodosulfuron-methyl-sodium, iofensulfuron, iofensulfuron-sodium, mesosulfuron, metazosulfuron, metsulfuron, metsulfuron-methyl, nicosulfuron, orthosulfamuron, oxasulfuron, primisulfuron, primisulfuron-methyl, propyrisulfuron, prosulfuron, pyrazosulfuron, pyrazosulfuron-ethyl, rimsulfuron, sulfometuron, sulfometuron-methyl, sulfosulfuron, thifensulfuron, thifensulfuron-methyl, triasulfuron, tribenuron, tribenuron-methyl, trifloxysulfuron, triflusulfuron, triflusulfuron-methyl and tritosulfuron, imidazolinones such as imazamethabenz, imazamethabenz-methyl, imazamox, imazapic, imazapyr, imazaquin and imazethapyr, triazolopyrimidine herbicides and sulfonanilides such as cloransulam, cloransulam-methyl, diclosulam, flumetsulam, florasulam, metosulam, penoxsulam, pyrimisulfan and pyroxsulam, pyrimidinylbenzoates such as bispyribac, bispyribac-sodium, pyribenzoxim, pyriftalid, pyriminobac, pyriminobac-methyl, pyrithiobac, pyrithiobac-sodium, 4-[[[2-[(4,6-dimethoxy-2-pyrimidinyl)oxy]phenyl]methyl]amino]-benzoic acid-1-methylethyl ester (CAS 420138-41-6), 4-[[[2-[(4,6-dimethoxy-2-pyrimidinyl)oxy]phenyl]methyl]amino]-benzoic acid propyl ester (CAS 420138-40-5), N-(4-bromophenyl)-2-[(4,6-dimethoxy-2-pyrimidinyl)oxy] benzenemethanamine (CAS 420138-01-8), sulfonylaminocarbonyl-triazolinone herbicides such as flucarbazone, flucarbazone-sodium, propoxycarbazone, propoxycarbazone-sodium, thiencarbazone and thiencarbazone-methyl; and triafamone;

among these, a preferred embodiment of the invention relates to those compositions comprising at least one imidazolinone herbicide;

b3) from the group of the photosynthesis inhibitors:

amicarbazone, inhibitors of the photosystem II, e.g. 1-(6-tert-butylpyrimidin-4-yl)-2-hydroxy-4-methoxy-3-methyl-2H-pyrrol-5-one (CAS 1654744-66-7), 1-(5-tert-butylisoxazol-3-yl)-2-hydroxy-4-methoxy-3-methyl-2H-pyrrol-5-one (CAS 1637455-12-9), 1-(5-tert-butylisoxazol-3-yl)-4-chloro-2-hydroxy-3-methyl-2H-pyrrol-5-one (CAS 1637453-94-1), 1-(5-tert-butyl-1-methyl-pyrazol-3-yl)-4-chloro-2-hydroxy-3-methyl-2H-pyrrol-5-one (CAS 1654057-29-0), 1-(5-tert-butyl-1-methylpyrazol-3-yl)-3-chloro-2-hydroxy-4-methyl-2H-pyrrol-5-one (CAS 1654747-80-4), 4-hydroxy-1-methoxy-5-methyl-3-[4-(trifluoromethyl)-2-pyridyl]imidazolidin-2-one; (CAS 2023785-78-4), 4-hydroxy-1,5-dimethyl-3-[4-(trifluoromethyl)-2-pyridyl]imidazolidin-2-one (CAS 2023785-79-5), 5-ethoxy-4-hydroxy-1-methyl-3-[4-(trifluoromethyl)-2-pyridyl]imidazolidin-2-one (CAS 1701416-69-4), 4-hydroxy-1-methyl-3-[4-(trifluoromethyl)-2-pyridyl]imidazolidin-2-one (CAS 1708087-22-2), 4-hydroxy-1,5-dimethyl-3-[1-methyl-5-(trifluoromethyl)pyrazol-3-yl]imidazolidin-2-one (CAS 2023785-80-8), 1-(5-tert-butylisoxazol-3-yl)-4-ethoxy-5-hydroxy-3-methyl-imidazolidin-2-one (CAS 1844836-64-1), triazine herbicides, including of chlorotriazine, triazinones, triazindiones, methylthiotriazines and pyridazinones such as ametryn, atrazine, chloridazone, cyanazine, desmetryn, dimethametryn, hexazinone, metribuzin, prometon, prometryn, propazine, simazine, simetryn, terbumeton, terbuthylazin, terbutryn and trietazin, aryl urea such as chlorbromuron, chlorotoluron, chloroxuron, dimefuron, diuron, fluometuron, isoproturon, isouron, linuron, metamitron, methabenzthiazuron, metobenzuron, metoxuron, monolinuron, neburon, siduron, tebuthiuron and thiadiazuron, phenyl carbamates such as desmedipham, karbutilat, phenmedipham, phenmedipham-ethyl, nitrile herbicides such as bromofenoxim, bromoxynil and its salts and esters, ioxynil and its salts and esters, uraciles such as bromacil, lenacil and terbacil, and bentazon and bentazon-sodium, pyridate, pyridafol, pentanochlor and propanil and inhibitors of the photosystem I such as diquat, diquat-dibromide, paraquat, paraquat-dichloride and paraquat-dimetilsulfate. Among these, a preferred embodiment of the invention relates to those compositions comprising at least one aryl urea herbicide. Among these, likewise a preferred embodiment of the invention relates to those compositions comprising at least one triazine herbicide. Among these, likewise a preferred embodiment of the invention relates to those compositions comprising at least one nitrile herbicide;

b4) from the group of the protoporphyrinogen-IX oxidase inhibitors:

acifluorfen, acifluorfen-sodium, azafenidin, bencarbazone, benzfendizone, bifenox, butafenacil, carfentrazone, carfentrazone-ethyl, chlomethoxyfen, chlorphthalim, cinidon-ethyl, fluazolate, flufenpyr, flufenpyr-ethyl, flumiclorac, flumiclorac-pentyl, flumioxazin, fluoroglycofen, fluoroglycofen-ethyl, fluthiacet, fluthiacet-methyl, fomesafen, halosafen, lactofen, oxadiargyl, oxadiazon, oxyfluorfen, pentoxazone, profluazol, pyraclonil, pyraflufen, pyraflufen-ethyl, saflufenacil, sulfentrazone, thidiazimin, tiafenacil, trifludimoxazin, ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate (CAS 353292-31-6; S-3100), N-ethyl-3-(2,6-dichloro-4-trifluoromethylphenoxy)-5-methyl-1H-pyrazole-1-carboxamide (CAS 452098-92-9), N-tetrahydrofurfuryl-3-(2,6-dichloro-4-trifluoromethylphenoxy)-5-methyl-1H-pyrazole-1-carboxamide (CAS 915396-43-9), N-ethyl-3-(2-chloro-6-fluoro-4-trifluoromethylphenoxy)-5-methyl-1H-pyrazole-1-carboxamide (CAS 452099-05-7), N-tetrahydrofurfuryl-3-(2-chloro-6-fluoro-4-trifluoromethylphenoxy)-5-methyl-1H-pyrazole-1-carboxamide (CAS 452100-03-7), 3-[7-fluoro-3-oxo-4-(prop-2-ynyl)-3,4-dihydro-2H-benzo[1,4]oxazin-6-yl]-1,5-dimethyl-6-thioxo-[1,3,5]triazinan-2,4-dione (CAS 451484-50-7), 2-(2,2,7-trifluoro-3-oxo-4-prop-2-ynyl-3,4-dihydro-2H-benzo[1,4]oxazin-6-yl)-4,5,6,7-tetrahydroisoindole-1,3-dione (CAS 1300118-96-0), 1-methyl-6-trifluoromethyl-3-(2,2,7-trifluoro-3-oxo-4-prop-2-ynyl-3,4-dihydro-2H-benzo[1,4]oxazin-6-yl)-1H-pyrimidine-2,4-dione (CAS 1304113-05-0), methyl (E)-4-[2-chloro-5-[4-chloro-5-(difluoromethoxy)-1H-methyl-pyrazol-3-yl]-4-fluorophenoxy]-3-methoxy-but-2-enoate (CAS 948893-00-3), and 3-[7-chloro-5-fluoro-2-(trifluoromethyl)-1H-benzimidazol-4-yl]-1-methyl-6-(trifluoromethyl)-1H-pyrimidine-2,4-dione (CAS 212754-$C_2$-4);

b5) from the group of the bleacher herbicides:

PDS inhibitors: beflubutamid, diflufenican, fluridone, flurochloridone, flurtamone, norflurazon, picolinafen, and 4-(3-trifluoromethylphenoxy)-2-(4-trifluoromethylphenyl) pyrimidine (CAS 180608-33-7), HPPD inhibitors: benzobicyclon, benzofenap, bicyclopyrone, clomazone, fenquinotrione, isoxaflutole, mesotrione, oxotrione (CAS 1486617-21-3), pyrasulfotole, pyrazolynate, pyrazoxyfen, sulcotrione, tefuryltrione, tembotrione, tolpyralate, topramezone, bleacher, unknown target: aclonifen, amitrole flumeturon, 2-chloro-3-methylsulfanyl-N-(1-methyltetrazol-5-yl)-4-(trifluoromethyl)benzamide (CAS 1361139-71-0), 2-(2,4-dichlorophenyl)methyl-4,4-dimethyl-3-isoxazolidone (CAS 81777-95-9) and 2-(2,5-dichlorophenyl)methyl-4,4-dimethyl-3-isoxazolidinone (CAS 81778-66-7);

b6) from the group of the EPSP synthase inhibitors: glyphosate, glyphosate-isopropylammonium, glyposate-potassium and glyphosate-trimesium (sulfosate);

b7) from the group of the glutamine synthase inhibitors: bilanaphos (bialaphos), bilanaphossodium, glufosinate, glufosinate-P and glufosinate-ammonium;

b8) from the group of the DHP synthase inhibitors: asulam;

b9) from the group of the mitosis inhibitors:

compounds of group K1: dinitroanilines such as benfluralin, butralin, dinitramine, ethalfluralin, fluchloralin, oryzalin, pendimethalin, prodiamine and trifluralin, phosphoramidates such as amiprophos, amiprophos-methyl, and butamiphos, benzoic acid herbicides such as chlorthal, chlorthal-dimethyl, pyridines such as dithiopyr and thiazopyr, benzamides such as propyzamide and tebutam; compounds of group K2: carbetamide, chlorpropham, flamprop, flamprop-isopropyl, flamprop-methyl, flamprop-M-isopropyl, flamprop-M-methyl and propham; among these, compounds of group K1, in particular dinitroanilines are preferred;

b10) from the group of the VLCFA inhibitors:

chloroacetamides such as acetochlor, alachlor, amidochlor, butachlor, dimethachlor, dimethenamid, dimethenamid-P, metazachlor, metolachlor, metolachlor-S, pethoxamid, pretilachlor, propachlor, propisochlor and thenylchlor, oxyacetanilides such as flufenacet and mefenacet, acetanilides such as diphenamid, naproanilide, napropamide and napropamide-M, tetrazolinones such fentrazamide, and other herbicides such as anilofos, cafenstrole, fenoxasulfone, ipfencarbazone, piperophos, pyroxasulfone and isoxazoline compounds of the formulae II.1, II.2, II.3, II.4, II.5, II.6, II.7, II.8 and II.9 the isoxazoline compounds of the formula (II) are known in the art, e.g. from WO 2006/024820, WO 2006/037945, WO 2007/071900 and WO 2007/096576;

among the VLCFA inhibitors, preference is given to chloroacetamides and oxyacetamides;

b11) from the group of the cellulose biosynthesis inhibitors: chlorthiamid, dichlobenil, flupoxam, indaziflam, isoxaben, triaziflam and 1-cyclohexyl-5-pentafluorphenyloxy-1⁴-[1,2,4,6]thiatriazin-3-ylamine (CAS 175899-01-1);

b12) from the group of the decoupler herbicides: dinoseb, dinoterb and DNOC and its salts;

b13) from the group of the auxinic herbicides:

2,4-D and its salts and esters such as clacyfos, 2,4-DB and its salts and esters, aminocyclopyrachlor and its salts and esters, aminopyralid and its salts such as aminopyralid-dimethylammonium, aminopyralid-tris(2-hydroxypropyl) ammonium and its esters, benazolin, benazolin-ethyl, chloramben and its salts and esters, clomeprop, clopyralid and its salts and esters, dicamba and its salts and esters, dichlorprop and its salts and esters, dichlorprop-P and its salts and esters, flopyrauxifen, fluroxypyr, fluroxypyr-butometyl, fluroxypyr-meptyl, halauxifen and its salts and esters (CAS 943832-60-8); MCPA and its salts and esters, MCPA-thioethyl, MCPB and its salts and esters, mecoprop and its salts and esters, mecoprop-P and its salts and esters, picloram and its salts and esters, quinclorac, quinmerac, TBA (2,3,6) and its salts and esters, triclopyr and its salts and esters, florpyrauxifen, florpyrauxifen-benzyl (CAS 1390661-72-9) and 4-amino-3-chloro-5-fluoro-6-(7-fluoro-1H-indol-6-yl)picolinic acid (CAS 1629965-65-6);

b14) from the group of the auxin transport inhibitors: diflufenzopyr, diflufenzopyr-sodium, naptalam and naptalam-sodium;

b15) from the group of the other herbicides: bromobutide, chlorflurenol, chlorflurenol-methyl, cinmethylin, cumyluron, cyclopyrimorate (CAS 499223-49-3 and its salts and esters, dalapon, dazomet, difenzoquat, difenzoquat-metilsulfate, dimethipin, DSMA, dymron, endothal and its salts, etobenzanid, flurenol, flurenol-butyl, flurprimidol, fosamine, fosamine-ammonium, indanofan, maleic hydrazide, mefluidide, metam, methiozolin (CAS 403640-27-7), methyl azide, methyl bromide, methyl-dymron, methyl iodide, MSMA, oleic acid, oxaziclomefone, pelargonic acid, pyributicarb, quinoclamine and tridiphane.

Preferred herbicides B that can be used in combination with the pyrimidine compounds of the formula (I) according to the present invention are:

b1) from the group of the lipid biosynthesis inhibitors:

clethodim, clodinafop-propargyl, cycloxydim, cyhalofop-butyl, diclofop-methyl, fenoxaprop-P-ethyl, fluazifop-P-butyl, haloxyfop-P-methyl, metamifop, pinoxaden, profoxydim, propaquizafop, quizalofop-P-ethyl, quizalofop-P-tefuryl, sethoxydim, tepraloxydim, tralkoxydim, 4-(4'-Chloro-4-cyclopropyl-2'-fluoro[1,1'-biphenyl]-3-yl)-5-hydroxy-2,2,6,6-tetramethyl-2H-pyran-3(6H)-one (CAS 1312337-72-6); 4-(2',4'-Dichloro-4-cyclopropyl[1,1'-biphenyl]-3-yl)-5-hydroxy-2,2,6,6-tetramethyl-2H-pyran-3(6H)- one (CAS 1312337-45-3); 4-(4'-Chloro-4-ethyl-2'-fluoro[1,1'-biphenyl]-3-yl)-5-hydroxy-2,2,6,6-tetramethyl-2H-pyran-3(6H)-one (CAS 1033757-93-5); 4-(2',4'-Dichloro-4-ethyl[1,1'-biphenyl]-3-yl)-2,2,6,6-tetramethyl-2H-pyran-3,5(4H,6H)-dione (CAS 1312340-84-3); 5-(Acetyloxy)-4-(4'-chloro-4-cyclopropyl-2'-fluoro[1,1'-biphenyl]-3-yl)-3,6-dihydro-2,2,6,6-tetramethyl-2H-pyran-3-one (CAS 1312337-48-6); 5-(Acetyloxy)-4-(2',4'-dichloro-4-cyclopropyl-[1,1'-biphenyl]-3-yl)-3,6-dihydro-2,2,6,6-tetramethyl-2H-pyran-3-one; 5-(Acetyloxy)-4-(4'-chloro-4-ethyl-2'-fluoro[1,1'-biphenyl]-3-yl)-3,6-dihydro-2,2,6,6-tetramethyl-2H-pyran-3-one (CAS 1312340-82-1); 5-(Acetyloxy)-4-(2',4'-dichloro-4-ethyl[1,1'-biphenyl]-3-yl)-3,6-dihydro-2,2,6,6-tetramethyl-2H-pyran-3-one (CAS 1033760-55-2); 4-(4'-Chloro-4-cyclopropyl-2'-fluoro[1,1'-biphenyl]-3-yl)-5,6-dihydro-2,2,6,6-tetramethyl-5-oxo-2H-pyran-3-yl carbonic acid methyl ester (CAS 1312337-51-1); 4-(2',4'-Dichloro-4-cyclopropyl-[1,1'-biphenyl]-3-yl)-5,6-dihydro-2,2,6,6-tetramethyl-5-oxo-2H-pyran-3-yl carbonic acid methyl ester; 4-(4'-Chloro-4-ethyl-2'-fluoro[1,1'-biphenyl]-3-yl)-5,6-dihydro-2,2,6,6-tetramethyl-5-oxo-2H-pyran-3-yl carbonic acid methyl ester (CAS 1312340-83-2); 4-(2',4'-Dichloro-4-ethyl[1,1'-biphenyl]-3-yl)-5,6-dihydro-2,2,6,6-tetramethyl-5-oxo-2H-pyran-3-yl carbonic acid methyl ester (CAS 1033760-58-5); benfuresate, dimepiperate, EPTC, esprocarb, ethofumesate, molinate, orbencarb, prosulfocarb, thiobencarb and triallate;

b2) from the group of the ALS inhibitors:
amidosulfuron, azimsulfuron, bensulfuron-methyl, bispyribac-sodium, chlorimuron-ethyl, chlorsulfuron, cloransulam-methyl, cyclosulfamuron, diclosulam, ethametsulfuron-methyl, ethoxysulfuron, flazasulfuron, florasulam, flucarbazone-sodium, flucetosulfuron, flumetsulam, flupyrsulfuron-methyl-sodium, foramsulfuron, halosulfuron-methyl, imazamethabenz-methyl, imazamox, imazapic, imazapyr, imazaquin, imazethapyr, imazosulfuron, iodosulfuron, iodosulfuron-methyl-sodium, iofensulfuron, iofensulfuron-sodium, mesosulfuron, metazosulfuron, metosulam, metsulfuron-methyl, nicosulfuron, orthosulfamuron, oxasulfuron, penoxsulam, primisulfuron-methyl, propoxycarbazon-sodium, propyrisulfuron, prosulfuron, pyrazosulfuron-ethyl, pyribenzoxim, pyrimisulfan, pyriftalid, pyriminobac-methyl, pyrithiobac-sodium, pyroxsulam, rimsulfuron, sulfometuron-methyl, sulfosulfuron, thiencarbazone-methyl, thifensulfuron-methyl, triasulfuron, tribenuron-methyl, trifloxysulfuron, triflusulfuron-methyl, tritosulfuron and triafamone;

b3) from the group of the photosynthesis inhibitors:
ametryn, amicarbazone, atrazine, bentazone, bentazone-sodium, bromoxynil and its salts and esters, chloridazone, chlorotoluron, cyanazine, desmedipham, diquat-dibromide, diuron, fluometuron, hexazinone, ioxynil and its salts and esters, isoproturon, lenacil, linuron, metamitron, methabenzthiazuron, metribuzin, paraquat, paraquat-dichloride, phenmedipham, propanil, pyridate, simazine, terbutryn, terbuthylazine, thidiazuron, 1-(6-tert-butylpyrimidin-4-yl)-2-hydroxy-4-methoxy-3-methyl-2H-pyrrol-5-one (CAS 1654744-66-7), 1-(5-tert-butylisoxazol-3-yl)-2-hydroxy-4-methoxy-3-methyl-2H-pyrrol-5-one (CAS 1637455-12-9), 1-(5-tert-butylisoxazol-3-yl)-4-chloro-2-hydroxy-3-methyl-2H-pyrrol-5-one (CAS 1637453-94-1), 1-(5-tert-butyl-1-methyl-pyrazol-3-yl)-4-chloro-2-hydroxy-3-methyl-2H-pyrrol-5-one (CAS 1654057-29-0), 1-(5-tert-butyl-1-methylpyrazol-3-yl)-3-chloro-2-hydroxy-4-methyl-2H-pyrrol-5-one (CAS 1654747-80-4), 4-hydroxy-1-methoxy-5-methyl-3-[4-(trifluoromethyl)-2-pyridyl]imidazolidin-2-one; (CAS 2023785-78-4), 4-hydroxy-1,5-dimethyl-3-[4-(trifluoromethyl)-2-pyridyl]imidazolidin-2-one (CAS 2023785-79-5), 5-ethoxy-4-hydroxy-1-methyl-3-[4-(trifluoromethyl)-2-pyridyl]imidazolidin-2-one (CAS 1701416-69-4), 4-hydroxy-1-methyl-3-[4-(trifluoromethyl)-2-pyridyl]imidazolidin-2-one (CAS 1708087-22-2), 4-hydroxy-1,5-dimethyl-3-[1-methyl-5-(trifluoromethyl)pyrazol-3-yl]imidazolidin-2-one (CAS 2023785-80-8) and 1-(5-tert-butylisoxazol-3-yl)-4-ethoxy-5-hydroxy-3-methyl-imidazolidin-2-one (CAS 1844836-64-1);

b4) from the group of the protoporphyrinogen-IX oxidase inhibitors:
acifluorfen-sodium, bencarbazone, benzfendizone, butafenacil, carfentrazone-ethyl, cinidon-ethyl, flufenpyr-ethyl, flumiclorac-pentyl, flumioxazin, fluoroglycofen-ethyl, fomesafen, lactofen, oxadiargyl, oxadiazon, oxyfluorfen, pentoxazone, pyraflufen, pyraflufen-ethyl, saflufenacil, sulfentrazone, tiafenacil, trifludimoxazin, ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate (CAS 353292-31-6; S-3100), N-ethyl-3-(2,6-dichloro-4-trifluoromethylphenoxy)-5-methyl-1H-pyrazole-1-carboxamide (CAS 452098-92-9), N-tetrahydrofurfuryl-3-(2,6-dichloro-4-trifluoromethylphenoxy)-5-methyl-1H-pyrazole-1-carboxamide (CAS 915396-43-9), N-ethyl-3-(2-chloro-6-fluoro-4-trifluoromethylphenoxy)-5-methyl-1H-pyrazole-1-carboxamide (CAS 452099-05-7), N-tetrahydrofurfuryl-3-(2-chloro-6-fluoro-4-trifluoromethylphenoxy)-5-methyl-1H-pyrazole-1-carboxamide (CAS 452100-03-7), 3-[7-fluoro-3-oxo-4-(prop-2-ynyl)-3,4-dihydro-2H-benzo[1,4]oxazin-6-yl]-1,5-dimethyl-6-thioxo-[1,3,5]triazinan-2,4-dione (CAS 451484-50-7), 2-(2,2,7-trifluoro-3-oxo-4-prop-2-ynyl-3,4-dihydro-2H-benzo[1,4]oxazin-6-yl)-4,5,6,7-tetrahydro-isoindole-1,3-dione (CAS 1300118-96-0); 1-methyl-6-trifluoromethyl-3-(2,2,7-trifluoro-3-oxo-4-prop-2-ynyl-3,4-dihydro-2H-benzo[1,4]oxazin-6-yl)-1H-pyrimidine-2,4-dione (CAS 1304113-05-0), and 3-[7-chloro-5-fluoro-2-(trifluoromethyl)-1H-benzimidazol-4-yl]-1-methyl-6-(trifluoromethyl)-1H-pyrimidine-2,4-dione (CAS 212754-$C_2$-4);

b5) from the group of the bleacher herbicides:
aclonifen, amitrole, beflubutamid, benzobicyclon, bicyclopyrone, clomazone, diflufenican, fenquinotrione, flumeturon, flurochloridone, flurtamone, isoxaflutole, mesotrione, oxotrione (CAS 1486617-21-3), norflurazon, picolinafen, pyrasulfotole, pyrazolynate, sulcotrione, tefuryltrione, tembotrione, tolpyralate, topramezone, 4-(3-trifluoromethylphenoxy)-2-(4-trifluoromethylphenyl)pyrimidine (CAS 180608-33-7), 2-chloro-3-methylsulfanyl-N-(1-methyltetrazol-5-yl)-4-(trifluoromethyl)benzamide (CAS 1361139-71-0,2-(2,4-dichlorophenyl)methyl-4,4-dimethyl-3-isoxazolidone (CAS 81777-95-9) and 2-(2,5-dichlorophenyl)methyl-4,4-dimethyl-3-isoxazolidinone (CAS 81778-66-7);

b6) from the group of the EPSP synthase inhibitors:
glyphosate, glyphosate-isopropylammonium, glyphosate-potassium and glyphosate-trimesium (sulfosate);

b7) from the group of the glutamine synthase inhibitors:
glufosinate, glufosinate-P, glufosinate-ammonium;

b8) from the group of the DHP synthase inhibitors:
asulam;

b9) from the group of the mitosis inhibitors:
benfluralin, dithiopyr, ethalfluralin, flamprop, flamprop-isopropyl, flamprop-methyl, flamprop-M-isopropyl, flamprop-M-methyl, oryzalin, pendimethalin, thiazopyr and trifluralin;

b10) from the group of the VLCFA inhibitors: acetochlor, alachlor, amidochlor, anilofos, butachlor, cafenstrole, dimethenamid, dimethenamid-P, fentrazamide, flufenacet, mefenacet, metazachlor, metolachlor, S-metolachlor, naproanilide, napropamide, napropamide-M, pretilachlor, fenoxasulfone, ipfencarbazone, pyroxasulfone thenylchlor and isoxazoline-compounds of the formulae II.1, II.2, II.3, II.4, II.5, II.6, II.7, II.8 and II.9 as mentioned above;

b11) from the group of the cellulose biosynthesis inhibitors: dichlobenil, flupoxam, indaziflam, isoxaben, triaziflam and 1-cyclohexyl-5-pentafluorphenyloxy-1$^4$-[1,2,4,6]thiatriazin-3-ylamine (CAS 175899-01-1);

b13) from the group of the auxinic herbicides:
2,4-D and its salts and esters, aminocyclopyrachlor and its salts and esters, aminopyralid and its salts such as aminopyralid-dimethylammonium, aminopyralid-tris(2-hydroxypropyl)ammonium and its esters, clopyralid and its salts and esters, dicamba and its salts and esters, dichlorprop-P and its salts and esters, flopyrauxifen, fluroxypyr-meptyl, halauxifen and its salts and esters (CAS 943832-60-8), MCPA and its salts and esters, MCPB and its salts and esters, mecoprop-P and its salts and esters, picloram and its salts and esters, quinclorac, quinmerac, triclopyr and its salts and esters, florpyrauxifen, florpyrauxifen-benzyl (CAS 1390661-72-9) and 4-amino-3-chloro-5-fluoro-6-(7-fluoro-1H-indol-6-yl)picolinic acid (CAS 1629965-65-6);

b14) from the group of the auxin transport inhibitors: diflufenzopyr and diflufenzopyr-sodium;

b15) from the group of the other herbicides: bromobutide, cinmethylin, cumyluron, cyclopyrimorate (CAS 499223-49-3) and its salts and esters, dalapon, difenzoquat, difenzoquat-metilsulfate, DSMA, dymron (=daimuron), indanofan, metam, methylbromide, MSMA, oxaziclomefone, pyributicarb and tridiphane.

Particularly preferred herbicides B that can be used in combination with the pyrimidine compounds of the formula (I) according to the present invention are:

b1) from the group of the lipid biosynthesis inhibitors: clodinafop-propargyl, cycloxydim, cyhalofop-butyl, fenoxaprop-P-ethyl, pinoxaden, profoxydim, tepraloxydim, tralkoxydim, 4-(4'-Chloro-4-cyclopropyl-2'-fluoro[1,1'-biphenyl]-3-yl)-5-hydroxy-2,2,6,6-tetramethyl-2H-pyran-3 (6H)-one (CAS 1312337-72-6); 4-(2',4'-Dichloro-4-cyclopropyl[1,1'-biphenyl]-3-yl)-5-hydroxy-2,2,6,6-tetramethyl-2H-pyran-3(6H)-one (CAS 1312337-45-3); 4-(4'-Chloro-4-ethyl-2'-fluoro[1,1'-biphenyl]-3-yl)-5-hydroxy-2,2,6,6-tetramethyl-2H-pyran-3(6H)-one (CAS 1033757-93-5); 4-(2',4'-Dichloro-4-ethyl[1,1'-biphenyl]-3-yl)-2,2,6,6-tetramethyl-2H-pyran-3,5(4H,6H)-dione (CAS 1312340-84-3); 5-(Acetyloxy)-4-(4'-chloro-4-cyclopropyl-2'-fluoro[1,1'-biphenyl]-3-yl)-3,6-dihydro-2,2,6,6-tetramethyl-2H-pyran-3-one (CAS 1312337-48-6); 5-(Acetyloxy)-4-(2',4'-dichloro-4-cyclopropyl-[1,1'-biphenyl]-3-yl)-3,6-dihydro-2, 2,6,6-tetramethyl-2H-pyran-3-one; 5-(Acetyloxy)-4-(4'-chloro-4-ethyl-2'-fluoro[1,1'-biphenyl]-3-yl)-3,6-dihydro-2, 2,6,6-tetramethyl-2H-pyran-3-one (CAS 1312340-82-1); 5-(Acetyloxy)-4-(2',4'-dichloro-4-ethyl[1,1'-biphenyl]-3-yl)-3,6-dihydro-2,2,6,6-tetramethyl-2H-pyran-3-one (CAS 1033760-55-2); 4-(4'-Chloro-4-cyclopropyl-2'-fluoro[1,1'-biphenyl]-3-yl)-5,6-dihydro-2,2,6,6-tetramethyl-5-oxo-2H-pyran-3-yl carbonic acid methyl ester (CAS 1312337-51-1); 4-(2',4'-Dichloro-4-cyclopropyl-[1,1'-biphenyl]-3-yl)-5,6-dihydro-2,2,6,6-tetramethyl-5-oxo-2H-pyran-3-yl carbonic acid methyl ester; 4-(4'-Chloro-4-ethyl-2'-fluoro[1,1'-biphenyl]-3-yl)-5,6-dihydro-2,2,6,6-tetramethyl-5-oxo-2H-pyran-3-yl carbonic acid methyl ester (CAS 1312340-83-2); 4-(2',4'-Dichloro-4-ethyl[1,1'-biphenyl]-3-yl)-5,6-dihydro-2,2,6,6-tetramethyl-5-oxo-2H-pyran-3-yl carbonic acid methyl ester (CAS 1033760-58-5); esprocarb, prosulfocarb, thiobencarb and triallate;

b2) from the group of the ALS inhibitors: bensulfuron-methyl, bispyribac-sodium, cyclosulfamuron, diclosulam, flumetsulam, flupyrsulfuron-methyl-sodium, foramsulfuron, imazamox, imazapic, imazapyr, imazaquin, imazethapyr, imazosulfuron, iodosulfuron, iodosulfuron-methyl-sodium, iofensulfuron, iofensulfuron-sodium, mesosulfuron, metazosulfuron, nicosulfuron, penoxsulam, propoxycarbazon-sodium, propyrisulfuron, pyrazosulfuron-ethyl, pyroxsulam, rimsulfuron, sulfosulfuron, thiencarbazon-methyl, tritosulfuron and triafamone;

b3) from the group of the photosynthesis inhibitors: ametryn, atrazine, diuron, fluometuron, hexazinone, isoproturon, linuron, metribuzin, paraquat, paraquat-dichloride, propanil, terbutryn, terbuthylazine, 1-(5-tert-butylisoxazol-3-yl)-2-hydroxy-4-methoxy-3-methyl-2H-pyrrol-5-one (CAS 1637455-12-9), 1-(5-tert-butylisoxazol-3-yl)-4-chloro-2-hydroxy-3-methyl-2H-pyrrol-5-one (CAS 1637453-94-1), 1-(5-tert-butylisoxazol-3-yl)-4-ethoxy-5-hydroxy-3-methyl-imidazolidin-2-one (CAS 1844836-64-1);

b4) from the group of the protoporphyrinogen-IX oxidase inhibitors: flumioxazin, oxyfluorfen, pyraflufen, pyraflufen-ethyl, saflufenacil, sulfentrazone, trifludimoxazin, ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate (CAS 353292-31-6; S-3100, 3-[7-fluoro-3-oxo-4-(prop-2-ynyl)-3,4-dihydro-2H-benzo[1,4]oxazin-6-yl]-1,5-dimethyl-6-thioxo-[1,3,5]triazinan-2,4-dione (CAS 451484-50-7), 2-(2,2,7-trifluoro-3-oxo-4-prop-2-ynyl-3,4-dihydro-2H-benzo[1,4]oxazin-6-yl)-4,5,6,7-tetrahydro-isoindole-1,3-dione (CAS 1300118-96-0), and 1-methyl-6-trifluoromethyl-3-(2,2,7-trifluoro-3-oxo-4-prop-2-ynyl-3,4-dihydro-2H-benzo[1,4]oxazin-6-yl)-1H-pyrimidine-2,4-dione (CAS 1304113-05-0);

b5) from the group of the bleacher herbicides: amitrole, bicyclopyrone, clomazone, diflufenican, fenquinotrione, flumeturon, flurochloridone, isoxaflutole, mesotrione, oxotrione (CAS 1486617-21-3), picolinafen, sulcotrione, tefuryltrione, tembotrione, tolpyralate, topramezone, 2-chloro-3-methylsulfanyl-N-(1-methyltetrazol-5-yl)-4-(trifluoromethyl)benzamide (CAS 1361139-71-0), 2-(2,4-dichlorophenyl)methyl-4,4-dimethyl-3-isoxazolidone (CAS 81777-95-9); and 2-(2,5-dichlorophenyl)methyl-4,4-dimethyl-3-isoxazolidinone (CAS 81778-66-7);

b6) from the group of the EPSP synthase inhibitors: glyphosate, glyphosate-isopropylammonium and glyphosate-trimesium (sulfosate);

b7) from the group of the glutamine synthase inhibitors: glufosinate, glufosinate-P and glufosinate-ammonium;

b9) from the group of the mitosis inhibitors: pendimethalin and trifluralin;

b10) from the group of the VLCFA inhibitors: acetochlor, cafenstrole, dimethenamid-P, fentrazamide, flufenacet, mefenacet, metazachlor, metolachlor, S-metolachlor, fenoxasulfone, ipfencarbazone and pyroxasulfone; likewise, preference is given to isoxazoline compounds of the formulae II.1, II.2, II.3, II.4, II.5, II.6, II.7, II.8 and II.9 as mentioned above;

b11) from the group of the cellulose biosynthesis inhibitors: indaziflam, isoxaben and triaziflam;

b13) from the group of the auxinic herbicides: 2,4-D and its salts and esters such as clacyfos, and aminocyclopyrachlor and its salts and esters, aminopyralid and its salts and its esters, clopyralid and its salts and esters, dicamba and its salts and esters, flopyrauxifen, fluroxypyr-meptyl, halauxifen, halauxifen-methyl, quinclorac, quinmerac, florpyrauxifen, florpyrauxifen-benzyl (CAS 1390661-72-9) and 4-amino-3-chloro-5-fluoro-6-(7-fluoro-1H-indol-6-yl) picolinic acid (CAS 1629965-65-6);

b14) from the group of the auxin transport inhibitors: diflufenzopyr and diflufenzopyr-sodium, b15) from the group of the other herbicides: cinmethylin, dymon (=daimuron), indanofan, oxaziclomefone.

Particularly preferred herbicides B are the herbicides B as defined above; in particular, the herbicides B.1-B.202 listed below in table B:

TABLE B

| | Herbicide B |
|---|---|
| B.1 | clethodim |
| B.2 | clodinafop-propargyl |
| B.3 | cycloxydim |
| B.4 | cyhalofop-butyl |
| B.5 | fenoxaprop-ethyl |
| B.6 | fenoxaprop-P-ethyl |
| B.7 | metamifop |
| B.8 | pinoxaden |
| B.9 | profoxydim |
| B.10 | sethoxydim |
| B.11 | tepraloxydim |
| B.12 | tralkoxydim |
| B.13 | esprocarb |
| B.14 | ethofumesate |
| B.15 | molinate |
| B.16 | prosulfocarb |
| B.17 | thiobencarb |
| B.18 | triallate |
| B.19 | bensulfuron-methyl |
| B.20 | bispyribac-sodium |
| B.21 | cloransulam-methyl |
| B.22 | chlorsulfuron |
| B.23 | clorimuron |
| B.24 | cyclosulfamuron |
| B.25 | diclosulam |
| B.26 | florasulam |
| B.27 | flumetsulam |
| B.28 | flupyrsulfuron-methyl-sodium |
| B.29 | foramsulfuron |
| B.30 | imazamox |
| B.31 | imazamox-ammonium |
| B.32 | imazapic |
| B.33 | imazapic-ammonium |
| B.34 | imazapic-isopropylammonium |
| B.35 | imazapyr |
| B.36 | imazapyr-ammonium |
| B.37 | imazapyr-isopropylammonium |
| B.38 | imazaquin |
| B.39 | imazaquin-ammonium |
| B.40 | imazethapyr |
| B.41 | imazethapyr-ammonium |
| B.42 | imazethapyr-isopropylammonium |
| B.43 | imazosulfuron |
| B.44 | iodosulfuron-methyl-sodium |
| B.45 | iofensulfuron |
| B.46 | iofensulfuron-sodium |
| B.47 | mesosulfuron-methyl |
| B.48 | metazosulfuron |
| B.49 | metsulfuron-methyl |
| B.50 | metosulam |
| B.51 | nicosulfuron |
| B.52 | penoxsulam |
| B.53 | propoxycarbazon-sodium |
| B.54 | pyrazosulfuron-ethyl |
| B.55 | pyribenzoxim |
| B.56 | pyriftalid |
| B.57 | pyroxsulam |
| B.58 | propyrisulfuron |
| B.59 | rimsulfuron |
| B.60 | sulfosulfuron |
| B.61 | thiencarbazone-methyl |
| B.62 | thifensulfuron-methyl |
| B.63 | tribenuron-methyl |
| B.64 | tritosulfuron |
| B.65 | triafamone |
| B.66 | ametryne |
| B.67 | atrazine |
| B.68 | bentazon |
| B.69 | bromoxynil |
| B.70 | bromoxynil-octanoate |
| B.71 | bromoxynil-heptanoate |
| B.72 | bromoxynil-potassium |
| B.73 | diuron |
| B.74 | fluometuron |
| B.75 | hexazinone |
| B.76 | isoproturon |
| B.77 | linuron |
| B.78 | metamitron |
| B.79 | metribuzin |
| B.80 | propanil |
| B.81 | simazin |
| B.82 | terbuthylazine |
| B.83 | terbutryn |
| B.84 | paraquat-dichloride |
| B.85 | acifluorfen |
| B.86 | butafenacil |
| B.87 | carfentrazone-ethyl |
| B.88 | flumioxazin |
| B.89 | fomesafen |
| B.90 | oxadiargyl |
| B.91 | oxyfluorfen |
| B.92 | pyraflufen |
| B.93 | pyraflufen-ethyl |
| B.94 | saflufenacil |
| B.95 | sulfentrazone |
| B.96 | trifludimoxazin |
| B.97 | ethyl [3-[2-chloro-4-fluoro-5-(1-methyl-6-trifluoromethyl-2,4-dioxo-1,2,3,4-tetrahydropyrimidin-3-yl)phenoxy]-2-pyridyl-oxy]acetate |
| B.98 | benzobicyclon |
| B.99 | bicyclopyrone |
| B.100 | clomazone |
| B.101 | diflufenican |
| B.102 | flurochloridone |
| B.103 | isoxaflutole |
| B.104 | mesotrione |
| B.105 | norflurazone |
| B.106 | picolinafen |
| B.107 | sulcotrione |
| B.108 | tefuryltrione |
| B.109 | tembotrione |
| B.110 | tolpyralate |
| B.111 | topramezone |
| B.112 | topramezone-sodium |
| B.113 | amitrole |
| B.114 | fluometuron |
| B.115 | fenquinotrione |
| B.116 | glyphosate |
| B.117 | glyphosate-ammonium |
| B.118 | glyphosate-dimethylammonium |
| B.119 | glyphosate-isopropylammonium |
| B.120 | glyphosate-trimesium (sulfosate) |
| B.121 | glyphosate-potassium |
| B.122 | glufosinate |
| B.123 | glufosinate-ammonium |
| B.124 | glufosinate-P |
| B.125 | glufosinate-P-ammonium |
| B.126 | pendimethalin |
| B.127 | trifluralin |
| B.128 | acetochlor |
| B.129 | butachlor |
| B.130 | cafenstrole |
| B.131 | dimethenamid-P |
| B.132 | fentrazamide |
| B.133 | flufenacet |
| B.134 | mefenacet |
| B.135 | metazachlor |
| B.136 | metolachlor |

TABLE B-continued

| | Herbicide B |
|---|---|
| B.137 | S-metolachlor |
| B.138 | pretilachlor |
| B.139 | fenoxasulfone |
| B.140 | indaziflam |
| B.141 | isoxaben |
| B.142 | triaziflam |
| B.143 | ipfencarbazone |
| B.144 | pyroxasulfone |
| B.145 | 2,4-D |
| B.146 | 2,4-D-isobutyl |
| B.147 | 2,4-D-dimethylammonium |
| B.148 | 2,4-D-N,N,N-trimethylethanolammonium |
| B.149 | aminopyralid |
| B.150 | aminopyralid-methyl |
| B.151 | aminopyralid-dimethylammonium |
| B.152 | aminopyralid-tris(2-hydroxypropyl)ammonium |
| B.153 | clopyralid |
| B.154 | clopyralid-methyl |
| B.155 | clopyralid-olamine |
| B.156 | dicamba |
| B.157 | dicamba-butotyl |
| B.158 | dicamba-diglycolamine |
| B.159 | dicamba-dimethylammonium |
| B.160 | dicamba-diolamine |
| B.161 | dicamba-isopropylammonium |
| B.162 | dicamba-potassium |
| B.163 | dicamba-sodium |
| B.164 | dicamba-trolamine |
| B.165 | dicamba-N,N-bis-(3-aminopropyl)methylamine |
| B.166 | dicamba-diethylenetriamine |
| B.167 | fluroxypyr |
| B.168 | fluroxypyr-meptyl |
| B.169 | halauxifen |
| B.170 | halauxifen-methyl |
| B.171 | MCPA |
| B.172 | MCPA-2-ethylhexyl |
| B.173 | MCPA-dimethylammonium |
| B.174 | quinclorac |
| B.175 | quinclorac-dimethylammonium |
| B.176 | quinmerac |
| B.177 | quinmerac-dimethylammonium |
| B.178 | florpyrauxifen |
| B.179 | florpyrauxifen-benzyl |
| B.180 | aminocyclopyrachlor |
| B.181 | aminocyclopyrachlor-potassium |
| B.182 | aminocyclopyrachlor-methyl |
| B.183 | diflufenzopyr |
| B.184 | diflufenzopyr-sodium |
| B.185 | dymron |
| B.186 | indanofan |
| B.187 | oxaziclomefone |
| B.188 | II.1 |
| B.189 | II.2 |
| B.190 | II.3 |
| B.191 | II.4 |
| B.192 | II.5 |
| B.193 | II.6 |
| B.194 | II.7 |
| B.195 | II.8 |
| B.196 | II.9 |
| B.197 | 4-amino-3-chloro-5-fluoro-6-(7-fluoro-1H-indol-6-yl)picolinic acid |
| B.198 | flopyrauxifen |
| B.199 | oxotrione |
| B.200 | cinmethylin |
| B.201 | 2-chloro-3-methylsulfanyl-N-(1-methyltetrazol-5-yl)-4-(trifluoromethyl)benzamide |
| B.202 | 2-(2,4-dichlorophenyl)methyl-4,4-dimethyl-3-isoxazolidone |

In another embodiment of the present invention the compositions according to the present invention comprise at least one pyrimidine compound of formula (I) and at least one safener C.

Safeners are chemical compounds which prevent or reduce damage on useful plants without having a major impact on the herbicidal action of the herbicidal active components of the present compositions towards unwanted plants. They can be applied either before sowings (e.g. on seed treatments, shoots or seedlings) or in the pre-emergence application or post-emergence application of the useful plant. The safeners and the pyrimidine compounds of formula (I) and/or the herbicides B can be applied simultaneously or in succession.

Suitable safeners are e.g. (quinolin-8-oxy)acetic acids, 1-phenyl-5-haloalkyl-1H-1,2,4-triazol-3-carboxylic acids, 1-phenyl-4,5-dihydro-5-alkyl-1H-pyrazol-3,5-dicarboxylic acids, 4,5-dihydro-5,5-diaryl-3-isoxazol carboxylic acids, dichloroacetamides, alpha-oximinophenylacetonitriles, acetophenonoximes, 4,6-dihalo-2-phenylpyrimidines, N-[[4-(aminocarbonyl)phenyl]sulfonyl]-2-benzoic amides, 1,8-naphthalic anhydride, 2-halo-4-(haloalkyl)-5-thiazol carboxylic acids, phosphorthiolates and N-alkyl-O-phenyl-carbamates and their agriculturally acceptable salts and their agriculturally acceptable derivatives such amides, esters, and thioesters, provided they have an acid group.

Examples of preferred safeners C are benoxacor, cloquintocet, cyometrinil, cyprosulfamide, dichlormid, dicyclonon, dietholate, fenchlorazole, fenclorim, flurazole, fluxofenim, furilazole, isoxadifen, mefenpyr, mephenate, naphthalic anhydride, oxabetrinil, 4-(dichloroacetyl)-1-oxa-4-azaspiro[4.5]decane (MON4660, CAS 71526-07-3), 2,2,5-trimethyl-3-(dichloroacetyl)-1,3-oxazolidine (R-29148, CAS 52836-31-4), metcamifen and BPCMS (CAS 54091-06-4).

Especially preferred safeners C are benoxacor, cloquintocet, cyprosulfamide, dichlormid, fenchlorazole, fenclorim, flurazole, fluxofenim, furilazole, isoxadifen, mefenpyr, naphthalic anhydride, oxabetrinil, 4-(dichloroacetyl)-1-oxa-4-azaspiro[4.5]decane (MON4660, CAS 71526-07-3), 2,2,5-trimethyl-3-(dichloroacetyl)-1,3-oxazolidine (R-29148, CAS 52836-31-4) and metcamifen.

Particularly preferred safeners C are benoxacor, cloquintocet, cyprosulfamide, dichlormid, fenchlorazole, fenclorim, furilazole, isoxadifen, mefenpyr, naphtalic anhydride, 4-(dichloroacetyl)-1-oxa-4-azaspiro[4.5]decane (MON4660, CAS 71526-07-3), 2,2,5-trimethyl-3-(dichloroacetyl)-1,3-oxazolidine (R-29148, CAS 52836-31-4) and metcamifen.

Particularly preferred safeners C, which, as component C, are constituent of the composition according to the invention are the safeners C as defined above; in particular the safeners C.1-C.17 listed below in table C:

TABLE C

| | Safener C |
|---|---|
| C.1 | benoxacor |
| C.2 | cloquintocet |
| C.3 | cloquintocet-mexyl |
| C.4 | cyprosulfamide |
| C.5 | dichlormid |
| C.6 | fenchlorazole |
| C.7 | fenchlorazole-ethyl |
| C.8 | fenclorim |
| C.9 | furilazole |
| C.10 | isoxadifen |
| C.11 | isoxadifen-ethyl |
| C.12 | mefenpyr |
| C.13 | mefenpyr-diethyl |

TABLE C-continued

| | Safener C |
|---|---|
| C.14 | naphtalic acid anhydride |
| C.15 | 4-(dichloroacetyl)-1-oxa-4-azaspiro[4.5]decane (MON4660, CAS 71526-07-3) |
| C.16 | 2,2,5-trimethyl-3-(dichloroacetyl)-1,3-oxazolidine (R-29148, CAS 52836-31-4) |
| C.17 | metcamifen |

The active compounds of groups b1) to b15) and the active compounds Care known herbicides and safeners, see, e.g., The Compendium of Pesticide Common Names (http://www.alanwood.net/pesticides/); Farm Chemicals Handbook 2000 volume 86, Meister Publishing Company, 2000; B. Hock, C. Fedtke, R. R. Schmidt, Herbizide [Herbicides], Georg Thieme Verlag, Stuttgart 1995; W. H. Ahrens, Herbicide Handbook, 7th edition, Weed Science Society of America, 1994; and K. K. Hatzios, Herbicide Handbook, Supplement for the 7th edition, Weed Science Society of America, 1998. 2,2,5-Trimethyl-3-(dichloroacetyl)-1,3-oxazolidine [CAS No. 52836-31-4] is also referred to as R-29148. 4-(Dichloroacetyl)-1-oxa-4-azaspiro[4.5]decane [CAS No. 71526-07-3] is also referred to as AD-67 and MON 4660.

The assignment of the active compounds to the respective mechanisms of action is based on current knowledge. If several mechanisms of action apply to one active compound, this substance was only assigned to one mechanism of action.

Active compounds B and C having a carboxyl group can be employed in the form of the acid, in the form of an agriculturally suitable salt as mentioned above or else in the form of an agriculturally acceptable derivative in the compositions according to the invention.

In the case of dicamba, suitable salts include those, where the counterion is an agriculturally acceptable cation. E.g., suitable salts of dicamba are dicamba-sodium, dicamba-potassium, dicamba-methylammonium, dicamba-dimethylammonium, dicamba-isopropylammonium, dicamba-diglycolamine, dicamba-olamine, dicamba-diolamine, dicamba-trolamine, dicamba-N,N-bis-(3-aminopropyl)methylamine and dicamba-diethylenetriamine. Examples of a suitable ester are dicamba-methyl and dicamba-butotyl.

Suitable salts of 2,4-D are 2,4-D-ammonium, 2,4-D-dimethylammonium, 2,4-D-diethylammonium, 2,4-D-diethanolammonium (2,4-D-diolamine), 2,4-D-triethanolammonium, 2,4-D-isopropylammonium, 2,4-D-triisopropanolammonium, 2,4-D-heptylammonium, 2,4-D-dodecylammonium, 2,4-D-tetradecylammonium, 2,4-D-triethylammonium, 2,4-D-tris(2-hydroxypropyl)ammonium, 2,4-D-tris(isopropyl)ammonium, 2,4-D-trolamine, 2,4-D-lithium, 2,4-D-sodium. Examples of suitable esters of 2,4-D are 2,4-D-butotyl, 2,4-D-2-butoxypropyl, 2,4-D-3-butoxypropyl, 2,4-D-butyl, 2,4-D-ethyl, 2,4-D-ethylhexyl, 2,4-D-isobutyl, 2,4-D-isooctyl, 2,4-Disopropyl, 2,4-D-meptyl, 2,4-D-methyl, 2,4-D-octyl, 2,4-D-pentyl, 2,4-D-propyl, 2,4-D-tefuryl and clacyfos.

Suitable salts of 2,4-DB are e.g. 2,4-DB-sodium, 2,4-DB-potassium and 2,4-DB-dimethylammonium. Suitable esters of 2,4-DB are e.g. 2,4-DB-butyl and 2,4-DB-isoctyl.

Suitable salts of dichlorprop are e.g. dichlorprop-sodium, dichlorprop-potassium and dichlorprop-dimethylammonium. Examples of suitable esters of dichlorprop are dichlorprop-butotyl and dichlorprop-isoctyl.

Suitable salts and esters of MCPA include MCPA-butotyl, MCPA-butyl, MCPA-dimethylammonium, MCPA-diolamine, MCPA-ethyl, MCPA-thioethyl, MCPA-2-ethylhexyl, MCPA-isobutyl, MCPA-isoctyl, MCPA-isopropyl, MCPA-isopropylammonium, MCPA-methyl, MCPA-olamine, MCPA-potassium, MCPA-sodium and MCPA-trolamine.

A suitable salt of MCPB is MCPB sodium. A suitable ester of MCPB is MCPB-ethyl.

Suitable salts of clopyralid are clopyralid-potassium, clopyralid-olamine and clopyralid-tris-(2-hydroxypropyl) ammonium. Example of suitable esters of clopyralid is clopyralid-methyl.

Examples of a suitable ester of fluroxypyr are fluroxypyr-meptyl and fluroxypyr-2-butoxy-1-methylethyl, wherein fluroxypyr-meptyl is preferred.

Suitable salts of picloram are picloram-dimethylammonium, picloram-potassium, picloram-triisopropanolammonium, picloram-triisopropylammonium and picloram-trolamine. A suitable ester of picloram is picloram-isoctyl.

A suitable salt of triclopyr is triclopyr-triethylammonium. Suitable esters of triclopyr are e.g. triclopyr-ethyl and triclopyr-butotyl.

Suitable salts and esters of chloramben include chloramben-ammonium, chlorambendiolamine, chloramben-methyl, chloramben-methylammonium and chloramben-sodium. Suitable salts and esters of 2,3,6-TBA include 2,3,6-TBA-dimethylammonium, 2,3,6-TBA-lithium, 2,3,6-TBA-potassium and 2,3,6-TBA-sodium.

Suitable salts and esters of aminopyralid include aminopyralid-potassium, aminopyralid-dimethylammonium, and aminopyralid-tris(2-hydroxypropyl)ammonium.

Suitable salts of glyphosate are e.g. glyphosate-ammonium, glyphosate-diammonium, glyphoste-dimethylammonium, glyphosate-isopropylammonium, glyphosate-potassium, glyphosate-sodium, glyphosate-trimesium as well as the ethanolamine and diethanolamine salts, preferably glyphosate-diammonium, glyphosate-isopropylammonium and glyphosate-trimesium (sulfosate).

A suitable salt of glufosinate is e.g. glufosinate-ammonium.

A suitable salt of glufosinate-P is e.g. glufosinate-P-ammonium.

Suitable salts and esters of bromoxynil are e.g. bromoxynil-butyrate, bromoxynil-heptanoate, bromoxynil-octanoate, bromoxynil-potassium and bromoxynil-sodium.

Suitable salts and esters of ioxonil are e.g. ioxonil-octanoate, ioxonil-potassium and ioxonil-sodium.

Suitable salts and esters of mecoprop include mecoprop-butotyl, mecoprop-dimethylammonium, mecoprop-diolamine, mecoprop-ethadyl, mecoprop-2-ethylhexyl, mecoprop-isoctyl, mecoprop-methyl, mecoprop-potassium, mecoprop-sodium and mecoprop-trolamine.

Suitable salts of mecoprop-P are e.g. mecoprop-P-butotyl, mecoprop-P-dimethylammonium, mecoprop-P-2-ethylhexyl, mecoprop-P-isobutyl, mecoprop-P-potassium and mecoprop-P-sodium.

A suitable salt of diflufenzopyr is e.g. diflufenzopyr-sodium.

A suitable salt of naptalam is e.g. naptalam-sodium.

Suitable salts and esters of aminocyclopyrachlor are e.g. aminocyclopyrachlor-dimethylammonium, aminocyclopyrachlor-methyl, aminocyclopyrachlor-triisopropanolammonium, aminocyclopyrachlor-sodium and aminocyclopyrachlor-potassium.

A suitable salt of quinclorac is e.g. quinclorac-dimethylammonium.

A suitable salt of quinmerac is e.g. quinmerac-dimethylammonium.

A suitable salt of imazamox is e.g. imazamox-ammonium.

Suitable salts of imazapic are e.g. imazapic-ammonium and imazapic-isopropylammonium.

Suitable salts of imazapyr are e.g. imazapyr-ammonium and imazapyr-isopropylammonium.

A suitable salt of imazaquin is e.g. imazaquin-ammonium.

Suitable salts of imazethapyr are e.g. imazethapyr-ammonium and imazethapyr-isopropylammonium.

A suitable salt of topramezone is e.g. topramezone-sodium.

According to a preferred embodiment of the invention, the composition comprises as herbicidal active compound B or component B at least one, preferably exactly one herbicide B.

According to another preferred embodiment of the invention, the composition comprises as herbicidal active compounds B or component B at least two, preferably exactly two herbicides B different from each other.

According to another preferred embodiment of the invention, the composition comprises as herbicidal active compounds B or component B at least three, preferably exactly three herbicides B different from each other.

According to another preferred embodiment of the invention, the composition comprises as safening component C or component C at least one, preferably exactly one safener C.

According to another preferred embodiment of the invention, the composition comprises as component B at least one, preferably exactly one herbicide B, and as component C at least one, preferably exactly one, safener C.

According to another preferred embodiment of the invention, the composition comprises at least two, preferably exactly two, herbicides B different from each other, and as component C at least one, preferably exactly one, safener C.

According to another preferred embodiment of the invention, the composition comprises at least three, preferably exactly three, herbicides B different from each other, and as component C at least one, preferably exactly one, safener C.

According to another preferred embodiment of the invention, the composition comprises as component A at least one, preferably exactly one compound of formula (I), preferably of formula (I.A), especially preferred the compound (1.1.I-3), (1.1.I-4), (1.1.I-10), (1.2.I-3), (1.2.I-4), or (1.2.I-10), and as component B at least one, preferably exactly one, herbicide B.

According to another preferred embodiment of the invention, the composition comprises as component A at least one, preferably exactly one compound of formula (I), preferably of formula (I.A), especially preferred the compound (1.1.I-3), (1.1.I-4), (1.1.I-10), (1.2.I-3), (1.2.I-4), or (1.2.I-10), and at least two, preferably exactly two, herbicides B different from each other.

According to another preferred embodiment of the invention, the composition comprises as component A at least one, preferably exactly one compound of formula (I), preferably of formula (I.A), especially preferred the compound (1.1.I-3), (1.1.I-4), (1.1.I-10), (1.2.I-3), (1.2.I-4), or (1.2.I-10), and at least three, preferably exactly three, herbicides B different from each other.

According to another preferred embodiment of the invention, the composition comprises as component A at least one, preferably exactly one compound of formula (I), preferably of formula (I.A), especially preferred the compound (1.1.I-3), (1.1.I-4), (1.1.I-10), (1.2.I-3), (1.2.I-4), or (1.2.I-10), and as component C at least one, preferably exactly one, safener C.

According to another preferred embodiment of the invention, the composition comprises as component A at least one, preferably exactly one compound of formula (I), preferably of formula (I.A), especially preferred the compound (1.1.I-3), (1.1.I-4), (1.1.I-10), (1.2.I-3), (1.2.I-4), or (1.2.I-10), as component B at least one, preferably exactly one, herbicide B, and as component C at least one, preferably exactly one safener C.

According to another preferred embodiment of the invention, the composition comprises as component A at least one, preferably exactly one compound of formula (I), preferably of formula (I.A), especially preferred the compound (1.1.I-3), (1.1.I-4), (1.1.I-10), (1.2.I-3), (1.2.I-4), or (1.2.I-10), at least two, preferably exactly two herbicides B different from each other, and as component C at least one, preferably exactly one, safener C.

According to another preferred embodiment of the invention, the composition comprises as component A at least one, preferably exactly one compound of formula (I), preferably of formula (I.A), especially preferred the compound (1.1.I-3), (1.1.I-4), (1.1.I-10), (1.2.I-3), (1.2.I-4), or (1.2.I-10), at least three, preferably exactly three herbicides B different from each other, and as component C at least one, preferably exactly one, safener C.

According to another preferred embodiment of the invention, the composition comprises as component A at least one, preferably exactly one compound of formula (I), preferably of formula (I.C), especially preferred the compound (1.5.I-3), (1.5.I-4), or (1.5.I-10), and as component B at least one, preferably exactly one, herbicide B.

According to another preferred embodiment of the invention, the composition comprises as component A at least one, preferably exactly one compound of formula (I), preferably of formula (I.C), especially preferred the compound (1.5.I-3), (1.5.I-4), or (1.5.I-10), and at least two, preferably exactly two, herbicides B different from each other.

According to another preferred embodiment of the invention, the composition comprises as component A at least one, preferably exactly one compound of formula (I), preferably of formula (I.C), especially preferred the compound (1.5.I-3), (1.5.I-4), or (1.5.I-10), and at least three, preferably exactly three, herbicides B different from each other.

According to another preferred embodiment of the invention, the composition comprises as component A at least one, preferably exactly one compound of formula (I), preferably of formula (I.C), especially preferred the compound (1.5.I-3), (1.5.I-4), or (1.5.I-10), and as component C at least one, preferably exactly one, safener C.

According to another preferred embodiment of the invention, the composition comprises as component A at least one, preferably exactly one compound of formula (I), preferably of formula (I.C), especially preferred the compound (1.5.I-3), (1.5.I-4), or (1.5.I-10), as component B at least one, preferably exactly one, herbicide B, and as component C at least one, preferably exactly one safener C.

According to another preferred embodiment of the invention, the composition comprises as component A at least one, preferably exactly one compound of formula (I), preferably of formula (I.C), especially preferred the compound (1.5.I-3), (1.5.I-4), or (1.5.I-10), at least two, preferably exactly two herbicides B different from each other, and as component C at least one, preferably exactly one, safener C.

According to another preferred embodiment of the invention, the composition comprises as component A at least one, preferably exactly one compound of formula (I), preferably of formula (I.C), especially preferred the compound (1.5.I-3), (1.5.I-4), or (1.5.I-10), at least three, preferably exactly three herbicides B different from each other, and as component C at least one, preferably exactly one, safener C.

According to another preferred embodiment of the invention, the composition comprises as component A at least one, preferably exactly one compound of formula (I), preferably of formula (I.F), especially preferred the compound (1.17.I-3), (1.17.I-4), or (1.17.I-10), and as component B at least one, preferably exactly one, herbicide B.

According to another preferred embodiment of the invention, the composition comprises as component A at least one, preferably exactly one compound of formula (I), preferably of formula (I.F), especially preferred the compound (1.17.I-3), (1.17.I-4), or (1.17.I-10), and at least two, preferably exactly two, herbicides B different from each other.

According to another preferred embodiment of the invention, the composition comprises as component A at least one, preferably exactly one compound of formula (I), preferably of formula (I.F), especially preferred the compound (1.17.I-3), (1.17.I-4), or (1.17.I-10), and at least three, preferably exactly three, herbicides B different from each other.

According to another preferred embodiment of the invention, the composition comprises as component A at least one, preferably exactly one compound of formula (I), preferably of formula (I.F), especially preferred the compound (1.17.I-3), (1.17.I-4), or (1.17.I-10), and as component C at least one, preferably exactly one, safener C.

According to another preferred embodiment of the invention, the composition comprises as component A at least one, preferably exactly one compound of formula (I), preferably of formula (I.F), especially preferred the compound (1.17.I-3), (1.17.I-4), or (1.17.I-10), as component B at least one, preferably exactly one, herbicide B, and as component C at least one, preferably exactly one safener C.

According to another preferred embodiment of the invention, the composition comprises as component A at least one, preferably exactly one compound of formula (I), preferably of formula (I.F), especially preferred the compound (1.17.I-3), (1.17.I-4), or (1.17.I-10), at least two, preferably exactly two herbicides B different from each other, and as component C at least one, preferably exactly one, safener C.

According to another preferred embodiment of the invention, the composition comprises as component A at least one, preferably exactly one compound of formula (I), preferably of formula (I.F), especially preferred the compound (1.17.I-3), (1.17.I-4), or (1.17.I-10), at least three, preferably exactly three herbicides B different from each other, and as component C at least one, preferably exactly one, safener C.

According to another preferred embodiment of the invention, the composition comprises, in addition to a pyrimidine compounds of formula (I), especially an active compound from the group consisting of (1.1.I-3), (1.1.I-4), (1.1.I-10), (1.2.I-3), (1.2.I-4), (1.5.I-3), (1.5.I-4) and (1.17.I-3), at least one and especially exactly one herbicidally active compound from group b1), in particular selected from the group consisting of clethodim, clodinafop-propargyl, cycloxydim, cyhalofop-butyl, fenoxaprop-ethyl, fenoxaprop-P-ethyl, metamifop, pinoxaden, profoxydim, sethoxydim, tepraloxydim, tralkoxydim, esprocarb, ethofumesate, molinate, prosulfocarb, thiobencarb and triallate.

According to another preferred embodiment of the invention, the composition comprises, in addition to a pyrimidine compounds of formula (I), especially an active compound from the group consisting of (1.1.I-3), (1.1.I-4), (1.1.I-10), (1.2.I-3), (1.2.I-4), (1.5.I-3), (1.5.I-4) and (1.17.I-3), at least one and especially exactly one herbicidally active compound from group b2), in particular selected from the group consisting of bensulfuron-methyl, bispyribac-sodium, cloransulam-methyl, chlorsulfuron, clorimuron, cyclosulfamuron, diclosulam, florasulam, flumetsulam, flupyrsulfuron-methyl-sodium, foramsulfuron, imazamox, imazamox-ammonium, imazapic, imazapic-ammonium, imazapic-isopropylammonium, imazapyr, imazapyr-ammonium, imazethapyr-isopropylammonium, imazaquin, imazaquin-ammonium, imazethapyr, imazethapyr-ammonium, imazethapyr-isopropylammonium, imazosulfuron, iodosulfuron-methyl-sodium, iofensulfuron, iofensulfuron-sodium, mesosulfuron-methyl, metazosulfuron, metsulfuron-methyl, metosulam, nicosulfuron, penoxsulam, propoxycarbazon-sodium, pyrazosulfuron-ethyl, pyribenzoxim, pyriftalid, pyroxsulam, propyrisulfuron, rimsulfuron, sulfosulfuron, thiencarbazon-methyl, thifensulfuron-methyl, tribenuron-methyl, tritosulfuron and triafamone.

According to another preferred embodiment of the invention, the composition comprises, in addition to a pyrimidine compounds of formula (I), especially an active compound from the group consisting (1.1.I-3), (1.1.I-4), (1.1.I-10), (1.2.I-3), (1.2.I-4), (1.5.I-3), (1.5.I-4) and (1.17.I-3), at least one and especially exactly one herbicidally active compound from group b3), in particular selected from the group consisting of ametryn, atrazine, bentazon, bromoxynil, bromoxynil-octanoate, bromoxynil-heptanoate, bromoxynil-potassium, diuron, fluometuron, hexazinone, isoproturon, linuron, metamitron, metribuzin, paraquat-dichloride, propanil, simazin, terbutryn and terbuthylazine.

According to another preferred embodiment of the invention, the composition comprises, in addition to a pyrimidine compounds of formula (I), especially an active compound from the group consisting of (1.1.I-3), (1.1.I-4), (1.1.I-10), (1.2.I-3), (1.2.I-4), (1.5.I-3), (1.5.I-4) and (1.17.I-3), at least one and especially exactly one herbicidally active compound from group b4), in particular selected from the group consisting of acifluorfen, butafencil, carfenetrazone-ethyl, flumioxazin, fomesafen, oxadiargyl, oxyfluorfen, pyraflufen, pyraflufen-ethyl, saflufenacil, sulfentrazone, trifludimoxazin, ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate (CAS 353292-31-6; S-3100).

According to another preferred embodiment of the invention, the composition comprises, in addition to a pyrimidine compounds of formula (I), especially an active compound from the group consisting of (1.1.I-3), (1.1.I-4), (1.1.I-10), (1.2.I-3), (1.2.I-4), (1.5.I-3), (1.5.I-4) and (1.17.I-3), at least one and especially exactly one herbicidally active compound from group b5), in particular selected from the group consisting of amitrole, benzobicyclon, bicyclopyrone, clomazone, diflufenican, fenquintrone, fluometuron, flurochloridone, isoxaflutole, mesotrione, norflurazone, oxotrione (CAS 1486617-21-3), picolinafen, sulcotrione, tefuryltrione, tembotrione, tolpyralate, topramezone, topramezone-sodium and 2-chloro-3-methylsulfanyl-N-(1-methyltetrazol-5-yl)-4-(trifluoromethyl)benzamide (CAS 1361139-71-0).

According to another preferred embodiment of the invention, the composition comprises, in addition to a pyrimidine compounds of formula (I), especially an active compound from the group consisting of (1.1.I-3), (1.1.I-4), (1.1.I-10), (1.2.I-3), (1.2.I-4), (1.5.I-3), (1.5.I-4) and (1.17.I-3), at least one and especially exactly one herbicidally active compound from group b6), in particular selected from the group consisting of glyphosate, glyphosate-ammonium, glyphosate-dimethylammonium, glyphosate-isopropylammonium and glyphosate-trimesium (sulfosate) and glyphosate-potassium.

According to another preferred embodiment of the invention, the composition comprises, in addition to a pyrimidine compounds of formula (I), especially an active compound from the group consisting of (1.1.I-3), (1.1.I-4), (1.1.I-10), (1.2.I-3), (1.2.I-4), (1.5.I-3), (1.5.I-4) and (1.17.I-3), at least one and especially exactly one herbicidally active compound from group b7), in particular selected from the group consisting of glufosinate, glufosinate-ammonium, glufosinate-P and glufosinate-P-ammonium.

According to another preferred embodiment of the invention, the composition comprises, in addition to a pyrimidine compounds of formula (I), especially an active compound from the group consisting of (1.1.I-3), (1.1.I-4), (1.1.I-10), (1.2.I-3), (1.2.I-4), (1.5.I-3), (1.5.I-4) and (1.17.I-3), at least one and especially exactly one herbicidally active compound from group b9), in particular selected from the group consisting of pendimethalin and trifluralin.

According to another preferred embodiment of the invention, the composition comprises, in addition to a pyrimidine compounds of formula (I), especially an active compound from the group consisting of (1.1.I-3), (1.1.I-4), (1.1.I-10), (1.2.I-3), (1.2.I-4), (1.5.I-3), (1.5.I-4) and (1.17.I-3), at least one and especially exactly one herbicidally active compound from group b10), in particular selected from the group consisting of acetochlor, butachlor, cafenstrole, dimethenamid-P, fentrazamide, flufenacet, mefenacet, metazachlor, metolachlor, S-metolachlor, fenoxasulfone, ipfencarbazone and pyroxasulfone. Likewise, preference is given to compositions comprising in addition to a pyrimidine compounds of formula (I), especially an active compound from the group consisting of (1.1.I-3), (1.1.I-4), (1.1.I-10), (1.2.I-3), (1.2.I-4), (1.5.I-3), (1.5.I-4) and (1.17.I-3), at least one and especially exactly one herbicidally active compound from group b10), in particular selected from the group consisting of isoxazoline compounds of the formulae 11.1, 11.2, 11.3, 11.4, 11.5, 11.6, 11.7, 11.8 and 11.9, as defined above.

According to another preferred embodiment of the invention, the composition comprises, in addition to a pyrimidine compounds of formula (I), especially an active compound from the group consisting of (1.1.I-3), (1.1.I-4), (1.1.I-10), (1.2.I-3), (1.2.I-4), (1.5.I-3), (1.5.I-4) and (1.17.I-3), at least one and especially exactly one herbicidally active compound from group b11), in particular indaziflam, isoxaben and triaziflam.

According to another preferred embodiment of the invention, the composition comprises, in addition to a pyrimidine compounds of formula (I), especially an active compound from the group consisting of (1.1.I-3), (1.1.I-4), (1.1.I-10), (1.2.I-3), (1.2.I-4), (1.5.I-3), (1.5.I-4) and (1.17.I-3), at least one and especially exactly one herbicidally active compound from group b13), in particular selected from the group consisting of 2,4-D, 2,4-D-isobutyl, 2,4-D-dimethylammonium, 2,4-D-N,N,N-trimethylethanolammonium, aminocyclopyrachlor, aminocyclopyrachlor-potassium, aminocyclopyrachlor-methyl, aminopyralid, aminopyralid-methyl, aminopyralid-dimethylammonium, aminopyralid-tris(2-hydroxypropyl)ammonium, clopyralid, clopyralid-methyl, clopyralid-olamine, dicamba, dicamba-butotyl, dicamba-diglycolamine, dicamba-dimethylammonium, dicamba-diolamine, dicamba-isopropylammonium, dicamba-potassium, dicamba-sodium, dicamba-trolamine, dicamba-N,N-bis-(3-aminopropyl)methylamine, dicamba-diethylenetriamine, flopyrauxifen, fluroxypyr, fluroxypyr-meptyl, halauxifen, halauxifen-methyl, MCPA, MCPA-2-ethylhexyl, MCPA-dimethylammonium, quinclorac, quinclorac-dimethylammonium, quinmerac, quinmerac-dimethylammonium, florpyrauxifen, florpyrauxifen-benzyl (CAS 1390661-72-9), and 4-amino-3-chloro-5-fluoro-6-(7-fluoro-1H-indol-6-yl)picolinic acid (CAS 1629965-65-6).

According to another preferred embodiment of the invention, the composition comprises, in addition to a pyrimidine compounds of formula (I), especially an active compound from the group consisting of (1.1.I-3), (1.1.I-4), (1.1.I-10), (1.2.I-3), (1.2.I-4), (1.5.I-3), (1.5.I-4) and (1.17.I-3), at least one and especially exactly one herbicidally active compound from group b14), in particular selected from the group consisting of diflufenzopyr, diflufenzopyr-sodium, dymron, indanofan and diflufenzopyr-sodium.

According to another preferred embodiment of the invention, the composition comprises, in addition to a pyrimidine compounds of formula (I), especially an active compound from the group consisting of (1.1.I-3), (1.1.I-4), (1.1.I-10), (1.2.I-3), (1.2.I-4), (1.5.I-3), (1.5.I-4) and (1.17.I-3), at least one and especially exactly one herbicidally active compound from group b15), in particular selected from the group consisting of cinmethylin, dymron (=daimuron), indanofan and oxaziclomefone.

According to another preferred embodiment of the invention, the composition comprises, in addition to a pyrimidine compounds of formula (I), especially an active compound from the group consisting of (1.1.I-3), (1.1.I-4), (1.1.I-10), (1.2.I-3), (1.2.I-4), (1.5.I-3), (1.5.I-4) and (1.17.I-3), at least one and especially exactly one safener C, in particular selected from the group consisting of benoxacor, cloquintocet, cyprosulfamide, dichlormid, fenchlorazole, fenclorim, furilazole, isoxadifen, mefenpyr, 4-(dichloroacetyl)-1-oxa-4-azaspiro[4.5]decane (MON4660, CAS 71526-07-3) and 2,2,5-trimethyl-3-(dichloroacetyl)-1,3-oxazolidine (R-29148, CAS 52836-31-4).

Here and below, the term "binary compositions" includes compositions comprising one or more, e.g. 1, 2 or 3, active compounds of the formula (I) and either one or more, e.g. 1, 2 or 3, herbicides B or one or more safeners C.

Correspondingly, the term "ternary compositions" includes compositions comprising one or more, e.g. 1, 2 or 3, active compounds of the formula (I), one or more, e.g. 1, 2 or 3, herbicides B and one or more, e.g. 1, 2 or 3, safeners C.

In binary compositions comprising at least one pyrimidine of formula (I) as component A and at least one herbicide B, the weight ratio of the active compounds A:B is generally in the range of from 1:1000 to 1000:1, preferably in the range of from 1:500 to 500:1, in particular in the range of from 1:250 to 250:1 and particularly preferably in the range of from 1:75 to 75:1.

In binary compositions comprising at least one pyrimidine of formula (I) as component A and at least one safener C, the weight ratio of the active compounds A:C is generally in the range of from 1:1000 to 1000:1, preferably in the range of from 1:500 to 500:1, in particular in the range of from 1:250 to 250:1 and particularly preferably in the range of from 1:75 to 75:1.

In ternary compositions comprising at least one pyrimidine of formula (I) as component A, at least one herbicide B and at least one safener C, the relative proportions by weight of the components A:B are generally in the range of from 1:1000 to 1000:1, preferably in the range of from 1:500 to 500:1, in particular in the range of from 1:250 to 250:1 and particularly preferably in the range of from 1:75 to 75:1, the weight ratio of the components A:C is generally in the range of from 1:1000 to 1000:1, preferably in the range of from 1:500 to 500:1, in particular in the range of from 1:250 to 250:1 and particularly preferably in the range of from 1:75 to 75:1, and the weight ratio of the components B:C is generally in the range of from 1:1000 to 1000:1, preferably in the range of from 1:500 to 500:1, in particular in the range of from 1:250 to 250:1 and particularly preferably in the range of from 1:75 to 75:1. The weight ratio of components A+B to component C is preferably in the range of from 1:500 to 500:1, in particular in the range of from 1:250 to 250:1 and particularly preferably in the range of from 1:75 to 75:1.

The weight ratios of the individual components in the preferred mixtures mentioned below are within the limits given above, in particular within the preferred limits.

Particularly preferred are the compositions mentioned below comprising the pyrimidine compounds of formula I as defined and the substance(s) as defined in the respective row of table T;

especially preferred comprising as only herbicidal active compounds the pyrimidine compounds of formula I as defined and the substance(s) as defined in the respective row of table T;

most preferably comprising as only active compounds the pyrimidine compounds of formula I as defined and the substance(s) as defined in the respective row of table T.

Particularly preferred are compositions 1.1 to 1.3653, comprising the compound 1.1.I-3 and the substance(s) as defined in the respective row of table T:

TABLE T (compositions 1.1 to 1.3653):

| comp. no. | herbicide B | safener C |
|---|---|---|
| 1.1 | B.1 | — |
| 1.2 | B.2 | — |
| 1.3 | B.3 | — |
| 1.4 | B.4 | — |
| 1.5 | B.5 | — |
| 1.6 | B.6 | — |
| 1.7 | B.7 | — |
| 1.8 | B.8 | — |
| 1.9 | B.9 | — |
| 1.10 | B.10 | — |
| 1.11 | B.11 | — |
| 1.12 | B.12 | — |
| 1.13 | B.13 | — |
| 1.14 | B.14 | — |
| 1.15 | B.15 | — |
| 1.16 | B.16 | — |
| 1.17 | B.17 | — |
| 1.18 | B.18 | — |
| 1.19 | B.19 | — |
| 1.20 | B.20 | — |
| 1.21 | B.21 | — |
| 1.22 | B.22 | — |
| 1.23 | B.23 | — |
| 1.24 | B.24 | — |
| 1.25 | B.25 | — |
| 1.26 | B.26 | — |
| 1.27 | B.27 | — |
| 1.28 | B.28 | — |
| 1.29 | B.29 | — |
| 1.30 | B.30 | — |
| 1.31 | B.31 | — |
| 1.32 | B.32 | — |
| 1.33 | B.33 | — |
| 1.34 | B.34 | — |
| 1.35 | B.35 | — |
| 1.36 | B.36 | — |
| 1.37 | B.37 | — |
| 1.38 | B.38 | — |
| 1.39 | B.39 | — |
| 1.40 | B.40 | — |
| 1.41 | B.41 | — |
| 1.42 | B.42 | — |
| 1.43 | B.43 | — |
| 1.44 | B.44 | — |
| 1.45 | B.45 | — |
| 1.46 | B.46 | — |
| 1.47 | B.47 | — |
| 1.48 | B.48 | — |
| 1.49 | B.49 | — |
| 1.50 | B.50 | — |
| 1.51 | B.51 | — |
| 1.52 | B.52 | — |
| 1.53 | B.53 | — |
| 1.54 | B.54 | — |
| 1.55 | B.55 | — |
| 1.56 | B.56 | — |
| 1.57 | B.57 | — |
| 1.58 | B.58 | — |
| 1.59 | B.59 | — |
| 1.60 | B.60 | — |
| 1.61 | B.61 | — |
| 1.62 | B.62 | — |
| 1.63 | B.63 | — |
| 1.64 | B.64 | — |
| 1.65 | B.65 | — |
| 1.66 | B.66 | — |
| 1.67 | B.67 | — |
| 1.68 | B.68 | — |
| 1.69 | B.69 | — |
| 1.70 | B.70 | — |
| 1.71 | B.71 | — |
| 1.72 | B.72 | — |
| 1.73 | B.73 | — |
| 1.74 | B.74 | — |
| 1.75 | B.75 | — |
| 1.76 | B.76 | — |
| 1.77 | B.77 | — |
| 1.78 | B.78 | — |
| 1.79 | B.79 | — |
| 1.80 | B.80 | — |
| 1.81 | B.81 | — |
| 1.82 | B.82 | — |
| 1.83 | B.83 | — |
| 1.84 | B.84 | — |
| 1.85 | B.85 | — |
| 1.86 | B.86 | — |
| 1.87 | B.87 | — |
| 1.88 | B.88 | — |
| 1.89 | B.89 | — |
| 1.90 | B.90 | — |
| 1.91 | B.91 | — |
| 1.92 | B.92 | — |
| 1.93 | B.93 | — |
| 1.94 | B.94 | — |
| 1.95 | B.95 | — |
| 1.96 | B.96 | — |
| 1.97 | B.97 | — |
| 1.98 | B.98 | — |
| 1.99 | B.99 | — |
| 1.100 | B.100 | — |
| 1.101 | B.101 | — |
| 1.102 | B.102 | — |
| 1.103 | B.103 | — |
| 1.104 | B.104 | — |
| 1.105 | B.105 | — |
| 1.106 | B.106 | — |
| 1.107 | B.107 | — |
| 1.108 | B.108 | — |
| 1.109 | B.109 | — |
| 1.110 | B.110 | — |
| 1.111 | B.111 | — |
| 1.112 | B.112 | — |
| 1.113 | B.113 | — |
| 1.114 | B.114 | — |
| 1.115 | B.115 | — |
| 1.116 | B.116 | — |
| 1.117 | B.117 | — |
| 1.118 | B.118 | — |
| 1.119 | B.119 | — |
| 1.120 | B.120 | — |

TABLE T-continued (compositions 1.1 to 1.3653):

| comp. no. | herbicide B | safener C |
|---|---|---|
| 1.121 | B.121 | — |
| 1.122 | B.122 | — |
| 1.123 | B.123 | — |
| 1.124 | B.124 | — |
| 1.125 | B.125 | — |
| 1.126 | B.126 | — |
| 1.127 | B.127 | — |
| 1.128 | B.128 | — |
| 1.129 | B.129 | — |
| 1.130 | B.130 | — |
| 1.131 | B.131 | — |
| 1.132 | B.132 | — |
| 1.133 | B.133 | — |
| 1.134 | B.134 | — |
| 1.135 | B.135 | — |
| 1.136 | B.136 | — |
| 1.137 | B.137 | — |
| 1.138 | B.138 | — |
| 1.139 | B.139 | — |
| 1.140 | B.140 | — |
| 1.141 | B.141 | — |
| 1.142 | B.142 | — |
| 1.143 | B.143 | — |
| 1.144 | B.144 | — |
| 1.145 | B.145 | — |
| 1.146 | B.146 | — |
| 1.147 | B.147 | — |
| 1.148 | B.148 | — |
| 1.149 | B.149 | — |
| 1.150 | B.150 | — |
| 1.151 | B.151 | — |
| 1.152 | B.152 | — |
| 1.153 | B.153 | — |
| 1.154 | B.154 | — |
| 1.155 | B.155 | — |
| 1.156 | B.156 | — |
| 1.157 | B.157 | — |
| 1.158 | B.158 | — |
| 1.159 | B.159 | — |
| 1.160 | B.160 | — |
| 1.161 | B.161 | — |
| 1.162 | B.162 | — |
| 1.163 | B.163 | — |
| 1.164 | B.164 | — |
| 1.165 | B.165 | — |
| 1.166 | B.166 | — |
| 1.167 | B.167 | — |
| 1.168 | B.168 | — |
| 1.169 | B.169 | — |
| 1.170 | B.170 | — |
| 1.171 | B.171 | — |
| 1.172 | B.172 | — |
| 1.173 | B.173 | — |
| 1.174 | B.174 | — |
| 1.175 | B.175 | — |
| 1.176 | B.176 | — |
| 1.177 | B.177 | — |
| 1.178 | B.178 | — |
| 1.179 | B.179 | — |
| 1.180 | B.180 | — |
| 1.181 | B.181 | — |
| 1.182 | B.182 | — |
| 1.183 | B.183 | — |
| 1.184 | B.184 | — |
| 1.185 | B.185 | — |
| 1.186 | B.186 | — |
| 1.187 | B.187 | — |
| 1.188 | B.188 | — |
| 1.189 | B.189 | — |
| 1.190 | B.190 | — |
| 1.191 | B.191 | — |
| 1.192 | B.192 | — |
| 1.193 | B.193 | — |
| 1.194 | B.194 | — |
| 1.195 | B.195 | — |
| 1.196 | B.196 | — |
| 1.197 | B.197 | — |
| 1.198 | B.198 | — |
| 1.199 | B.199 | — |
| 1.200 | B.200 | — |
| 1.201 | B.201 | — |
| 1.202 | B.202 | — |
| 1.203 | B.1 | C.1 |
| 1.204 | B.2 | C.1 |
| 1.205 | B.3 | C.1 |
| 1.206 | B.4 | C.1 |
| 1.207 | B.5 | C.1 |
| 1.208 | B.6 | C.1 |
| 1.209 | B.7 | C.1 |
| 1.210 | B.8 | C.1 |
| 1.211 | B.9 | C.1 |
| 1.212 | B.10 | C.1 |
| 1.213 | B.11 | C.1 |
| 1.214 | B.12 | C.1 |
| 1.215 | B.13 | C.1 |
| 1.216 | B.14 | C.1 |
| 1.217 | B.15 | C.1 |
| 1.218 | B.16 | C.1 |
| 1.219 | B.17 | C.1 |
| 1.220 | B.18 | C.1 |
| 1.221 | B.19 | C.1 |
| 1.222 | B.20 | C.1 |
| 1.223 | B.21 | C.1 |
| 1.224 | B.22 | C.1 |
| 1.225 | B.23 | C.1 |
| 1.226 | B.24 | C.1 |
| 1.227 | B.25 | C.1 |
| 1.228 | B.26 | C.1 |
| 1.229 | B.27 | C.1 |
| 1.230 | B.28 | C.1 |
| 1.231 | B.29 | C.1 |
| 1.232 | B.30 | C.1 |
| 1.233 | B.31 | C.1 |
| 1.234 | B.32 | C.1 |
| 1.235 | B.33 | C.1 |
| 1.236 | B.34 | C.1 |
| 1.237 | B.35 | C.1 |
| 1.238 | B.36 | C.1 |
| 1.239 | B.37 | C.1 |
| 1.240 | B.38 | C.1 |
| 1.241 | B.39 | C.1 |
| 1.242 | B.40 | C.1 |
| 1.243 | B.41 | C.1 |
| 1.244 | B.42 | C.1 |
| 1.245 | B.43 | C.1 |
| 1.246 | B.44 | C.1 |
| 1.247 | B.45 | C.1 |
| 1.248 | B.46 | C.1 |
| 1.249 | B.47 | C.1 |
| 1.250 | B.48 | C.1 |
| 1.251 | B.49 | C.1 |
| 1.252 | B.50 | C.1 |
| 1.253 | B.51 | C.1 |
| 1.254 | B.52 | C.1 |
| 1.255 | B.53 | C.1 |
| 1.256 | B.54 | C.1 |
| 1.257 | B.55 | C.1 |
| 1.258 | B.56 | C.1 |
| 1.259 | B.57 | C.1 |
| 1.260 | B.58 | C.1 |
| 1.261 | B.59 | C.1 |
| 1.262 | B.60 | C.1 |
| 1.263 | B.61 | C.1 |
| 1.264 | B.62 | C.1 |
| 1.265 | B.63 | C.1 |
| 1.266 | B.64 | C.1 |
| 1.267 | B.65 | C.1 |
| 1.268 | B.66 | C.1 |
| 1.269 | B.67 | C.1 |
| 1.270 | B.68 | C.1 |

TABLE T-continued (compositions 1.1 to 1.3653):

| comp. no. | herbicide B | safener C |
|---|---|---|
| 1.271 | B.69 | C.1 |
| 1.272 | B.70 | C.1 |
| 1.273 | B.71 | C.1 |
| 1.274 | B.72 | C.1 |
| 1.275 | B.73 | C.1 |
| 1.276 | B.74 | C.1 |
| 1.277 | B.75 | C.1 |
| 1.278 | B.76 | C.1 |
| 1.279 | B.77 | C.1 |
| 1.280 | B.78 | C.1 |
| 1.281 | B.79 | C.1 |
| 1.282 | B.80 | C.1 |
| 1.283 | B.81 | C.1 |
| 1.284 | B.82 | C.1 |
| 1.285 | B.83 | C.1 |
| 1.286 | B.84 | C.1 |
| 1.287 | B.85 | C.1 |
| 1.288 | B.86 | C.1 |
| 1.289 | B.87 | C.1 |
| 1.290 | B.88 | C.1 |
| 1.291 | B.89 | C.1 |
| 1.292 | B.90 | C.1 |
| 1.293 | B.91 | C.1 |
| 1.294 | B.92 | C.1 |
| 1.295 | B.93 | C.1 |
| 1.296 | B.94 | C.1 |
| 1.297 | B.95 | C.1 |
| 1.298 | B.96 | C.1 |
| 1.299 | B.97 | C.1 |
| 1.300 | B.98 | C.1 |
| 1.301 | B.99 | C.1 |
| 1.302 | B.100 | C.1 |
| 1.303 | B.101 | C.1 |
| 1.304 | B.102 | C.1 |
| 1.305 | B.103 | C.1 |
| 1.306 | B.104 | C.1 |
| 1.307 | B.105 | C.1 |
| 1.308 | B.106 | C.1 |
| 1.309 | B.107 | C.1 |
| 1.310 | B.108 | C.1 |
| 1.311 | B.109 | C.1 |
| 1.312 | B.110 | C.1 |
| 1.313 | B.111 | C.1 |
| 1.314 | B.112 | C.1 |
| 1.315 | B.113 | C.1 |
| 1.316 | B.114 | C.1 |
| 1.317 | B.115 | C.1 |
| 1.318 | B.116 | C.1 |
| 1.319 | B.117 | C.1 |
| 1.320 | B.118 | C.1 |
| 1.321 | B.119 | C.1 |
| 1.322 | B.120 | C.1 |
| 1.323 | B.121 | C.1 |
| 1.324 | B.122 | C.1 |
| 1.325 | B.123 | C.1 |
| 1.326 | B.124 | C.1 |
| 1.327 | B.125 | C.1 |
| 1.328 | B.126 | C.1 |
| 1.329 | B.127 | C.1 |
| 1.330 | B.128 | C.1 |
| 1.331 | B.129 | C.1 |
| 1.332 | B.130 | C.1 |
| 1.333 | B.131 | C.1 |
| 1.334 | B.132 | C.1 |
| 1.335 | B.133 | C.1 |
| 1.336 | B.134 | C.1 |
| 1.337 | B.135 | C.1 |
| 1.338 | B.136 | C.1 |
| 1.339 | B.137 | C.1 |
| 1.340 | B.138 | C.1 |
| 1.341 | B.139 | C.1 |
| 1.342 | B.140 | C.1 |
| 1.343 | B.141 | C.1 |
| 1.344 | B.142 | C.1 |
| 1.345 | B.143 | C.1 |
| 1.346 | B.144 | C.1 |
| 1.347 | B.145 | C.1 |
| 1.348 | B.146 | C.1 |
| 1.349 | B.147 | C.1 |
| 1.350 | B.148 | C.1 |
| 1.351 | B.149 | C.1 |
| 1.352 | B.150 | C.1 |
| 1.353 | B.151 | C.1 |
| 1.354 | B.152 | C.1 |
| 1.355 | B.153 | C.1 |
| 1.356 | B.154 | C.1 |
| 1.357 | B.155 | C.1 |
| 1.358 | B.156 | C.1 |
| 1.359 | B.157 | C.1 |
| 1.360 | B.158 | C.1 |
| 1.361 | B.159 | C.1 |
| 1.362 | B.160 | C.1 |
| 1.363 | B.161 | C.1 |
| 1.364 | B.162 | C.1 |
| 1.365 | B.163 | C.1 |
| 1.366 | B.164 | C.1 |
| 1.367 | B.165 | C.1 |
| 1.368 | B.166 | C.1 |
| 1.369 | B.167 | C.1 |
| 1.370 | B.168 | C.1 |
| 1.371 | B.169 | C.1 |
| 1.372 | B.170 | C.1 |
| 1.373 | B.171 | C.1 |
| 1.374 | B.172 | C.1 |
| 1.375 | B.173 | C.1 |
| 1.376 | B.174 | C.1 |
| 1.377 | B.175 | C.1 |
| 1.378 | B.176 | C.1 |
| 1.379 | B.177 | C.1 |
| 1.380 | B.178 | C.1 |
| 1.381 | B.179 | C.1 |
| 1.382 | B.180 | C.1 |
| 1.383 | B.181 | C.1 |
| 1.384 | B.182 | C.1 |
| 1.385 | B.183 | C.1 |
| 1.386 | B.184 | C.1 |
| 1.387 | B.185 | C.1 |
| 1.388 | B.186 | C.1 |
| 1.389 | B.187 | C.1 |
| 1.390 | B.188 | C.1 |
| 1.391 | B.189 | C.1 |
| 1.392 | B.190 | C.1 |
| 1.393 | B.191 | C.1 |
| 1.394 | B.192 | C.1 |
| 1.395 | B.193 | C.1 |
| 1.396 | B.194 | C.1 |
| 1.397 | B.195 | C.1 |
| 1.398 | B.196 | C.1 |
| 1.399 | B.197 | C.1 |
| 1.400 | B.198 | C.1 |
| 1.401 | B.199 | C.1 |
| 1.402 | B.200 | C.1 |
| 1.403 | B.201 | C.1 |
| 1.404 | B.202 | C.1 |
| 1.405 | B.1 | C.2 |
| 1.406 | B.2 | C.2 |
| 1.407 | B.3 | C.2 |
| 1.408 | B.4 | C.2 |
| 1.409 | B.5 | C.2 |
| 1.410 | B.6 | C.2 |
| 1.411 | B.7 | C.2 |
| 1.412 | B.8 | C.2 |
| 1.413 | B.9 | C.2 |
| 1.414 | B.10 | C.2 |
| 1.415 | B.11 | C.2 |
| 1.416 | B.12 | C.2 |
| 1.417 | B.13 | C.2 |
| 1.418 | B.14 | C.2 |
| 1.419 | B.15 | C.2 |
| 1.420 | B.16 | C.2 |

TABLE T-continued (compositions 1.1 to 1.3653):

| comp. no. | herbi-cide B | safener C |
|---|---|---|
| 1.421 | B.17 | C.2 |
| 1.422 | B.18 | C.2 |
| 1.423 | B.19 | C.2 |
| 1.424 | B.20 | C.2 |
| 1.425 | B.21 | C.2 |
| 1.426 | B.22 | C.2 |
| 1.427 | B.23 | C.2 |
| 1.428 | B.24 | C.2 |
| 1.429 | B.25 | C.2 |
| 1.430 | B.26 | C.2 |
| 1.431 | B.27 | C.2 |
| 1.432 | B.28 | C.2 |
| 1.433 | B.29 | C.2 |
| 1.434 | B.30 | C.2 |
| 1.435 | B.31 | C.2 |
| 1.436 | B.32 | C.2 |
| 1.437 | B.33 | C.2 |
| 1.438 | B.34 | C.2 |
| 1.439 | B.35 | C.2 |
| 1.440 | B.36 | C.2 |
| 1.441 | B.37 | C.2 |
| 1.442 | B.38 | C.2 |
| 1.443 | B.39 | C.2 |
| 1.444 | B.40 | C.2 |
| 1.445 | B.41 | C.2 |
| 1.446 | B.42 | C.2 |
| 1.447 | B.43 | C.2 |
| 1.448 | B.44 | C.2 |
| 1.449 | B.45 | C.2 |
| 1.450 | B.46 | C.2 |
| 1.451 | B.47 | C.2 |
| 1.452 | B.48 | C.2 |
| 1.453 | B.49 | C.2 |
| 1.454 | B.50 | C.2 |
| 1.455 | B.51 | C.2 |
| 1.456 | B.52 | C.2 |
| 1.457 | B.53 | C.2 |
| 1.458 | B.54 | C.2 |
| 1.459 | B.55 | C.2 |
| 1.460 | B.56 | C.2 |
| 1.461 | B.57 | C.2 |
| 1.462 | B.58 | C.2 |
| 1.463 | B.59 | C.2 |
| 1.464 | B.60 | C.2 |
| 1.465 | B.61 | C.2 |
| 1.466 | B.62 | C.2 |
| 1.467 | B.63 | C.2 |
| 1.468 | B.64 | C.2 |
| 1.469 | B.65 | C.2 |
| 1.470 | B.66 | C.2 |
| 1.471 | B.67 | C.2 |
| 1.472 | B.68 | C.2 |
| 1.473 | B.69 | C.2 |
| 1.474 | B.70 | C.2 |
| 1.475 | B.71 | C.2 |
| 1.476 | B.72 | C.2 |
| 1.477 | B.73 | C.2 |
| 1.478 | B.74 | C.2 |
| 1.479 | B.75 | C.2 |
| 1.480 | B.76 | C.2 |
| 1.481 | B.77 | C.2 |
| 1.482 | B.78 | C.2 |
| 1.483 | B.79 | C.2 |
| 1.484 | B.80 | C.2 |
| 1.485 | B.81 | C.2 |
| 1.486 | B.82 | C.2 |
| 1.487 | B.83 | C.2 |
| 1.488 | B.84 | C.2 |
| 1.489 | B.85 | C.2 |
| 1.490 | B.86 | C.2 |
| 1.491 | B.87 | C.2 |
| 1.492 | B.88 | C.2 |
| 1.493 | B.89 | C.2 |
| 1.494 | B.90 | C.2 |
| 1.495 | B.91 | C.2 |
| 1.496 | B.92 | C.2 |
| 1.497 | B.93 | C.2 |
| 1.498 | B.94 | C.2 |
| 1.499 | B.95 | C.2 |
| 1.500 | B.96 | C.2 |
| 1.501 | B.97 | C.2 |
| 1.502 | B.98 | C.2 |
| 1.503 | B.99 | C.2 |
| 1.504 | B.100 | C.2 |
| 1.505 | B.101 | C.2 |
| 1.506 | B.102 | C.2 |
| 1.507 | B.103 | C.2 |
| 1.508 | B.104 | C.2 |
| 1.509 | B.105 | C.2 |
| 1.510 | B.106 | C.2 |
| 1.511 | B.107 | C.2 |
| 1.512 | B.108 | C.2 |
| 1.513 | B.109 | C.2 |
| 1.514 | B.110 | C.2 |
| 1.515 | B.111 | C.2 |
| 1.516 | B.112 | C.2 |
| 1.517 | B.113 | C.2 |
| 1.518 | B.114 | C.2 |
| 1.519 | B.115 | C.2 |
| 1.520 | B.116 | C.2 |
| 1.521 | B.117 | C.2 |
| 1.522 | B.118 | C.2 |
| 1.523 | B.119 | C.2 |
| 1.524 | B.120 | C.2 |
| 1.525 | B.121 | C.2 |
| 1.526 | B.122 | C.2 |
| 1.527 | B.123 | C.2 |
| 1.528 | B.124 | C.2 |
| 1.529 | B.125 | C.2 |
| 1.530 | B.126 | C.2 |
| 1.531 | B.127 | C.2 |
| 1.532 | B.128 | C.2 |
| 1.533 | B.129 | C.2 |
| 1.534 | B.130 | C.2 |
| 1.535 | B.131 | C.2 |
| 1.536 | B.132 | C.2 |
| 1.537 | B.133 | C.2 |
| 1.538 | B.134 | C.2 |
| 1.539 | B.135 | C.2 |
| 1.540 | B.136 | C.2 |
| 1.541 | B.137 | C.2 |
| 1.542 | B.138 | C.2 |
| 1.543 | B.139 | C.2 |
| 1.544 | B.140 | C.2 |
| 1.545 | B.141 | C.2 |
| 1.546 | B.142 | C.2 |
| 1.547 | B.143 | C.2 |
| 1.548 | B.144 | C.2 |
| 1.549 | B.145 | C.2 |
| 1.550 | B.146 | C.2 |
| 1.551 | B.147 | C.2 |
| 1.552 | B.148 | C.2 |
| 1.553 | B.149 | C.2 |
| 1.554 | B.150 | C.2 |
| 1.555 | B.151 | C.2 |
| 1.556 | B.152 | C.2 |
| 1.557 | B.153 | C.2 |
| 1.558 | B.154 | C.2 |
| 1.559 | B.155 | C.2 |
| 1.560 | B.156 | C.2 |
| 1.561 | B.157 | C.2 |
| 1.562 | B.158 | C.2 |
| 1.563 | B.159 | C.2 |
| 1.564 | B.160 | C.2 |
| 1.565 | B.161 | C.2 |
| 1.566 | B.162 | C.2 |
| 1.567 | B.163 | C.2 |
| 1.568 | B.164 | C.2 |
| 1.569 | B.165 | C.2 |
| 1.570 | B.166 | C.2 |

TABLE T-continued (compositions 1.1 to 1.3653):

| comp. no. | herbicide B | safener C |
|---|---|---|
| 1.571 | B.167 | C.2 |
| 1.572 | B.168 | C.2 |
| 1.573 | B.169 | C.2 |
| 1.574 | B.170 | C.2 |
| 1.575 | B.171 | C.2 |
| 1.576 | B.172 | C.2 |
| 1.577 | B.173 | C.2 |
| 1.578 | B.174 | C.2 |
| 1.579 | B.175 | C.2 |
| 1.580 | B.176 | C.2 |
| 1.581 | B.177 | C.2 |
| 1.582 | B.178 | C.2 |
| 1.583 | B.179 | C.2 |
| 1.584 | B.180 | C.2 |
| 1.585 | B.181 | C.2 |
| 1.586 | B.182 | C.2 |
| 1.587 | B.183 | C.2 |
| 1.588 | B.184 | C.2 |
| 1.589 | B.185 | C.2 |
| 1.590 | B.186 | C.2 |
| 1.591 | B.187 | C.2 |
| 1.592 | B.188 | C.2 |
| 1.593 | B.189 | C.2 |
| 1.594 | B.190 | C.2 |
| 1.595 | B.191 | C.2 |
| 1.596 | B.192 | C.2 |
| 1.597 | B.193 | C.2 |
| 1.598 | B.194 | C.2 |
| 1.599 | B.195 | C.2 |
| 1.600 | B.196 | C.2 |
| 1.601 | B.197 | C.2 |
| 1.602 | B.198 | C.2 |
| 1.603 | B.199 | C.2 |
| 1.604 | B.200 | C.2 |
| 1.605 | B.201 | C.2 |
| 1.606 | B.202 | C.2 |
| 1.607 | B.1 | C.3 |
| 1.608 | B.2 | C.3 |
| 1.609 | B.3 | C.3 |
| 1.610 | B.4 | C.3 |
| 1.611 | B.5 | C.3 |
| 1.612 | B.6 | C.3 |
| 1.613 | B.7 | C.3 |
| 1.614 | B.8 | C.3 |
| 1.615 | B.9 | C.3 |
| 1.616 | B.10 | C.3 |
| 1.617 | B.11 | C.3 |
| 1.618 | B.12 | C.3 |
| 1.619 | B.13 | C.3 |
| 1.620 | B.14 | C.3 |
| 1.621 | B.15 | C.3 |
| 1.622 | B.16 | C.3 |
| 1.623 | B.17 | C.3 |
| 1.624 | B.18 | C.3 |
| 1.625 | B.19 | C.3 |
| 1.626 | B.20 | C.3 |
| 1.627 | B.21 | C.3 |
| 1.628 | B.22 | C.3 |
| 1.629 | B.23 | C.3 |
| 1.630 | B.24 | C.3 |
| 1.631 | B.25 | C.3 |
| 1.632 | B.26 | C.3 |
| 1.633 | B.27 | C.3 |
| 1.634 | B.28 | C.3 |
| 1.635 | B.29 | C.3 |
| 1.636 | B.30 | C.3 |
| 1.637 | B.31 | C.3 |
| 1.638 | B.32 | C.3 |
| 1.639 | B.33 | C.3 |
| 1.640 | B.34 | C.3 |
| 1.641 | B.35 | C.3 |
| 1.642 | B.36 | C.3 |
| 1.643 | B.37 | C.3 |
| 1.644 | B.38 | C.3 |
| 1.645 | B.39 | C.3 |
| 1.646 | B.40 | C.3 |
| 1.647 | B.41 | C.3 |
| 1.648 | B.42 | C.3 |
| 1.649 | B.43 | C.3 |
| 1.650 | B.44 | C.3 |
| 1.651 | B.45 | C.3 |
| 1.652 | B.46 | C.3 |
| 1.653 | B.47 | C.3 |
| 1.654 | B.48 | C.3 |
| 1.655 | B.49 | C.3 |
| 1.656 | B.50 | C.3 |
| 1.657 | B.51 | C.3 |
| 1.658 | B.52 | C.3 |
| 1.659 | B.53 | C.3 |
| 1.660 | B.54 | C.3 |
| 1.661 | B.55 | C.3 |
| 1.662 | B.56 | C.3 |
| 1.663 | B.57 | C.3 |
| 1.664 | B.58 | C.3 |
| 1.665 | B.59 | C.3 |
| 1.666 | B.60 | C.3 |
| 1.667 | B.61 | C.3 |
| 1.668 | B.62 | C.3 |
| 1.669 | B.63 | C.3 |
| 1.670 | B.64 | C.3 |
| 1.671 | B.65 | C.3 |
| 1.672 | B.66 | C.3 |
| 1.673 | B.67 | C.3 |
| 1.674 | B.68 | C.3 |
| 1.675 | B.69 | C.3 |
| 1.676 | B.70 | C.3 |
| 1.677 | B.71 | C.3 |
| 1.678 | B.72 | C.3 |
| 1.679 | B.73 | C.3 |
| 1.680 | B.74 | C.3 |
| 1.681 | B.75 | C.3 |
| 1.682 | B.76 | C.3 |
| 1.683 | B.77 | C.3 |
| 1.684 | B.78 | C.3 |
| 1.685 | B.79 | C.3 |
| 1.686 | B.80 | C.3 |
| 1.687 | B.81 | C.3 |
| 1.688 | B.82 | C.3 |
| 1.689 | B.83 | C.3 |
| 1.690 | B.84 | C.3 |
| 1.691 | B.85 | C.3 |
| 1.692 | B.86 | C.3 |
| 1.693 | B.87 | C.3 |
| 1.694 | B.88 | C.3 |
| 1.695 | B.89 | C.3 |
| 1.696 | B.90 | C.3 |
| 1.697 | B.91 | C.3 |
| 1.698 | B.92 | C.3 |
| 1.699 | B.93 | C.3 |
| 1.700 | B.94 | C.3 |
| 1.701 | B.95 | C.3 |
| 1.702 | B.96 | C.3 |
| 1.703 | B.97 | C.3 |
| 1.704 | B.98 | C.3 |
| 1.705 | B.99 | C.3 |
| 1.706 | B.100 | C.3 |
| 1.707 | B.101 | C.3 |
| 1.708 | B.102 | C.3 |
| 1.709 | B.103 | C.3 |
| 1.710 | B.104 | C.3 |
| 1.711 | B.105 | C.3 |
| 1.712 | B.106 | C.3 |
| 1.713 | B.107 | C.3 |
| 1.714 | B.108 | C.3 |
| 1.715 | B.109 | C.3 |
| 1.716 | B.110 | C.3 |
| 1.717 | B.111 | C.3 |
| 1.718 | B.112 | C.3 |
| 1.719 | B.113 | C.3 |
| 1.720 | B.114 | C.3 |

TABLE T-continued (compositions 1.1 to 1.3653):

| comp. no. | herbi-cide B | safener C |
|---|---|---|
| 1.721 | B.115 | C.3 |
| 1.722 | B.116 | C.3 |
| 1.723 | B.117 | C.3 |
| 1.724 | B.118 | C.3 |
| 1.725 | B.119 | C.3 |
| 1.726 | B.120 | C.3 |
| 1.727 | B.121 | C.3 |
| 1.728 | B.122 | C.3 |
| 1.729 | B.123 | C.3 |
| 1.730 | B.124 | C.3 |
| 1.731 | B.125 | C.3 |
| 1.732 | B.126 | C.3 |
| 1.733 | B.127 | C.3 |
| 1.734 | B.128 | C.3 |
| 1.735 | B.129 | C.3 |
| 1.736 | B.130 | C.3 |
| 1.737 | B.131 | C.3 |
| 1.738 | B.132 | C.3 |
| 1.739 | B.133 | C.3 |
| 1.740 | B.134 | C.3 |
| 1.741 | B.135 | C.3 |
| 1.742 | B.136 | C.3 |
| 1.743 | B.137 | C.3 |
| 1.744 | B.138 | C.3 |
| 1.745 | B.139 | C.3 |
| 1.746 | B.140 | C.3 |
| 1.747 | B.141 | C.3 |
| 1.748 | B.142 | C.3 |
| 1.749 | B.143 | C.3 |
| 1.750 | B.144 | C.3 |
| 1.751 | B.145 | C.3 |
| 1.752 | B.146 | C.3 |
| 1.753 | B.147 | C.3 |
| 1.754 | B.148 | C.3 |
| 1.755 | B.149 | C.3 |
| 1.756 | B.150 | C.3 |
| 1.757 | B.151 | C.3 |
| 1.758 | B.152 | C.3 |
| 1.759 | B.153 | C.3 |
| 1.760 | B.154 | C.3 |
| 1.761 | B.155 | C.3 |
| 1.762 | B.156 | C.3 |
| 1.763 | B.157 | C.3 |
| 1.764 | B.158 | C.3 |
| 1.765 | B.159 | C.3 |
| 1.766 | B.160 | C.3 |
| 1.767 | B.161 | C.3 |
| 1.768 | B.162 | C.3 |
| 1.769 | B.163 | C.3 |
| 1.770 | B.164 | C.3 |
| 1.771 | B.165 | C.3 |
| 1.772 | B.166 | C.3 |
| 1.773 | B.167 | C.3 |
| 1.774 | B.168 | C.3 |
| 1.775 | B.169 | C.3 |
| 1.776 | B.170 | C.3 |
| 1.777 | B.171 | C.3 |
| 1.778 | B.172 | C.3 |
| 1.779 | B.173 | C.3 |
| 1.780 | B.174 | C.3 |
| 1.781 | B.175 | C.3 |
| 1.782 | B.176 | C.3 |
| 1.783 | B.177 | C.3 |
| 1.784 | B.178 | C.3 |
| 1.785 | B.179 | C.3 |
| 1.786 | B.180 | C.3 |
| 1.787 | B.181 | C.3 |
| 1.788 | B.182 | C.3 |
| 1.789 | B.183 | C.3 |
| 1.790 | B.184 | C.3 |
| 1.791 | B.185 | C.3 |
| 1.792 | B.186 | C.3 |
| 1.793 | B.187 | C.3 |
| 1.794 | B.188 | C.3 |
| 1.795 | B.189 | C.3 |
| 1.796 | B.190 | C.3 |
| 1.797 | B.191 | C.3 |
| 1.798 | B.192 | C.3 |
| 1.799 | B.193 | C.3 |
| 1.800 | B.194 | C.3 |
| 1.801 | B.195 | C.3 |
| 1.802 | B.196 | C.3 |
| 1.803 | B.197 | C.3 |
| 1.804 | B.198 | C.3 |
| 1.805 | B.199 | C.3 |
| 1.806 | B.200 | C.3 |
| 1.807 | B.201 | C.3 |
| 1.808 | B.202 | C.3 |
| 1.809 | B.1 | C.4 |
| 1.810 | B.2 | C.4 |
| 1.811 | B.3 | C.4 |
| 1.812 | B.4 | C.4 |
| 1.813 | B.5 | C.4 |
| 1.814 | B.6 | C.4 |
| 1.815 | B.7 | C.4 |
| 1.816 | B.8 | C.4 |
| 1.817 | B.9 | C.4 |
| 1.818 | B.10 | C.4 |
| 1.819 | B.11 | C.4 |
| 1.820 | B.12 | C.4 |
| 1.821 | B.13 | C.4 |
| 1.822 | B.14 | C.4 |
| 1.823 | B.15 | C.4 |
| 1.824 | B.16 | C.4 |
| 1.825 | B.17 | C.4 |
| 1.826 | B.18 | C.4 |
| 1.827 | B.19 | C.4 |
| 1.828 | B.20 | C.4 |
| 1.829 | B.21 | C.4 |
| 1.830 | B.22 | C.4 |
| 1.831 | B.23 | C.4 |
| 1.832 | B.24 | C.4 |
| 1.833 | B.25 | C.4 |
| 1.834 | B.26 | C.4 |
| 1.835 | B.27 | C.4 |
| 1.836 | B.28 | C.4 |
| 1.837 | B.29 | C.4 |
| 1.838 | B.30 | C.4 |
| 1.839 | B.31 | C.4 |
| 1.840 | B.32 | C.4 |
| 1.841 | B.33 | C.4 |
| 1.842 | B.34 | C.4 |
| 1.843 | B.35 | C.4 |
| 1.844 | B.36 | C.4 |
| 1.845 | B.37 | C.4 |
| 1.846 | B.38 | C.4 |
| 1.847 | B.39 | C.4 |
| 1.848 | B.40 | C.4 |
| 1.849 | B.41 | C.4 |
| 1.850 | B.42 | C.4 |
| 1.851 | B.43 | C.4 |
| 1.852 | B.44 | C.4 |
| 1.853 | B.45 | C.4 |
| 1.854 | B.46 | C.4 |
| 1.855 | B.47 | C.4 |
| 1.856 | B.48 | C.4 |
| 1.857 | B.49 | C.4 |
| 1.858 | B.50 | C.4 |
| 1.859 | B.51 | C.4 |
| 1.860 | B.52 | C.4 |
| 1.861 | B.53 | C.4 |
| 1.862 | B.54 | C.4 |
| 1.863 | B.55 | C.4 |
| 1.864 | B.56 | C.4 |
| 1.865 | B.57 | C.4 |
| 1.866 | B.58 | C.4 |
| 1.867 | B.59 | C.4 |
| 1.868 | B.60 | C.4 |
| 1.869 | B.61 | C.4 |
| 1.870 | B.62 | C.4 |

TABLE T-continued (compositions 1.1 to 1.3653):

| comp. no. | herbicide B | safener C |
|---|---|---|
| 1.871 | B.63 | C.4 |
| 1.872 | B.64 | C.4 |
| 1.873 | B.65 | C.4 |
| 1.874 | B.66 | C.4 |
| 1.875 | B.67 | C.4 |
| 1.876 | B.68 | C.4 |
| 1.877 | B.69 | C.4 |
| 1.878 | B.70 | C.4 |
| 1.879 | B.71 | C.4 |
| 1.880 | B.72 | C.4 |
| 1.881 | B.73 | C.4 |
| 1.882 | B.74 | C.4 |
| 1.883 | B.75 | C.4 |
| 1.884 | B.76 | C.4 |
| 1.885 | B.77 | C.4 |
| 1.886 | B.78 | C.4 |
| 1.887 | B.79 | C.4 |
| 1.888 | B.80 | C.4 |
| 1.889 | B.81 | C.4 |
| 1.890 | B.82 | C.4 |
| 1.891 | B.83 | C.4 |
| 1.892 | B.84 | C.4 |
| 1.893 | B.85 | C.4 |
| 1.894 | B.86 | C.4 |
| 1.895 | B.87 | C.4 |
| 1.896 | B.88 | C.4 |
| 1.897 | B.89 | C.4 |
| 1.898 | B.90 | C.4 |
| 1.899 | B.91 | C.4 |
| 1.900 | B.92 | C.4 |
| 1.901 | B.93 | C.4 |
| 1.902 | B.94 | C.4 |
| 1.903 | B.95 | C.4 |
| 1.904 | B.96 | C.4 |
| 1.905 | B.97 | C.4 |
| 1.906 | B.98 | C.4 |
| 1.907 | B.99 | C.4 |
| 1.908 | B.100 | C.4 |
| 1.909 | B.101 | C.4 |
| 1.910 | B.102 | C.4 |
| 1.911 | B.103 | C.4 |
| 1.912 | B.104 | C.4 |
| 1.913 | B.105 | C.4 |
| 1.914 | B.106 | C.4 |
| 1.915 | B.107 | C.4 |
| 1.916 | B.108 | C.4 |
| 1.917 | B.109 | C.4 |
| 1.918 | B.110 | C.4 |
| 1.919 | B.111 | C.4 |
| 1.920 | B.112 | C.4 |
| 1.921 | B.113 | C.4 |
| 1.922 | B.114 | C.4 |
| 1.923 | B.115 | C.4 |
| 1.924 | B.116 | C.4 |
| 1.925 | B.117 | C.4 |
| 1.926 | B.118 | C.4 |
| 1.927 | B.119 | C.4 |
| 1.928 | B.120 | C.4 |
| 1.929 | B.121 | C.4 |
| 1.930 | B.122 | C.4 |
| 1.931 | B.123 | C.4 |
| 1.932 | B.124 | C.4 |
| 1.933 | B.125 | C.4 |
| 1.934 | B.126 | C.4 |
| 1.935 | B.127 | C.4 |
| 1.936 | B.128 | C.4 |
| 1.937 | B.129 | C.4 |
| 1.938 | B.130 | C.4 |
| 1.939 | B.131 | C.4 |
| 1.940 | B.132 | C.4 |
| 1.941 | B.133 | C.4 |
| 1.942 | B.134 | C.4 |
| 1.943 | B.135 | C.4 |
| 1.944 | B.136 | C.4 |
| 1.945 | B.137 | C.4 |
| 1.946 | B.138 | C.4 |
| 1.947 | B.139 | C.4 |
| 1.948 | B.140 | C.4 |
| 1.949 | B.141 | C.4 |
| 1.950 | B.142 | C.4 |
| 1.951 | B.143 | C.4 |
| 1.952 | B.144 | C.4 |
| 1.953 | B.145 | C.4 |
| 1.954 | B.146 | C.4 |
| 1.955 | B.147 | C.4 |
| 1.956 | B.148 | C.4 |
| 1.957 | B.149 | C.4 |
| 1.958 | B.150 | C.4 |
| 1.959 | B.151 | C.4 |
| 1.960 | B.152 | C.4 |
| 1.961 | B.153 | C.4 |
| 1.962 | B.154 | C.4 |
| 1.963 | B.155 | C.4 |
| 1.964 | B.156 | C.4 |
| 1.965 | B.157 | C.4 |
| 1.966 | B.158 | C.4 |
| 1.967 | B.159 | C.4 |
| 1.968 | B.160 | C.4 |
| 1.969 | B.161 | C.4 |
| 1.970 | B.162 | C.4 |
| 1.971 | B.163 | C.4 |
| 1.972 | B.164 | C.4 |
| 1.973 | B.165 | C.4 |
| 1.974 | B.166 | C.4 |
| 1.975 | B.167 | C.4 |
| 1.976 | B.168 | C.4 |
| 1.977 | B.169 | C.4 |
| 1.978 | B.170 | C.4 |
| 1.979 | B.171 | C.4 |
| 1.980 | B.172 | C.4 |
| 1.981 | B.173 | C.4 |
| 1.982 | B.174 | C.4 |
| 1.983 | B.175 | C.4 |
| 1.984 | B.176 | C.4 |
| 1.985 | B.177 | C.4 |
| 1.986 | B.178 | C.4 |
| 1.987 | B.179 | C.4 |
| 1.988 | B.180 | C.4 |
| 1.989 | B.181 | C.4 |
| 1.990 | B.182 | C.4 |
| 1.991 | B.183 | C.4 |
| 1.992 | B.184 | C.4 |
| 1.993 | B.185 | C.4 |
| 1.994 | B.186 | C.4 |
| 1.995 | B.187 | C.4 |
| 1.996 | B.188 | C.4 |
| 1.997 | B.189 | C.4 |
| 1.998 | B.190 | C.4 |
| 1.999 | B.191 | C.4 |
| 1.1000 | B.192 | C.4 |
| 1.1001 | B.193 | C.4 |
| 1.1002 | B.194 | C.4 |
| 1.1003 | B.195 | C.4 |
| 1.1004 | B.196 | C.4 |
| 1.1005 | B.197 | C.4 |
| 1.1006 | B.198 | C.4 |
| 1.1007 | B.199 | C.4 |
| 1.1008 | B.200 | C.4 |
| 1.1009 | B.201 | C.4 |
| 1.1010 | B.202 | C.4 |
| 1.1011 | B.1 | C.5 |
| 1.1012 | B.2 | C.5 |
| 1.1013 | B.3 | C.5 |
| 1.1014 | B.4 | C.5 |
| 1.1015 | B.5 | C.5 |
| 1.1016 | B.6 | C.5 |
| 1.1017 | B.7 | C.5 |
| 1.1018 | B.8 | C.5 |
| 1.1019 | B.9 | C.5 |
| 1.1020 | B.10 | C.5 |

TABLE T-continued (compositions 1.1 to 1.3653):

| comp. no. | herbicide B | safener C |
|---|---|---|
| 1.1021 | B.11 | C.5 |
| 1.1022 | B.12 | C.5 |
| 1.1023 | B.13 | C.5 |
| 1.1024 | B.14 | C.5 |
| 1.1025 | B.15 | C.5 |
| 1.1026 | B.16 | C.5 |
| 1.1027 | B.17 | C.5 |
| 1.1028 | B.18 | C.5 |
| 1.1029 | B.19 | C.5 |
| 1.1030 | B.20 | C.5 |
| 1.1031 | B.21 | C.5 |
| 1.1032 | B.22 | C.5 |
| 1.1033 | B.23 | C.5 |
| 1.1034 | B.24 | C.5 |
| 1.1035 | B.25 | C.5 |
| 1.1036 | B.26 | C.5 |
| 1.1037 | B.27 | C.5 |
| 1.1038 | B.28 | C.5 |
| 1.1039 | B.29 | C.5 |
| 1.1040 | B.30 | C.5 |
| 1.1041 | B.31 | C.5 |
| 1.1042 | B.32 | C.5 |
| 1.1043 | B.33 | C.5 |
| 1.1044 | B.34 | C.5 |
| 1.1045 | B.35 | C.5 |
| 1.1046 | B.36 | C.5 |
| 1.1047 | B.37 | C.5 |
| 1.1048 | B.38 | C.5 |
| 1.1049 | B.39 | C.5 |
| 1.1050 | B.40 | C.5 |
| 1.1051 | B.41 | C.5 |
| 1.1052 | B.42 | C.5 |
| 1.1053 | B.43 | C.5 |
| 1.1054 | B.44 | C.5 |
| 1.1055 | B.45 | C.5 |
| 1.1056 | B.46 | C.5 |
| 1.1057 | B.47 | C.5 |
| 1.1058 | B.48 | C.5 |
| 1.1059 | B.49 | C.5 |
| 1.1060 | B.50 | C.5 |
| 1.1061 | B.51 | C.5 |
| 1.1062 | B.52 | C.5 |
| 1.1063 | B.53 | C.5 |
| 1.1064 | B.54 | C.5 |
| 1.1065 | B.55 | C.5 |
| 1.1066 | B.56 | C.5 |
| 1.1067 | B.57 | C.5 |
| 1.1068 | B.58 | C.5 |
| 1.1069 | B.59 | C.5 |
| 1.1070 | B.60 | C.5 |
| 1.1071 | B.61 | C.5 |
| 1.1072 | B.62 | C.5 |
| 1.1073 | B.63 | C.5 |
| 1.1074 | B.64 | C.5 |
| 1.1075 | B.65 | C.5 |
| 1.1076 | B.66 | C.5 |
| 1.1077 | B.67 | C.5 |
| 1.1078 | B.68 | C.5 |
| 1.1079 | B.69 | C.5 |
| 1.1080 | B.70 | C.5 |
| 1.1081 | B.71 | C.5 |
| 1.1082 | B.72 | C.5 |
| 1.1083 | B.73 | C.5 |
| 1.1084 | B.74 | C.5 |
| 1.1085 | B.75 | C.5 |
| 1.1086 | B.76 | C.5 |
| 1.1087 | B.77 | C.5 |
| 1.1088 | B.78 | C.5 |
| 1.1089 | B.79 | C.5 |
| 1.1090 | B.80 | C.5 |
| 1.1091 | B.81 | C.5 |
| 1.1092 | B.82 | C.5 |
| 1.1093 | B.83 | C.5 |
| 1.1094 | B.84 | C.5 |
| 1.1095 | B.85 | C.5 |
| 1.1096 | B.86 | C.5 |
| 1.1097 | B.87 | C.5 |
| 1.1098 | B.88 | C.5 |
| 1.1099 | B.89 | C.5 |
| 1.1100 | B.90 | C.5 |
| 1.1101 | B.91 | C.5 |
| 1.1102 | B.92 | C.5 |
| 1.1103 | B.93 | C.5 |
| 1.1104 | B.94 | C.5 |
| 1.1105 | B.95 | C.5 |
| 1.1106 | B.96 | C.5 |
| 1.1107 | B.97 | C.5 |
| 1.1108 | B.98 | C.5 |
| 1.1109 | B.99 | C.5 |
| 1.1110 | B.100 | C.5 |
| 1.1111 | B.101 | C.5 |
| 1.1112 | B.102 | C.5 |
| 1.1113 | B.103 | C.5 |
| 1.1114 | B.104 | C.5 |
| 1.1115 | B.105 | C.5 |
| 1.1116 | B.106 | C.5 |
| 1.1117 | B.107 | C.5 |
| 1.1118 | B.108 | C.5 |
| 1.1119 | B.109 | C.5 |
| 1.1120 | B.110 | C.5 |
| 1.1121 | B.111 | C.5 |
| 1.1122 | B.112 | C.5 |
| 1.1123 | B.113 | C.5 |
| 1.1124 | B.114 | C.5 |
| 1.1125 | B.115 | C.5 |
| 1.1126 | B.116 | C.5 |
| 1.1127 | B.117 | C.5 |
| 1.1128 | B.118 | C.5 |
| 1.1129 | B.119 | C.5 |
| 1.1130 | B.120 | C.5 |
| 1.1131 | B.121 | C.5 |
| 1.1132 | B.122 | C.5 |
| 1.1133 | B.123 | C.5 |
| 1.1134 | B.124 | C.5 |
| 1.1135 | B.125 | C.5 |
| 1.1136 | B.126 | C.5 |
| 1.1137 | B.127 | C.5 |
| 1.1138 | B.128 | C.5 |
| 1.1139 | B.129 | C.5 |
| 1.1140 | B.130 | C.5 |
| 1.1141 | B.131 | C.5 |
| 1.1142 | B.132 | C.5 |
| 1.1143 | B.133 | C.5 |
| 1.1144 | B.134 | C.5 |
| 1.1145 | B.135 | C.5 |
| 1.1146 | B.136 | C.5 |
| 1.1147 | B.137 | C.5 |
| 1.1148 | B.138 | C.5 |
| 1.1149 | B.139 | C.5 |
| 1.1150 | B.140 | C.5 |
| 1.1151 | B.141 | C.5 |
| 1.1152 | B.142 | C.5 |
| 1.1153 | B.143 | C.5 |
| 1.1154 | B.144 | C.5 |
| 1.1155 | B.145 | C.5 |
| 1.1156 | B.146 | C.5 |
| 1.1157 | B.147 | C.5 |
| 1.1158 | B.148 | C.5 |
| 1.1159 | B.149 | C.5 |
| 1.1160 | B.150 | C.5 |
| 1.1161 | B.151 | C.5 |
| 1.1162 | B.152 | C.5 |
| 1.1163 | B.153 | C.5 |
| 1.1164 | B.154 | C.5 |
| 1.1165 | B.155 | C.5 |
| 1.1166 | B.156 | C.5 |
| 1.1167 | B.157 | C.5 |
| 1.1168 | B.158 | C.5 |
| 1.1169 | B.159 | C.5 |
| 1.1170 | B.160 | C.5 |

TABLE T-continued (compositions 1.1 to 1.3653):

| comp. no. | herbicide B | safener C |
|---|---|---|
| 1.1171 | B.161 | C.5 |
| 1.1172 | B.162 | C.5 |
| 1.1173 | B.163 | C.5 |
| 1.1174 | B.164 | C.5 |
| 1.1175 | B.165 | C.5 |
| 1.1176 | B.166 | C.5 |
| 1.1177 | B.167 | C.5 |
| 1.1178 | B.168 | C.5 |
| 1.1179 | B.169 | C.5 |
| 1.1180 | B.170 | C.5 |
| 1.1181 | B.171 | C.5 |
| 1.1182 | B.172 | C.5 |
| 1.1183 | B.173 | C.5 |
| 1.1184 | B.174 | C.5 |
| 1.1185 | B.175 | C.5 |
| 1.1186 | B.176 | C.5 |
| 1.1187 | B.177 | C.5 |
| 1.1188 | B.178 | C.5 |
| 1.1189 | B.179 | C.5 |
| 1.1190 | B.180 | C.5 |
| 1.1191 | B.181 | C.5 |
| 1.1192 | B.182 | C.5 |
| 1.1193 | B.183 | C.5 |
| 1.1194 | B.184 | C.5 |
| 1.1195 | B.185 | C.5 |
| 1.1196 | B.186 | C.5 |
| 1.1197 | B.187 | C.5 |
| 1.1198 | B.188 | C.5 |
| 1.1199 | B.189 | C.5 |
| 1.1200 | B.190 | C.5 |
| 1.1201 | B.191 | C.5 |
| 1.1202 | B.192 | C.5 |
| 1.1203 | B.193 | C.5 |
| 1.1204 | B.194 | C.5 |
| 1.1205 | B.195 | C.5 |
| 1.1206 | B.196 | C.5 |
| 1.1207 | B.197 | C.5 |
| 1.1208 | B.198 | C.5 |
| 1.1209 | B.199 | C.5 |
| 1.1210 | B.200 | C.5 |
| 1.1211 | B.201 | C.5 |
| 1.1212 | B.202 | C.5 |
| 1.1213 | B.1 | C.6 |
| 1.1214 | B.2 | C.6 |
| 1.1215 | B.3 | C.6 |
| 1.1216 | B.4 | C.6 |
| 1.1217 | B.5 | C.6 |
| 1.1218 | B.6 | C.6 |
| 1.1219 | B.7 | C.6 |
| 1.1220 | B.8 | C.6 |
| 1.1221 | B.9 | C.6 |
| 1.1222 | B.10 | C.6 |
| 1.1223 | B.11 | C.6 |
| 1.1224 | B.12 | C.6 |
| 1.1225 | B.13 | C.6 |
| 1.1226 | B.14 | C.6 |
| 1.1227 | B.15 | C.6 |
| 1.1228 | B.16 | C.6 |
| 1.1229 | B.17 | C.6 |
| 1.1230 | B.18 | C.6 |
| 1.1231 | B.19 | C.6 |
| 1.1232 | B.20 | C.6 |
| 1.1233 | B.21 | C.6 |
| 1.1234 | B.22 | C.6 |
| 1.1235 | B.23 | C.6 |
| 1.1236 | B.24 | C.6 |
| 1.1237 | B.25 | C.6 |
| 1.1238 | B.26 | C.6 |
| 1.1239 | B.27 | C.6 |
| 1.1240 | B.28 | C.6 |
| 1.1241 | B.29 | C.6 |
| 1.1242 | B.30 | C.6 |
| 1.1243 | B.31 | C.6 |
| 1.1244 | B.32 | C.6 |
| 1.1245 | B.33 | C.6 |
| 1.1246 | B.34 | C.6 |
| 1.1247 | B.35 | C.6 |
| 1.1248 | B.36 | C.6 |
| 1.1249 | B.37 | C.6 |
| 1.1250 | B.38 | C.6 |
| 1.1251 | B.39 | C.6 |
| 1.1252 | B.40 | C.6 |
| 1.1253 | B.41 | C.6 |
| 1.1254 | B.42 | C.6 |
| 1.1255 | B.43 | C.6 |
| 1.1256 | B.44 | C.6 |
| 1.1257 | B.45 | C.6 |
| 1.1258 | B.46 | C.6 |
| 1.1259 | B.47 | C.6 |
| 1.1260 | B.48 | C.6 |
| 1.1261 | B.49 | C.6 |
| 1.1262 | B.50 | C.6 |
| 1.1263 | B.51 | C.6 |
| 1.1264 | B.52 | C.6 |
| 1.1265 | B.53 | C.6 |
| 1.1266 | B.54 | C.6 |
| 1.1267 | B.55 | C.6 |
| 1.1268 | B.56 | C.6 |
| 1.1269 | B.57 | C.6 |
| 1.1270 | B.58 | C.6 |
| 1.1271 | B.59 | C.6 |
| 1.1272 | B.60 | C.6 |
| 1.1273 | B.61 | C.6 |
| 1.1274 | B.62 | C.6 |
| 1.1275 | B.63 | C.6 |
| 1.1276 | B.64 | C.6 |
| 1.1277 | B.65 | C.6 |
| 1.1278 | B.66 | C.6 |
| 1.1279 | B.67 | C.6 |
| 1.1280 | B.68 | C.6 |
| 1.1281 | B.69 | C.6 |
| 1.1282 | B.70 | C.6 |
| 1.1283 | B.71 | C.6 |
| 1.1284 | B.72 | C.6 |
| 1.1285 | B.73 | C.6 |
| 1.1286 | B.74 | C.6 |
| 1.1287 | B.75 | C.6 |
| 1.1288 | B.76 | C.6 |
| 1.1289 | B.77 | C.6 |
| 1.1290 | B.78 | C.6 |
| 1.1291 | B.79 | C.6 |
| 1.1292 | B.80 | C.6 |
| 1.1293 | B.81 | C.6 |
| 1.1294 | B.82 | C.6 |
| 1.1295 | B.83 | C.6 |
| 1.1296 | B.84 | C.6 |
| 1.1297 | B.85 | C.6 |
| 1.1298 | B.86 | C.6 |
| 1.1299 | B.87 | C.6 |
| 1.1300 | B.88 | C.6 |
| 1.1301 | B.89 | C.6 |
| 1.1302 | B.90 | C.6 |
| 1.1303 | B.91 | C.6 |
| 1.1304 | B.92 | C.6 |
| 1.1305 | B.93 | C.6 |
| 1.1306 | B.94 | C.6 |
| 1.1307 | B.95 | C.6 |
| 1.1308 | B.96 | C.6 |
| 1.1309 | B.97 | C.6 |
| 1.1310 | B.98 | C.6 |
| 1.1311 | B.99 | C.6 |
| 1.1312 | B.100 | C.6 |
| 1.1313 | B.101 | C.6 |
| 1.1314 | B.102 | C.6 |
| 1.1315 | B.103 | C.6 |
| 1.1316 | B.104 | C.6 |
| 1.1317 | B.105 | C.6 |
| 1.1318 | B.106 | C.6 |
| 1.1319 | B.107 | C.6 |
| 1.1320 | B.108 | C.6 |

TABLE T-continued (compositions 1.1 to 1.3653):

| comp. no. | herbi-cide B | safener C |
|---|---|---|
| 1.1321 | B.109 | C.6 |
| 1.1322 | B.110 | C.6 |
| 1.1323 | B.111 | C.6 |
| 1.1324 | B.112 | C.6 |
| 1.1325 | B.113 | C.6 |
| 1.1326 | B.114 | C.6 |
| 1.1327 | B.115 | C.6 |
| 1.1328 | B.116 | C.6 |
| 1.1329 | B.117 | C.6 |
| 1.1330 | B.118 | C.6 |
| 1.1331 | B.119 | C.6 |
| 1.1332 | B.120 | C.6 |
| 1.1333 | B.121 | C.6 |
| 1.1334 | B.122 | C.6 |
| 1.1335 | B.123 | C.6 |
| 1.1336 | B.124 | C.6 |
| 1.1337 | B.125 | C.6 |
| 1.1338 | B.126 | C.6 |
| 1.1339 | B.127 | C.6 |
| 1.1340 | B.128 | C.6 |
| 1.1341 | B.129 | C.6 |
| 1.1342 | B.130 | C.6 |
| 1.1343 | B.131 | C.6 |
| 1.1344 | B.132 | C.6 |
| 1.1345 | B.133 | C.6 |
| 1.1346 | B.134 | C.6 |
| 1.1347 | B.135 | C.6 |
| 1.1348 | B.136 | C.6 |
| 1.1349 | B.137 | C.6 |
| 1.1350 | B.138 | C.6 |
| 1.1351 | B.139 | C.6 |
| 1.1352 | B.140 | C.6 |
| 1.1353 | B.141 | C.6 |
| 1.1354 | B.142 | C.6 |
| 1.1355 | B.143 | C.6 |
| 1.1356 | B.144 | C.6 |
| 1.1357 | B.145 | C.6 |
| 1.1358 | B.146 | C.6 |
| 1.1359 | B.147 | C.6 |
| 1.1360 | B.148 | C.6 |
| 1.1361 | B.149 | C.6 |
| 1.1362 | B.150 | C.6 |
| 1.1363 | B.151 | C.6 |
| 1.1364 | B.152 | C.6 |
| 1.1365 | B.153 | C.6 |
| 1.1366 | B.154 | C.6 |
| 1.1367 | B.155 | C.6 |
| 1.1368 | B.156 | C.6 |
| 1.1369 | B.157 | C.6 |
| 1.1370 | B.158 | C.6 |
| 1.1371 | B.159 | C.6 |
| 1.1372 | B.160 | C.6 |
| 1.1373 | B.161 | C.6 |
| 1.1374 | B.162 | C.6 |
| 1.1375 | B.163 | C.6 |
| 1.1376 | B.164 | C.6 |
| 1.1377 | B.165 | C.6 |
| 1.1378 | B.166 | C.6 |
| 1.1379 | B.167 | C.6 |
| 1.1380 | B.168 | C.6 |
| 1.1381 | B.169 | C.6 |
| 1.1382 | B.170 | C.6 |
| 1.1383 | B.171 | C.6 |
| 1.1384 | B.172 | C.6 |
| 1.1385 | B.173 | C.6 |
| 1.1386 | B.174 | C.6 |
| 1.1387 | B.175 | C.6 |
| 1.1388 | B.176 | C.6 |
| 1.1389 | B.177 | C.6 |
| 1.1390 | B.178 | C.6 |
| 1.1391 | B.179 | C.6 |
| 1.1392 | B.180 | C.6 |
| 1.1393 | B.181 | C.6 |
| 1.1394 | B.182 | C.6 |
| 1.1395 | B.183 | C.6 |
| 1.1396 | B.184 | C.6 |
| 1.1397 | B.185 | C.6 |
| 1.1398 | B.186 | C.6 |
| 1.1399 | B.187 | C.6 |
| 1.1400 | B.188 | C.6 |
| 1.1401 | B.189 | C.6 |
| 1.1402 | B.190 | C.6 |
| 1.1403 | B.191 | C.6 |
| 1.1404 | B.192 | C.6 |
| 1.1405 | B.193 | C.6 |
| 1.1406 | B.194 | C.6 |
| 1.1407 | B.195 | C.6 |
| 1.1408 | B.196 | C.6 |
| 1.1409 | B.197 | C.6 |
| 1.1410 | B.198 | C.6 |
| 1.1411 | B.199 | C.6 |
| 1.1412 | B.200 | C.6 |
| 1.1413 | B.201 | C.6 |
| 1.1414 | B.202 | C.6 |
| 1.1415 | B.1 | C.7 |
| 1.1416 | B.2 | C.7 |
| 1.1417 | B.3 | C.7 |
| 1.1418 | B.4 | C.7 |
| 1.1419 | B.5 | C.7 |
| 1.1420 | B.6 | C.7 |
| 1.1421 | B.7 | C.7 |
| 1.1422 | B.8 | C.7 |
| 1.1423 | B.9 | C.7 |
| 1.1424 | B.10 | C.7 |
| 1.1425 | B.11 | C.7 |
| 1.1426 | B.12 | C.7 |
| 1.1427 | B.13 | C.7 |
| 1.1428 | B.14 | C.7 |
| 1.1429 | B.15 | C.7 |
| 1.1430 | B.16 | C.7 |
| 1.1431 | B.17 | C.7 |
| 1.1432 | B.18 | C.7 |
| 1.1433 | B.19 | C.7 |
| 1.1434 | B.20 | C.7 |
| 1.1435 | B.21 | C.7 |
| 1.1436 | B.22 | C.7 |
| 1.1437 | B.23 | C.7 |
| 1.1438 | B.24 | C.7 |
| 1.1439 | B.25 | C.7 |
| 1.1440 | B.26 | C.7 |
| 1.1441 | B.27 | C.7 |
| 1.1442 | B.28 | C.7 |
| 1.1443 | B.29 | C.7 |
| 1.1444 | B.30 | C.7 |
| 1.1445 | B.31 | C.7 |
| 1.1446 | B.32 | C.7 |
| 1.1447 | B.33 | C.7 |
| 1.1448 | B.34 | C.7 |
| 1.1449 | B.35 | C.7 |
| 1.1450 | B.36 | C.7 |
| 1.1451 | B.37 | C.7 |
| 1.1452 | B.38 | C.7 |
| 1.1453 | B.39 | C.7 |
| 1.1454 | B.40 | C.7 |
| 1.1455 | B.41 | C.7 |
| 1.1456 | B.42 | C.7 |
| 1.1457 | B.43 | C.7 |
| 1.1458 | B.44 | C.7 |
| 1.1459 | B.45 | C.7 |
| 1.1460 | B.46 | C.7 |
| 1.1461 | B.47 | C.7 |
| 1.1462 | B.48 | C.7 |
| 1.1463 | B.49 | C.7 |
| 1.1464 | B.50 | C.7 |
| 1.1465 | B.51 | C.7 |
| 1.1466 | B.52 | C.7 |
| 1.1467 | B.53 | C.7 |
| 1.1468 | B.54 | C.7 |
| 1.1469 | B.55 | C.7 |
| 1.1470 | B.56 | C.7 |

TABLE T-continued (compositions 1.1 to 1.3653):

| comp. no. | herbicide B | safener C |
|---|---|---|
| 1.1471 | B.57 | C.7 |
| 1.1472 | B.58 | C.7 |
| 1.1473 | B.59 | C.7 |
| 1.1474 | B.60 | C.7 |
| 1.1475 | B.61 | C.7 |
| 1.1476 | B.62 | C.7 |
| 1.1477 | B.63 | C.7 |
| 1.1478 | B.64 | C.7 |
| 1.1479 | B.65 | C.7 |
| 1.1480 | B.66 | C.7 |
| 1.1481 | B.67 | C.7 |
| 1.1482 | B.68 | C.7 |
| 1.1483 | B.69 | C.7 |
| 1.1484 | B.70 | C.7 |
| 1.1485 | B.71 | C.7 |
| 1.1486 | B.72 | C.7 |
| 1.1487 | B.73 | C.7 |
| 1.1488 | B.74 | C.7 |
| 1.1489 | B.75 | C.7 |
| 1.1490 | B.76 | C.7 |
| 1.1491 | B.77 | C.7 |
| 1.1492 | B.78 | C.7 |
| 1.1493 | B.79 | C.7 |
| 1.1494 | B.80 | C.7 |
| 1.1495 | B.81 | C.7 |
| 1.1496 | B.82 | C.7 |
| 1.1497 | B.83 | C.7 |
| 1.1498 | B.84 | C.7 |
| 1.1499 | B.85 | C.7 |
| 1.1500 | B.86 | C.7 |
| 1.1501 | B.87 | C.7 |
| 1.1502 | B.88 | C.7 |
| 1.1503 | B.89 | C.7 |
| 1.1504 | B.90 | C.7 |
| 1.1505 | B.91 | C.7 |
| 1.1506 | B.92 | C.7 |
| 1.1507 | B.93 | C.7 |
| 1.1508 | B.94 | C.7 |
| 1.1509 | B.95 | C.7 |
| 1.1510 | B.96 | C.7 |
| 1.1511 | B.97 | C.7 |
| 1.1512 | B.98 | C.7 |
| 1.1513 | B.99 | C.7 |
| 1.1514 | B.100 | C.7 |
| 1.1515 | B.101 | C.7 |
| 1.1516 | B.102 | C.7 |
| 1.1517 | B.103 | C.7 |
| 1.1518 | B.104 | C.7 |
| 1.1519 | B.105 | C.7 |
| 1.1520 | B.106 | C.7 |
| 1.1521 | B.107 | C.7 |
| 1.1522 | B.108 | C.7 |
| 1.1523 | B.109 | C.7 |
| 1.1524 | B.110 | C.7 |
| 1.1525 | B.111 | C.7 |
| 1.1526 | B.112 | C.7 |
| 1.1527 | B.113 | C.7 |
| 1.1528 | B.114 | C.7 |
| 1.1529 | B.115 | C.7 |
| 1.1530 | B.116 | C.7 |
| 1.1531 | B.117 | C.7 |
| 1.1532 | B.118 | C.7 |
| 1.1533 | B.119 | C.7 |
| 1.1534 | B.120 | C.7 |
| 1.1535 | B.121 | C.7 |
| 1.1536 | B.122 | C.7 |
| 1.1537 | B.123 | C.7 |
| 1.1538 | B.124 | C.7 |
| 1.1539 | B.125 | C.7 |
| 1.1540 | B.126 | C.7 |
| 1.1541 | B.127 | C.7 |
| 1.1542 | B.128 | C.7 |
| 1.1543 | B.129 | C.7 |
| 1.1544 | B.130 | C.7 |
| 1.1545 | B.131 | C.7 |
| 1.1546 | B.132 | C.7 |
| 1.1547 | B.133 | C.7 |
| 1.1548 | B.134 | C.7 |
| 1.1549 | B.135 | C.7 |
| 1.1550 | B.136 | C.7 |
| 1.1551 | B.137 | C.7 |
| 1.1552 | B.138 | C.7 |
| 1.1553 | B.139 | C.7 |
| 1.1554 | B.140 | C.7 |
| 1.1555 | B.141 | C.7 |
| 1.1556 | B.142 | C.7 |
| 1.1557 | B.143 | C.7 |
| 1.1558 | B.144 | C.7 |
| 1.1559 | B.145 | C.7 |
| 1.1560 | B.146 | C.7 |
| 1.1561 | B.147 | C.7 |
| 1.1562 | B.148 | C.7 |
| 1.1563 | B.149 | C.7 |
| 1.1564 | B.150 | C.7 |
| 1.1565 | B.151 | C.7 |
| 1.1566 | B.152 | C.7 |
| 1.1567 | B.153 | C.7 |
| 1.1568 | B.154 | C.7 |
| 1.1569 | B.155 | C.7 |
| 1.1570 | B.156 | C.7 |
| 1.1571 | B.157 | C.7 |
| 1.1572 | B.158 | C.7 |
| 1.1573 | B.159 | C.7 |
| 1.1574 | B.160 | C.7 |
| 1.1575 | B.161 | C.7 |
| 1.1576 | B.162 | C.7 |
| 1.1577 | B.163 | C.7 |
| 1.1578 | B.164 | C.7 |
| 1.1579 | B.165 | C.7 |
| 1.1580 | B.166 | C.7 |
| 1.1581 | B.167 | C.7 |
| 1.1582 | B.168 | C.7 |
| 1.1583 | B.169 | C.7 |
| 1.1584 | B.170 | C.7 |
| 1.1585 | B.171 | C.7 |
| 1.1586 | B.172 | C.7 |
| 1.1587 | B.173 | C.7 |
| 1.1588 | B.174 | C.7 |
| 1.1589 | B.175 | C.7 |
| 1.1590 | B.176 | C.7 |
| 1.1591 | B.177 | C.7 |
| 1.1592 | B.178 | C.7 |
| 1.1593 | B.179 | C.7 |
| 1.1594 | B.180 | C.7 |
| 1.1595 | B.181 | C.7 |
| 1.1596 | B.182 | C.7 |
| 1.1597 | B.183 | C.7 |
| 1.1598 | B.184 | C.7 |
| 1.1599 | B.185 | C.7 |
| 1.1600 | B.186 | C.7 |
| 1.1601 | B.187 | C.7 |
| 1.1602 | B.188 | C.7 |
| 1.1603 | B.189 | C.7 |
| 1.1604 | B.190 | C.7 |
| 1.1605 | B.191 | C.7 |
| 1.1606 | B.192 | C.7 |
| 1.1607 | B.193 | C.7 |
| 1.1608 | B.194 | C.7 |
| 1.1609 | B.195 | C.7 |
| 1.1610 | B.196 | C.7 |
| 1.1611 | B.197 | C.7 |
| 1.1612 | B.198 | C.7 |
| 1.1613 | B.199 | C.7 |
| 1.1614 | B.200 | C.7 |
| 1.1615 | B.201 | C.7 |
| 1.1616 | B.202 | C.7 |
| 1.1617 | B.1 | C.8 |
| 1.1618 | B.2 | C.8 |
| 1.1619 | B.3 | C.8 |
| 1.1620 | B.4 | C.8 |

TABLE T-continued (compositions 1.1 to 1.3653):

| comp. no. | herbi-cide B | safener C |
|---|---|---|
| 1.1621 | B.5 | C.8 |
| 1.1622 | B.6 | C.8 |
| 1.1623 | B.7 | C.8 |
| 1.1624 | B.8 | C.8 |
| 1.1625 | B.9 | C.8 |
| 1.1626 | B.10 | C.8 |
| 1.1627 | B.11 | C.8 |
| 1.1628 | B.12 | C.8 |
| 1.1629 | B.13 | C.8 |
| 1.1630 | B.14 | C.8 |
| 1.1631 | B.15 | C.8 |
| 1.1632 | B.16 | C.8 |
| 1.1633 | B.17 | C.8 |
| 1.1634 | B.18 | C.8 |
| 1.1635 | B.19 | C.8 |
| 1.1636 | B.20 | C.8 |
| 1.1637 | B.21 | C.8 |
| 1.1638 | B.22 | C.8 |
| 1.1639 | B.23 | C.8 |
| 1.1640 | B.24 | C.8 |
| 1.1641 | B.25 | C.8 |
| 1.1642 | B.26 | C.8 |
| 1.1643 | B.27 | C.8 |
| 1.1644 | B.28 | C.8 |
| 1.1645 | B.29 | C.8 |
| 1.1646 | B.30 | C.8 |
| 1.1647 | B.31 | C.8 |
| 1.1648 | B.32 | C.8 |
| 1.1649 | B.33 | C.8 |
| 1.1650 | B.34 | C.8 |
| 1.1651 | B.35 | C.8 |
| 1.1652 | B.36 | C.8 |
| 1.1653 | B.37 | C.8 |
| 1.1654 | B.38 | C.8 |
| 1.1655 | B.39 | C.8 |
| 1.1656 | B.40 | C.8 |
| 1.1657 | B.41 | C.8 |
| 1.1658 | B.42 | C.8 |
| 1.1659 | B.43 | C.8 |
| 1.1660 | B.44 | C.8 |
| 1.1661 | B.45 | C.8 |
| 1.1662 | B.46 | C.8 |
| 1.1663 | B.47 | C.8 |
| 1.1664 | B.48 | C.8 |
| 1.1665 | B.49 | C.8 |
| 1.1666 | B.50 | C.8 |
| 1.1667 | B.51 | C.8 |
| 1.1668 | B.52 | C.8 |
| 1.1669 | B.53 | C.8 |
| 1.1670 | B.54 | C.8 |
| 1.1671 | B.55 | C.8 |
| 1.1672 | B.56 | C.8 |
| 1.1673 | B.57 | C.8 |
| 1.1674 | B.58 | C.8 |
| 1.1675 | B.59 | C.8 |
| 1.1676 | B.60 | C.8 |
| 1.1677 | B.61 | C.8 |
| 1.1678 | B.62 | C.8 |
| 1.1679 | B.63 | C.8 |
| 1.1680 | B.64 | C.8 |
| 1.1681 | B.65 | C.8 |
| 1.1682 | B.66 | C.8 |
| 1.1683 | B.67 | C.8 |
| 1.1684 | B.68 | C.8 |
| 1.1685 | B.69 | C.8 |
| 1.1686 | B.70 | C.8 |
| 1.1687 | B.71 | C.8 |
| 1.1688 | B.72 | C.8 |
| 1.1689 | B.73 | C.8 |
| 1.1690 | B.74 | C.8 |
| 1.1691 | B.75 | C.8 |
| 1.1692 | B.76 | C.8 |
| 1.1693 | B.77 | C.8 |
| 1.1694 | B.78 | C.8 |
| 1.1695 | B.79 | C.8 |
| 1.1696 | B.80 | C.8 |
| 1.1697 | B.81 | C.8 |
| 1.1698 | B.82 | C.8 |
| 1.1699 | B.83 | C.8 |
| 1.1700 | B.84 | C.8 |
| 1.1701 | B.85 | C.8 |
| 1.1702 | B.86 | C.8 |
| 1.1703 | B.87 | C.8 |
| 1.1704 | B.88 | C.8 |
| 1.1705 | B.89 | C.8 |
| 1.1706 | B.90 | C.8 |
| 1.1707 | B.91 | C.8 |
| 1.1708 | B.92 | C.8 |
| 1.1709 | B.93 | C.8 |
| 1.1710 | B.94 | C.8 |
| 1.1711 | B.95 | C.8 |
| 1.1712 | B.96 | C.8 |
| 1.1713 | B.97 | C.8 |
| 1.1714 | B.98 | C.8 |
| 1.1715 | B.99 | C.8 |
| 1.1716 | B.100 | C.8 |
| 1.1717 | B.101 | C.8 |
| 1.1718 | B.102 | C.8 |
| 1.1719 | B.103 | C.8 |
| 1.1720 | B.104 | C.8 |
| 1.1721 | B.105 | C.8 |
| 1.1722 | B.106 | C.8 |
| 1.1723 | B.107 | C.8 |
| 1.1724 | B.108 | C.8 |
| 1.1725 | B.109 | C.8 |
| 1.1726 | B.110 | C.8 |
| 1.1727 | B.111 | C.8 |
| 1.1728 | B.112 | C.8 |
| 1.1729 | B.113 | C.8 |
| 1.1730 | B.114 | C.8 |
| 1.1731 | B.115 | C.8 |
| 1.1732 | B.116 | C.8 |
| 1.1733 | B.117 | C.8 |
| 1.1734 | B.118 | C.8 |
| 1.1735 | B.119 | C.8 |
| 1.1736 | B.120 | C.8 |
| 1.1737 | B.121 | C.8 |
| 1.1738 | B.122 | C.8 |
| 1.1739 | B.123 | C.8 |
| 1.1740 | B.124 | C.8 |
| 1.1741 | B.125 | C.8 |
| 1.1742 | B.126 | C.8 |
| 1.1743 | B.127 | C.8 |
| 1.1744 | B.128 | C.8 |
| 1.1745 | B.129 | C.8 |
| 1.1746 | B.130 | C.8 |
| 1.1747 | B.131 | C.8 |
| 1.1748 | B.132 | C.8 |
| 1.1749 | B.133 | C.8 |
| 1.1750 | B.134 | C.8 |
| 1.1751 | B.135 | C.8 |
| 1.1752 | B.136 | C.8 |
| 1.1753 | B.137 | C.8 |
| 1.1754 | B.138 | C.8 |
| 1.1755 | B.139 | C.8 |
| 1.1756 | B.140 | C.8 |
| 1.1757 | B.141 | C.8 |
| 1.1758 | B.142 | C.8 |
| 1.1759 | B.143 | C.8 |
| 1.1760 | B.144 | C.8 |
| 1.1761 | B.145 | C.8 |
| 1.1762 | B.146 | C.8 |
| 1.1763 | B.147 | C.8 |
| 1.1764 | B.148 | C.8 |
| 1.1765 | B.149 | C.8 |
| 1.1766 | B.150 | C.8 |
| 1.1767 | B.151 | C.8 |
| 1.1768 | B.152 | C.8 |
| 1.1769 | B.153 | C.8 |
| 1.1770 | B.154 | C.8 |

TABLE T-continued (compositions 1.1 to 1.3653):

| comp. no. | herbicide B | safener C |
|---|---|---|
| 1.1771 | B.155 | C.8 |
| 1.1772 | B.156 | C.8 |
| 1.1773 | B.157 | C.8 |
| 1.1774 | B.158 | C.8 |
| 1.1775 | B.159 | C.8 |
| 1.1776 | B.160 | C.8 |
| 1.1777 | B.161 | C.8 |
| 1.1778 | B.162 | C.8 |
| 1.1779 | B.163 | C.8 |
| 1.1780 | B.164 | C.8 |
| 1.1781 | B.165 | C.8 |
| 1.1782 | B.166 | C.8 |
| 1.1783 | B.167 | C.8 |
| 1.1784 | B.168 | C.8 |
| 1.1785 | B.169 | C.8 |
| 1.1786 | B.170 | C.8 |
| 1.1787 | B.171 | C.8 |
| 1.1788 | B.172 | C.8 |
| 1.1789 | B.173 | C.8 |
| 1.1790 | B.174 | C.8 |
| 1.1791 | B.175 | C.8 |
| 1.1792 | B.176 | C.8 |
| 1.1793 | B.177 | C.8 |
| 1.1794 | B.178 | C.8 |
| 1.1795 | B.179 | C.8 |
| 1.1796 | B.180 | C.8 |
| 1.1797 | B.181 | C.8 |
| 1.1798 | B.182 | C.8 |
| 1.1799 | B.183 | C.8 |
| 1.1800 | B.184 | C.8 |
| 1.1801 | B.185 | C.8 |
| 1.1802 | B.186 | C.8 |
| 1.1803 | B.187 | C.8 |
| 1.1804 | B.188 | C.8 |
| 1.1805 | B.189 | C.8 |
| 1.1806 | B.190 | C.8 |
| 1.1807 | B.191 | C.8 |
| 1.1808 | B.192 | C.8 |
| 1.1809 | B.193 | C.8 |
| 1.1810 | B.194 | C.8 |
| 1.1811 | B.195 | C.8 |
| 1.1812 | B.196 | C.8 |
| 1.1813 | B.197 | C.8 |
| 1.1814 | B.198 | C.8 |
| 1.1815 | B.199 | C.8 |
| 1.1816 | B.200 | C.8 |
| 1.1817 | B.201 | C.8 |
| 1.1818 | B.202 | C.8 |
| 1.1819 | B.1 | C.9 |
| 1.1820 | B.2 | C.9 |
| 1.1821 | B.3 | C.9 |
| 1.1822 | B.4 | C.9 |
| 1.1823 | B.5 | C.9 |
| 1.1824 | B.6 | C.9 |
| 1.1825 | B.7 | C.9 |
| 1.1826 | B.8 | C.9 |
| 1.1827 | B.9 | C.9 |
| 1.1828 | B.10 | C.9 |
| 1.1829 | B.11 | C.9 |
| 1.1830 | B.12 | C.9 |
| 1.1831 | B.13 | C.9 |
| 1.1832 | B.14 | C.9 |
| 1.1833 | B.15 | C.9 |
| 1.1834 | B.16 | C.9 |
| 1.1835 | B.17 | C.9 |
| 1.1836 | B.18 | C.9 |
| 1.1837 | B.19 | C.9 |
| 1.1838 | B.20 | C.9 |
| 1.1839 | B.21 | C.9 |
| 1.1840 | B.22 | C.9 |
| 1.1841 | B.23 | C.9 |
| 1.1842 | B.24 | C.9 |
| 1.1843 | B.25 | C.9 |
| 1.1844 | B.26 | C.9 |
| 1.1845 | B.27 | C.9 |
| 1.1846 | B.28 | C.9 |
| 1.1847 | B.29 | C.9 |
| 1.1848 | B.30 | C.9 |
| 1.1849 | B.31 | C.9 |
| 1.1850 | B.32 | C.9 |
| 1.1851 | B.33 | C.9 |
| 1.1852 | B.34 | C.9 |
| 1.1853 | B.35 | C.9 |
| 1.1854 | B.36 | C.9 |
| 1.1855 | B.37 | C.9 |
| 1.1856 | B.38 | C.9 |
| 1.1857 | B.39 | C.9 |
| 1.1858 | B.40 | C.9 |
| 1.1859 | B.41 | C.9 |
| 1.1860 | B.42 | C.9 |
| 1.1861 | B.43 | C.9 |
| 1.1862 | B.44 | C.9 |
| 1.1863 | B.45 | C.9 |
| 1.1864 | B.46 | C.9 |
| 1.1865 | B.47 | C.9 |
| 1.1866 | B.48 | C.9 |
| 1.1867 | B.49 | C.9 |
| 1.1868 | B.50 | C.9 |
| 1.1869 | B.51 | C.9 |
| 1.1870 | B.52 | C.9 |
| 1.1871 | B.53 | C.9 |
| 1.1872 | B.54 | C.9 |
| 1.1873 | B.55 | C.9 |
| 1.1874 | B.56 | C.9 |
| 1.1875 | B.57 | C.9 |
| 1.1876 | B.58 | C.9 |
| 1.1877 | B.59 | C.9 |
| 1.1878 | B.60 | C.9 |
| 1.1879 | B.61 | C.9 |
| 1.1880 | B.62 | C.9 |
| 1.1881 | B.63 | C.9 |
| 1.1882 | B.64 | C.9 |
| 1.1883 | B.65 | C.9 |
| 1.1884 | B.66 | C.9 |
| 1.1885 | B.67 | C.9 |
| 1.1886 | B.68 | C.9 |
| 1.1887 | B.69 | C.9 |
| 1.1888 | B.70 | C.9 |
| 1.1889 | B.71 | C.9 |
| 1.1890 | B.72 | C.9 |
| 1.1891 | B.73 | C.9 |
| 1.1892 | B.74 | C.9 |
| 1.1893 | B.75 | C.9 |
| 1.1894 | B.76 | C.9 |
| 1.1895 | B.77 | C.9 |
| 1.1896 | B.78 | C.9 |
| 1.1897 | B.79 | C.9 |
| 1.1898 | B.80 | C.9 |
| 1.1899 | B.81 | C.9 |
| 1.1900 | B.82 | C.9 |
| 1.1901 | B.83 | C.9 |
| 1.1902 | B.84 | C.9 |
| 1.1903 | B.85 | C.9 |
| 1.1904 | B.86 | C.9 |
| 1.1905 | B.87 | C.9 |
| 1.1906 | B.88 | C.9 |
| 1.1907 | B.89 | C.9 |
| 1.1908 | B.90 | C.9 |
| 1.1909 | B.91 | C.9 |
| 1.1910 | B.92 | C.9 |
| 1.1911 | B.93 | C.9 |
| 1.1912 | B.94 | C.9 |
| 1.1913 | B.95 | C.9 |
| 1.1914 | B.96 | C.9 |
| 1.1915 | B.97 | C.9 |
| 1.1916 | B.98 | C.9 |
| 1.1917 | B.99 | C.9 |
| 1.1918 | B.100 | C.9 |
| 1.1919 | B.101 | C.9 |
| 1.1920 | B.102 | C.9 |

TABLE T-continued (compositions 1.1 to 1.3653):

| comp. no. | herbi-cide B | safener C |
|---|---|---|
| 1.1921 | B.103 | C.9 |
| 1.1922 | B.104 | C.9 |
| 1.1923 | B.105 | C.9 |
| 1.1924 | B.106 | C.9 |
| 1.1925 | B.107 | C.9 |
| 1.1926 | B.108 | C.9 |
| 1.1927 | B.109 | C.9 |
| 1.1928 | B.110 | C.9 |
| 1.1929 | B.111 | C.9 |
| 1.1930 | B.112 | C.9 |
| 1.1931 | B.113 | C.9 |
| 1.1932 | B.114 | C.9 |
| 1.1933 | B.115 | C.9 |
| 1.1934 | B.116 | C.9 |
| 1.1935 | B.117 | C.9 |
| 1.1936 | B.118 | C.9 |
| 1.1937 | B.119 | C.9 |
| 1.1938 | B.120 | C.9 |
| 1.1939 | B.121 | C.9 |
| 1.1940 | B.122 | C.9 |
| 1.1941 | B.123 | C.9 |
| 1.1942 | B.124 | C.9 |
| 1.1943 | B.125 | C.9 |
| 1.1944 | B.126 | C.9 |
| 1.1945 | B.127 | C.9 |
| 1.1946 | B.128 | C.9 |
| 1.1947 | B.129 | C.9 |
| 1.1948 | B.130 | C.9 |
| 1.1949 | B.131 | C.9 |
| 1.1950 | B.132 | C.9 |
| 1.1951 | B.133 | C.9 |
| 1.1952 | B.134 | C.9 |
| 1.1953 | B.135 | C.9 |
| 1.1954 | B.136 | C.9 |
| 1.1955 | B.137 | C.9 |
| 1.1956 | B.138 | C.9 |
| 1.1957 | B.139 | C.9 |
| 1.1958 | B.140 | C.9 |
| 1.1959 | B.141 | C.9 |
| 1.1960 | B.142 | C.9 |
| 1.1961 | B.143 | C.9 |
| 1.1962 | B.144 | C.9 |
| 1.1963 | B.145 | C.9 |
| 1.1964 | B.146 | C.9 |
| 1.1965 | B.147 | C.9 |
| 1.1966 | B.148 | C.9 |
| 1.1967 | B.149 | C.9 |
| 1.1968 | B.150 | C.9 |
| 1.1969 | B.151 | C.9 |
| 1.1970 | B.152 | C.9 |
| 1.1971 | B.153 | C.9 |
| 1.1972 | B.154 | C.9 |
| 1.1973 | B.155 | C.9 |
| 1.1974 | B.156 | C.9 |
| 1.1975 | B.157 | C.9 |
| 1.1976 | B.158 | C.9 |
| 1.1977 | B.159 | C.9 |
| 1.1978 | B.160 | C.9 |
| 1.1979 | B.161 | C.9 |
| 1.1980 | B.162 | C.9 |
| 1.1981 | B.163 | C.9 |
| 1.1982 | B.164 | C.9 |
| 1.1983 | B.165 | C.9 |
| 1.1984 | B.166 | C.9 |
| 1.1985 | B.167 | C.9 |
| 1.1986 | B.168 | C.9 |
| 1.1987 | B.169 | C.9 |
| 1.1988 | B.170 | C.9 |
| 1.1989 | B.171 | C.9 |
| 1.1990 | B.172 | C.9 |
| 1.1991 | B.173 | C.9 |
| 1.1992 | B.174 | C.9 |
| 1.1993 | B.175 | C.9 |
| 1.1994 | B.176 | C.9 |
| 1.1995 | B.177 | C.9 |
| 1.1996 | B.178 | C.9 |
| 1.1997 | B.179 | C.9 |
| 1.1998 | B.180 | C.9 |
| 1.1999 | B.181 | C.9 |
| 1.2000 | B.182 | C.9 |
| 1.2001 | B.183 | C.9 |
| 1.2002 | B.184 | C.9 |
| 1.2003 | B.185 | C.9 |
| 1.2004 | B.186 | C.9 |
| 1.2005 | B.187 | C.9 |
| 1.2006 | B.188 | C.9 |
| 1.2007 | B.189 | C.9 |
| 1.2008 | B.190 | C.9 |
| 1.2009 | B.191 | C.9 |
| 1.2010 | B.192 | C.9 |
| 1.2011 | B.193 | C.9 |
| 1.2012 | B.194 | C.9 |
| 1.2013 | B.195 | C.9 |
| 1.2014 | B.196 | C.9 |
| 1.2015 | B.197 | C.9 |
| 1.2016 | B.198 | C.9 |
| 1.2017 | B.199 | C.9 |
| 1.2018 | B.200 | C.9 |
| 1.2019 | B.201 | C.9 |
| 1.2020 | B.202 | C.9 |
| 1.2021 | B.1 | C.10 |
| 1.2022 | B.2 | C.10 |
| 1.2023 | B.3 | C.10 |
| 1.2024 | B.4 | C.10 |
| 1.2025 | B.5 | C.10 |
| 1.2026 | B.6 | C.10 |
| 1.2027 | B.7 | C.10 |
| 1.2028 | B.8 | C.10 |
| 1.2029 | B.9 | C.10 |
| 1.2030 | B.10 | C.10 |
| 1.2031 | B.11 | C.10 |
| 1.2032 | B.12 | C.10 |
| 1.2033 | B.13 | C.10 |
| 1.2034 | B.14 | C.10 |
| 1.2035 | B.15 | C.10 |
| 1.2036 | B.16 | C.10 |
| 1.2037 | B.17 | C.10 |
| 1.2038 | B.18 | C.10 |
| 1.2039 | B.19 | C.10 |
| 1.2040 | B.20 | C.10 |
| 1.2041 | B.21 | C.10 |
| 1.2042 | B.22 | C.10 |
| 1.2043 | B.23 | C.10 |
| 1.2044 | B.24 | C.10 |
| 1.2045 | B.25 | C.10 |
| 1.2046 | B.26 | C.10 |
| 1.2047 | B.27 | C.10 |
| 1.2048 | B.28 | C.10 |
| 1.2049 | B.29 | C.10 |
| 1.2050 | B.30 | C.10 |
| 1.2051 | B.31 | C.10 |
| 1.2052 | B.32 | C.10 |
| 1.2053 | B.33 | C.10 |
| 1.2054 | B.34 | C.10 |
| 1.2055 | B.35 | C.10 |
| 1.2056 | B.36 | C.10 |
| 1.2057 | B.37 | C.10 |
| 1.2058 | B.38 | C.10 |
| 1.2059 | B.39 | C.10 |
| 1.2060 | B.40 | C.10 |
| 1.2061 | B.41 | C.10 |
| 1.2062 | B.42 | C.10 |
| 1.2063 | B.43 | C.10 |
| 1.2064 | B.44 | C.10 |
| 1.2065 | B.45 | C.10 |
| 1.2066 | B.46 | C.10 |
| 1.2067 | B.47 | C.10 |
| 1.2068 | B.48 | C.10 |
| 1.2069 | B.49 | C.10 |
| 1.2070 | B.50 | C.10 |

TABLE T-continued (compositions 1.1 to 1.3653):

| comp. no. | herbicide B | safener C |
|---|---|---|
| 1.2071 | B.51 | C.10 |
| 1.2072 | B.52 | C.10 |
| 1.2073 | B.53 | C.10 |
| 1.2074 | B.54 | C.10 |
| 1.2075 | B.55 | C.10 |
| 1.2076 | B.56 | C.10 |
| 1.2077 | B.57 | C.10 |
| 1.2078 | B.58 | C.10 |
| 1.2079 | B.59 | C.10 |
| 1.2080 | B.60 | C.10 |
| 1.2081 | B.61 | C.10 |
| 1.2082 | B.62 | C.10 |
| 1.2083 | B.63 | C.10 |
| 1.2084 | B.64 | C.10 |
| 1.2085 | B.65 | C.10 |
| 1.2086 | B.66 | C.10 |
| 1.2087 | B.67 | C.10 |
| 1.2088 | B.68 | C.10 |
| 1.2089 | B.69 | C.10 |
| 1.2090 | B.70 | C.10 |
| 1.2091 | B.71 | C.10 |
| 1.2092 | B.72 | C.10 |
| 1.2093 | B.73 | C.10 |
| 1.2094 | B.74 | C.10 |
| 1.2095 | B.75 | C.10 |
| 1.2096 | B.76 | C.10 |
| 1.2097 | B.77 | C.10 |
| 1.2098 | B.78 | C.10 |
| 1.2099 | B.79 | C.10 |
| 1.2100 | B.80 | C.10 |
| 1.2101 | B.81 | C.10 |
| 1.2102 | B.82 | C.10 |
| 1.2103 | B.83 | C.10 |
| 1.2104 | B.84 | C.10 |
| 1.2105 | B.85 | C.10 |
| 1.2106 | B.86 | C.10 |
| 1.2107 | B.87 | C.10 |
| 1.2108 | B.88 | C.10 |
| 1.2109 | B.89 | C.10 |
| 1.2110 | B.90 | C.10 |
| 1.2111 | B.91 | C.10 |
| 1.2112 | B.92 | C.10 |
| 1.2113 | B.93 | C.10 |
| 1.2114 | B.94 | C.10 |
| 1.2115 | B.95 | C.10 |
| 1.2116 | B.96 | C.10 |
| 1.2117 | B.97 | C.10 |
| 1.2118 | B.98 | C.10 |
| 1.2119 | B.99 | C.10 |
| 1.2120 | B.100 | C.10 |
| 1.2121 | B.101 | C.10 |
| 1.2122 | B.102 | C.10 |
| 1.2123 | B.103 | C.10 |
| 1.2124 | B.104 | C.10 |
| 1.2125 | B.105 | C.10 |
| 1.2126 | B.106 | C.10 |
| 1.2127 | B.107 | C.10 |
| 1.2128 | B.108 | C.10 |
| 1.2129 | B.109 | C.10 |
| 1.2130 | B.110 | C.10 |
| 1.2131 | B.111 | C.10 |
| 1.2132 | B.112 | C.10 |
| 1.2133 | B.113 | C.10 |
| 1.2134 | B.114 | C.10 |
| 1.2135 | B.115 | C.10 |
| 1.2136 | B.116 | C.10 |
| 1.2137 | B.117 | C.10 |
| 1.2138 | B.118 | C.10 |
| 1.2139 | B.119 | C.10 |
| 1.2140 | B.120 | C.10 |
| 1.2141 | B.121 | C.10 |
| 1.2142 | B.122 | C.10 |
| 1.2143 | B.123 | C.10 |
| 1.2144 | B.124 | C.10 |
| 1.2145 | B.125 | C.10 |
| 1.2146 | B.126 | C.10 |
| 1.2147 | B.127 | C.10 |
| 1.2148 | B.128 | C.10 |
| 1.2149 | B.129 | C.10 |
| 1.2150 | B.130 | C.10 |
| 1.2151 | B.131 | C.10 |
| 1.2152 | B.132 | C.10 |
| 1.2153 | B.133 | C.10 |
| 1.2154 | B.134 | C.10 |
| 1.2155 | B.135 | C.10 |
| 1.2156 | B.136 | C.10 |
| 1.2157 | B.137 | C.10 |
| 1.2158 | B.138 | C.10 |
| 1.2159 | B.139 | C.10 |
| 1.2160 | B.140 | C.10 |
| 1.2161 | B.141 | C.10 |
| 1.2162 | B.142 | C.10 |
| 1.2163 | B.143 | C.10 |
| 1.2164 | B.144 | C.10 |
| 1.2165 | B.145 | C.10 |
| 1.2166 | B.146 | C.10 |
| 1.2167 | B.147 | C.10 |
| 1.2168 | B.148 | C.10 |
| 1.2169 | B.149 | C.10 |
| 1.2170 | B.150 | C.10 |
| 1.2171 | B.151 | C.10 |
| 1.2172 | B.152 | C.10 |
| 1.2173 | B.153 | C.10 |
| 1.2174 | B.154 | C.10 |
| 1.2175 | B.155 | C.10 |
| 1.2176 | B.156 | C.10 |
| 1.2177 | B.157 | C.10 |
| 1.2178 | B.158 | C.10 |
| 1.2179 | B.159 | C.10 |
| 1.2180 | B.160 | C.10 |
| 1.2181 | B.161 | C.10 |
| 1.2182 | B.162 | C.10 |
| 1.2183 | B.163 | C.10 |
| 1.2184 | B.164 | C.10 |
| 1.2185 | B.165 | C.10 |
| 1.2186 | B.166 | C.10 |
| 1.2187 | B.167 | C.10 |
| 1.2188 | B.168 | C.10 |
| 1.2189 | B.169 | C.10 |
| 1.2190 | B.170 | C.10 |
| 1.2191 | B.171 | C.10 |
| 1.2192 | B.172 | C.10 |
| 1.2193 | B.173 | C.10 |
| 1.2194 | B.174 | C.10 |
| 1.2195 | B.175 | C.10 |
| 1.2196 | B.176 | C.10 |
| 1.2197 | B.177 | C.10 |
| 1.2198 | B.178 | C.10 |
| 1.2199 | B.179 | C.10 |
| 1.2200 | B.180 | C.10 |
| 1.2201 | B.181 | C.10 |
| 1.2202 | B.182 | C.10 |
| 1.2203 | B.183 | C.10 |
| 1.2204 | B.184 | C.10 |
| 1.2205 | B.185 | C.10 |
| 1.2206 | B.186 | C.10 |
| 1.2207 | B.187 | C.10 |
| 1.2208 | B.188 | C.10 |
| 1.2209 | B.189 | C.10 |
| 1.2210 | B.190 | C.10 |
| 1.2211 | B.191 | C.10 |
| 1.2212 | B.192 | C.10 |
| 1.2213 | B.193 | C.10 |
| 1.2214 | B.194 | C.10 |
| 1.2215 | B.195 | C.10 |
| 1.2216 | B.196 | C.10 |
| 1.2217 | B.197 | C.10 |
| 1.2218 | B.198 | C.10 |
| 1.2219 | B.199 | C.10 |
| 1.2220 | B.200 | C.10 |

TABLE T-continued (compositions 1.1 to 1.3653):

| comp. no. | herbicide B | safener C |
|---|---|---|
| 1.2221 | B.201 | C.10 |
| 1.2222 | B.202 | C.10 |
| 1.2223 | B.1 | C.11 |
| 1.2224 | B.2 | C.11 |
| 1.2225 | B.3 | C.11 |
| 1.2226 | B.4 | C.11 |
| 1.2227 | B.5 | C.11 |
| 1.2228 | B.6 | C.11 |
| 1.2229 | B.7 | C.11 |
| 1.2230 | B.8 | C.11 |
| 1.2231 | B.9 | C.11 |
| 1.2232 | B.10 | C.11 |
| 1.2233 | B.11 | C.11 |
| 1.2234 | B.12 | C.11 |
| 1.2235 | B.13 | C.11 |
| 1.2236 | B.14 | C.11 |
| 1.2237 | B.15 | C.11 |
| 1.2238 | B.16 | C.11 |
| 1.2239 | B.17 | C.11 |
| 1.2240 | B.18 | C.11 |
| 1.2241 | B.19 | C.11 |
| 1.2242 | B.20 | C.11 |
| 1.2243 | B.21 | C.11 |
| 1.2244 | B.22 | C.11 |
| 1.2245 | B.23 | C.11 |
| 1.2246 | B.24 | C.11 |
| 1.2247 | B.25 | C.11 |
| 1.2248 | B.26 | C.11 |
| 1.2249 | B.27 | C.11 |
| 1.2250 | B.28 | C.11 |
| 1.2251 | B.29 | C.11 |
| 1.2252 | B.30 | C.11 |
| 1.2253 | B.31 | C.11 |
| 1.2254 | B.32 | C.11 |
| 1.2255 | B.33 | C.11 |
| 1.2256 | B.34 | C.11 |
| 1.2257 | B.35 | C.11 |
| 1.2258 | B.36 | C.11 |
| 1.2259 | B.37 | C.11 |
| 1.2260 | B.38 | C.11 |
| 1.2261 | B.39 | C.11 |
| 1.2262 | B.40 | C.11 |
| 1.2263 | B.41 | C.11 |
| 1.2264 | B.42 | C.11 |
| 1.2265 | B.43 | C.11 |
| 1.2266 | B.44 | C.11 |
| 1.2267 | B.45 | C.11 |
| 1.2268 | B.46 | C.11 |
| 1.2269 | B.47 | C.11 |
| 1.2270 | B.48 | C.11 |
| 1.2271 | B.49 | C.11 |
| 1.2272 | B.50 | C.11 |
| 1.2273 | B.51 | C.11 |
| 1.2274 | B.52 | C.11 |
| 1.2275 | B.53 | C.11 |
| 1.2276 | B.54 | C.11 |
| 1.2277 | B.55 | C.11 |
| 1.2278 | B.56 | C.11 |
| 1.2279 | B.57 | C.11 |
| 1.2280 | B.58 | C.11 |
| 1.2281 | B.59 | C.11 |
| 1.2282 | B.60 | C.11 |
| 1.2283 | B.61 | C.11 |
| 1.2284 | B.62 | C.11 |
| 1.2285 | B.63 | C.11 |
| 1.2286 | B.64 | C.11 |
| 1.2287 | B.65 | C.11 |
| 1.2288 | B.66 | C.11 |
| 1.2289 | B.67 | C.11 |
| 1.2290 | B.68 | C.11 |
| 1.2291 | B.69 | C.11 |
| 1.2292 | B.70 | C.11 |
| 1.2293 | B.71 | C.11 |
| 1.2294 | B.72 | C.11 |
| 1.2295 | B.73 | C.11 |
| 1.2296 | B.74 | C.11 |
| 1.2297 | B.75 | C.11 |
| 1.2298 | B.76 | C.11 |
| 1.2299 | B.77 | C.11 |
| 1.2300 | B.78 | C.11 |
| 1.2301 | B.79 | C.11 |
| 1.2302 | B.80 | C.11 |
| 1.2303 | B.81 | C.11 |
| 1.2304 | B.82 | C.11 |
| 1.2305 | B.83 | C.11 |
| 1.2306 | B.84 | C.11 |
| 1.2307 | B.85 | C.11 |
| 1.2308 | B.86 | C.11 |
| 1.2309 | B.87 | C.11 |
| 1.2310 | B.88 | C.11 |
| 1.2311 | B.89 | C.11 |
| 1.2312 | B.90 | C.11 |
| 1.2313 | B.91 | C.11 |
| 1.2314 | B.92 | C.11 |
| 1.2315 | B.93 | C.11 |
| 1.2316 | B.94 | C.11 |
| 1.2317 | B.95 | C.11 |
| 1.2318 | B.96 | C.11 |
| 1.2319 | B.97 | C.11 |
| 1.2320 | B.98 | C.11 |
| 1.2321 | B.99 | C.11 |
| 1.2322 | B.100 | C.11 |
| 1.2323 | B.101 | C.11 |
| 1.2324 | B.102 | C.11 |
| 1.2325 | B.103 | C.11 |
| 1.2326 | B.104 | C.11 |
| 1.2327 | B.105 | C.11 |
| 1.2328 | B.106 | C.11 |
| 1.2329 | B.107 | C.11 |
| 1.2330 | B.108 | C.11 |
| 1.2331 | B.109 | C.11 |
| 1.2332 | B.110 | C.11 |
| 1.2333 | B.111 | C.11 |
| 1.2334 | B.112 | C.11 |
| 1.2335 | B.113 | C.11 |
| 1.2336 | B.114 | C.11 |
| 1.2337 | B.115 | C.11 |
| 1.2338 | B.116 | C.11 |
| 1.2339 | B.117 | C.11 |
| 1.2340 | B.118 | C.11 |
| 1.2341 | B.119 | C.11 |
| 1.2342 | B.120 | C.11 |
| 1.2343 | B.121 | C.11 |
| 1.2344 | B.122 | C.11 |
| 1.2345 | B.123 | C.11 |
| 1.2346 | B.124 | C.11 |
| 1.2347 | B.125 | C.11 |
| 1.2348 | B.126 | C.11 |
| 1.2349 | B.127 | C.11 |
| 1.2350 | B.128 | C.11 |
| 1.2351 | B.129 | C.11 |
| 1.2352 | B.130 | C.11 |
| 1.2353 | B.131 | C.11 |
| 1.2354 | B.132 | C.11 |
| 1.2355 | B.133 | C.11 |
| 1.2356 | B.134 | C.11 |
| 1.2357 | B.135 | C.11 |
| 1.2358 | B.136 | C.11 |
| 1.2359 | B.137 | C.11 |
| 1.2360 | B.138 | C.11 |
| 1.2361 | B.139 | C.11 |
| 1.2362 | B.140 | C.11 |
| 1.2363 | B.141 | C.11 |
| 1.2364 | B.142 | C.11 |
| 1.2365 | B.143 | C.11 |
| 1.2366 | B.144 | C.11 |
| 1.2367 | B.145 | C.11 |
| 1.2368 | B.146 | C.11 |
| 1.2369 | B.147 | C.11 |
| 1.2370 | B.148 | C.11 |

TABLE T-continued (compositions 1.1 to 1.3653):

| comp. no. | herbicide B | safener C |
|---|---|---|
| 1.2371 | B.149 | C.11 |
| 1.2372 | B.150 | C.11 |
| 1.2373 | B.151 | C.11 |
| 1.2374 | B.152 | C.11 |
| 1.2375 | B.153 | C.11 |
| 1.2376 | B.154 | C.11 |
| 1.2377 | B.155 | C.11 |
| 1.2378 | B.156 | C.11 |
| 1.2379 | B.157 | C.11 |
| 1.2380 | B.158 | C.11 |
| 1.2381 | B.159 | C.11 |
| 1.2382 | B.160 | C.11 |
| 1.2383 | B.161 | C.11 |
| 1.2384 | B.162 | C.11 |
| 1.2385 | B.163 | C.11 |
| 1.2386 | B.164 | C.11 |
| 1.2387 | B.165 | C.11 |
| 1.2388 | B.166 | C.11 |
| 1.2389 | B.167 | C.11 |
| 1.2390 | B.168 | C.11 |
| 1.2391 | B.169 | C.11 |
| 1.2392 | B.170 | C.11 |
| 1.2393 | B.171 | C.11 |
| 1.2394 | B.172 | C.11 |
| 1.2395 | B.173 | C.11 |
| 1.2396 | B.174 | C.11 |
| 1.2397 | B.175 | C.11 |
| 1.2398 | B.176 | C.11 |
| 1.2399 | B.177 | C.11 |
| 1.2400 | B.178 | C.11 |
| 1.2401 | B.179 | C.11 |
| 1.2402 | B.180 | C.11 |
| 1.2403 | B.181 | C.11 |
| 1.2404 | B.182 | C.11 |
| 1.2405 | B.183 | C.11 |
| 1.2406 | B.184 | C.11 |
| 1.2407 | B.185 | C.11 |
| 1.2408 | B.186 | C.11 |
| 1.2409 | B.187 | C.11 |
| 1.2410 | B.188 | C.11 |
| 1.2411 | B.189 | C.11 |
| 1.2412 | B.190 | C.11 |
| 1.2413 | B.191 | C.11 |
| 1.2414 | B.192 | C.11 |
| 1.2415 | B.193 | C.11 |
| 1.2416 | B.194 | C.11 |
| 1.2417 | B.195 | C.11 |
| 1.2418 | B.196 | C.11 |
| 1.2419 | B.197 | C.11 |
| 1.2420 | B.198 | C.11 |
| 1.2421 | B.199 | C.11 |
| 1.2422 | B.200 | C.11 |
| 1.2423 | B.201 | C.11 |
| 1.2424 | B.202 | C.11 |
| 1.2425 | B.1 | C.12 |
| 1.2426 | B.2 | C.12 |
| 1.2427 | B.3 | C.12 |
| 1.2428 | B.4 | C.12 |
| 1.2429 | B.5 | C.12 |
| 1.2430 | B.6 | C.12 |
| 1.2431 | B.7 | C.12 |
| 1.2432 | B.8 | C.12 |
| 1.2433 | B.9 | C.12 |
| 1.2434 | B.10 | C.12 |
| 1.2435 | B.11 | C.12 |
| 1.2436 | B.12 | C.12 |
| 1.2437 | B.13 | C.12 |
| 1.2438 | B.14 | C.12 |
| 1.2439 | B.15 | C.12 |
| 1.2440 | B.16 | C.12 |
| 1.2441 | B.17 | C.12 |
| 1.2442 | B.18 | C.12 |
| 1.2443 | B.19 | C.12 |
| 1.2444 | B.20 | C.12 |
| 1.2445 | B.21 | C.12 |
| 1.2446 | B.22 | C.12 |
| 1.2447 | B.23 | C.12 |
| 1.2448 | B.24 | C.12 |
| 1.2449 | B.25 | C.12 |
| 1.2450 | B.26 | C.12 |
| 1.2451 | B.27 | C.12 |
| 1.2452 | B.28 | C.12 |
| 1.2453 | B.29 | C.12 |
| 1.2454 | B.30 | C.12 |
| 1.2455 | B.31 | C.12 |
| 1.2456 | B.32 | C.12 |
| 1.2457 | B.33 | C.12 |
| 1.2458 | B.34 | C.12 |
| 1.2459 | B.35 | C.12 |
| 1.2460 | B.36 | C.12 |
| 1.2461 | B.37 | C.12 |
| 1.2462 | B.38 | C.12 |
| 1.2463 | B.39 | C.12 |
| 1.2464 | B.40 | C.12 |
| 1.2465 | B.41 | C.12 |
| 1.2466 | B.42 | C.12 |
| 1.2467 | B.43 | C.12 |
| 1.2468 | B.44 | C.12 |
| 1.2469 | B.45 | C.12 |
| 1.2470 | B.46 | C.12 |
| 1.2471 | B.47 | C.12 |
| 1.2472 | B.48 | C.12 |
| 1.2473 | B.49 | C.12 |
| 1.2474 | B.50 | C.12 |
| 1.2475 | B.51 | C.12 |
| 1.2476 | B.52 | C.12 |
| 1.2477 | B.53 | C.12 |
| 1.2478 | B.54 | C.12 |
| 1.2479 | B.55 | C.12 |
| 1.2480 | B.56 | C.12 |
| 1.2481 | B.57 | C.12 |
| 1.2482 | B.58 | C.12 |
| 1.2483 | B.59 | C.12 |
| 1.2484 | B.60 | C.12 |
| 1.2485 | B.61 | C.12 |
| 1.2486 | B.62 | C.12 |
| 1.2487 | B.63 | C.12 |
| 1.2488 | B.64 | C.12 |
| 1.2489 | B.65 | C.12 |
| 1.2490 | B.66 | C.12 |
| 1.2491 | B.67 | C.12 |
| 1.2492 | B.68 | C.12 |
| 1.2493 | B.69 | C.12 |
| 1.2494 | B.70 | C.12 |
| 1.2495 | B.71 | C.12 |
| 1.2496 | B.72 | C.12 |
| 1.2497 | B.73 | C.12 |
| 1.2498 | B.74 | C.12 |
| 1.2499 | B.75 | C.12 |
| 1.2500 | B.76 | C.12 |
| 1.2501 | B.77 | C.12 |
| 1.2502 | B.78 | C.12 |
| 1.2503 | B.79 | C.12 |
| 1.2504 | B.80 | C.12 |
| 1.2505 | B.81 | C.12 |
| 1.2506 | B.82 | C.12 |
| 1.2507 | B.83 | C.12 |
| 1.2508 | B.84 | C.12 |
| 1.2509 | B.85 | C.12 |
| 1.2510 | B.86 | C.12 |
| 1.2511 | B.87 | C.12 |
| 1.2512 | B.88 | C.12 |
| 1.2513 | B.89 | C.12 |
| 1.2514 | B.90 | C.12 |
| 1.2515 | B.91 | C.12 |
| 1.2516 | B.92 | C.12 |
| 1.2517 | B.93 | C.12 |
| 1.2518 | B.94 | C.12 |
| 1.2519 | B.95 | C.12 |
| 1.2520 | B.96 | C.12 |

TABLE T-continued (compositions 1.1 to 1.3653):

| comp. no. | herbi-cide B | safener C |
|---|---|---|
| 1.2521 | B.97 | C.12 |
| 1.2522 | B.98 | C.12 |
| 1.2523 | B.99 | C.12 |
| 1.2524 | B.100 | C.12 |
| 1.2525 | B.101 | C.12 |
| 1.2526 | B.102 | C.12 |
| 1.2527 | B.103 | C.12 |
| 1.2528 | B.104 | C.12 |
| 1.2529 | B.105 | C.12 |
| 1.2530 | B.106 | C.12 |
| 1.2531 | B.107 | C.12 |
| 1.2532 | B.108 | C.12 |
| 1.2533 | B.109 | C.12 |
| 1.2534 | B.110 | C.12 |
| 1.2535 | B.111 | C.12 |
| 1.2536 | B.112 | C.12 |
| 1.2537 | B.113 | C.12 |
| 1.2538 | B.114 | C.12 |
| 1.2539 | B.115 | C.12 |
| 1.2540 | B.116 | C.12 |
| 1.2541 | B.117 | C.12 |
| 1.2542 | B.118 | C.12 |
| 1.2543 | B.119 | C.12 |
| 1.2544 | B.120 | C.12 |
| 1.2545 | B.121 | C.12 |
| 1.2546 | B.122 | C.12 |
| 1.2547 | B.123 | C.12 |
| 1.2548 | B.124 | C.12 |
| 1.2549 | B.125 | C.12 |
| 1.2550 | B.126 | C.12 |
| 1.2551 | B.127 | C.12 |
| 1.2552 | B.128 | C.12 |
| 1.2553 | B.129 | C.12 |
| 1.2554 | B.130 | C.12 |
| 1.2555 | B.131 | C.12 |
| 1.2556 | B.132 | C.12 |
| 1.2557 | B.133 | C.12 |
| 1.2558 | B.134 | C.12 |
| 1.2559 | B.135 | C.12 |
| 1.2560 | B.136 | C.12 |
| 1.2561 | B.137 | C.12 |
| 1.2562 | B.138 | C.12 |
| 1.2563 | B.139 | C.12 |
| 1.2564 | B.140 | C.12 |
| 1.2565 | B.141 | C.12 |
| 1.2566 | B.142 | C.12 |
| 1.2567 | B.143 | C.12 |
| 1.2568 | B.144 | C.12 |
| 1.2569 | B.145 | C.12 |
| 1.2570 | B.146 | C.12 |
| 1.2571 | B.147 | C.12 |
| 1.2572 | B.148 | C.12 |
| 1.2573 | B.149 | C.12 |
| 1.2574 | B.150 | C.12 |
| 1.2575 | B.151 | C.12 |
| 1.2576 | B.152 | C.12 |
| 1.2577 | B.153 | C.12 |
| 1.2578 | B.154 | C.12 |
| 1.2579 | B.155 | C.12 |
| 1.2580 | B.156 | C.12 |
| 1.2581 | B.157 | C.12 |
| 1.2582 | B.158 | C.12 |
| 1.2583 | B.159 | C.12 |
| 1.2584 | B.160 | C.12 |
| 1.2585 | B.161 | C.12 |
| 1.2586 | B.162 | C.12 |
| 1.2587 | B.163 | C.12 |
| 1.2588 | B.164 | C.12 |
| 1.2589 | B.165 | C.12 |
| 1.2590 | B.166 | C.12 |
| 1.2591 | B.167 | C.12 |
| 1.2592 | B.168 | C.12 |
| 1.2593 | B.169 | C.12 |
| 1.2594 | B.170 | C.12 |
| 1.2595 | B.171 | C.12 |
| 1.2596 | B.172 | C.12 |
| 1.2597 | B.173 | C.12 |
| 1.2598 | B.174 | C.12 |
| 1.2599 | B.175 | C.12 |
| 1.2600 | B.176 | C.12 |
| 1.2601 | B.177 | C.12 |
| 1.2602 | B.178 | C.12 |
| 1.2603 | B.179 | C.12 |
| 1.2604 | B.180 | C.12 |
| 1.2605 | B.181 | C.12 |
| 1.2606 | B.182 | C.12 |
| 1.2607 | B.183 | C.12 |
| 1.2608 | B.184 | C.12 |
| 1.2609 | B.185 | C.12 |
| 1.2610 | B.186 | C.12 |
| 1.2611 | B.187 | C.12 |
| 1.2612 | B.188 | C.12 |
| 1.2613 | B.189 | C.12 |
| 1.2614 | B.190 | C.12 |
| 1.2615 | B.191 | C.12 |
| 1.2616 | B.192 | C.12 |
| 1.2617 | B.193 | C.12 |
| 1.2618 | B.194 | C.12 |
| 1.2619 | B.195 | C.12 |
| 1.2620 | B.196 | C.12 |
| 1.2621 | B.197 | C.12 |
| 1.2622 | B.198 | C.12 |
| 1.2623 | B.199 | C.12 |
| 1.2624 | B.200 | C.12 |
| 1.2625 | B.201 | C.12 |
| 1.2626 | B.202 | C.12 |
| 1.2627 | B.1 | C.13 |
| 1.2628 | B.2 | C.13 |
| 1.2629 | B.3 | C.13 |
| 1.2630 | B.4 | C.13 |
| 1.2631 | B.5 | C.13 |
| 1.2632 | B.6 | C.13 |
| 1.2633 | B.7 | C.13 |
| 1.2634 | B.8 | C.13 |
| 1.2635 | B.9 | C.13 |
| 1.2636 | B.10 | C.13 |
| 1.2637 | B.11 | C.13 |
| 1.2638 | B.12 | C.13 |
| 1.2639 | B.13 | C.13 |
| 1.2640 | B.14 | C.13 |
| 1.2641 | B.15 | C.13 |
| 1.2642 | B.16 | C.13 |
| 1.2643 | B.17 | C.13 |
| 1.2644 | B.18 | C.13 |
| 1.2645 | B.19 | C.13 |
| 1.2646 | B.20 | C.13 |
| 1.2647 | B.21 | C.13 |
| 1.2648 | B.22 | C.13 |
| 1.2649 | B.23 | C.13 |
| 1.2650 | B.24 | C.13 |
| 1.2651 | B.25 | C.13 |
| 1.2652 | B.26 | C.13 |
| 1.2653 | B.27 | C.13 |
| 1.2654 | B.28 | C.13 |
| 1.2655 | B.29 | C.13 |
| 1.2656 | B.30 | C.13 |
| 1.2657 | B.31 | C.13 |
| 1.2658 | B.32 | C.13 |
| 1.2659 | B.33 | C.13 |
| 1.2660 | B.34 | C.13 |
| 1.2661 | B.35 | C.13 |
| 1.2662 | B.36 | C.13 |
| 1.2663 | B.37 | C.13 |
| 1.2664 | B.38 | C.13 |
| 1.2665 | B.39 | C.13 |
| 1.2666 | B.40 | C.13 |
| 1.2667 | B.41 | C.13 |
| 1.2668 | B.42 | C.13 |
| 1.2669 | B.43 | C.13 |
| 1.2670 | B.44 | C.13 |

TABLE T-continued (compositions 1.1 to 1.3653):

| comp. no. | herbicide B | safener C |
|---|---|---|
| 1.2671 | B.45 | C.13 |
| 1.2672 | B.46 | C.13 |
| 1.2673 | B.47 | C.13 |
| 1.2674 | B.48 | C.13 |
| 1.2675 | B.49 | C.13 |
| 1.2676 | B.50 | C.13 |
| 1.2677 | B.51 | C.13 |
| 1.2678 | B.52 | C.13 |
| 1.2679 | B.53 | C.13 |
| 1.2680 | B.54 | C.13 |
| 1.2681 | B.55 | C.13 |
| 1.2682 | B.56 | C.13 |
| 1.2683 | B.57 | C.13 |
| 1.2684 | B.58 | C.13 |
| 1.2685 | B.59 | C.13 |
| 1.2686 | B.60 | C.13 |
| 1.2687 | B.61 | C.13 |
| 1.2688 | B.62 | C.13 |
| 1.2689 | B.63 | C.13 |
| 1.2690 | B.64 | C.13 |
| 1.2691 | B.65 | C.13 |
| 1.2692 | B.66 | C.13 |
| 1.2693 | B.67 | C.13 |
| 1.2694 | B.68 | C.13 |
| 1.2695 | B.69 | C.13 |
| 1.2696 | B.70 | C.13 |
| 1.2697 | B.71 | C.13 |
| 1.2698 | B.72 | C.13 |
| 1.2699 | B.73 | C.13 |
| 1.2700 | B.74 | C.13 |
| 1.2701 | B.75 | C.13 |
| 1.2702 | B.76 | C.13 |
| 1.2703 | B.77 | C.13 |
| 1.2704 | B.78 | C.13 |
| 1.2705 | B.79 | C.13 |
| 1.2706 | B.80 | C.13 |
| 1.2707 | B.81 | C.13 |
| 1.2708 | B.82 | C.13 |
| 1.2709 | B.83 | C.13 |
| 1.2710 | B.84 | C.13 |
| 1.2711 | B.85 | C.13 |
| 1.2712 | B.86 | C.13 |
| 1.2713 | B.87 | C.13 |
| 1.2714 | B.88 | C.13 |
| 1.2715 | B.89 | C.13 |
| 1.2716 | B.90 | C.13 |
| 1.2717 | B.91 | C.13 |
| 1.2718 | B.92 | C.13 |
| 1.2719 | B.93 | C.13 |
| 1.2720 | B.94 | C.13 |
| 1.2721 | B.95 | C.13 |
| 1.2722 | B.96 | C.13 |
| 1.2723 | B.97 | C.13 |
| 1.2724 | B.98 | C.13 |
| 1.2725 | B.99 | C.13 |
| 1.2726 | B.100 | C.13 |
| 1.2727 | B.101 | C.13 |
| 1.2728 | B.102 | C.13 |
| 1.2729 | B.103 | C.13 |
| 1.2730 | B.104 | C.13 |
| 1.2731 | B.105 | C.13 |
| 1.2732 | B.106 | C.13 |
| 1.2733 | B.107 | C.13 |
| 1.2734 | B.108 | C.13 |
| 1.2735 | B.109 | C.13 |
| 1.2736 | B.110 | C.13 |
| 1.2737 | B.111 | C.13 |
| 1.2738 | B.112 | C.13 |
| 1.2739 | B.113 | C.13 |
| 1.2740 | B.114 | C.13 |
| 1.2741 | B.115 | C.13 |
| 1.2742 | B.116 | C.13 |
| 1.2743 | B.117 | C.13 |
| 1.2744 | B.118 | C.13 |
| 1.2745 | B.119 | C.13 |
| 1.2746 | B.120 | C.13 |
| 1.2747 | B.121 | C.13 |
| 1.2748 | B.122 | C.13 |
| 1.2749 | B.123 | C.13 |
| 1.2750 | B.124 | C.13 |
| 1.2751 | B.125 | C.13 |
| 1.2752 | B.126 | C.13 |
| 1.2753 | B.127 | C.13 |
| 1.2754 | B.128 | C.13 |
| 1.2755 | B.129 | C.13 |
| 1.2756 | B.130 | C.13 |
| 1.2757 | B.131 | C.13 |
| 1.2758 | B.132 | C.13 |
| 1.2759 | B.133 | C.13 |
| 1.2760 | B.134 | C.13 |
| 1.2761 | B.135 | C.13 |
| 1.2762 | B.136 | C.13 |
| 1.2763 | B.137 | C.13 |
| 1.2764 | B.138 | C.13 |
| 1.2765 | B.139 | C.13 |
| 1.2766 | B.140 | C.13 |
| 1.2767 | B.141 | C.13 |
| 1.2768 | B.142 | C.13 |
| 1.2769 | B.143 | C.13 |
| 1.2770 | B.144 | C.13 |
| 1.2771 | B.145 | C.13 |
| 1.2772 | B.146 | C.13 |
| 1.2773 | B.147 | C.13 |
| 1.2774 | B.148 | C.13 |
| 1.2775 | B.149 | C.13 |
| 1.2776 | B.150 | C.13 |
| 1.2777 | B.151 | C.13 |
| 1.2778 | B.152 | C.13 |
| 1.2779 | B.153 | C.13 |
| 1.2780 | B.154 | C.13 |
| 1.2781 | B.155 | C.13 |
| 1.2782 | B.156 | C.13 |
| 1.2783 | B.157 | C.13 |
| 1.2784 | B.158 | C.13 |
| 1.2785 | B.159 | C.13 |
| 1.2786 | B.160 | C.13 |
| 1.2787 | B.161 | C.13 |
| 1.2788 | B.162 | C.13 |
| 1.2789 | B.163 | C.13 |
| 1.2790 | B.164 | C.13 |
| 1.2791 | B.165 | C.13 |
| 1.2792 | B.166 | C.13 |
| 1.2793 | B.167 | C.13 |
| 1.2794 | B.168 | C.13 |
| 1.2795 | B.169 | C.13 |
| 1.2796 | B.170 | C.13 |
| 1.2797 | B.171 | C.13 |
| 1.2798 | B.172 | C.13 |
| 1.2799 | B.173 | C.13 |
| 1.2800 | B.174 | C.13 |
| 1.2801 | B.175 | C.13 |
| 1.2802 | B.176 | C.13 |
| 1.2803 | B.177 | C.13 |
| 1.2804 | B.178 | C.13 |
| 1.2805 | B.179 | C.13 |
| 1.2806 | B.180 | C.13 |
| 1.2807 | B.181 | C.13 |
| 1.2808 | B.182 | C.13 |
| 1.2809 | B.183 | C.13 |
| 1.2810 | B.184 | C.13 |
| 1.2811 | B.185 | C.13 |
| 1.2812 | B.186 | C.13 |
| 1.2813 | B.187 | C.13 |
| 1.2814 | B.188 | C.13 |
| 1.2815 | B.189 | C.13 |
| 1.2816 | B.190 | C.13 |
| 1.2817 | B.191 | C.13 |
| 1.2818 | B.192 | C.13 |
| 1.2819 | B.193 | C.13 |
| 1.2820 | B.194 | C.13 |

TABLE T-continued (compositions 1.1 to 1.3653):

| comp. no. | herbicide B | safener C |
|---|---|---|
| 1.2821 | B.195 | C.13 |
| 1.2822 | B.196 | C.13 |
| 1.2823 | B.197 | C.13 |
| 1.2824 | B.198 | C.13 |
| 1.2825 | B.199 | C.13 |
| 1.2826 | B.200 | C.13 |
| 1.2827 | B.201 | C.13 |
| 1.2828 | B.202 | C.13 |
| 1.2829 | B.1 | C.14 |
| 1.2830 | B.2 | C.14 |
| 1.2831 | B.3 | C.14 |
| 1.2832 | B.4 | C.14 |
| 1.2833 | B.5 | C.14 |
| 1.2834 | B.6 | C.14 |
| 1.2835 | B.7 | C.14 |
| 1.2836 | B.8 | C.14 |
| 1.2837 | B.9 | C.14 |
| 1.2838 | B.10 | C.14 |
| 1.2839 | B.11 | C.14 |
| 1.2840 | B.12 | C.14 |
| 1.2841 | B.13 | C.14 |
| 1.2842 | B.14 | C.14 |
| 1.2843 | B.15 | C.14 |
| 1.2844 | B.16 | C.14 |
| 1.2845 | B.17 | C.14 |
| 1.2846 | B.18 | C.14 |
| 1.2847 | B.19 | C.14 |
| 1.2848 | B.20 | C.14 |
| 1.2849 | B.21 | C.14 |
| 1.2850 | B.22 | C.14 |
| 1.2851 | B.23 | C.14 |
| 1.2852 | B.24 | C.14 |
| 1.2853 | B.25 | C.14 |
| 1.2854 | B.26 | C.14 |
| 1.2855 | B.27 | C.14 |
| 1.2856 | B.28 | C.14 |
| 1.2857 | B.29 | C.14 |
| 1.2858 | B.30 | C.14 |
| 1.2859 | B.31 | C.14 |
| 1.2860 | B.32 | C.14 |
| 1.2861 | B.33 | C.14 |
| 1.2862 | B.34 | C.14 |
| 1.2863 | B.35 | C.14 |
| 1.2864 | B.36 | C.14 |
| 1.2865 | B.37 | C.14 |
| 1.2866 | B.38 | C.14 |
| 1.2867 | B.39 | C.14 |
| 1.2868 | B.40 | C.14 |
| 1.2869 | B.41 | C.14 |
| 1.2870 | B.42 | C.14 |
| 1.2871 | B.43 | C.14 |
| 1.2872 | B.44 | C.14 |
| 1.2873 | B.45 | C.14 |
| 1.2874 | B.46 | C.14 |
| 1.2875 | B.47 | C.14 |
| 1.2876 | B.48 | C.14 |
| 1.2877 | B.49 | C.14 |
| 1.2878 | B.50 | C.14 |
| 1.2879 | B.51 | C.14 |
| 1.2880 | B.52 | C.14 |
| 1.2881 | B.53 | C.14 |
| 1.2882 | B.54 | C.14 |
| 1.2883 | B.55 | C.14 |
| 1.2884 | B.56 | C.14 |
| 1.2885 | B.57 | C.14 |
| 1.2886 | B.58 | C.14 |
| 1.2887 | B.59 | C.14 |
| 1.2888 | B.60 | C.14 |
| 1.2889 | B.61 | C.14 |
| 1.2890 | B.62 | C.14 |
| 1.2891 | B.63 | C.14 |
| 1.2892 | B.64 | C.14 |
| 1.2893 | B.65 | C.14 |
| 1.2894 | B.66 | C.14 |
| 1.2895 | B.67 | C.14 |
| 1.2896 | B.68 | C.14 |
| 1.2897 | B.69 | C.14 |
| 1.2898 | B.70 | C.14 |
| 1.2899 | B.71 | C.14 |
| 1.2900 | B.72 | C.14 |
| 1.2901 | B.73 | C.14 |
| 1.2902 | B.74 | C.14 |
| 1.2903 | B.75 | C.14 |
| 1.2904 | B.76 | C.14 |
| 1.2905 | B.77 | C.14 |
| 1.2906 | B.78 | C.14 |
| 1.2907 | B.79 | C.14 |
| 1.2908 | B.80 | C.14 |
| 1.2909 | B.81 | C.14 |
| 1.2910 | B.82 | C.14 |
| 1.2911 | B.83 | C.14 |
| 1.2912 | B.84 | C.14 |
| 1.2913 | B.85 | C.14 |
| 1.2914 | B.86 | C.14 |
| 1.2915 | B.87 | C.14 |
| 1.2916 | B.88 | C.14 |
| 1.2917 | B.89 | C.14 |
| 1.2918 | B.90 | C.14 |
| 1.2919 | B.91 | C.14 |
| 1.2920 | B.92 | C.14 |
| 1.2921 | B.93 | C.14 |
| 1.2922 | B.94 | C.14 |
| 1.2923 | B.95 | C.14 |
| 1.2924 | B.96 | C.14 |
| 1.2925 | B.97 | C.14 |
| 1.2926 | B.98 | C.14 |
| 1.2927 | B.99 | C.14 |
| 1.2928 | B.100 | C.14 |
| 1.2929 | B.101 | C.14 |
| 1.2930 | B.102 | C.14 |
| 1.2931 | B.103 | C.14 |
| 1.2932 | B.104 | C.14 |
| 1.2933 | B.105 | C.14 |
| 1.2934 | B.106 | C.14 |
| 1.2935 | B.107 | C.14 |
| 1.2936 | B.108 | C.14 |
| 1.2937 | B.109 | C.14 |
| 1.2938 | B.110 | C.14 |
| 1.2939 | B.111 | C.14 |
| 1.2940 | B.112 | C.14 |
| 1.2941 | B.113 | C.14 |
| 1.2942 | B.114 | C.14 |
| 1.2943 | B.115 | C.14 |
| 1.2944 | B.116 | C.14 |
| 1.2945 | B.117 | C.14 |
| 1.2946 | B.118 | C.14 |
| 1.2947 | B.119 | C.14 |
| 1.2948 | B.120 | C.14 |
| 1.2949 | B.121 | C.14 |
| 1.2950 | B.122 | C.14 |
| 1.2951 | B.123 | C.14 |
| 1.2952 | B.124 | C.14 |
| 1.2953 | B.125 | C.14 |
| 1.2954 | B.126 | C.14 |
| 1.2955 | B.127 | C.14 |
| 1.2956 | B.128 | C.14 |
| 1.2957 | B.129 | C.14 |
| 1.2958 | B.130 | C.14 |
| 1.2959 | B.131 | C.14 |
| 1.2960 | B.132 | C.14 |
| 1.2961 | B.133 | C.14 |
| 1.2962 | B.134 | C.14 |
| 1.2963 | B.135 | C.14 |
| 1.2964 | B.136 | C.14 |
| 1.2965 | B.137 | C.14 |
| 1.2966 | B.138 | C.14 |
| 1.2967 | B.139 | C.14 |
| 1.2968 | B.140 | C.14 |
| 1.2969 | B.141 | C.14 |
| 1.2970 | B.142 | C.14 |

TABLE T-continued (compositions 1.1 to 1.3653):

| comp. no. | herbicide B | safener C |
|---|---|---|
| 1.2971 | B.143 | C.14 |
| 1.2972 | B.144 | C.14 |
| 1.2973 | B.145 | C.14 |
| 1.2974 | B.146 | C.14 |
| 1.2975 | B.147 | C.14 |
| 1.2976 | B.148 | C.14 |
| 1.2977 | B.149 | C.14 |
| 1.2978 | B.150 | C.14 |
| 1.2979 | B.151 | C.14 |
| 1.2980 | B.152 | C.14 |
| 1.2981 | B.153 | C.14 |
| 1.2982 | B.154 | C.14 |
| 1.2983 | B.155 | C.14 |
| 1.2984 | B.156 | C.14 |
| 1.2985 | B.157 | C.14 |
| 1.2986 | B.158 | C.14 |
| 1.2987 | B.159 | C.14 |
| 1.2988 | B.160 | C.14 |
| 1.2989 | B.161 | C.14 |
| 1.2990 | B.162 | C.14 |
| 1.2991 | B.163 | C.14 |
| 1.2992 | B.164 | C.14 |
| 1.2993 | B.165 | C.14 |
| 1.2994 | B.166 | C.14 |
| 1.2995 | B.167 | C.14 |
| 1.2996 | B.168 | C.14 |
| 1.2997 | B.169 | C.14 |
| 1.2998 | B.170 | C.14 |
| 1.2999 | B.171 | C.14 |
| 1.3000 | B.172 | C.14 |
| 1.3001 | B.173 | C.14 |
| 1.3002 | B.174 | C.14 |
| 1.3003 | B.175 | C.14 |
| 1.3004 | B.176 | C.14 |
| 1.3005 | B.177 | C.14 |
| 1.3006 | B.178 | C.14 |
| 1.3007 | B.179 | C.14 |
| 1.3008 | B.180 | C.14 |
| 1.3009 | B.181 | C.14 |
| 1.3010 | B.182 | C.14 |
| 1.3011 | B.183 | C.14 |
| 1.3012 | B.184 | C.14 |
| 1.3013 | B.185 | C.14 |
| 1.3014 | B.186 | C.14 |
| 1.3015 | B.187 | C.14 |
| 1.3016 | B.188 | C.14 |
| 1.3017 | B.189 | C.14 |
| 1.3018 | B.190 | C.14 |
| 1.3019 | B.191 | C.14 |
| 1.3020 | B.192 | C.14 |
| 1.3021 | B.193 | C.14 |
| 1.3022 | B.194 | C.14 |
| 1.3023 | B.195 | C.14 |
| 1.3024 | B.196 | C.14 |
| 1.3025 | B.197 | C.14 |
| 1.3026 | B.198 | C.14 |
| 1.3027 | B.199 | C.14 |
| 1.3028 | B.200 | C.14 |
| 1.3029 | B.201 | C.14 |
| 1.3030 | B.202 | C.14 |
| 1.3031 | B.1 | C.15 |
| 1.3032 | B.2 | C.15 |
| 1.3033 | B.3 | C.15 |
| 1.3034 | B.4 | C.15 |
| 1.3035 | B.5 | C.15 |
| 1.3036 | B.6 | C.15 |
| 1.3037 | B.7 | C.15 |
| 1.3038 | B.8 | C.15 |
| 1.3039 | B.9 | C.15 |
| 1.3040 | B.10 | C.15 |
| 1.3041 | B.11 | C.15 |
| 1.3042 | B.12 | C.15 |
| 1.3043 | B.13 | C.15 |
| 1.3044 | B.14 | C.15 |
| 1.3045 | B.15 | C.15 |
| 1.3046 | B.16 | C.15 |
| 1.3047 | B.17 | C.15 |
| 1.3048 | B.18 | C.15 |
| 1.3049 | B.19 | C.15 |
| 1.3050 | B.20 | C.15 |
| 1.3051 | B.21 | C.15 |
| 1.3052 | B.22 | C.15 |
| 1.3053 | B.23 | C.15 |
| 1.3054 | B.24 | C.15 |
| 1.3055 | B.25 | C.15 |
| 1.3056 | B.26 | C.15 |
| 1.3057 | B.27 | C.15 |
| 1.3058 | B.28 | C.15 |
| 1.3059 | B.29 | C.15 |
| 1.3060 | B.30 | C.15 |
| 1.3061 | B.31 | C.15 |
| 1.3062 | B.32 | C.15 |
| 1.3063 | B.33 | C.15 |
| 1.3064 | B.34 | C.15 |
| 1.3065 | B.35 | C.15 |
| 1.3066 | B.36 | C.15 |
| 1.3067 | B.37 | C.15 |
| 1.3068 | B.38 | C.15 |
| 1.3069 | B.39 | C.15 |
| 1.3070 | B.40 | C.15 |
| 1.3071 | B.41 | C.15 |
| 1.3072 | B.42 | C.15 |
| 1.3073 | B.43 | C.15 |
| 1.3074 | B.44 | C.15 |
| 1.3075 | B.45 | C.15 |
| 1.3076 | B.46 | C.15 |
| 1.3077 | B.47 | C.15 |
| 1.3078 | B.48 | C.15 |
| 1.3079 | B.49 | C.15 |
| 1.3080 | B.50 | C.15 |
| 1.3081 | B.51 | C.15 |
| 1.3082 | B.52 | C.15 |
| 1.3083 | B.53 | C.15 |
| 1.3084 | B.54 | C.15 |
| 1.3085 | B.55 | C.15 |
| 1.3086 | B.56 | C.15 |
| 1.3087 | B.57 | C.15 |
| 1.3088 | B.58 | C.15 |
| 1.3089 | B.59 | C.15 |
| 1.3090 | B.60 | C.15 |
| 1.3091 | B.61 | C.15 |
| 1.3092 | B.62 | C.15 |
| 1.3093 | B.63 | C.15 |
| 1.3094 | B.64 | C.15 |
| 1.3095 | B.65 | C.15 |
| 1.3096 | B.66 | C.15 |
| 1.3097 | B.67 | C.15 |
| 1.3098 | B.68 | C.15 |
| 1.3099 | B.69 | C.15 |
| 1.3100 | B.70 | C.15 |
| 1.3101 | B.71 | C.15 |
| 1.3102 | B.72 | C.15 |
| 1.3103 | B.73 | C.15 |
| 1.3104 | B.74 | C.15 |
| 1.3105 | B.75 | C.15 |
| 1.3106 | B.76 | C.15 |
| 1.3107 | B.77 | C.15 |
| 1.3108 | B.78 | C.15 |
| 1.3109 | B.79 | C.15 |
| 1.3110 | B.80 | C.15 |
| 1.3111 | B.81 | C.15 |
| 1.3112 | B.82 | C.15 |
| 1.3113 | B.83 | C.15 |
| 1.3114 | B.84 | C.15 |
| 1.3115 | B.85 | C.15 |
| 1.3116 | B.86 | C.15 |
| 1.3117 | B.87 | C.15 |
| 1.3118 | B.88 | C.15 |
| 1.3119 | B.89 | C.15 |
| 1.3120 | B.90 | C.15 |

TABLE T-continued (compositions 1.1 to 1.3653):

| comp. no. | herbicide B | safener C |
|---|---|---|
| 1.3121 | B.91 | C.15 |
| 1.3122 | B.92 | C.15 |
| 1.3123 | B.93 | C.15 |
| 1.3124 | B.94 | C.15 |
| 1.3125 | B.95 | C.15 |
| 1.3126 | B.96 | C.15 |
| 1.3127 | B.97 | C.15 |
| 1.3128 | B.98 | C.15 |
| 1.3129 | B.99 | C.15 |
| 1.3130 | B.100 | C.15 |
| 1.3131 | B.101 | C.15 |
| 1.3132 | B.102 | C.15 |
| 1.3133 | B.103 | C.15 |
| 1.3134 | B.104 | C.15 |
| 1.3135 | B.105 | C.15 |
| 1.3136 | B.106 | C.15 |
| 1.3137 | B.107 | C.15 |
| 1.3138 | B.108 | C.15 |
| 1.3139 | B.109 | C.15 |
| 1.3140 | B.110 | C.15 |
| 1.3141 | B.111 | C.15 |
| 1.3142 | B.112 | C.15 |
| 1.3143 | B.113 | C.15 |
| 1.3144 | B.114 | C.15 |
| 1.3145 | B.115 | C.15 |
| 1.3146 | B.116 | C.15 |
| 1.3147 | B.117 | C.15 |
| 1.3148 | B.118 | C.15 |
| 1.3149 | B.119 | C.15 |
| 1.3150 | B.120 | C.15 |
| 1.3151 | B.121 | C.15 |
| 1.3152 | B.122 | C.15 |
| 1.3153 | B.123 | C.15 |
| 1.3154 | B.124 | C.15 |
| 1.3155 | B.125 | C.15 |
| 1.3156 | B.126 | C.15 |
| 1.3157 | B.127 | C.15 |
| 1.3158 | B.128 | C.15 |
| 1.3159 | B.129 | C.15 |
| 1.3160 | B.130 | C.15 |
| 1.3161 | B.131 | C.15 |
| 1.3162 | B.132 | C.15 |
| 1.3163 | B.133 | C.15 |
| 1.3164 | B.134 | C.15 |
| 1.3165 | B.135 | C.15 |
| 1.3166 | B.136 | C.15 |
| 1.3167 | B.137 | C.15 |
| 1.3168 | B.138 | C.15 |
| 1.3169 | B.139 | C.15 |
| 1.3170 | B.140 | C.15 |
| 1.3171 | B.141 | C.15 |
| 1.3172 | B.142 | C.15 |
| 1.3173 | B.143 | C.15 |
| 1.3174 | B.144 | C.15 |
| 1.3175 | B.145 | C.15 |
| 1.3176 | B.146 | C.15 |
| 1.3177 | B.147 | C.15 |
| 1.3178 | B.148 | C.15 |
| 1.3179 | B.149 | C.15 |
| 1.3180 | B.150 | C.15 |
| 1.3181 | B.151 | C.15 |
| 1.3182 | B.152 | C.15 |
| 1.3183 | B.153 | C.15 |
| 1.3184 | B.154 | C.15 |
| 1.3185 | B.155 | C.15 |
| 1.3186 | B.156 | C.15 |
| 1.3187 | B.157 | C.15 |
| 1.3188 | B.158 | C.15 |
| 1.3189 | B.159 | C.15 |
| 1.3190 | B.160 | C.15 |
| 1.3191 | B.161 | C.15 |
| 1.3192 | B.162 | C.15 |
| 1.3193 | B.163 | C.15 |
| 1.3194 | B.164 | C.15 |
| 1.3195 | B.165 | C.15 |
| 1.3196 | B.166 | C.15 |
| 1.3197 | B.167 | C.15 |
| 1.3198 | B.168 | C.15 |
| 1.3199 | B.169 | C.15 |
| 1.3200 | B.170 | C.15 |
| 1.3201 | B.171 | C.15 |
| 1.3202 | B.172 | C.15 |
| 1.3203 | B.173 | C.15 |
| 1.3204 | B.174 | C.15 |
| 1.3205 | B.175 | C.15 |
| 1.3206 | B.176 | C.15 |
| 1.3207 | B.177 | C.15 |
| 1.3208 | B.178 | C.15 |
| 1.3209 | B.179 | C.15 |
| 1.3210 | B.180 | C.15 |
| 1.3211 | B.181 | C.15 |
| 1.3212 | B.182 | C.15 |
| 1.3213 | B.183 | C.15 |
| 1.3214 | B.184 | C.15 |
| 1.3215 | B.185 | C.15 |
| 1.3216 | B.186 | C.15 |
| 1.3217 | B.187 | C.15 |
| 1.3218 | B.188 | C.15 |
| 1.3219 | B.189 | C.15 |
| 1.3220 | B.190 | C.15 |
| 1.3221 | B.191 | C.15 |
| 1.3222 | B.192 | C.15 |
| 1.3223 | B.193 | C.15 |
| 1.3224 | B.194 | C.15 |
| 1.3225 | B.195 | C.15 |
| 1.3226 | B.196 | C.15 |
| 1.3227 | B.197 | C.15 |
| 1.3228 | B.198 | C.15 |
| 1.3229 | B.199 | C.15 |
| 1.3230 | B.200 | C.15 |
| 1.3231 | B.201 | C.15 |
| 1.3232 | B.202 | C.15 |
| 1.3233 | B.1 | C.16 |
| 1.3234 | B.2 | C.16 |
| 1.3235 | B.3 | C.16 |
| 1.3236 | B.4 | C.16 |
| 1.3237 | B.5 | C.16 |
| 1.3238 | B.6 | C.16 |
| 1.3239 | B.7 | C.16 |
| 1.3240 | B.8 | C.16 |
| 1.3241 | B.9 | C.16 |
| 1.3242 | B.10 | C.16 |
| 1.3243 | B.11 | C.16 |
| 1.3244 | B.12 | C.16 |
| 1.3245 | B.13 | C.16 |
| 1.3246 | B.14 | C.16 |
| 1.3247 | B.15 | C.16 |
| 1.3248 | B.16 | C.16 |
| 1.3249 | B.17 | C.16 |
| 1.3250 | B.18 | C.16 |
| 1.3251 | B.19 | C.16 |
| 1.3252 | B.20 | C.16 |
| 1.3253 | B.21 | C.16 |
| 1.3254 | B.22 | C.16 |
| 1.3255 | B.23 | C.16 |
| 1.3256 | B.24 | C.16 |
| 1.3257 | B.25 | C.16 |
| 1.3258 | B.26 | C.16 |
| 1.3259 | B.27 | C.16 |
| 1.3260 | B.28 | C.16 |
| 1.3261 | B.29 | C.16 |
| 1.3262 | B.30 | C.16 |
| 1.3263 | B.31 | C.16 |
| 1.3264 | B.32 | C.16 |
| 1.3265 | B.33 | C.16 |
| 1.3266 | B.34 | C.16 |
| 1.3267 | B.35 | C.16 |
| 1.3268 | B.36 | C.16 |
| 1.3269 | B.37 | C.16 |
| 1.3270 | B.38 | C.16 |

TABLE T-continued (compositions 1.1 to 1.3653):

| comp. no. | herbi-cide B | safener C |
|---|---|---|
| 1.3271 | B.39 | C.16 |
| 1.3272 | B.40 | C.16 |
| 1.3273 | B.41 | C.16 |
| 1.3274 | B.42 | C.16 |
| 1.3275 | B.43 | C.16 |
| 1.3276 | B.44 | C.16 |
| 1.3277 | B.45 | C.16 |
| 1.3278 | B.46 | C.16 |
| 1.3279 | B.47 | C.16 |
| 1.3280 | B.48 | C.16 |
| 1.3281 | B.49 | C.16 |
| 1.3282 | B.50 | C.16 |
| 1.3283 | B.51 | C.16 |
| 1.3284 | B.52 | C.16 |
| 1.3285 | B.53 | C.16 |
| 1.3286 | B.54 | C.16 |
| 1.3287 | B.55 | C.16 |
| 1.3288 | B.56 | C.16 |
| 1.3289 | B.57 | C.16 |
| 1.3290 | B.58 | C.16 |
| 1.3291 | B.59 | C.16 |
| 1.3292 | B.60 | C.16 |
| 1.3293 | B.61 | C.16 |
| 1.3294 | B.62 | C.16 |
| 1.3295 | B.63 | C.16 |
| 1.3296 | B.64 | C.16 |
| 1.3297 | B.65 | C.16 |
| 1.3298 | B.66 | C.16 |
| 1.3299 | B.67 | C.16 |
| 1.3300 | B.68 | C.16 |
| 1.3301 | B.69 | C.16 |
| 1.3302 | B.70 | C.16 |
| 1.3303 | B.71 | C.16 |
| 1.3304 | B.72 | C.16 |
| 1.3305 | B.73 | C.16 |
| 1.3306 | B.74 | C.16 |
| 1.3307 | B.75 | C.16 |
| 1.3308 | B.76 | C.16 |
| 1.3309 | B.77 | C.16 |
| 1.3310 | B.78 | C.16 |
| 1.3311 | B.79 | C.16 |
| 1.3312 | B.80 | C.16 |
| 1.3313 | B.81 | C.16 |
| 1.3314 | B.82 | C.16 |
| 1.3315 | B.83 | C.16 |
| 1.3316 | B.84 | C.16 |
| 1.3317 | B.85 | C.16 |
| 1.3318 | B.86 | C.16 |
| 1.3319 | B.87 | C.16 |
| 1.3320 | B.88 | C.16 |
| 1.3321 | B.89 | C.16 |
| 1.3322 | B.90 | C.16 |
| 1.3323 | B.91 | C.16 |
| 1.3324 | B.92 | C.16 |
| 1.3325 | B.93 | C.16 |
| 1.3326 | B.94 | C.16 |
| 1.3327 | B.95 | C.16 |
| 1.3328 | B.96 | C.16 |
| 1.3329 | B.97 | C.16 |
| 1.3330 | B.98 | C.16 |
| 1.3331 | B.99 | C.16 |
| 1.3332 | B.100 | C.16 |
| 1.3333 | B.101 | C.16 |
| 1.3334 | B.102 | C.16 |
| 1.3335 | B.103 | C.16 |
| 1.3336 | B.104 | C.16 |
| 1.3337 | B.105 | C.16 |
| 1.3338 | B.106 | C.16 |
| 1.3339 | B.107 | C.16 |
| 1.3340 | B.108 | C.16 |
| 1.3341 | B.109 | C.16 |
| 1.3342 | B.110 | C.16 |
| 1.3343 | B.111 | C.16 |
| 1.3344 | B.112 | C.16 |
| 1.3345 | B.113 | C.16 |
| 1.3346 | B.114 | C.16 |
| 1.3347 | B.115 | C.16 |
| 1.3348 | B.116 | C.16 |
| 1.3349 | B.117 | C.16 |
| 1.3350 | B.118 | C.16 |
| 1.3351 | B.119 | C.16 |
| 1.3352 | B.120 | C.16 |
| 1.3353 | B.121 | C.16 |
| 1.3354 | B.122 | C.16 |
| 1.3355 | B.123 | C.16 |
| 1.3356 | B.124 | C.16 |
| 1.3357 | B.125 | C.16 |
| 1.3358 | B.126 | C.16 |
| 1.3359 | B.127 | C.16 |
| 1.3360 | B.128 | C.16 |
| 1.3361 | B.129 | C.16 |
| 1.3362 | B.130 | C.16 |
| 1.3363 | B.131 | C.16 |
| 1.3364 | B.132 | C.16 |
| 1.3365 | B.133 | C.16 |
| 1.3366 | B.134 | C.16 |
| 1.3367 | B.135 | C.16 |
| 1.3368 | B.136 | C.16 |
| 1.3369 | B.137 | C.16 |
| 1.3370 | B.138 | C.16 |
| 1.3371 | B.139 | C.16 |
| 1.3372 | B.140 | C.16 |
| 1.3373 | B.141 | C.16 |
| 1.3374 | B.142 | C.16 |
| 1.3375 | B.143 | C.16 |
| 1.3376 | B.144 | C.16 |
| 1.3377 | B.145 | C.16 |
| 1.3378 | B.146 | C.16 |
| 1.3379 | B.147 | C.16 |
| 1.3380 | B.148 | C.16 |
| 1.3381 | B.149 | C.16 |
| 1.3382 | B.150 | C.16 |
| 1.3383 | B.151 | C.16 |
| 1.3384 | B.152 | C.16 |
| 1.3385 | B.153 | C.16 |
| 1.3386 | B.154 | C.16 |
| 1.3387 | B.155 | C.16 |
| 1.3388 | B.156 | C.16 |
| 1.3389 | B.157 | C.16 |
| 1.3390 | B.158 | C.16 |
| 1.3391 | B.159 | C.16 |
| 1.3392 | B.160 | C.16 |
| 1.3393 | B.161 | C.16 |
| 1.3394 | B.162 | C.16 |
| 1.3395 | B.163 | C.16 |
| 1.3396 | B.164 | C.16 |
| 1.3397 | B.165 | C.16 |
| 1.3398 | B.166 | C.16 |
| 1.3399 | B.167 | C.16 |
| 1.3400 | B.168 | C.16 |
| 1.3401 | B.169 | C.16 |
| 1.3402 | B.170 | C.16 |
| 1.3403 | B.171 | C.16 |
| 1.3404 | B.172 | C.16 |
| 1.3405 | B.173 | C.16 |
| 1.3406 | B.174 | C.16 |
| 1.3407 | B.175 | C.16 |
| 1.3408 | B.176 | C.16 |
| 1.3409 | B.177 | C.16 |
| 1.3410 | B.178 | C.16 |
| 1.3411 | B.179 | C.16 |
| 1.3412 | B.180 | C.16 |
| 1.3413 | B.181 | C.16 |
| 1.3414 | B.182 | C.16 |
| 1.3415 | B.183 | C.16 |
| 1.3416 | B.184 | C.16 |
| 1.3417 | B.185 | C.16 |
| 1.3418 | B.186 | C.16 |
| 1.3419 | B.187 | C.16 |
| 1.3420 | B.188 | C.16 |

TABLE T-continued (compositions 1.1 to 1.3653):

| comp. no. | herbi-cide B | safener C |
|---|---|---|
| 1.3421 | B.189 | C.16 |
| 1.3422 | B.190 | C.16 |
| 1.3423 | B.191 | C.16 |
| 1.3424 | B.192 | C.16 |
| 1.3425 | B.193 | C.16 |
| 1.3426 | B.194 | C.16 |
| 1.3427 | B.195 | C.16 |
| 1.3428 | B.196 | C.16 |
| 1.3429 | B.197 | C.16 |
| 1.3430 | B.198 | C.16 |
| 1.3431 | B.199 | C.16 |
| 1.3432 | B.200 | C.16 |
| 1.3433 | B.201 | C.16 |
| 1.3434 | B.202 | C.16 |
| 1.3435 | B.1 | C.17 |
| 1.3436 | B.2 | C.17 |
| 1.3437 | B.3 | C.17 |
| 1.3438 | B.4 | C.17 |
| 1.3439 | B.5 | C.17 |
| 1.3440 | B.6 | C.17 |
| 1.3441 | B.7 | C.17 |
| 1.3442 | B.8 | C.17 |
| 1.3443 | B.9 | C.17 |
| 1.3444 | B.10 | C.17 |
| 1.3445 | B.11 | C.17 |
| 1.3446 | B.12 | C.17 |
| 1.3447 | B.13 | C.17 |
| 1.3448 | B.14 | C.17 |
| 1.3449 | B.15 | C.17 |
| 1.3450 | B.16 | C.17 |
| 1.3451 | B.17 | C.17 |
| 1.3452 | B.18 | C.17 |
| 1.3453 | B.19 | C.17 |
| 1.3454 | B.20 | C.17 |
| 1.3455 | B.21 | C.17 |
| 1.3456 | B.22 | C.17 |
| 1.3457 | B.23 | C.17 |
| 1.3458 | B.24 | C.17 |
| 1.3459 | B.25 | C.17 |
| 1.3460 | B.26 | C.17 |
| 1.3461 | B.27 | C.17 |
| 1.3462 | B.28 | C.17 |
| 1.3463 | B.29 | C.17 |
| 1.3464 | B.30 | C.17 |
| 1.3465 | B.31 | C.17 |
| 1.3466 | B.32 | C.17 |
| 1.3467 | B.33 | C.17 |
| 1.3468 | B.34 | C.17 |
| 1.3469 | B.35 | C.17 |
| 1.3470 | B.36 | C.17 |
| 1.3471 | B.37 | C.17 |
| 1.3472 | B.38 | C.17 |
| 1.3473 | B.39 | C.17 |
| 1.3474 | B.40 | C.17 |
| 1.3475 | B.41 | C.17 |
| 1.3476 | B.42 | C.17 |
| 1.3477 | B.43 | C.17 |
| 1.3478 | B.44 | C.17 |
| 1.3479 | B.45 | C.17 |
| 1.3480 | B.46 | C.17 |
| 1.3481 | B.47 | C.17 |
| 1.3482 | B.48 | C.17 |
| 1.3483 | B.49 | C.17 |
| 1.3484 | B.50 | C.17 |
| 1.3485 | B.51 | C.17 |
| 1.3486 | B.52 | C.17 |
| 1.3487 | B.53 | C.17 |
| 1.3488 | B.54 | C.17 |
| 1.3489 | B.55 | C.17 |
| 1.3490 | B.56 | C.17 |
| 1.3491 | B.57 | C.17 |
| 1.3492 | B.58 | C.17 |
| 1.3493 | B.59 | C.17 |
| 1.3494 | B.60 | C.17 |
| 1.3495 | B.61 | C.17 |
| 1.3496 | B.62 | C.17 |
| 1.3497 | B.63 | C.17 |
| 1.3498 | B.64 | C.17 |
| 1.3499 | B.65 | C.17 |
| 1.3500 | B.66 | C.17 |
| 1.3501 | B.67 | C.17 |
| 1.3502 | B.68 | C.17 |
| 1.3503 | B.69 | C.17 |
| 1.3504 | B.70 | C.17 |
| 1.3505 | B.71 | C.17 |
| 1.3506 | B.72 | C.17 |
| 1.3507 | B.73 | C.17 |
| 1.3508 | B.74 | C.17 |
| 1.3509 | B.75 | C.17 |
| 1.3510 | B.76 | C.17 |
| 1.3511 | B.77 | C.17 |
| 1.3512 | B.78 | C.17 |
| 1.3513 | B.79 | C.17 |
| 1.3514 | B.80 | C.17 |
| 1.3515 | B.81 | C.17 |
| 1.3516 | B.82 | C.17 |
| 1.3517 | B.83 | C.17 |
| 1.3518 | B.84 | C.17 |
| 1.3519 | B.85 | C.17 |
| 1.3520 | B.86 | C.17 |
| 1.3521 | B.87 | C.17 |
| 1.3522 | B.88 | C.17 |
| 1.3523 | B.89 | C.17 |
| 1.3524 | B.90 | C.17 |
| 1.3525 | B.91 | C.17 |
| 1.3526 | B.92 | C.17 |
| 1.3527 | B.93 | C.17 |
| 1.3528 | B.94 | C.17 |
| 1.3529 | B.95 | C.17 |
| 1.3530 | B.96 | C.17 |
| 1.3531 | B.97 | C.17 |
| 1.3532 | B.98 | C.17 |
| 1.3533 | B.99 | C.17 |
| 1.3534 | B.100 | C.17 |
| 1.3535 | B.101 | C.17 |
| 1.3536 | B.102 | C.17 |
| 1.3537 | B.103 | C.17 |
| 1.3538 | B.104 | C.17 |
| 1.3539 | B.105 | C.17 |
| 1.3540 | B.106 | C.17 |
| 1.3541 | B.107 | C.17 |
| 1.3542 | B.108 | C.17 |
| 1.3543 | B.109 | C.17 |
| 1.3544 | B.110 | C.17 |
| 1.3545 | B.111 | C.17 |
| 1.3546 | B.112 | C.17 |
| 1.3547 | B.113 | C.17 |
| 1.3548 | B.114 | C.17 |
| 1.3549 | B.115 | C.17 |
| 1.3550 | B.116 | C.17 |
| 1.3551 | B.117 | C.17 |
| 1.3552 | B.118 | C.17 |
| 1.3553 | B.119 | C.17 |
| 1.3554 | B.120 | C.17 |
| 1.3555 | B.121 | C.17 |
| 1.3556 | B.122 | C.17 |
| 1.3557 | B.123 | C.17 |
| 1.3558 | B.124 | C.17 |
| 1.3559 | B.125 | C.17 |
| 1.3560 | B.126 | C.17 |
| 1.3561 | B.127 | C.17 |
| 1.3562 | B.128 | C.17 |
| 1.3563 | B.129 | C.17 |
| 1.3564 | B.130 | C.17 |
| 1.3565 | B.131 | C.17 |
| 1.3566 | B.132 | C.17 |
| 1.3567 | B.133 | C.17 |
| 1.3568 | B.134 | C.17 |
| 1.3569 | B.135 | C.17 |
| 1.3570 | B.136 | C.17 |

TABLE T-continued (compositions 1.1 to 1.3653):

| comp. no. | herbi-cide B | safener C |
|---|---|---|
| 1.3571 | B.137 | C.17 |
| 1.3572 | B.138 | C.17 |
| 1.3573 | B.139 | C.17 |
| 1.3574 | B.140 | C.17 |
| 1.3575 | B.141 | C.17 |
| 1.3576 | B.142 | C.17 |
| 1.3577 | B.143 | C.17 |
| 1.3578 | B.144 | C.17 |
| 1.3579 | B.145 | C.17 |
| 1.3580 | B.146 | C.17 |
| 1.3581 | B.147 | C.17 |
| 1.3582 | B.148 | C.17 |
| 1.3583 | B.149 | C.17 |
| 1.3584 | B.150 | C.17 |
| 1.3585 | B.151 | C.17 |
| 1.3586 | B.152 | C.17 |
| 1.3587 | B.153 | C.17 |
| 1.3588 | B.154 | C.17 |
| 1.3589 | B.155 | C.17 |
| 1.3590 | B.156 | C.17 |
| 1.3591 | B.157 | C.17 |
| 1.3592 | B.158 | C.17 |
| 1.3593 | B.159 | C.17 |
| 1.3594 | B.160 | C.17 |
| 1.3595 | B.161 | C.17 |
| 1.3596 | B.162 | C.17 |
| 1.3597 | B.163 | C.17 |
| 1.3598 | B.164 | C.17 |
| 1.3599 | B.165 | C.17 |
| 1.3600 | B.166 | C.17 |
| 1.3601 | B.167 | C.17 |
| 1.3602 | B.168 | C.17 |
| 1.3603 | B.169 | C.17 |
| 1.3604 | B.170 | C.17 |
| 1.3605 | B.171 | C.17 |
| 1.3606 | B.172 | C.17 |
| 1.3607 | B.173 | C.17 |
| 1.3608 | B.174 | C.17 |
| 1.3609 | B.175 | C.17 |
| 1.3610 | B.176 | C.17 |
| 1.3611 | B.177 | C.17 |
| 1.3612 | B.178 | C.17 |
| 1.3613 | B.179 | C.17 |
| 1.3614 | B.180 | C.17 |
| 1.3615 | B.181 | C.17 |
| 1.3616 | B.182 | C.17 |
| 1.3617 | B.183 | C.17 |
| 1.3618 | B.184 | C.17 |
| 1.3619 | B.185 | C.17 |
| 1.3620 | B.186 | C.17 |
| 1.3621 | B.187 | C.17 |
| 1.3622 | B.188 | C.17 |
| 1.3623 | B.189 | C.17 |
| 1.3624 | B.190 | C.17 |
| 1.3625 | B.191 | C.17 |
| 1.3626 | B.192 | C.17 |
| 1.3627 | B.193 | C.17 |
| 1.3628 | B.194 | C.17 |
| 1.3629 | B.195 | C.17 |
| 1.3630 | B.196 | C.17 |
| 1.3631 | B.197 | C.17 |
| 1.3632 | B.198 | C.17 |
| 1.3633 | B.199 | C.17 |
| 1.3634 | B.200 | C.17 |
| 1.3635 | B.201 | C.17 |
| 1.3636 | B.202 | C.17 |
| 1.3637 | — | C.1 |
| 1.3638 | — | C.2 |
| 1.3639 | — | C.3 |
| 1.3640 | — | C.4 |
| 1.3641 | — | C.5 |
| 1.3642 | — | C.6 |
| 1.3643 | — | C.7 |
| 1.3644 | — | C.8 |
| 1.3645 | — | C.9 |
| 1.3646 | — | C.10 |
| 1.3647 | — | C.11 |
| 1.3648 | — | C.12 |
| 1.3649 | — | C.13 |
| 1.3650 | — | C.14 |
| 1.3651 | — | C.15 |
| 1.3652 | — | C.16 |
| 1.3653 | — | C.17 |

The specific number for each single composition is deductible as follows:

Composition 1.203 e.g. comprises the compound 1.1.I-3, clethodim (B.1) and benoxacor (C.1) (see table B, entry B.1 and table C, entry C.1).

Also especially preferred are compositions 2.1 to 2.3653 which differ from the compositions 1.1 to 1.3653 only in that they comprise the active compound (1.1.I-4) in place of the compound (1.1.I-3).

Also especially preferred are compositions 3.1 to 3.3653 which differ from the compositions 1.1 to 1.3653 only in that they comprise the active compound (1.1.I-10) in place of the compound (1.1.I-3).

Also especially preferred are compositions 4.1 to 4.3653 which differ from the compositions 1.1 to 1.3653 only in that they comprise the active compound (1.2.I-3) in place of the compound (1.1.I-3).

Also especially preferred are compositions 5.1 to 5.3653 which differ from the compositions 1.1 to 1.3653 only in that they comprise the active compound (1.2.I-4) in place of the compound (1.1.I-3).

Also especially preferred are compositions 6.1 to 6.3653 which differ from the compositions 1.1 to 1.3653 only in that they comprise the active compound (1.2.I-10) in place of the compound (1.1.I-3).

Also especially preferred are compositions 7.1 to 7.3653 which differ from the compositions 1.1 to 1.3653 only in that they comprise the active compound (1.5.I-3) in place of the compound (1.1.I-3).

Also especially preferred are compositions 8.1 to 8.3653 which differ from the compositions 1.1 to 1.3653 only in that they comprise the active compound (1.5.I-4) in place of the compound (1.1.I-3).

Also especially preferred are compositions 9.1 to 9.3653 which differ from the compositions 1.1 to 1.3653 only in that they comprise the active compound (1.5.I-10) in place of the compound (1.1.I-3).

Also especially preferred are compositions 10.1 to 10.3653 which differ from the compositions 1.1 to 1.3653 only in that they comprise the active compound (1.17.I-3) in place of the compound (1.1.I-3).

Also especially preferred are compositions 11.1 to 11.3653 which differ from the compositions 1.1 to 1.3653 only in that they comprise the active compound (1.17.I-4) in place of the compound (1.1.I-3).

Also especially preferred are compositions 12.1 to 12.3653 which differ from the compositions 1.1 to 1.3653 only in that they comprise the active compound (1.17.I-10) in place of the compound (1.1.I-3).

Also especially preferred are compositions 13.1 to 13.3653 which differ from the compositions 1.1 to 1.3653 only in that they additionally comprise B.2 as further herbicide B.

Also especially preferred are compositions 14.1 to 14.3653 which differ from the compositions 1.1 to 1.3653 only in that they additionally comprise B.8 as further herbicide B.

Also especially preferred are compositions 15.1 to 15.3653 which differ from the compositions 1.1 to 1.3653 only in that they additionally comprise B.30 as further herbicide B.

Also especially preferred are compositions 16.1 to 16.3653 which differ from the compositions 1.1 to 1.3653 only in that they additionally comprise B.32 as further herbicide B.

Also especially preferred are compositions 17.1 to 17.3653 which differ from the compositions 1.1 to 1.3653 only in that they additionally comprise B.35 as further herbicide B.

Also especially preferred are compositions 18.1 to 18.3653 which differ from the compositions 1.1 to 1.3653 only in that they additionally comprise B.38 as further herbicide B.

Also especially preferred are compositions 19.1 to 19.3653 which differ from the compositions 1.1 to 1.3653 only in that they additionally comprise B.40 as further herbicide B.

Also especially preferred are compositions 20.1 to 20.3653 which differ from the compositions 1.1 to 1.3653 only in that they additionally comprise B.51 as further herbicide B.

Also especially preferred are compositions 21.1 to 21.3653 which differ from the compositions 1.1 to 1.3653 only in that they additionally comprise B.55 as further herbicide B.

Also especially preferred are compositions 22.1 to 22.3653 which differ from the compositions 1.1 to 1.3653 only in that they additionally comprise B.56 as further herbicide B.

Also especially preferred are compositions 23.1 to 23.3653 which differ from the compositions 1.1 to 1.3653 only in that they additionally comprise B.64 as further herbicide B.

Also especially preferred are compositions 24.1 to 24.3653 which differ from the compositions 1.1 to 1.3653 only in that they additionally comprise B.66 as further herbicide B.

Also especially preferred are compositions 25.1 to 25.3653 which differ from the compositions 1.1 to 1.3653 only in that they additionally comprise B.67 as further herbicide B.

Also especially preferred are compositions 26.1 to 26.3653 which differ from the compositions 1.1 to 1.3653 only in that they additionally comprise B.68 as further herbicide B.

Also especially preferred are compositions 27.1 to 27.3653 which differ from the compositions 1.1 to 1.3653 only in that they additionally comprise B.69 as further herbicide B.

Also especially preferred are compositions 28.1 to 28.3653 which differ from the compositions 1.1 to 1.3653 only in that they additionally comprise B.73 as further herbicide B.

Also especially preferred are compositions 29.1 to 29.3653 which differ from the compositions 1.1 to 1.3653 only in that they additionally comprise B.76 as further herbicide B.

Also especially preferred are compositions 30.1 to 30.3653 which differ from the compositions 1.1 to 1.3653 only in that they additionally comprise B.81 as further herbicide B.

Also especially preferred are compositions 31.1 to 31.3653 which differ from the compositions 1.1 to 1.3653 only in that they additionally comprise B.82 as further herbicide B.

Also especially preferred are compositions 32.1 to 32.3653 which differ from the compositions 1.1 to 1.3653 only in that they additionally comprise B.85 as further herbicide B.

Also especially preferred are compositions 33.1 to 33.3653 which differ from the compositions 1.1 to 1.3653 only in that they additionally comprise B.88 as further herbicide B.

Also especially preferred are compositions 34.1 to 34.3653 which differ from the compositions 1.1 to 1.3653 only in that they additionally comprise B.89 as further herbicide B.

Also especially preferred are compositions 35.1 to 35.3653 which differ from the compositions 1.1 to 1.3653 only in that they additionally comprise B.94 as further herbicide B.

Also especially preferred are compositions 36.1 to 36.3653 which differ from the compositions 1.1 to 1.3653 only in that they additionally comprise B.95 as further herbicide B.

Also especially preferred are compositions 37.1 to 37.3653 which differ from the compositions 1.1 to 1.3653 only in that they additionally comprise B.98 as further herbicide B.

Also especially preferred are compositions 38.1 to 38.3653 which differ from the compositions 1.1 to 1.3653 only in that they additionally comprise B.100 as further herbicide B.

Also especially preferred are compositions 39.1 to 39.3653 which differ from the compositions 1.1 to 1.3653 only in that they additionally comprise B.103 as further herbicide B.

Also especially preferred are compositions 40.1 to 40.3653 which differ from the compositions 1.1 to 1.3653 only in that they additionally comprise B.103 and B.67 as further herbicides B.

Also especially preferred are compositions 41.1 to 41.3653 which differ from the compositions 1.1 to 1.3653 only in that they additionally comprise B.103 and B.76 as further herbicides B.

Also especially preferred are compositions 42.1 to 42.3653 which differ from the compositions 1.1 to 1.3653 only in that they additionally comprise B.103 and B.82 as further herbicides B.

Also especially preferred are compositions 43.1 to 43.3653 which differ from the compositions 1.1 to 1.3653 only in that they additionally comprise B.104 as further herbicide B.

Also especially preferred are compositions 44.1 to 44.3653 which differ from the compositions 1.1 to 1.3653 only in that they additionally comprise B.104 and B.67 as further herbicides B.

Also especially preferred are compositions 45.1 to 45.3653 which differ from the compositions 1.1 to 1.3653 only in that they additionally comprise B.104 and B.76 as further herbicides B.

Also especially preferred are compositions 46.1 to 46.3653 which differ from the compositions 1.1 to 1.3653 only in that they additionally comprise B.104 and B.82 as further herbicides B.

Also especially preferred are compositions 47.1 to 47.3653 which differ from the compositions 1.1 to 1.3653 only in that they additionally comprise B.106 as further herbicide B.

Also especially preferred are compositions 48.1 to 48.3653 which differ from the compositions 1.1 to 1.3653 only in that they additionally comprise B.107 as further herbicide B.

Also especially preferred are compositions 49.1 to 49.3653 which differ from the compositions 1.1 to 1.3653 only in that they additionally comprise B. 107 and B.67 as further herbicides B.

Also especially preferred are compositions 50.1 to 50.3653 which differ from the compositions 1.1 to 1.3653 only in that they additionally comprise B. 107 and B.76 as further herbicides B.

Also especially preferred are compositions 51.1 to 51.3653 which differ from the compositions 1.1 to 1.3653 only in that they additionally comprise B. 107 and B.82 as further herbicides B.

Also especially preferred are compositions 52.1 to 52.3653 which differ from the compositions 1.1 to 1.3653 only in that they additionally comprise B.109 as further herbicide B.

Also especially preferred are compositions 53.1 to 53.3653 which differ from the compositions 1.1 to 1.3653 only in that they additionally comprise B.111 as further herbicide B.

Also especially preferred are compositions 54.1 to 54.3653 which differ from the compositions 1.1 to 1.3653 only in that they additionally comprise B.111 and B.67 as further herbicides B.

Also especially preferred are compositions 55.1 to 55.3653 which differ from the compositions 1.1 to 1.3653 only in that they additionally comprise B.111 and B.76 as further herbicides B.

Also especially preferred are compositions 56.1 to 56.3653 which differ from the compositions 1.1 to 1.3653 only in that they additionally comprise B.111 and B.82 tas further herbicides B.

Also especially preferred are compositions 57.1 to 57.3653 which differ from the compositions 1.1 to 1.3653 only in that they additionally comprise B. 116 as further herbicide B.

Also especially preferred are compositions 58.1 to 58.3653 which differ from the compositions 1.1 to 1.3653 only in that they additionally comprise B.116 and B.67 as further herbicides B.

Also especially preferred are compositions 59.1 to 59.3653 which differ from the compositions 1.1 to 1.3653 only in that they additionally comprise B.116 and B.94 as further herbicides B.

Also especially preferred are compositions 60.1 to 60.3653 which differ from the compositions 1.1 to 1.3653 only in that they additionally comprise B.116 and B.103 as further herbicides B.

Also especially preferred are compositions 61.1 to 61.3653 which differ from the compositions 1.1 to 1.3653 only in that they additionally comprise B.116 and B.128 as further herbicides B.

Also especially preferred are compositions 62.1 to 62.3653 which differ from the compositions 1.1 to 1.3653 only in that they additionally comprise B.116 and B.104 as further herbicides B.

Also especially preferred are compositions 63.1 to 63.3653 which differ from the compositions 1.1 to 1.3653 only in that they additionally comprise B.116 and B.107 as further herbicides B.

Also especially preferred are compositions 64.1 to 64.3653 which differ from the compositions 1.1 to 1.3653 only in that they additionally comprise B.116 and B.111 as further herbicides B.

Also especially preferred are compositions 65.1 to 65.3653 which differ from the compositions 1.1 to 1.3653 only in that they additionally comprise B.122 as further herbicide B.

Also especially preferred are compositions 66.1 to 66.3653 which differ from the compositions 1.1 to 1.3653 only in that they additionally comprise B.126 as further herbicide B.

Also especially preferred are compositions 67.1 to 67.3653 which differ from the compositions 1.1 to 1.3653 only in that they additionally comprise B.128 as further herbicide B.

Also especially preferred are compositions 68.1 to 68.3653 which differ from the compositions 1.1 to 1.3653 only in that they additionally comprise B.131 as further herbicide B.

Also especially preferred are compositions 69.1 to 69.3653 which differ from the compositions 1.1 to 1.3653 only in that they additionally comprise B.132 as further herbicide B.

Also especially preferred are compositions 70.1 to 70.3653 which differ from the compositions 1.1 to 1.3653 only in that they additionally comprise B.133 as further herbicide B.

Also especially preferred are compositions 71.1 to 71.3653 which differ from the compositions 1.1 to 1.3653 only in that they additionally comprise B.135 as further herbicide B.

Also especially preferred are compositions 72.1 to 72.3653 which differ from the compositions 1.1 to 1.3653 only in that they additionally comprise B.137 as further herbicide B.

Also especially preferred are compositions 73.1 to 73.3653 which differ from the compositions 11.1 to 1.3653 only in that they additionally comprise B.138 as further herbicide B.

Also especially preferred are compositions 74.1 to 74.3653 which differ from the compositions 1.1 to 1.3653 only in that they additionally comprise B.140 i as further herbicide B.

Also especially preferred are compositions 75.1 to 75.3653 which differ from the compositions 1.1 to 1.3653 only in that they additionally comprise B.145 as further herbicide B.

Also especially preferred are compositions 76.1 to 76.3653 which differ from the compositions 1.1 to 1.3653 only in that they additionally comprise B.153 as further herbicide B.

Also especially preferred are compositions 77.1 to 77.3653 which differ from the compositions 1.1 to 1.3653 only in that they additionally comprise B.156 as further herbicide B.

Also especially preferred are compositions 78.1 to 78.3653 which differ from the compositions 1.1 to 1.3653 only in that they additionally comprise B.171 as further herbicide B.

Also especially preferred are compositions 79.1 to 79.3653 which differ from the compositions 1.1 to 1.3653 only in that they additionally comprise B.174 as further herbicide B.

The invention also relates to agrochemical compositions comprising at least an auxiliary and at least one pyrimidine compound of formula (I) according to the invention.

An agrochemical composition comprises a pesticidal effective amount of a pyrimidine compound of formula (I). The term "effective amount" denotes an amount of the composition or of the compounds I, which is sufficient for controlling unwanted plants, especially for controlling unwanted plants in cultivated plants and which does not result in a substantial damage to the treated plants. Such an amount can vary in a broad range and is dependent on various factors, such as the plants to be controlled, the treated cultivated plant or material, the climatic conditions and the specific pyrimidine compound of formula (I) used.

The pyrimidine compounds of formula (I), their N-oxides, salts or derivatives can be converted into customary types of agrochemical compositions, e.g. solutions, emulsions, suspensions, dusts, powders, pastes, granules, pressings, capsules, and mixtures thereof. Examples for agrochemical composition types are suspensions (e.g. SC, OD, FS), emulsifiable concentrates (e.g. EC), emulsions (e.g. EW, EO, ES, ME), capsules (e.g. CS, ZC), pastes, pastilles, wettable powders or dusts (e.g. WP, SP, WS, DP, DS), pressings (e.g. BR, TB, DT), granules (e.g. WG, SG, GR, FG, GG, MG), insecticidal articles (e.g. LN), as well as gel formulations for the treatment of plant propagation materials such as seeds (e.g. GF). These and further agrochemical compositions types are defined in the "Catalogue of pesticide formulation types and international coding system", Technical Monograph No. 2, $6^{th}$ Ed. May 2008, CropLife International.

The agrochemical compositions are prepared in a known manner, such as described by Mollet and Grubemann, Formulation technology, Wiley VCH, Weinheim, 2001; or Knowles, New developments in crop protection product formulation, Agrow Reports DS243, T&F Informa, London, 2005.

Suitable auxiliaries are solvents, liquid carriers, solid carriers or fillers, surfactants, dispersants, emulsifiers, wetters, adjuvants, solubilizers, penetration enhancers, protective colloids, adhesion agents, thickeners, humectants, repellents, attractants, feeding stimulants, compatibilizers, bactericides, anti-freezing agents, anti-foaming agents, colorants, tackifiers and binders.

Suitable solvents and liquid carriers are water and organic solvents, such as mineral oil fractions of medium to high boiling point, e.g. kerosene, diesel oil; oils of vegetable or animal origin; aliphatic, cyclic, and aromatic hydrocarbons, e. g. toluene, paraffin, tetrahydronaphthalene, alkylated naphthalenes; alcohols, e.g. ethanol, propanol, butanol, benzylalcohol, cyclohexanol; glycols; DMSO; ketones, e.g. cyclohexanone; esters, e.g. lactates, carbonates, fatty acid esters, gamma-butyrolactone; fatty acids; phosphonates; amines; amides, e.g. N-methylpyrrolidone, fatty acid dimethylamides; and mixtures thereof.

Suitable solid carriers or fillers are mineral earths, e.g. silicates, silica gels, talc, kaolins, limestone, lime, chalk, clays, dolomite, diatomaceous earth, bentonite, calcium sulfate, magnesium sulfate, magnesium oxide; polysaccharides, e.g. cellulose, starch; fertilizers, e.g. ammonium sulfate, ammonium phosphate, ammonium nitrate,ureas; products of vegetable origin, e.g. cereal meal, tree bark meal, wood meal, nutshell meal, and mixtures thereof.

Suitable surfactants are surface-active compounds, such as anionic, cationic, non-ionic, and amphoteric surfactants, block polymers, polyelectrolytes, and mixtures thereof. Such surfactants can be used as emulsifier, dispersant, solubilizer, wetter, penetration enhancer, protective colloid, or adjuvant. Examples of surfactants are listed in McCutcheon's, Vol. 1: Emulsifiers & Detergents, McCutcheon's Directories, Glen Rock, USA, 2008 (International Ed. or North American Ed.).

Suitable anionic surfactants are alkali, alkaline earth or ammonium salts of sulfonates, sulfates, phosphates, carboxylates, and mixtures thereof. Examples of sulfonates are alkylarylsulfonates, diphenylsulfonates, alpha-olefin sulfonates, lignine sulfonates, sulfonates of fatty acids and oils, sulfonates of ethoxylated alkylphenols, sulfonates of alkoxylated arylphenols, sulfonates of condensed naphthalenes, sulfonates of dodecyl- and tridecylbenzenes, sulfonates of naphthalenes and alkylnaphthalenes, sulfosuccinates or sulfosuccinamates. Examples of sulfates are sulfates of fatty acids and oils, of ethoxylated alkylphenols, of alcohols, of ethoxylated alcohols, or of fatty acid esters. Examples of phosphates are phosphate esters. Examples of carboxylates are alkyl carboxylates, and carboxylated alcohol or alkylphenol ethoxylates.

Suitable nonionic surfactants are alkoxylates, N-substituted fatty acid amides, amine oxides, esters, sugar-based surfactants, polymeric surfactants, and mixtures thereof. Examples of alkoxylates are compounds such as alcohols, alkylphenols, amines, amides, arylphenols, fatty acids, or fatty acid esters which have been alkoxylated with 1 to 50 equivalents. Ethylene oxide and/or propylene oxide may be employed for the alkoxylation, preferably ethylene oxide. Examples of N-substituted fatty acid amides are fatty acid glucamides or fatty acid alkanolamides. Examples of esters are fatty acid esters, glycerol esters, or monoglycerides. Examples of sugar-based surfactants are sorbitans, ethoxylated sorbitans, sucrose, and glucose esters, or alkylpolyglucosides. Examples of polymeric surfactants are home- or copolymers of vinylpyrrolidone, vinylalcohols, or vinylacetate.

Suitable cationic surfactants are quaternary surfactants, e.g. quaternary ammonium compounds with one or two hydrophobic groups, or salts of long-chain primary amines. Suitable amphoteric surfactants are alkylbetains and imidazolines. Suitable block polymers are block polymers of the A-B or A-B-A type comprising blocks of polyethylene oxide and polypropylene oxide, or of the A-B-C type comprising alkanol, polyethylene oxide and polypropylene oxide. Suitable polyelectrolytes are polyacids or polybases. Examples of polyacids are alkali salts of polyacrylic acid or polyacid comb polymers. Examples of polybases are polyvinylamines or polyethyleneamines.

Suitable adjuvants are compounds, which have a neglectable or even no pesticidal activity themselves, and which improve the biological performance of the pyrimidine compounds of formula (I) on the target. Examples are surfactants, mineral or vegetable oils, and other auxiliaries. Further examples are listed by Knowles, Adjuvants, and additives, Agrow Reports DS256, T&F Informa UK, 2006, chapter 5.

Suitable thickeners are polysaccharides (e.g. xanthan gum, carboxymethylcellulose), inorganic clays (organically modified or unmodified), polycarboxylates, and silicates.

Suitable bactericides are bronopol and isothiazolinone derivatives such as alkylisothiazolinones and benzisothiazolinones.

Suitable anti-freezing agents are ethylene glycol, propylene glycol, urea, and glycerin.

Suitable anti-foaming agents are silicones, long chain alcohols, and salts of fatty acids.

Suitable colorants (e.g. in red, blue, or green) are pigments of low water solubility and water-soluble dyes. Examples are inorganic colorants (e.g. iron oxide, titan oxide, iron hexacyanoferrate) and organic colorants (e.g. alizarin-, azo-, and phthalocyanine colorants).

Suitable tackifiers or binders are polyvinylpyrrolidons, polyvinylacetates, polyvinyl alcohols, polyacrylates, biological or synthetic waxes, and cellulose ethers.

Examples for agrochemical composition types and their preparation are:

i) Water-soluble concentrates (SL, LS)

10-60 wt % of a pyrimidine compound of formula (I) according to the invention and 5-15 wt % wetting agent (e.g. alcohol alkoxylates) are dissolved in water and/or in a water-soluble solvent (e.g. alcohols) ad 100 wt %. The active substance dissolves upon dilution with water.

ii) Dispersible concentrates (DC)

5-25 wt % of a pyrimidine compound of formula (I) according to the invention and 1-10 wt % dispersant (e. g. polyvinylpyrrolidone) are dissolved in organic solvent (e.g. cyclohexanone) ad 100 wt %. Dilution with water gives a dispersion.

iii) Emulsifiable concentrates (EC)

15-70 wt % of a pyrimidine compound of formula (I) according to the invention and 5-10 wt % emulsifiers (e.g. calcium dodecylbenzenesulfonate and castor oil ethoxylate) are dissolved in water-insoluble organic solvent (e.g. aromatic hydrocarbon) ad 100 wt %. Dilution with water gives an emulsion.

iv) Emulsions (EW, EO, ES)

5-40 wt % of a pyrimidine compound of formula (I) according to the invention and 1-10 wt % emulsifiers (e.g. calcium dodecylbenzenesulfonate and castor oil ethoxylate) are dissolved in 20-40 wt % water-insoluble organic solvent (e.g. aromatic hydrocarbon). This mixture is introduced into water ad 100 wt % by means of an emulsifying machine and made into a homogeneous emulsion. Dilution with water gives an emulsion.

v) Suspensions (SC, OD, FS)

In an agitated ball mill, 20-60 wt % of a pyrimidine compound of formula (I) according to the invention are comminuted with addition of 2-10 wt % dispersants and wetting agents (e.g. sodium lignosulfonate and alcohol ethoxylate), 0.1-2 wt % thickener (e.g. xanthan gum) and water ad 100 wt % to give a fine active substance suspension. Dilution with water gives a stable suspension of the active substance. For FS type composition up to 40 wt % binder (e.g. polyvinylalcohol) is added.

vi) Water-dispersible granules and water-soluble granules (WG, SG)

50-80 wt % of a pyrimidine compound of formula (I) according to the invention are ground finely with addition of dispersants and wetting agents (e.g. sodium lignosulfonate and alcohol ethoxylate) ad 100 wt % and prepared as water-dispersible or water-soluble granules by means of technical appliances (e. g. extrusion, spray tower, fluidized bed). Dilution with water gives a stable dispersion or solution of the active substance.

vii) Water-dispersible powders and water-soluble powders (WP, SP, WS)

50-80 wt % of a pyrimidine compound of formula (I) according to the invention are ground in a rotor-stator mill with addition of 1-5 wt % dispersants (e.g. sodium lignosulfonate), 1-3 wt % wetting agents (e.g. alcohol ethoxylate) and solid carrier (e.g. silica gel) ad 100 wt %. Dilution with water gives a stable dispersion or solution of the active substance.

viii) Gel (GW, GF)

In an agitated ball mill, 5-25 wt % of a pyrimidine compound of formula (I) according to the invention are comminuted with addition of 3-10 wt % dispersants (e.g. sodium lignosulfonate), 1-5 wt % thickener (e.g. carboxymethylcellulose) and water ad 100 wt % to give a fine suspension of the active substance. Dilution with water gives a stable suspension of the active substance.

iv) Microemulsion (ME)

5-20 wt % of a pyrimidine compound of formula (I) according to the invention are added to 5-30 wt % organic solvent blend (e.g. fatty acid dimethylamide and cyclohexanone), 10-25 wt % surfactant blend (e.g. alcohol ethoxylate and arylphenol ethoxylate), and water ad 100%. This mixture is stirred for 1 h to produce spontaneously a thermodynamically stable microemulsion.

iv) Microcapsules (CS)

An oil phase comprising 5-50 wt % of a pyrimidine compound of formula (I) according to the invention, 0-40 wt % water insoluble organic solvent (e.g. aromatic hydrocarbon), 2-15 wt % acrylic monomers (e.g. methylmethacrylate, methacrylic acid, and a di- or triacrylate) are dispersed into an aqueous solution of a protective colloid (e.g. polyvinyl alcohol). Radical polymerization initiated by a radical initiator results in the formation of poly(meth)acrylate microcapsules. Alternatively, an oil phase comprising 5-50 wt % of a pyrimidine compound of formula (I) according to the invention, 0-40 wt % water insoluble organic solvent (e.g. aromatic hydrocarbon), and an isocyanate monomer (e.g. diphenylmethene-4,4'-diisocyanate) are dispersed into an aqueous solution of a protective colloid (e.g. polyvinyl alcohol). The addition of a polyamine (e.g. hexamethylenediamine) results in the formation of polyurea microcapsules. The monomers amount to 1-10 wt %. The wt % relate to the total CS composition.

ix) Dustable powders (DP, DS)

1-10 wt % of a pyrimidine compound of formula (I) according to the invention are ground finely and mixed intimately with solid carrier (e.g. finely divided kaolin) ad 100 wt %.

x) Granules (GR, FG)

0.5-30 wt % of a pyrimidine compound of formula (I) according to the invention is ground finely and associated with solid carrier (e.g. silicate) ad 100 wt %. Granulation is achieved by extrusion, spray-drying or the fluidized bed.

xi) Ultra-low volume liquids (UL)

1-50 wt % of a pyrimidine compound of formula (I) according to the invention are dissolved in organic solvent (e.g. aromatic hydrocarbon) ad 100 wt %.

The agrochemical compositions types i) to xi) may optionally comprise further auxiliaries, such as 0.1-1 wt % bactericides, 5-15 wt % anti-freezing agents, 0.1-1 wt % anti-foaming agents, and 0.1-1 wt % colorants.

The agrochemical compositions comprising generally comprise between 0.01 and 95%, preferably between 0.1 and 90%, and in particular between 0.5 and 75%, by weight of the pyrimidine compound of formula (I). The pyrimidine compounds of formula (I) are employed in a purity of from 90% to 100%, preferably from 95% to 100% (according to NMR spectrum).

Solutions for seed treatment (LS), suspoemulsions (SE), flowable concentrates (FS), powders for dry treatment (DS), water-dispersible powders for slurry treatment (WS), water-soluble powders (SS), emulsions (ES), emulsifiable concentrates (EC) and gels (GF) are usually employed for the purposes of treatment of plant propagation materials, particularly seeds. The agrochemical compositions in question give, after two-to-tenfold dilution, active substance concentrations of from 0.01 to 60% by weight, preferably from 0.1 to 40% by weight, in the ready-to-use preparations. Application can be carried out before or during sowing.

Methods for applying pyrimidine compounds of formula (I) and agrochemical compositions thereof, on to plant propagation material, especially seeds, include dressing, coating, pelleting, dusting, soaking and in-furrow application methods of the propagation material. Preferably, pyrimidine compounds of formula (I) and agrochemical compositions thereof, are applied on to the plant propagation material by a method such that germination is not induced, e. g. by seed dressing, pelleting, coating and dusting.

Various types of oils, wetters, adjuvants, fertilizer, or micronutrients, and further pesticides (e.g. herbicides, insecticides, fungicides, growth regulators, safeners) may be added to the pyrimidine compounds of formula (I) and the agrochemical compositions comprising them as premix or, if appropriate not until immediately prior to use (tank mix). These agents can be admixed with the agrochemical compositions according to the invention in a weight ratio of 1:100 to 100:1, preferably 1:10 to 10:1.

The user applies the pyrimidine compound of formula (I) according to the invention and the agrochemical compositions comprising them usually from a pre-dosage device, a knapsack sprayer, a spray tank, a spray plane, or an irrigation system. Usually, the agrochemical composition is made up with water, buffer, and/or further auxiliaries to the desired application concentration and the ready-to-use spray liquor or the agrochemical composition according to the invention is thus obtained. Usually, 20 to 2000 liters, preferably 50 to 400 liters, of the ready-to-use spray liquor are applied per hectare of agricultural useful area.

According to one embodiment, either individual components of the agrochemical composition according to the invention or partially premixed components, e. g. components comprising pyrimidine compounds of formula (I) may be mixed by the user in a spray tank and further auxiliaries and additives may be added, if appropriate.

In a further embodiment, individual components of the agrochemical composition according to the invention such as parts of a kit or parts of a binary or ternary mixture may be mixed by the user himself in a spray tank and further auxiliaries may be added, if appropriate.

In a further embodiment, either individual components of the agrochemical composition according to the invention or partially premixed components, e. g components comprising pyrimidine compounds of formula (I) can be applied jointly (e.g. after tank mix) or consecutively.

The pyrimidine compounds of formula (I), are suitable as herbicides. They are suitable as such or as an appropriately formulated composition (agrochemical composition).

The pyrimidine compounds of formula (I), or the agrochemical compositions comprising the pyrimidine compounds of formula (I), control vegetation on non-crop areas very efficiently, especially at high rates of application. They act against broad-leaved weeds and grass weeds in crops such as wheat, rice, maize, soya, and cotton without causing any significant damage to the crop plants. This effect is mainly observed at low rates of application.

The pyrimidine compounds of formula (I), or the agrochemical compositions comprising them, are applied to the plants mainly by spraying the leaves. Here, the application can be carried out using, e.g., water as carrier by customary spraying techniques using spray liquor amounts of from about 100 to 1000 l/ha (e.g. from 300 to 400 l/ha). The pyrimidine compounds of formula (I), or the agrochemical compositions comprising them, may also be applied by the low-volume or the ultra-low-volume method, or in the form of micro granules.

Application of the pyrimidine compounds of formula (I), or the agrochemical compositions comprising them, can be done before, during, and/or after, preferably during and/or after, the emergence of the undesirable plants.

The pyrimidine compounds of formula (I), or the agrochemical compositions comprising them, can be applied pre-, post-emergence or pre-plant, or together with the seed of a crop plant. It is also possible to apply the pyrimidine compounds of formula (I), or the agrochemical compositions comprising them, by applying seed, pretreated with the pyrimidine compounds of formula (I), or the agrochemical compositions comprising them, of a crop plant. If the active ingredients are less well tolerated by certain crop plants, application techniques may be used in which the herbicidal compositions are sprayed, with the aid of the spraying equipment, in such a way that as far as possible they do not come into contact with the leaves of the sensitive crop plants, while the active ingredients reach the leaves of undesirable plants growing underneath, or the bare soil surface (post-directed, lay-by).

In a further embodiment, the pyrimidine compounds of formula (I), or the agrochemical compositions comprising them, can be applied by treating seed. The treatment of seeds comprises essentially all procedures familiar to the person skilled in the art (seed dressing, seed coating, seed dusting, seed soaking, seed film coating, seed multilayer coating, seed encrusting, seed dripping and seed pelleting) based on the pyrimidine compounds of formula (I), or the agrochemical compositions prepared therefrom. Here, the herbicidal compositions can be applied diluted or undiluted.

The term "seed" comprises seed of all types, such as, e.g., corns, seeds, fruits, tubers, seedlings and similar forms. Here, preferably, the term seed describes corns and seeds. The seed used can be seed of the useful plants mentioned above, but also the seed of transgenic plants or plants obtained by customary breeding methods.

When employed in plant protection, the amounts of active substances applied, i.e. the pyrimidine compounds of formula (I) without formulation auxiliaries, are, depending on the kind of effect desired, from 0.001 to 2 kg per ha, preferably from 0.005 to 2 kg per ha, more preferably from 0.05 to 0.9 kg per ha and in particular from 0.1 to 0.75 kg per ha.

In another embodiment of the invention, the application rate of the pyrimidine compounds of formula (I) is from 0.001 to 3 kg/ha, preferably from 0.005 to 2.5 kg/ha and in particular from 0.01 to 2 kg/ha of active substance (a.s.).

In another preferred embodiment of the invention, the rates of application of the pyrimidine compounds of formula (I) according to the present invention (total amount of pyrimidine compounds of formula (I)) are from 0.1 g/ha to 3000 g/ha, preferably 10 g/ha to 1000 g/ha, depending on the control target, the season, the target plants and the growth stage.

In another preferred embodiment of the invention, the application rates of the pyrimidine compounds of formula (I)

are in the range from 0.1 g/ha to 5000 g/ha and preferably in the range from 1 g/ha to 2500 g/ha or from 5 g/ha to 2000 g/ha.

In another preferred embodiment of the invention, the application rate of the pyrimidine compounds of formula (I) is 0.1 to 1000 g/ha, preferably 1 to 750 g/ha, more preferably 5 to 500 g/ha.

In treatment of plant propagation materials such as seeds, e. g. by dusting, coating or drenching seed, amounts of active substance of from 0.1 to 1000 g, preferably from 1 to 1000 g, more preferably from 1 to 100 g, and most preferably from 5 to 100 g, per 100 kilogram of plant propagation material (preferably seeds) are generally required.

In another embodiment of the invention, to treat the seed, the amounts of active substances applied, i.e. the pyrimidine compounds of formula (I) are generally employed in amounts of from 0.001 to 10 kg per 100 kg of seed.

When used in the protection of materials or stored products, the amount of active substance applied depends on the kind of application area and on the desired effect. Amounts customarily applied in the protection of materials are 0.001 g to 2 kg, preferably 0.005 g to 1 kg, of active substance per cubic meter of treated material.

Depending on the application method in question, the pyrimidine compounds of formula (I), or the agrochemical compositions comprising them, can additionally be employed in a further number of crop plants for eliminating undesirable plants. Examples of suitable crops are the following:

*Allium cepa, Ananas comosus, Arachis hypogaea, Asparagus officinalis, Avena sativa, Beta vulgaris* spec. *altissima, Beta vulgaris* spec. *rapa, Brassica napus* var. *napus, Brassica napus* var. *napobrassica, Brassica rapa* var. *silvestris, Brassica oleracea, Brassica nigra, Camellia sinensis, Carthamus tinctorius, Carya illinoinensis, Citrus limon, Citrus sinensis, Coffea arabica* (*Coffea canephora, Coffea liberica*), *Cucumis sativus, Cynodon dactylon, Daucus carota, Elaeis guineensis, Fragaria vesca, Glycine max, Gossypium hirsutum,* (*Gossypium arboreum, Gossypium herbaceum, Gossypium vitifolium*), *Helianthus annuus, Hevea brasiliensis, Hordeum vulgare, Humulus lupulus, Ipomoea batatas, Juglans regia, Lens culinaris, Linum usitatissimum, Lycopersicon lycopersicum, Malus* spec., *Manihot esculenta, Medicago sativa, Musa* spec., *Nicotiana tabacum* (*N. rustica*), *Olea europaea, Oryza sativa, Phaseolus lunatus, Phaseolus vulgaris, Picea abies, Pinus* spec., *Pistacia vera, Pisum sativum, Prunus avium, Prunus persica, Pyrus communis, Prunus armeniaca, Prunus cerasus, Prunus dulcis* and *Prunus domestica, Ribes sylvestre, Ricinus communis, Saccharum officinarum, Secale cereale, Sinapis alba, Solanum tuberosum, Sorghum bicolor* (s. *vulgare*), *Theobroma cacao, Trifolium pratense, Triticum aestivum,* Triticale, *Triticum durum, Vicia faba, Vitis vinifera,* and *Zea mays.*

Preferred crops are *Arachis hypogaea, Beta vulgaris* spec. *altissima, Brassica napus* var. *napus, Brassica oleracea, Citrus limon, Citrus sinensis, Coffea arabica* (*Coffea canephora, Coffea liberica*), *Cynodon dactylon, Glycine max, Gossypium hirsutum,* (*Gossypium arboreum, Gossypium herbaceum, Gossypium vitifolium*), *Helianthus annuus, Hordeum vulgare, Juglans regia, Lens culinaris, Linum usitatissimum, Lycopersicon lycopersicum, Malus* spec., *Medicago sativa, Nicotiana tabacum* (*N. rustica*), *Olea europaea, Oryza sativa, Phaseolus sativus, Phaseolus vulgaris, Pistacia vera, Pisum sativum, Prunus dulcis, Saccharum officinarum, Secale cereale, Solanum tuberosum, Sorghum bicolor* (s. *vulgare*), Triticale, *Triticum aestivum, Triticum durum, Vicia faba, Vitis vinifera,* and *Zea mays.*

Especially preferred crops are crops of cereals, corn, soybeans, rice, oilseed rape, cotton, potatoes, peanuts, or permanent crops.

The pyrimidine compounds of formula (I) according to the invention, or the agrochemical compositions comprising them, can also be used in genetically modified plants. The term "genetically modified plants" is to be understood as plants whose genetic material has been modified by the use of recombinant DNA techniques to include an inserted sequence of DNA that is not native to that plant species' genome or to exhibit a deletion of DNA that was native to that species' genome, wherein the modification(s) cannot readily be obtained by cross breeding, mutagenesis or natural recombination alone. Often, a particular genetically modified plant will be one that has obtained its genetic modification(s) by inheritance through a natural breeding or propagation process from an ancestral plant whose genome was the one directly treated by use of a recombinant DNA technique. Typically, one or more genes have been integrated into the genetic material of a genetically modified plant in order to improve certain properties of the plant. Such genetic modifications also include but are not limited to targeted post-translational modification of protein(s), oligo- or polypeptides. e. g., by inclusion therein of amino acid mutation(s) that permit, decrease, or promote glycosylation or polymer additions such as prenylation, acetylation farnesylation, or PEG moiety attachment.

Plants that have been modified by breeding, mutagenesis or genetic engineering, e.g. have been rendered tolerant to applications of specific classes of herbicides, such as auxin herbicides such as dicamba or 2,4-D; bleacher herbicides such as hydroxyphenylpyruvate dioxygenase (HPPD) inhibitors or phytoene desaturase (PDS) inhibitors; acetolactate synthase (ALS) inhibitors such as sulfonyl ureas or imidazolinones; enolpyruvyl shikimate 3-phosphate synthase (EPSP) inhibitors such as glyphosate; glutamine synthetase (GS) inhibitors such as glufosinate; protoporphyrinogen-IX oxidase inhibitors; lipid biosynthesis inhibitors such as acetyl CoA carboxylase (ACCase) inhibitors; or oxynil (i.e. bromoxynil or ioxynil) herbicides as a result of conventional methods of breeding or genetic engineering; furthermore, plants have been made resistant to multiple classes of herbicides through multiple genetic modifications, such as resistance to both glyphosate and glufosinate or to both glyphosate and a herbicide from another class such as ALS inhibitors, HPPD inhibitors, auxin herbicides, or ACCase inhibitors. These herbicide resistance technologies are, e.g., described in Pest Management Science 61, 2005, 246; 61, 2005, 258; 61, 2005, 277; 61, 2005, 269; 61, 2005, 286; 64, 2008, 326; 64, 2008, 332; Weed Science 57, 2009, 108; Australian Journal of Agricultural Research 58, 2007, 708; Science 316, 2007, 1185; and references quoted therein. Several cultivated plants have been rendered tolerant to herbicides by mutagenesis and conventional methods of breeding, e. g., Clearfield® summer rape (Canola, BASF SE, Germany) being tolerant to imidazolinones, e. g., imazamox, or ExpressSun® sunflowers (DuPont, USA) being tolerant to sulfonyl ureas, e. g., tribenuron. Genetic engineering methods have been used to render cultivated plants such as soybean, cotton, corn, beets and rape, tolerant to herbicides such as glyphosate, imidazolinones, and glufosinate, some of which are under development or commercially available under the brands or trade names RoundupReady® (glyphosate tolerant, Monsanto, USA), Cultivance® (imidazolinone tolerant, BASF SE, Germany), and LibertyLink® (glufosinate tolerant, Bayer CropScience, Germany).

Furthermore, plants are also covered that are by the use of recombinant DNA techniques capable to synthesize one or more insecticidal proteins, especially those known from the bacterial genus *Bacillus*, particularly from *Bacillus thuringiensis*, such as delta-endotoxins, e. g., CryIA(b), CryIA(c), CryIF, CryIF(a2), CryIIA(b), CryIIIA, CryIIIB(b1) or Cry9c; vegetative insecticidal proteins (VIP), e. g., VIP1, VIP2, VIP3, or VIP3A; insecticidal proteins of bacteria colonizing nematodes, e. g., *Photorhabdus* spp. or *Xenorhabdus* spp.; toxins produced by animals, such as scorpion toxins, arachnid toxins, wasp toxins, or other insect-specific neurotoxins; toxins produced by fungi, such as Streptomycetes toxins, plant lectins, such as pea or barley lectins; agglutinins; proteinase inhibitors, such as trypsin inhibitors, serine protease inhibitors, patatin, cystatin or papain inhibitors; ribosome-inactivating proteins (RIP), such as ricin, maize-RIP, abrin, luffin, saporin or bryodin; steroid metabolism enzymes, such as 3-hydroxy-steroid oxidase, ecdysteroid-IDP-glycosyl-transferase, cholesterol oxidases, ecdysone inhibitors or HMG-CoA-reductase; ion channel blockers, such as blockers of sodium or calcium channels; juvenile hormone esterase; diuretic hormone receptors (helicokinin receptors); stilbene synthase, bibenzyl synthase, chitinases or glucanases. In the context of the present invention these insecticidal proteins or toxins are to be understood expressly also as including pre-toxins, hybrid proteins, truncated or otherwise modified proteins. Hybrid proteins are characterized by a new combination of protein domains, (see, e. g., WO 02/015701). Further examples of such toxins or genetically modified plants capable of synthesizing such toxins are disclosed, e. g., in EP-A 374 753, WO 93/007278, WO 95/34656, EP-A 427 529, EP-A 451 878, WO 03/18810, and WO 03/52073. The methods for producing such genetically modified plants are generally known to the person skilled in the art and are described, e. g., in the publications mentioned above. These insecticidal proteins contained in the genetically modified plants impart to the plants producing these proteins tolerance to harmful pests from all taxonomic groups of arthropods, especially to beetles (Coeloptera), two-winged insects (Diptera), and moths (Lepidoptera) and to nematodes (Nematoda). Genetically modified plants capable to synthesize one or more insecticidal proteins are, e. g., described in the publications mentioned above, and some of which are commercially available such as YieldGard® (corn cultivars producing the Cry1Ab toxin), YieldGard® Plus (corn cultivars producing Cry1Ab and Cry3Bb1 toxins), Starlink® (corn cultivars producing the Cry9c toxin), Herculex® RW (corn cultivars producing Cry34Ab1, Cry35Ab1 and the enzyme Phosphinothricin-N-Acetyltransferase [PAT]); NuCOTN® 33B (cotton cultivars producing the Cry1Ac toxin), Bollgard® I (cotton cultivars producing the Cry1Ac toxin), Bollgard® II (cotton cultivars producing Cry1Ac and Cry2Ab2 toxins); VIPCOT® (cotton cultivars producing a VIP-toxin); NewLeaf® (potato cultivars producing the Cry3A toxin); Bt-Xtra®, NatureGard®, KnockOut®, BiteGard®, Protecta®, Bt11 (e. g., Agrisure® CB) and Bt176 from Syngenta Seeds SAS, France, (corn cultivars producing the Cry1Ab toxin and PAT enzyme), MIR604 from Syngenta Seeds SAS, France (corn cultivars producing a modified version of the Cry3A toxin, c.f. WO 03/018810), MON 863 from Monsanto Europe S.A., Belgium (corn cultivars producing the Cry3Bb1 toxin), IPC 531 from Monsanto Europe S.A., Belgium (cotton cultivars producing a modified version of the Cry1Ac toxin) and 1507 from Pioneer Overseas Corporation, Belgium (corn cultivars producing the Cry1F toxin and PAT enzyme).

Furthermore, plants are also covered that are by the use of recombinant DNA techniques capable to synthesize one or more proteins to increase the resistance or tolerance of those plants to bacterial, viral or fungal pathogens. Examples of such proteins are the so-called "pathogenesis-related proteins" (PR proteins, see, e.g., EP-A 392 225), plant disease resistance genes (e. g., potato cultivars, which express resistance genes acting against *Phytophthora infestans* derived from the Mexican wild potato, *Solanum bulbocastanum*) or T4-lyso-zym (e.g., potato cultivars capable of synthesizing these proteins with increased resistance against bacteria such as *Erwinia amylovora*). The methods for producing such genetically modified plants are generally known to the person skilled in the art and are described, e.g., in the publications mentioned above.

Furthermore, plants are also covered that are by the use of recombinant DNA techniques capable to synthesize one or more proteins to increase the productivity (e.g., bio-mass production, grain yield, starch content, oil content or protein content), tolerance to drought, salinity or other growth-limiting environmental factors or tolerance to pests and fungal, bacterial or viral pathogens of those plants.

Furthermore, plants are also covered that contain by the use of recombinant DNA techniques a modified amount of ingredients or new ingredients, specifically to improve human or animal nutrition, e. g., oil crops that produce health-promoting long-chain omega-3 fatty acids or unsaturated omega-9 fatty acids (e. g., Nexera® rape, Dow AgroSciences, Canada).

Furthermore, plants are also covered that contain by the use of recombinant DNA techniques a modified amount of ingredients or new ingredients, specifically to improve raw material production, e.g., potatoes that produce increased amounts of amylopectin (e.g. Amflora® potato, BASF SE, Germany).

The preparation of the pyrimidine compounds of formula (I) is illustrated by the following examples.

A PREPARATION EXAMPLES

Example 1: Methyl 5-(2-chloro-3-thienyl)-2-cyclopropyl-pyrimidine-4-carboxylate 5-Bromo-2-cyclopropyl-pyrimidine-4-carboxylic acid NaH (60% purity, 41.9 g,) is added in portions to EtOH (800 mL) at 0° C. The resulting mixture is warmed to ambient temperature and the cyclopropanecarboxamidine hydrochlorid (93.5 g,) is added in portions. The reaction is warmed to 50° C. and maintained at this temperature for 0.5 h and then cooled to ambient temperature before mucobromic acid (100 g,) is added in EtOH while keeping the internal temperature below 55° C. The mixture is allowed to cool to ambient temperature and stirred for additional 16 h. All solid components are removed by filtration and the resulting solution is concentrated under reduced pressure. Aq. HCl (1 mol/L) is added, the aqueous phase is washed with EtOAc (3×), the combined organic extracts are dried over MgSO$_4$ and the solid parts removed by filtration. The residue is concentrated under reduced pressure and the resulting solid titrated with ($^i$Pr)$_2$O. The solids are collected by filtration and dried yielding the title compound (68.0 g, yield 72%) as a colorless solid.

¹H NMR (400 MHz, CDCl₃): δ=8.91 (s, 1H), 2.38-2.26 (m, 1H), 1.34-1.14 (m, 4H) ppm; MS (ESI) m/z 244.9 [M+H⁺].

1.2 Methyl 5-bromo-2-cyclopropyl-pyrimidine-4-carboxylate

5-Bromo-2-cyclopropyl-pyrimidine-4-carboxylic acid (91.0 g,) is dissolved in MeOH (1200 mL) and conc. sulfuric acid (20 mL) is added dropwise at ambient temperature. The reaction is heated to reflux and stirred for 16 h. The resulting mixture is cooled to ambient temperature and neutralized with aq. sat. NaHCO₃. The residue is parted between EtOAc and aq. sat. NaHCO₃, the phases are separated, the aq. phase is extracted with EtOAc and the combined organics are dried over MgSO₄. Solid parts are removed by filtration and the organic phase is concentrated under reduced pressure. Column chromatography of the resulting crude product (ISCO-CombiFlash Rf, cyclohexane/EtOAc) yields the title compound (81.0 g, yield 84%) as a colorless solid.

¹H NMR (400 MHz, CDCl₃): δ=8.74 (s, 1H), 4.01 (s, 3H), 2.33-2.22 (m, 1H), 1.21-1.06 (m, 4H) ppm; MS (ESI) m/z 246.9 [M+H⁺].

1.3 Methyl 5-(2-chloro-3-thienyl)-2-cyclopropyl-pyrimidine-4-carboxylate

A mixture of methyl 5-bromo-2-cyclopropyl-pyrimidine-4-carboxylate (700 mg,), (2-chloro-3-thienyl)boronic acid (660 mg,), CsF (1.24 g,) and PdCl₂dppf (398 mg,) in toluene (30 mL) is heated under reflux under an atmosphere of argon for 1 h. Water and EtOAc are added, the phases are separated and organic phase is dried over MgSO₄. The solids are removed via filtration and resulting solution is concentrated under reduced pressure. Column chromatography of the crude product (ISCO-CombiFlash Rf, cyclohexane/EtOAc) yields the title compound (200 mg, yield 25%) as a yellow oil.

¹H NMR (400 MHz, CDCl₃): δ 8.68 (s, 1H), 7.20 (d, J=5.7 Hz, 1H), 6.92 (d, J=5.8 Hz, 1H), 3.85 (s, 3H), 2.42-2.36 (m, 1H), 1.26-1.13 (m, 4H) ppm; MS (ESI) m/z 295.1 [M+H⁺].

Example 2: Methyl 5-(3-bromo-2-pyridyl)-2-cyclopropyl-pyrimidine-4-carboxylate

2.1 Methyl 2-cyclopropyl-5-(4,4,5,5-tetramethyl-1,3,2-dioxaborolan-2-yl)pyrimidine-4-carboxylate A mixture of methyl 5-(2-chloro-3-thienyl)-2-cyclopropyl-pyrimidine-4-carboxylate (27.5 g), bis(pinacolato)diboron (54.3 g), KOAc (21.0 g) and PdCl₂dppf (8.74 mg) in dioxane (500 mL) is heated to 100° C. under an atmosphere of argon for 6 h. The mixture is cooled to ambient temperature, filtered over celite and the volatiles are removed under reduced pressure. Column chromatography of the crude product (ISCO-CombiFlash Rf, cyclohexane/EtOAc) yields the title compound (18.0 mg, yield 55%) as an oil.

¹H NMR (400 MHz, CDCl₃): δ 8.80 (s, 1H), 3.98 (s, 3H), 2.36-2.30 (m, 1H), 1.38 (s, 12H), 1.22-1.17 (m, 2H), 1.15-1.08 (m, 2H) ppm.

2.2 Methyl 5-(3-bromo-2-pyridyl)-2-cyclopropyl-pyrimidine-4-carboxylate

A mixture of methyl 2-cyclopropyl-5-(4,4,5,5-tetramethyl-1,3,2-dioxaborolan-2-yl)pyrimidine-4-carboxylate (1.00 g), 2,3-dibromopyridine (1.56 g), CsF (1.25 g) and PdCl₂dppf (403 mg) in toluene (20 mL) is heated under reflux under an atmosphere of argon for 3 h. The volatiles are removed under reduced pressure and column chromatography of the crude product (cyclohexane/EtOAc) yields the title compound (300 mg, yield 27%) as a colorless solid.

¹H NMR (400 MHz, CDCl₃): δ 8.78 (s, 1H), 8.62 (dd, J=4.7, 1.5 Hz, 1H), 7.99 (dd, J=8.1, 1.5 Hz, 1H), 7.23 (dd, J=8.1, 4.7 Hz, 1H), 3.82 (s, 3H), 2.47-2.41 (m, 1H), 1.39-1.25 (m, 2H), 1.20-1.15 (m, 2H) ppm; MS (ESI) m/z 336.0 [M+H⁺].

With appropriate modification of the starting materials, the procedures given in the synthesis examples below were used to obtain further compounds of formula I. The compounds obtained in this manner are listed in the Table Z that follows, together with physical data.

The products shown below were characterized by melting point determination, by the masses ([m/z]) or retention time (RT; [min.]) determined by HPLC-MS or HPLC spectrometry.

HPLC-MS=high performance liquid chromatography-coupled mass spectrometry; HPLC methods:

Method: Column: Phenomenex Kinetex 1.7 μm XB-C18 100A; 50×2.1 mm; mobile phase: A: water+0.1% trifluoroacetic acid (TFA); B: acetonitrile+0.1% TFA; gradient: 5-100% B in 1.50 minutes; 100% B 0.25 min; flow: 0.8-1.0 ml/min in 1.51 minutes at 60° C. MS: quadrupole electrospray ionization, 80 V (positive mode).

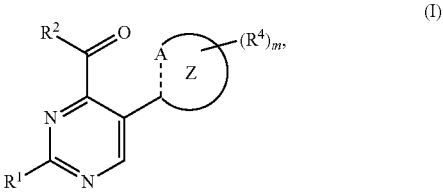

(I)

TABLE Z denotes point of attachment to the pyrimidine ring.

| Example | R¹ | R² | Z (R⁴)ₘ | HPLC/MS, Rₜ [min] | HPLC/MS, m/z |
|---|---|---|---|---|---|
| 1 | c-C₃H₅ | OH | 2-pyridyl, 3-CH₃ | 0.513 | 256.5 |
| 2 | c-C₃H₅ | OH | 4-pyridyl, 3-CH₃ | 0.557 | 255.8 |
| 3 | c-C₃H₅ | OH | thienyl, 3-CH₃ | 0.969 | 261.0 |

TABLE Z-continued denotes point of attachment to the pyrimidine ring.

| Example. | R¹ | R² | # —A—Z—(R⁴)ₘ | HPLC/MS, Rₜ [min] | HPLC/MS, m/z |
|---|---|---|---|---|---|
| 4 | c-C₃H₅ | OCH₃ | 3-methyl-2-thienyl (H₃C on thiophene, # at 2) | 1.163 | 275.1 |
| 5 | c-C₃H₅ | OCH₃ | 2-methyl-3-thienyl (# at 3, H₃C at 2) | 1.150 | 275.2 |
| 6 | c-C₃H₅ | OH | 4-methyl-3-thienyl (# at 3, CH₃ at 4) | 0.956 | 261.0 |
| 7 | c-C₃H₅ | OCH₃ | 4-methyl-3-thienyl (# at 3, CH₃ at 4) | 1.148 | 275.2 |
| 8 | c-C₃H₅ | OH | 2-methyl-3-thienyl (# at 3, H₃C at 2) | 0.953 | 261.0 |
| 9 | c-C₃H₅ | OH | 3-methoxy-2-pyridinyl (OCH₃ at 3, # at 2) | 0.677 | 228.0 |
| 10 | c-C₃H₅ | OH | 3-chloro-2-pyridinyl (Cl at 3, # at 2) | 0.845 | 232.0 |
| 11 | c-C₃H₅ | OCH₃ | 2-chloro-3-thienyl (# at 3, Cl at 2) | 1.157 | 295.1 |
| 12 | c-C₃H₅ | OH | 2-chloro-3-thienyl (# at 3, Cl at 2) | 0.984 | 281.0 |
| 13 | c-C₃H₅ | OH | 2-chloro-3-furyl (# at 3, Cl at 2) | 0.925 | 265.0 |
| 14 | c-C₃H₅ | OH | 2-bromo-3-furyl (# at 3, Br at 2) | 0.934 | 308.9 |
| 15 | c-C₃H₅ | OCH₃ | 2-chloro-3-furyl (# at 3, Cl at 2) | 1.100 | 279.0 |
| 16 | c-C₃H₅ | OCH₃ | 3-chloro-2-pyridinyl (Cl at 3, # at 2) | 0.996 | 290.0 |
| 17 | c-C₃H₅ | OCH₃ | 3-(difluoromethyl)-2-furyl (CHF₂ at 3, # at 2) | 1.078 | 295.0 |
| 18 | c-C₃H₅ | OCH₃ | 2-bromo-3-pyridinyl (Br at 2, # at 3) | 1.000 | 336.0 |
| 19 | c-C₃H₅ | OCH₃ | 2-fluoro-3-pyridinyl (F at 2, # at 3) | 0.973 | 274.1 |
| 20 | c-C₃H₅ | OH | 2-bromo-3-pyridinyl (Br at 2, # at 3) | 0.845 | 320.1 |
| 21 | c-C₃H₅ | OCH₃ | 5-fluoro-2-bromo-3-pyridinyl (F at 5, Br at 2, # at 3) | 1.076 | 352.0 |
| 22 | c-C₃H₅ | OCH₃ | 4-bromo-3-thienyl (# at 3, Br at 4) | 1.161 | 340.8 |

TABLE Z-continued
denotes point of attachment to the pyrimidine ring.
| Example | R¹ | R² | # 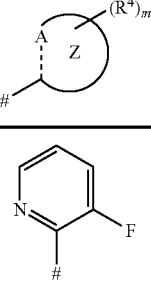 (R⁴)ₘ | HPLC/MS, Rₜ [min] | HPLC/MS, m/z |
|---|---|---|---|---|---|
| 23 | c-C₃H₅ | OH | 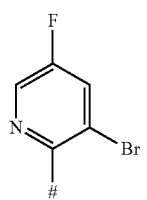 | 0.785 | 260.1 |
| 24 | c-C₃H₅ | OH | 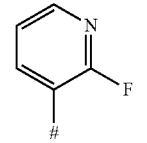 | 0.907 | 337.6 |
| 25 | c-C₃H₅ | OCH₃ |  | 0.951 | 274.0 |
| 26 | c-C₃H₅ | OH | 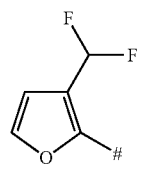 | 0.786 | 260.0 |
| 27 | c-C₃H₅ | OH | 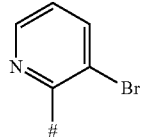 | 0.926 | 281.1 |
| 28 | c-C₃H₅ | OCH₃ | 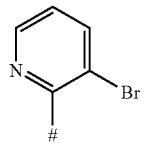 | 1.012 | 336.0 |
| 29 | c-C₃H₅ | OH | 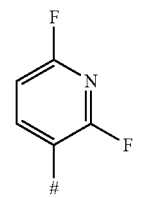 | 0.849 | 321.8 |
| 30 | c-C₃H₅ | OCH₃ | 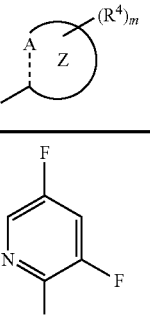 | 1.048 | 292.0 |
| 31 | c-C₃H₅ | OCH₃ | 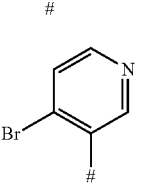 | 1.035 | 292.0 |
| 32 | c-C₃H₅ | OCH₃ | 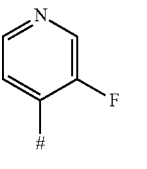 | 0.932 | 335.9 |
| 33 | c-C₃H₅ | OCH₃ | 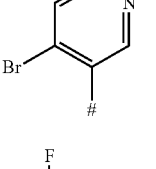 | 0.912 | 274.0 |
| 34 | c-C₃H₅ | OCH₃ | 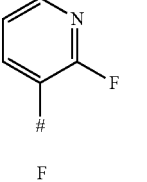 | 0.974 | 333.9 |
| 35 | c-C₃H₅ | OH | 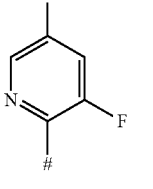 | 0.879 | 278.1 |
| 36 | c-C₃H₅ | OH | 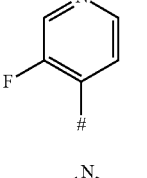 | 0.847 | 278.1 |
| 37 | c-C₃H₅ | OH | 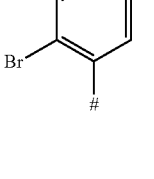 | 0.699 | 260.1 |
| 38 | c-C₃H₅ | OH |  | 0.797 | 320.0 |

TABLE Z-continued
denotes point of attachment to the pyrimidine ring.
| Example | R¹ | R² | # (structure) | HPLC/MS, $R_t$ [min] | HPLC/MS, m/z |
|---|---|---|---|---|---|
| 39 | c-C₃H₅ | OH | 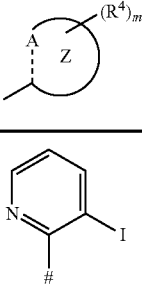 | 0.851 | 368.0 |
| 40 | c-C₃H₅ | OH | 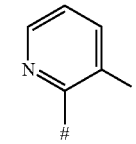 | 0.779 | 259.0 |
| 41 | c-C₃H₅ | OCH₃ | 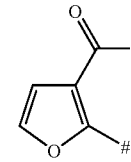 | 1.078 | 308.1 |
| 42 | c-C₃H₅ | OH | 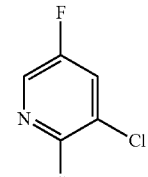 | 0.907 | 294.1 |
| 43 | C₂H₅ | OCH₃ | 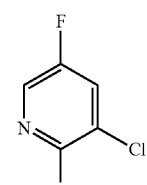 | 0.915 | 323.9 |
| 44 | C₂H₅ | OCH₃ | 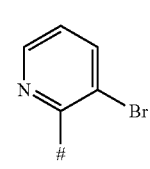 | 0.874 | 262.0 |
| 45 | OCH₃ | OCH₃ | 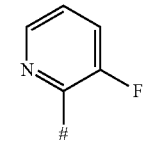 | 0.867 | 371.9 |
| 46 | OCH₃ | OCH₃ | 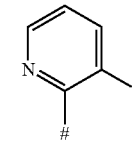 | 0.825 | 264.0 |
| 47 | C₂H₅ | OH | 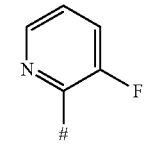 | 0.791 | 355.9 |
| 48 | C₂H₅ | OH | 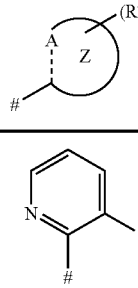 | 0.769 | 309.9 |
| 49 | C₂H₅ | OH | 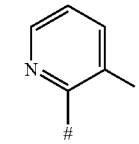 | 0.780 | 309.9 |
| 50 | C₂H₅ | OH | 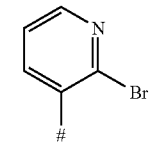 | 0.713 | 248.0 |
| 51 | OCH₃ | OH | 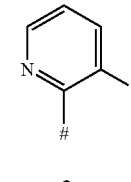 | 0.723 | 309.9 |
| 52 | OCH₃ | OH | 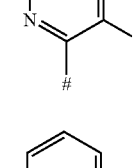 | 0.657 | 250.1 |
| 53 | OCH₃ | OCH₃ | 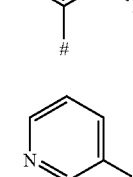 | 0.917 | 282.0 |
| 54 | C₂H₅ | OH | 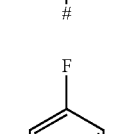 | 0.734 | 326.9 |

TABLE Z-continued denotes point of attachment to the pyrimidine ring.

| Example | R¹ | R² | # —A—Z—(R⁴)ₘ | HPLC/ MS, Rₜ [min] | HPLC/ MS, m/z |
|---|---|---|---|---|---|
| 55 | OCH₃ | OH | 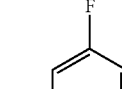 | 0.497 | 268.0 |
| 56 | C₂H₅ | OCH₃ | 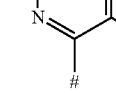 | 0.920 | 278.0 |
| 57 | C₂H₅ | OH | 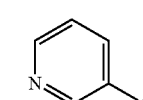 | 0.769 | 264.0 |
| 58 | OCH₃ | OCH₃ | 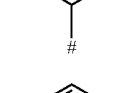 | 0.891 | 280.0 |
| 59 | OCH₃ | OH | 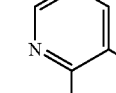 | 0.712 | 266.0 |
| 60 | c-C₃H₅ | OH | 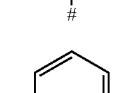 | 0.970 | 324.9 |
| 61 | c-C₃H₅ | OCH₃ | 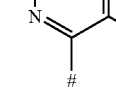 | 1.153 | 342.0 |
| 62 | c-C₃H₅ | OH | 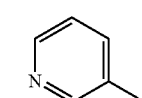 | 0.995 | 328.0 |
| 63 | c-C₃H₅ | OCH₃ | 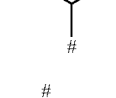 | 1.180 | 358.0 |
| 64 | c-C₃H₅ | OH | 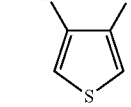 | 1.033 | 344.0 |

B USE EXAMPLES

The herbicidal activity of the pyrimidine compounds of formula (I) was demonstrated by the following greenhouse experiments:

The culture containers used were plastic flowerpots containing loamy sand with approximately 3.0% of humus as the substrate. The seeds of the test plants were sown separately for each species.

For the pre-emergence treatment, the active ingredients, which had been suspended or emulsified in water, were applied directly after sowing by means of finely distributing nozzles.

The containers were irrigated gently to promote germination and growth and subsequently covered with transparent plastic hoods until the plants had rooted. This cover caused uniform germination of the test plants, unless this had been impaired by the active ingredients.

For the post-emergence treatment, the test plants were first grown to a height of 3 to 15 cm, depending on the plant habit, and only then treated with the active ingredients which had been suspended or emulsified in water. For this purpose, the test plants were either sown directly and grown in the same containers, or they were first grown separately as seedlings and transplanted into the test containers a few days prior to treatment.

Depending on the species, the plants were kept at 10-25° C. or 20-35° C., respectively.

The test period extended over 2 to 4 weeks. During this time, the plants were tended, and their response to the individual treatments was evaluated.

Evaluation was carried out using a scale from 0 to 100. 100 means no emergence of the plants, or complete destruction of at least the aerial moieties, and 0 means no damage, or normal course of growth. A good herbicidal activity is given at values of at least 70 and a very good herbicidal activity is given at values of at least 85.

The plants used in the greenhouse experiments were of the following species:

| Bayer code | Scientific name |
|---|---|
| ABUTH | *Abutilon theophrasti* |
| ALOMY | *Alopecurus myosuroides* |
| AMARE | *Amaranthus retroflexus* |
| APESV | *Apera spica-venti* |
| AVEFA | *Avena fatua* |
| ECHCG | *Echinocloa crus-galli* |
| SETVI | *Setaria viridis* |

At an application rate of 2000 g/ha, example 3 applied by the post-emergence method showed very good herbicidal activity against ECHCG and AMARE, and applied by the pre-emergence method showed very good herbicidal activity against ECHCG and APESV.

At an application rate of 2000 g/ha, example 4 applied by the post-emergence method showed very good herbicidal activity against ECHCG, and applied by the pre-emergence method showed very good herbicidal activity against ECHCG.

At an application rate of 2000 g/ha, example 5 applied by the pre-emergence method showed very good herbicidal activity against ECHCG.

At an application rate of 2000 g/ha, example 6 applied by the post-emergence method showed very good herbicidal activity against ECHCG, and applied by the pre-emergence method showed very good herbicidal activity against APESV and ECHCG.

At an application rate of 2000 g/ha, example 7 applied by the post-emergence method showed very good herbicidal activity against ECHCG, and applied by the pre-emergence method showed very good herbicidal activity against ECHCG.

At an application rate of 2000 g/ha, example 8 applied by the pre-emergence method showed very good herbicidal activity against APESV and ECHCG.

At an application rate of 1000 g/ha, example 10 applied by the post-emergence method showed very good herbicidal activity against AVEFA and ALOMY, and good herbicidal activity against ECHCG, and applied by the pre-emergence method showed very good herbicidal activity against APESV and ECHCG.

At an application rate of 1000 g/ha, example 11 applied by the post-emergence method showed good herbicidal activity against AVEFA and very good activity against ALOMY, and applied by the pre-emergence method showed very good herbicidal activity against ECHCG.

At an application rate of 1000 g/ha, example 12 applied by the post-emergence method showed very good herbicidal activity against AVEFA and ALOMY, and applied by the pre-emergence method showed very good herbicidal activity against APESV and ECHCG.

At an application rate of 2000 g/ha, example 13 applied by the post-emergence method showed very good herbicidal activity against ALOMY and ECHCG, and applied by the pre-emergence method showed very good herbicidal activity against APESV and ECHCG.

At an application rate of 1000 g/ha, example 14 applied by the pre-emergence method showed very good herbicidal activity against ECHCG and good activity against APESV.

At an application rate of 2000 g/ha, example 15 applied by the pre-emergence method showed good herbicidal activity against ECHCG.

At an application rate of 1000 g/ha, example 16 applied by the post-emergence method showed very good herbicidal activity against ALOMY and ECHCG, and good herbicidal activity against AVEFA, and applied by the pre-emergence method showed good herbicidal activity against APESV and ECHCG.

At an application rate of 2000 g/ha, example 17 applied by the post-emergence method showed very good herbicidal activity against AMARE.

At an application rate of 2000 g/ha, example 18 applied by the post-emergence method showed very good herbicidal activity against AVEFA, AMARE and ECHCG, and applied by the pre-emergence method showed very good herbicidal activity against APESV and ECHCG.

At an application rate of 2000 g/ha, example 19 applied by the post-emergence method showed very good herbicidal activity against SETVI, AMARE and ECHCG.

At an application rate of 2000 g/ha, example 20 applied by the post-emergence method showed very good herbicidal activity against AVEFA and ECHCG, and applied by the pre-emergence method showed very good herbicidal activity against APESV and ECHCG.

At an application rate of 2000 g/ha, example 21 applied by the post-emergence method showed very good herbicidal activity against ALOMY, AVEFA and ECHCG, and applied by the pre-emergence method showed very good herbicidal activity against APESV and ECHCG.

At an application rate of 2000 g/ha, example 23 applied by the post-emergence method showed very good herbicidal activity against ALOMY and ECHCG, and applied by the pre-emergence method showed very good herbicidal activity against APESV and ECHCG.

At an application rate of 2000 g/ha, example 24 applied by the post-emergence method showed very good herbicidal activity against AMARE, AVEFA and ECHCG, and applied by the pre-emergence method showed very good herbicidal activity against ECHCG and APESV.

At an application rate of 1000 g/ha, example 25 applied by the post-emergence method, showed very good herbicidal activity against ECHCG.

At an application rate of 2000 g/ha, example 28 applied by the post-emergence method, showed very good herbicidal activity against ALOMY, and good herbicidal activity against SETVI, and applied by the pre-emergence method showed very good herbicidal activity against ECHCG and APESV.

At an application rate of 2000 g/ha, example 29 applied by the post-emergence method showed very good herbicidal activity against ALOMY, AVEFA and ECHCG, and applied by the pre-emergence method showed good herbicidal activity against APESV and ECHCG.

At an application rate of 2000 g/ha, example 31 applied by the post-emergence method showed very good herbicidal activity against SETVI, and good activity against ABUTH, and applied by the pre-emergence method showed very good herbicidal activity against APESV.

At an application rate of 2000 g/ha, example 32 applied by the post-emergence method showed very good herbicidal activity against AMARE, and applied by the pre-emergence method showed very good herbicidal activity against APESV, and ECHCG.

At an application rate of 2000 g/ha, example 33 applied by the post-emergence method showed very good herbicidal activity against AVEFA, AMARE and SETVI, and applied by the pre-emergence method showed good herbicidal activity against APESV.

At an application rate of 2000 g/ha, example 34 applied by the post-emergence method showed very good herbicidal activity against ALOMY, ECHCG and SETVI, and applied by the pre-emergence method showed very good herbicidal activity against ECHCG and APESV.

At an application rate of 2000 g/ha, example 36 applied by the post-emergence method showed very good herbicidal activity against ALOMY and AVEFA, and applied by the pre-emergence method showed very good herbicidal activity against ECHCG and APESV.

At an application rate of 2000 g/ha, example 37 applied by the post-emergence method showed good herbicidal activity against ALOMY and ECHCG, and applied by the pre-emergence method showed good herbicidal activity against APESV, and very good herbicidal activity against ECHCG.

At an application rate of 2000 g/ha, example 38 applied by the post-emergence method showed very good herbicidal activity against ALOMY, AVEFA, and AMARE, and applied by the pre-emergence method showed very good herbicidal activity against ECHCG and APESV.

At an application rate of 2000 g/ha, example 39 applied by the post-emergence method showed very good herbicidal activity against AVEFA, and good herbicidal activity against ECHCG and ALOMY, and applied by the pre-emergence method showed very good herbicidal activity against ECHCG and APESV.

At an application rate of 2000 g/ha, example 40 applied by the post-emergence method showed very good herbicidal activity against AMARE.

At an application rate of 2000 g/ha, example 41 applied by the post-emergence method showed very good herbicidal activity against ALOMY, AVEFA, and SETVI, and applied by the pre-emergence method showed very good herbicidal activity against ECHCG and APESV.

At an application rate of 2000 g/ha, example 42 applied by the post-emergence method showed very good herbicidal activity against ALOMY, AVEFA, and ECHCG, and applied by the pre-emergence method showed very good herbicidal activity against ECHCG and APESV.

At an application rate of 2000 g/ha, example 43 applied by the pre-emergence method showed very good herbicidal activity against ECHCG.

At an application rate of 2000 g/ha, example 46 applied by the post-emergence method showed good herbicidal activity against AMARE.

At an application rate of 2000 g/ha, example 48 applied by the post-emergence method showed very good herbicidal activity against SETVI.

At an application rate of 2000 g/ha, example 49 applied by the post-emergence method showed very good herbicidal activity against SETVI, and applied by the pre-emergence method showed very good herbicidal activity against ECHCG.

At an application rate of 1000 g/ha, example 50 applied by the post-emergence method showed very good herbicidal activity against ECHCG.

At an application rate of 2000 g/ha, example 51 applied by the post-emergence method showed good herbicidal activity against ALOMY, AVEFA, and ECHCG.

At an application rate of 2000 g/ha, example 53 applied by the post-emergence method showed good herbicidal activity against SETVI.

At an application rate of 1000 g/ha, example 54 applied by the post-emergence method showed very good herbicidal activity against AMARE and ECHCG.

At an application rate of 2000 g/ha, example 61 applied by the post-emergence method showed very good herbicidal activity against SETVI, ALOMY and AVEFA, and applied by the pre-emergence method showed good herbicidal activity against APESV and showed very good herbicidal activity against ECHCG.

At an application rate of 2000 g/ha, example 62 applied by the post-emergence method showed very good herbicidal activity against ECHCG, ALOMY and AVEFA, and applied by the pre-emergence method showed very good herbicidal activity against APESV and ECHCG.

At an application rate of 2000 g/ha, example 63 applied by the post-emergence method showed very good herbicidal activity against SETVI, ALOMY and ABUTH, and applied by the pre-emergence method showed very good herbicidal activity against APESV and ECHCG.

At an application rate of 2000 g/ha, example 64 applied by the post-emergence method showed very good herbicidal activity against ALOMY and AVEFA, and showed good herbicidal activity against ECHCG, and applied by the pre-emergence method showed very good herbicidal activity against APESV and ECHCG.

The invention claimed is:
1. A pyrimidine compound of formula (I)

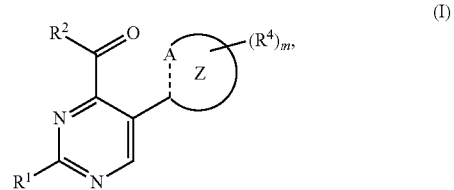

wherein
the dotted line ( ------ ) is a single bond or a double bond;
$R^1$ is $C_1$-$C_6$-alkyl, $C_1$-$C_6$-haloalkyl, OH—$C_1$-$C_6$-alkyl, $C_3$-$C_6$-alkenyl, $C_3$-$C_6$-haloalkenyl, $C_2$-$C_6$-alkynyl, $C_3$-$C_6$-haloalkynyl, $C_1$-$C_6$-alkoxy-$C_1$-$C_6$-alkyl, $C_1$-$C_6$-alkoxy, $C_3$-$C_6$-alkenyloxy, $C_3$-$C_6$-haloalkenyloxy, $C_3$-$C_6$-alkynyloxy, $C_3$-$C_6$-haloalkynyloxy, $C_1$-$C_6$-haloalkoxy, $C_3$-$C_6$-cycloalkoxy, $C_3$-$C_6$-halocycloalkoxy, $C_3$-$C_6$-cycloalkenyloxy, $C_3$-$C_6$-halocycloalkenyloxy, $C_1$-$C_6$-alkylthio, $C_1$-$C_6$-haloalkylthio, ($C_1$-$C_6$-alkyl)amino, di($C_1$-$C_6$-alkyl)amino, $C_1$-$C_6$-alkylsulfinyl, $C_1$-$C_6$-alkylsulfonyl, $C_3$-$C_6$-cycloalkyl, $C_3$-$C_6$-cycloalkenyl, $C_3$-$C_6$-halocycloalkyl, $C_3$-$C_6$-halocycloalkenyl, [1-($C_1$-$C_6$-alkyl)]-$C_3$-$C_6$-cycloalkyl, [1-($C_3$-$C_6$-alkenyl]-$C_3$-$C_6$-cycloalkyl, [1-($C_2$-$C_6$-alkynyl]-$C_3$-$C_6$-cycloalkyl, [1-($C_1$-$C_6$-haloalkyl]-$C_3$-$C_6$-cycloalkyl, [1-($C_3$-$C_6$-haloalkenyl]-$C_3$-$C_6$-cycloalkyl, [1-($C_3$-$C_6$-haloalkynyl)]-$C_3$-$C_6$-cycloalkyl, $C_3$-$C_6$-cycloalkyl-$C_1$-$C_6$-haloalkyl, $C_3$-$C_6$-cycloalkyl-$C_1$-$C_6$-alkoxy, $C_3$-$C_6$-cycloalkyl-$C_1$-$C_6$-haloalkoxy, phenyl, 5- or 6-membered heteroaryl, or 3- to 6-membered heterocyclyl;
wherein the cyclic groups of $R^1$ are unsubstituted or substituted by $R^a$;
$R^2$ is H, halogen, $C_1$-$C_6$-alkyl, $C_1$-$C_6$-haloalkyl, $C_1$-$C_6$-alkylcarbonyl-$C_1$-$C_6$-alkyl, $C_1$-$C_6$-alkoxycarbonyl-$C_1$-$C_6$-alkyl, $C_1$-$C_6$-haloalkylcarbonyl-$C_1$-$C_6$-alkyl, $C_1$-$C_6$-haloalkoxy-carbonyl-$C_1$-$C_6$-alkyl, $C_1$-$C_6$-alkylcarbonyl-$C_1$-$C_6$-haloalkyl, $C_1$-$C_6$-alkoxycarbonyl-$C_1$-$C_6$-haloalkyl, $C_1$-$C_6$-haloalkylcarbonyl-$C_1$-$C_6$-haloalkyl, $C_1$-$C_6$-haloalkoxycarbonyl-$C_1$-$C_6$-haloalkyl, OH, $C_1$-$C_6$-alkoxy, $C_1$-$C_6$-alkoxy-$C_1$-$C_6$-alkoxy, $C_1$-$C_6$-haloalkoxy-$C_1$-$C_6$-alkoxy, $C_1$-$C_6$-alkoxy-$C_1$-$C_6$-haloalkoxy, $C_1$-$C_6$-haloalkoxy-$C_1$-$C_6$-haloalkoxy, $C_1$-$C_6$-alkoxy-$C_1$-$C_6$-alkoxy-$C_1$-$C_6$-alkoxy, $C_1$-$C_6$-haloalkoxy, $C_1$-$C_6$-cyanoalkoxy, $C_1$-$C_6$-hydroxyalkoxy, $C_3$-$C_6$-alkenyloxy, $C_3$-$C_6$-alkenyloxy-$C_1$-$C_6$-alkoxy, $C_3$-$C_6$-haloalkenyloxy-$C_1$-$C_6$-haloalkoxy, $C_3$-$C_6$-alkenyloxy-$C_1$-$C_6$-haloalkoxy, $C_3$-$C_6$-haloalkenyloxy, $C_3$-$C_6$-alkynyloxy, $C_3$-$C_6$-haloalkynyloxy, $C_3$-$C_6$-alkynyloxy-$C_1$-$C_6$-alkoxy, $C_3$-$C_6$-haloalkynyloxy-$C_1$-$C_6$-haloalkoxy, $C_3$-$C_6$-alkynyloxy-$C_1$-$C_6$-haloalkoxy, $C_3$-$C_6$-alkynyloxy-$C_3$-$C_6$-alkenyloxy, $C_3$-$C_6$-haloalkynyloxy-$C_3$-$C_6$-alkenyloxy, $C_3$-$C_6$-alkynyloxy-$C_3$-$C_6$-haloalkenyloxy, $C_3$-$C_6$-haloalkynyloxy-$C_3$-$C_6$-haloalkenyloxy, $C_3$-$C_6$-alkynyloxy-$C_3$-$C_6$-alkynyloxy, $C_3$-$C_6$-haloalkynyloxy-$C_3$-$C_6$-alkynyloxy, $C_3$-$C_6$-alkynyloxy-$C_3$-$C_6$-haloalkynyloxy, $C_3$-$C_6$-halo-alkynyloxy-$C_3$-$C_6$-haloalkynyloxy, ($C_1$-$C_6$-alkyl)carbonyl-$C_1$-$C_6$-alkoxy, ($C_1$-$C_6$-haloalkyl)carbonyl-$C_1$-$C_6$-haloalkoxy, ($C_1$-$C_6$-haloalkyl)carbonyl-$C_1$-$C_6$-alkoxy, ($C_1$-$C_6$-al-kyl)carbonyl-$C_1$-$C_6$-haloalkoxy, ($C_1$-$C_6$-alkoxy)carbonyl-$C_1$-$C_6$-alkoxy, ($C_1$-$C_6$-haloalkoxy)-carbonyl-$C_1$-$C_6$-alkoxY, ($C_1$-$C_6$-alkoxy)carbonyl-$C_1$-$C_6$-haloalkoxy, ($C_1$-$C_6$-haloalkoxy)-carbonyl-$C_1$-$C_6$-haloalkoxy, ($C_1$-$C_6$-alkoxy-$C_1$-$C_6$-alkyl)carbonyl-$C_1$-$C_6$-alkoxy, ($C_1$-$C_6$-haloalkoxy-$C_1$-$C_6$-alkyl)carbonyl-$C_1$-$C_6$-alkoxy, ($C_1$-$C_6$-alkoxy-$C_1$-$C_6$-haloalkyl)carbonyl-$C_1$-$C_6$-alkoxy, ($C_1$-$C_6$-alkoxy-$C_1$-$C_6$-alkyl)carbonyl-$C_1$-$C_6$-haloalkoxy, ($C_1$-$C_6$-haloalkoxy-$C_1$-$C_6$-haloalkyl)carbonyl-$C_1$-$C_6$-alkoxy, ($C_1$-$C_6$-haloalkoxy-$C_1$-$C_6$-alkyl)carbonyl-$C_1$-$C_6$-halo-alkoxy, ($C_1$-$C_6$-alkoxy-$C_1$-$C_6$-haloalkyl)carbonyl-$C_1$-$C_6$-haloalkoxy, ($C_1$-$C_6$-haloalkoxy-$C_1$-$C_6$-haloalkyl)carbonyl-$C_1$-$C_6$-haloalkoxy, ($C_1$-$C_6$-alkylthio)carbonyl-$C_1$-$C_6$-alkoxy, ($C_1$-$C_6$-haloalkylthio)carbonyl-$C_1$-$C_6$-alkoxy, ($C_1$-$C_6$-alkylthio)carbonyl-$C_1$-$C_6$-haloalkoxy, ($C_1$-$C_6$-haloalkylthio)carbonyl-$C_1$-$C_6$-haloalkoxy, ($C_1$-$C_6$-alkylthio-$C_1$-$C_6$-alkyl)carbonyl-$C_1$-$C_6$-alkoxy, ($C_1$-$C_6$-haloalkylthio-$C_1$-$C_6$-alkyl)carbonyl-$C_1$-$C_6$-alkoxy, ($C_1$-$C_6$-alkylthio-$C_1$-$C_6$-haloalkyl)-carbonyl-$C_1$-$C_6$-alkoxy, ($C_1$-$C_6$-alkylthio-$C_1$-$C_6$-alkyl)carbonyl-$C_1$-$C_6$-haloalkoxy, ($C_1$-$C_6$-haloalkylthio-$C_1$-$C_6$-haloalkyl)carbonyl-$C_1$-$C_6$-alkoxy, ($C_1$-$C_6$-haloalkylthio-$C_1$-$C_6$-alkyl)carbonyl-$C_1$-$C_6$-haloalkoxy, ($C_1$-$C_6$-alkylthio-$C_1$-$C_6$-haloalkyl)carbonyl-$C_1$-$C_6$-halo-alkoxy, ($C_1$-$C_6$-haloalkylthio-$C_1$-$C_6$-haloalkyl)carbonyl-$C_1$-$C_6$-haloalkoxy, $C_3$-$C_6$-cycloalkoxy, $C_3$-$C_6$-halocycloalkoxy, ($C_3$-$C_6$-cycloalkyl)$C_1$-$C_6$-alkoxy, ($C_3$-$C_6$-halo-cycloalkyl)$C_1$-$C_6$-alkoxy, ($C_3$-$C_6$-cycloalkyl)$C_1$-$C_6$-haloalkoxy, $C_1$-$C_6$-alkylcarbonylmino, [($C_1$-$C_6$-alkyl)carbonyl]$C_1$-$C_6$-alkyl)amino, $C_1$-$C_6$-haloalkylcarbonylamino, [($C_1$-$C_6$-haloalkyl)carbonyl]($C_1$-$C_6$-alkyl)amino, $C_3$-$C_6$-cycloalkylcarbonylamino, [($C_3$-$C_6$-cyclo-alkyl)carbonyl]$C_1$-$C_6$-alkyl)amino, phenylcarbonylamino, (phenylcarbonyl)($C_1$-$C_6$-alkyl)amino, heterocyclylcarbonylamino, (heterocyclylcarbonyl)($C_1$-$C_6$-alkyl)-amino, heteroarylcarbonylamino, (heteroarylcarbonyl)($C_1$-$C_6$-alkyl)amino, [($C_1$-$C_6$-alkyl)-carbonyl]($C_1$-$C_6$-alkoxy)amino, [($C_1$-$C_6$-haloalkyl)carbonyl]($C_1$-$C_6$-alkoxy)amino, [($C_3$-$C_6$-cycloalkyl)carbonyl]($C_1$-$C_6$-alkyloxy)amino, (phenylcarbonyl)($C_1$-$C_6$-alkoxy)-amino, (heterocyclylcarbonyl)($C_1$-$C_6$-alkoxy)amino, (heteroarylcarbonyl)($C_1$-$C_6$-alkoxy)-amino, [($C_1$-$C_6$-alkyl)carbonyl](C2-$C_6$-alkenyl)amino, [($C_1$-$C_6$-haloalkyl)carbonyl](C2-$C_6$-alkenyl)amino, [($C_3$-$C_6$-cycloalkyl)carbonyl]($C_2$-$C_6$-alkenyl)amino, (phenyl-carbonyl)(C2-$C_6$-alkenyl)amino, (heterocyclylcarbonyl)($C_2$-$C_6$-alkenyl)amino, (heteroarylcarbonyl)($C_2$-$C_6$-alkenyl)amino, [($C_1$-$C_6$-alkyl)carbonyl]($C_3$-$C_6$-alkynyl)amino, [($C_1$-$C_6$-haloalkyl)carbonyl]($C_3$-$C_6$-alkynyl)amino, [($C_3$-$C_6$-cycloalkyl)carbonyl]($C_3$-$C_6$-alkynyl)amino, (phenylcarbonyl)($C_3$-$C_6$-alkynyl)amino, (heterocyclylcarbonyl)($C_3$-$C_6$-alkynyl)amino, (heteroarylcarbonyl)($C_3$-$C_6$-alkynyl)amino, [($C_2$-$C_6$-alkenyl)carbonyl]-amino, [($C_2$-$C_6$-alkenyl)carbonyl]($C_1$-$C_6$-alkyl)amino, [($C_2$-$C_6$-alkenyl)carbonyl]($C_1$-$C_6$-alkoxy)amino, [($C_3$-$C_6$-alkynyl)carbonyl]amino, [($C_3$-$C_6$-alkynyl)carbonyl]($C_1$-$C_6$-alkyl)amino, [($C_3$-$C_6$-alkynyl)carbonyl]($C_1$-$C_6$-alkoxy)amino, [di($C_1$-$C_6$-alkyl)amino]carbonylamino, [di($C_1$-$C_6$-alkyl)aminocarbonyl]($C_1$-$C_6$-alkyl)amino, [di($C_1$-$C_6$-alkyl)aminocarbonyl]($C_1$-$C_6$-alkoxy)amino, aminocarbonyl-$C_1$-$C_6$-alkoxy, ($C_3$-$C_6$-halo-cycloalkyl)$C_1$-$C_6$-haloalkoxy, aminocarbonyl-$C_1$-$C_6$-haloalkoxy, N—($C_1$-$C_6$-alkyl)-aminocarbonyl-$C_1$-$C_6$-alkoxy, N—($C_1$-$C_6$-alkyl)-aminocarbonyl-$C_1$-$C_6$-haloalkoxy, N,N-di($C_1$-$C_6$-alkyl)-aminocarbonyl-$C_1$-$C_6$-alkoxy, N,N-di($C_1$-$C_6$-alkyl)-aminocarbonyl-$C_1$-$C_6$-haloalkoxy, (diphenyl)C=N—O, ($C_1$-$C_6$-alkyl)(phenyl)C=N—O, [di($C_1$-$C_6$-alkyl)]C=N-0, ($C_1$-$C_6$-alkyl)$_3$-silyl-$C_1$-$C_6$-alkoxy, $C_1$-$C_6$-alkylthio, $C_1$-$C_6$-haloalkylthio, $C_1$-$C_6$-alkoxy-$C_1$-$C_6$-alkylthio, $C_1$-$C_6$-haloalkoxy-$C_1$-$C_6$-alkylthio, $C_1$-$C_6$-alkoxy-$C_1$-$C_6$-haloalkylthio, $C_1$-$C_6$-haloalkoxy-$C_1$-$C_6$-haloalkylthio, $C_1$-$C_6$-alkoxy-$C_1$-$C_6$-alkoxy-$C_1$-$C_6$-alkylthio, $C_1$-$C_6$-cyanoalkylthio, $C_3$-$C_6$-alkenylthio, $C_3$-$C_6$-haloalkenylthio, $C_3$-$C_6$-alkenyloxy-$C_1$-$C_6$-alkylthio, $C_3$-$C_6$-haloalkenyloxy-$C_1$-$C_6$-alkylthio, $C_3$-$C_6$-alkenyloxy-$C_1$-$C_6$-haloalkylthio, $C_3$-$C_6$-haloalkenyloxy-$C_1$-$C_6$-haloalkylthio, $C_3$-$C_6$-alkynylthio, $C_3$-$C_6$-haloalkynylthio, $C_3$-$C_6$-alkynyloxy-$C_1$-$C_6$-alkylthio, $C_3$-$C_6$-haloalkynyloxy-$C_1$-$C_6$-haloalkylthio, $C_3$-$C_6$-alkynyloxy-$C_1$-$C_6$-haloalkylthio, $C_3$-$C_6$-alkynyloxy-$C_3$-$C_6$-alkenylthio, $C_3$-$C_6$-haloalkynyloxy-$C_3$-$C_6$-alkenylthio, $C_3$-$C_6$-haloalkynyloxy-$C_3$-$C_6$-haloalkenylthio, $C_3$-$C_6$-haloalkynyloxy-$C_3$-$C_6$-haloalkenylthio, $C_3$-$C_6$-alkynyloxy-$C_3$-$C_6$-alkynylthio, $C_3$-$C_6$-haloalkynyloxy-$C_3$-$C_6$-alkynylthio, $C_3$-$C_6$-alkynyloxy-$C_3$-$C_6$-haloalkynylthio, $C_3$-$C_6$-haloalkynyloxy-$C_3$-$C_6$-haloalkynylthio, ($C_1$-$C_6$-alkyl)carbonyl-$C_1$-$C_6$-alkylthio, ($C_1$-$C_6$-haloalkyl)carbonyl-$C_1$-$C_6$-alkylthio, ($C_1$-$C_6$-alkyl)carbonyl-$C_1$-$C_6$-haloalkylthio, ($C_1$-$C_6$-haloalkyl)carbonyl-$C_1$-$C_6$-haloalkylthio, ($C_1$-$C_6$-alkoxy)carbonyl-$C_1$-$C_6$-alkylthio, ($C_1$-$C_6$-haloalkoxy)carbonyl-$C_1$-$C_6$-alkylthio, ($C_1$-$C_6$-alkoxy)carbonyl-$C_1$-$C_6$-haloalkylthio, ($C_1$-$C_6$-haloalkoxy)carbonyl-$C_1$-$C_6$-haloalkylthio, ($C_1$-$C_6$-alkoxy-$C_1$-$C_6$-alkyl)carbonyl-$C_1$-$C_6$-alkylthio, ($C_1$-$C_6$-haloalkoxy-$C_1$-$C_6$-alkyl)carbonyl-$C_1$-$C_6$-alkylthio, ($C_1$-$C_6$-alkoxy-$C_1$-$C_6$-haloalkyl)carbonyl-$C_1$-$C_6$-alkylthio, ($C_1$-$C_6$-alkoxy-$C_1$-$C_6$-alkyl)carbonyl-$C_1$-$C_6$-haloalkylthio, ($C_1$-$C_6$-haloalkoxy-$C_1$-$C_6$-haloalkyl)carbonyl-$C_1$-$C_6$-alkylthio, ($C_1$-$C_6$-haloalkoxy-$C_1$-$C_6$-alkyl)carbonyl-$C_1$-$C_6$-haloalkylthio, ($C_1$-$C_6$-alkoxy-$C_1$-$C_6$-haloalkyl)carbonyl-$C_1$-$C_6$-haloalkylthio, ($C_1$-$C_6$-haloalkoxy-$C_1$-$C_6$-haloalkylthio)carbonyl-$C_1$-$C_6$-haloalkylthio, ($C_1$-$C_6$-alkylthio)carbonyl-$C_1$-$C_6$-alkylthio, ($C_1$-$C_6$-haloalkylthio)carbonyl-$C_1$-$C_6$-alkylthio, ($C_1$-$C_6$-alkylthio)carbonyl-$C_1$-$C_6$-haloalkylthio, ($C_1$-$C_6$-haloalkyl-thio)carbonyl-$C_1$-$C_6$-haloalkylthio, ($C_1$-$C_6$-alkylthio-$C_1$-$C_6$-alkyl)carbonyl-$C_1$-$C_6$-alkylthio, ($C_1$-$C_6$-haloalkylthio-$C_1$-$C_6$-alkyl)carbonyl-$C_1$-$C_6$-alkylthio, ($C_1$-$C_6$-alkylthio-$C_1$-$C_6$-haloalkyl)carbonyl-$C_1$-$C_6$-alkylthio, ($C_1$-$C_6$-alkylthio-$C_1$-$C_6$-alkyl)carbonyl-$C_1$-$C_6$-haloalkylthio, ($C_1$-$C_6$-haloalkylthio-$C_1$-$C_6$-haloalkyl)carbonyl-$C_1$-$C_6$-alkylthio, ($C_1$-$C_6$-haloalkylthio-$C_1$-$C_6$-alkyl)carbonyl-$C_1$-$C_6$-haloalkylthio, ($C_1$-$C_6$-alkylthio-$C_1$-$C_6$-haloalkyl)carbonyl-$C_1$-$C_6$-haloalkylthio, ($C_1$-$C_6$-haloalkylthio-$C_1$-$C_6$-haloalkyl)carbonyl-$C_1$-$C_6$-haloalkylthio, $C_3$-$C_6$-cycloalkylthio, $C_3$-$C_6$-halocycloalkylthio, ($C_3$-$C_6$-cycloalkyl)$C_1$-$C_6$-alkylthio, ($C_3$-$C_6$-cyclo-alkyl)$C_1$-$C_6$-haloalkylthio, ($C_3$-$C_6$-halocycloalkyl)$C_1$-$C_6$-alkylthio, ($C_3$-$C_6$-halocycloalkyl)$C_1$-$C_6$-haloalkylthio, aminocarbonyl-$C_1$-$C_6$-alkylthio, aminocarbonyl-$C_1$-$C_6$-haloalkylthio, N—($C_1$-$C_6$-alkyl)-aminocarbonyl-$C_1$-$C_6$-alkylthio, N—($C_1$-$C_6$-haloalkyl)-aminocarbonyl-$C_1$-$C_6$-alkylthio, N—($C_1$-$C_6$-alkyl)- aminocarbonyl-$C_1$-$C_6$-haloalkylthio, N—($C_1$-$C_6$-haloalkyl)-aminocarbonyl-$C_1$-$C_6$-haloalkylthio, N,N-di($C_1$-$C_6$-alkyl)-aminocarbonyl-$C_1$-$C_6$-alkylthio, N,N-di($C_1$-$C_6$-haloalkyl)-aminocarbonyl-$C_1$-$C_6$-alkylthio, N,N-di($C_1$-$C_6$-alkyl)-aminocarbonyl-$C_1$-$C_6$-haloalkylthio, N,N-di($C_1$-$C_6$-haloalkyl)-aminocarbonyl-$C_1$-$C_6$-haloalkylthio, NH2, ($C_1$-$C_6$-alkyl)amino, hydroxyamino, ($C_1$-$C_6$-alkoxy)amino, ($C_1$-$C_6$-cycloalkoxy)amino, ($C_1$-$C_6$-al-kyl)sulfinylamino, ($C_1$-$C_6$-alkyl)sulfonylamino, (amino)sulfinylamino, [($C_1$-$C_6$-alkyl)amino]sulfinylamino, (amino)sulfonylamino, [($C_1$-$C_6$-alkyl)amino]sulfonylamino, [di($C_1$-$C_6$-al-kyl)amino]sulfonylamino, di($C_1$-$C_6$-alkyl)amino, (hydroxy)($C_1$-$C_6$-alkyl)amino, (hydroxy)($C_1$-$C_6$-cycloalkyl)amino, ($C_1$-$C_6$-alkoxy)($C_1$-$C_6$-alkyl)amino, ($C_1$-$C_6$-alkoxy)($C_3$-$C_6$-cycloalkyl)amino, ($C_3$-$C_6$-cycloalkoxy)($C_1$-$C_6$-alkyl)amino, ($C_3$-$C_6$-cycloalkoxy)($C_3$-$C_6$-cycloalkyl)amino, [($C_1$-$C_6$-alkyl)sulfinyl]($C_1$-$C_6$-alkyl)amino, [($C_1$-$C_6$-alkyl)sulfonyl]($C_1$-$C_6$-alkyl)amino, [di($C_1$-$C_6$-alkyl)amino]sulfinylamino, [di($C_1$-$C_6$-alkyl)amino]sulfonylamino, phenyloxy, phenyl-$C_1$-$C_6$-alkoxy, phenylthio, phenyl-$C_1$-$C_6$-alkylthio, phenylamino, ($C_1$-$C_6$-alkyl)(phenyl)amino, (heteroaryl)oxy, heteroaryl-$C_1$-$C_6$-alkoxy, (heterocyclyl)oxy, or heterocyclyl-$C_1$-$C_6$-alkoxy;

wherein the cyclic groups of $R^2$ are unsubstituted or substituted by $R^a$;

Z together with A is a 5 or 6 membered heteroaryl ring selected from rings A to G where # denotes the point of attachment to the pyrimidine ring,

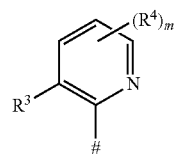

A

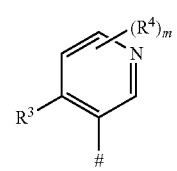

B

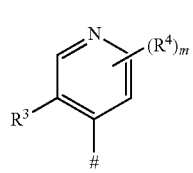

C

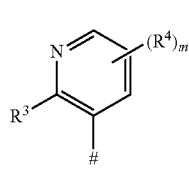

D

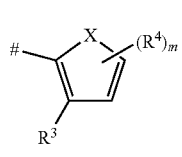

E

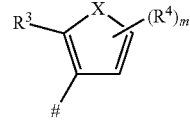

F

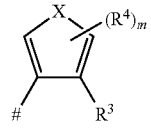

G $R^3$ is halogen, CHO, CN, $C_1$-$C_6$-haloalkyl, or $C_1$-$C_6$-alkoxy;

X is O, S, or $NR^{3,4}$;

$R^{3,4}$ is H, $C_1$-$C_6$-alkyl, $C_1$-$C_6$-haloalkyl, $C_1$-$C_6$-alkylcarbonyl, $C_3$-$C_6$-alkenyl, $C_3$-$C_6$-haloalkenyl, $C_3$-$C_6$-alkenyl, $C_3$-$C_6$-haloalkenyl, or $C_3$-$C_6$-cycloalkyl;

$R^4$ is halogen, CHO, CN, $C_1$-$C_6$-alkyl, $C_1$-$C_6$-haloalkyl, or $C_1$-$C_6$-alkoxy;

$R^a$ is halogen, CN, $NO_2$, $C_1$-$C_6$-alkyl, $C_1$-$C_6$-haloalkyl, $C_1$-$C_6$-alkoxy, or $C_1$-$C_6$-haloalkoxy;

m is 0 or 1;

and agriculturally acceptable salts of the compounds of formula (I).

2. The pyrimidine compound of formula (I) of claim 1, wherein $R^1$ is $C_1$-$C_6$-alkyl, $C_1$-$C_6$-alkoxy, $C_1$-$C_6$-haloalkoxy, $C_3$-$C_6$-alkenyloxy, $C_3$-$C_6$-haloalkenyloxy, $C_3$-$C_6$-alkynyloxy, $C_3$-$C_6$-haloalkynyloxy, $C_1$-$C_6$-alkylthio, or $C_3$-$C_6$-cycloalkyl, wherein the cycloalkyl substituent is unsubstituted.

3. The pyrimidine compound of formula (I) of claim 1, wherein $R^2$ is OH, $C_1$-$C_6$-alkoxy, $C_1$-$C_6$-haloalkoxy, $C_3$-$C_6$-alkynyloxy, $C_1$-$C_6$-alkylthio, phenyloxy, $C_1$-$C_6$-alkylcarbonylamino, $C_1$-$C_6$-haloalkylcarbonylamino, phenylcarbonylamino, heterocyclylcarbonylamino, heteroarylcarbonylamino, ($C_1$-$C_6$-alkoxy)amino, ($C_1$-$C_6$-alkoxy)($C_1$-$C_6$-alkyl)amino, hydroxy($C_1$-$C_6$-alkyl)amino, hydroxyamino, or phenyl-$C_1$-$C_6$-alkoxy, wherein the phenyl substituent is unsubstituted.

4. The pyrimidine compound of formula (I) of claim 1, wherein $R^1$ is $C_1$-$C_6$-alkyl, $C_1$-$C_6$-alkoxy, $C_1$-$C_6$-haloalkoxy, $C_3$-$C_6$-alkenyloxy, $C_3$-$C_6$-haloalkenyloxy $C_3$-$C_6$-alkynyloxy, $C_3$-$C_6$-haloalkynyloxy, $C_1$-$C_6$-alkylthio, or $C_3$-$C_6$-cycloalkyl, wherein the cycloalkyl substituent is unsubstituted; and $R^2$ is OH, $C_1$-$C_6$-alkoxy, $C_1$-$C_6$-haloalkoxy, $C_3$-$C_6$-alkynyloxy, $C_1$-$C_6$-alkylthio, phenyloxy, $C_1$-$C_6$-alkylcarbonylamino, $C_1$-$C_6$-haloalkylcarbonylamino, phenylcarbonylamino, heterocyclylcarbonylamino, heteroarylcarbonylamino, ($C_1$-$C_6$-alkoxy)amino, ($C_1$-$C_6$-alkoxy)($C_1$-$C_6$-alkyl)amino, hydroxy($C_1$-$C_6$-alkyl)amino, hydroxyamino, or phenyl-$C_1$-$C_6$-alkoxy, wherein the phenyl substituent is unsubstituted.

5. A herbicidal composition comprising:

A) at least one pyrimidine compound of formula I, including agriculturally acceptable salts of the compounds of formula (I), as defined in claim 1;

and

B) at least one herbicide B selected from the group consisting of herbicides of class b1) to b15):
- b1) lipid biosynthesis inhibitors;
- b2) acetolactate synthase inhibitors (ALS inhibitors);
- b3) photosynthesis inhibitors;
- b4) protoporphyrinogen-IX oxidase inhibitors,
- b5) bleacher herbicides;
- b6) enolpyruvyl shikimate 3-phosphate synthase inhibitors (EPSP inhibitors);
- b7) glutamine synthetase inhibitors;
- b8) 7,8-dihydropteroate synthase inhibitors (DHP inhibitors);
- b9) mitosis inhibitors;
- b10) inhibitors of the synthesis of very long chain fatty acids (VLCFA inhibitors);
- b11) cellulose biosynthesis inhibitors;
- b12) decoupler herbicides;
- b13) auxinic herbicides;
- b14) auxin transport inhibitors; and
- b15) other herbicides selected from the group consisting of bromobutide, chlorflurenol, chlorflurenol-methyl, cinmethylin, cumyluron, dalapon, dazomet, difenzoquat, difenzoquat-metilsulfate, dimethipin, DSMA, dymron, endothal and its salts, etobenzanid, flamprop, flamprop-isopropyl, flamprop-methyl, flamprop-M-isopropyl, flamprop-M-methyl, flurenol, flurenol-butyl, flurprimidol, fosamine, fosamine-ammonium, indanofan, indaziflam, maleic hydrazide, mefluidide, metam, methiozolin (CAS 403640-27-7), methyl azide, methyl bromide, methyl-dymron, methyl iodide, MSMA, oleic acid, oxaziclomefone, pelargonic acid, pyributicarb, quinoclamine, triaziflam, tridiphane and 6-chloro-3-(2-cyclopropyl-6-methylphenoxy)-4-pyridazinol, and its salts and esters;

including their agriculturally acceptable salts.

6. A composition comprising the composition of claim 5, and safeners.

7. The composition of claim 5, wherein the composition comprises at least one herbicide B selected from herbicides of class b1, b2, b3, b4, b5, b6, b9, b10, b13 and b14.

8. The composition of claim 5, wherein the composition comprises at least one herbicide B selected from herbicides of class b1, b2, b4, b5, b9, b10, b13 and b14.

9. The composition of claim 5, wherein the weight ratio of component A to component B is in the range of from 1:500 to 500:1.

10. A herbicidal composition comprising a herbicidal active amount of at least one pyrimidine compound of formula (I), including agriculturally acceptable salts of the compounds of formula (I), as defined in claim 1, and at least one inert liquid and/or solid carrier and, optionally, at least one surface-active substance.

11. A herbicidal composition comprising the composition of claim 5, and at least one inert liquid and/or solid carrier and, optionally, at least one surface-active substance.

12. A method of controlling undesired vegetation, which comprises allowing a herbicidal active amount of at least one pyrimidine compound of formula (I) of claim 1 or an agriculturally acceptable salt of the compounds of formula (I) to act on plants, their environment or on seed.

13. A method of controlling undesired vegetation, which comprises allowing a herbicidal active amount of the composition of claim 5 to act on plants, their environment or on seed.

14. The method of claim 12, wherein
$R^1$ is $C_1$-$C_6$-alkyl, $C_1$-$C_6$-alkoxy, $C_1$-$C_6$-haloalkoxy, $C_3$-$C_6$-alkenyloxy, $C_3$-$C_6$-haloalkenyloxy, $C_3$-$C_6$-alkynyloxy, $C_3$-$C_6$-haloalkynyloxy, $C_1$-$C_6$-alkylthio, or $C_3$-$C_6$-cycloalkyl, wherein the cycloalkyl substituent is unsubstituted.

15. The method of claim 12, wherein
$R^2$ is OH, $C_1$-$C_6$-alkoxy, $C_1$-$C_6$-haloalkoxy, $C_3$-$C_6$-alkynyloxy, $C_1$-$C_6$-alkylthio, phenyloxy, $C_1$-$C_6$-alkylcarbonylamino, $C_1$-$C_6$-haloalkylcarbonylamino, phenylcarbonylamino, heterocyclylcarbonylamino, heteroarylcarbonylamino, ($C_1$-$C_6$-alkoxy)amino, ($C_1$-$C_6$-alkoxy)($C_1$-$C_6$-alkyl)amino, hydroxy($C_1$-$C_6$-alkyl)amino, hydroxyamino, or phenyl-$C_1$-$C_6$-alkoxy, wherein the phenyl substituent is unsubstituted.

16. The method of claim 12, wherein
$R^1$ is $C_1$-$C_6$-alkyl, $C_1$-$C_6$-alkoxy, $C_1$-$C_6$-haloalkoxy, $C_3$-$C_6$-alkenyloxy, $C_3$-$C_6$-haloalkenyloxy $C_3$-$C_6$-alkynyloxy, $C_3$-$C_6$-haloalkynyloxy, $C_1$-$C_6$-alkylthio, or $C_3$-$C_6$-cycloalkyl, wherein the cycloalkyl substituent is unsubstituted; and
$R^2$ is OH, $C_1$-$C_6$-alkoxy, $C_1$-$C_6$-haloalkoxy, $C_3$-$C_6$-alkynyloxy, $C_1$-$C_6$-alkylthio, phenyloxy, $C_1$-$C_6$-alkylcarbonylamino, $C_1$-$C_6$-haloalkylcarbonylamino, phenylcarbonylamino, heterocyclylcarbonylamino, heteroarylcarbonylamino, ($C_1$-$C_6$-alkoxy)amino, ($C_1$-$C_6$-alkoxy)($C_1$-$C_6$-alkyl)amino, hydroxy($C_1$-$C_6$-alkyl)amino, hydroxyamino, or phenyl-$C_1$-$C_6$-alkoxy, wherein the phenyl substituent is unsubstituted.

* * * * *